United States Patent
Gray et al.

(10) Patent No.: US 10,450,310 B2
(45) Date of Patent: Oct. 22, 2019

(54) BIFUNCTIONAL MOLECULES FOR DEGRADATION OF EGFR AND METHODS OF USE

(71) Applicant: Dana-Farber Cancer Institute, Inc., Boston, MA (US)

(72) Inventors: Nathanael Gray, Boston, MA (US); Jaebong Jang, Boston, MA (US); Dries De Clercq, Boston, MA (US); Michael Eck, Boston, MA (US); Pasi Janne, Nedham, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/163,254

(22) Filed: Oct. 17, 2018

(65) Prior Publication Data

US 2019/0106417 A1 Apr. 11, 2019

Related U.S. Application Data

(63) Continuation of application No. PCT/US2017/028950, filed on Apr. 21, 2017.

(60) Provisional application No. 62/326,574, filed on Apr. 22, 2016.

(51) Int. Cl.
| | | |
|---|---|---|
| *C07D 417/14* | (2006.01) | |
| *A61K 47/54* | (2017.01) | |
| *A61P 35/00* | (2006.01) | |
| *A61K 47/18* | (2017.01) | |

(52) U.S. Cl.
CPC .......... *C07D 417/14* (2013.01); *A61K 47/18* (2013.01); *A61K 47/545* (2017.08); *A61P 35/00* (2018.01)

(58) Field of Classification Search
CPC .............................. C07D 401/14; C07D 403/14
See application file for complete search history.

(56) References Cited

U.S. PATENT DOCUMENTS

| | | | |
|---|---|---|---|
| 6,306,663 B1 | 10/2001 | Kenten et al. | |
| 7,041,298 B2 | 5/2006 | Deshaies et al. | |
| 7,208,157 B2 | 4/2007 | Deshaies et al. | |
| 9,694,084 B2 * | 7/2017 | Bradner | C07J 43/003 |
| 2013/0190340 A1 | 7/2013 | Hedstrom et al. | |
| 2014/0302523 A1 | 10/2014 | Crews et al. | |
| 2014/0356322 A1 | 12/2014 | Crews et al. | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0022642 A1 | 1/2016 | Crews et al. | |
| 2016/0045607 A1 | 2/2016 | Crew et al. | |
| 2016/0058872 A1 | 3/2016 | Crew et al. | |
| 2016/0176916 A1 | 6/2016 | Bradner et al. | |
| 2016/0214972 A1 | 7/2016 | Jin et al. | |
| 2016/0272639 A1 | 9/2016 | Crew et al. | |
| 2017/0008904 A1 | 1/2017 | Crew et al. | |
| 2017/0037004 A1 | 2/2017 | Crew et al. | |
| 2017/0065719 A1 | 3/2017 | Qian et al. | |
| 2018/0009779 A1 * | 1/2018 | Bradner | C07D 471/04 |
| 2018/0015087 A1 | 1/2018 | Liu et al. | |
| 2018/0085465 A1 | 3/2018 | Bradner et al. | |
| 2018/0134684 A1 * | 5/2018 | Bradner | C07D 471/04 |
| 2018/0193470 A1 * | 7/2018 | Crew | A61K 47/545 |
| 2019/0016703 A1 * | 1/2019 | Gray | A61K 47/545 |

FOREIGN PATENT DOCUMENTS

| | | | | |
|---|---|---|---|---|
| WO | WO 2013/106646 A2 | 7/2013 | | |
| WO | WO-2013106646 A2 * | 7/2013 | ........... | C07D 413/12 |
| WO | WO 2013/170147 A1 | 11/2013 | | |
| WO | WO 2015/160845 A1 | 10/2015 | | |
| WO | WO-2015160845 A2 * | 10/2015 | ........... | C07D 401/14 |
| WO | WO 2016/065139 A1 | 4/2016 | | |
| WO | WO 2016/077380 A1 | 5/2016 | | |
| WO | WO 2016/105518 A1 | 6/2016 | | |

(Continued)

OTHER PUBLICATIONS

Bartlett, et al. "The evolution of thalidomide and its IMiD derivatives as anticancer agents." Nat Rev Cancer 2004, 4(4):312-322.
Berndsen et al. "New insights into ubiquitin E3 ligase mechanism" Nat. Struct. Mol. Biol. 2014, 21:301-307.
Buckley et al. "HaloPROTACS: Use of Small Molecule PROTACS to Induce Degradation of HaloTag Fusion Proteins" ACS Chemical Biology 2015, 10:1831-1837.
Buckley et al. "Small-Molecule Control of Intracellular Protein Levels through Modulation of the Ubiquitin Proteasome System" Angewandte Reviews, 2014, 53:2312-2330.
Buckley et al. "Targeting the Von Hippel-Lindau E3 Ubiquitin Ligase Using Small Molecules to Disrupt the Vhl/Hif-1alpha Interaction" J. Am. Chem. Soc. 2012, 134:4465-4468.

(Continued)

*Primary Examiner* — Alexander R Pagano
(74) *Attorney, Agent, or Firm* — Knowles Intellectual Property Stratregies, LLC

(57) ABSTRACT

The present application provides bifunctional compounds of Formula (I):

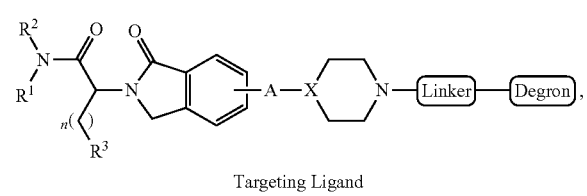

Targeting Ligand which act as protein degradation inducing moieties for EGFR and/or a mutant thereof. The present application also describes methods for the targeted degradation of EGFR and/or a mutant thereof through the use of the bifunctional compounds that link a ubiquitin ligase-binding moiety to a ligand that is capable of binding to EGFR and/or a mutant thereof which can be utilized in the treatment of disorders modulated by EGFR or a mutant thereof.

18 Claims, 8 Drawing Sheets

(56) References Cited

FOREIGN PATENT DOCUMENTS

| | | |
|---|---|---|
| WO | WO 2016/146985 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/117474 A1 | 7/2017 |
| WO | WO 2017/176708 A1 | 10/2017 |
| WO | WO 2017/176957 A1 | 10/2017 |
| WO | WO 2017/180417 A1 | 10/2017 |
| WO | WO 2017/185036 A1 | 10/2017 |
| WO | WO 2017/197036 A1 | 11/2017 |
| WO | WO 2017/197046 A1 | 11/2017 |
| WO | WO 2017/197051 A1 | 11/2017 |
| WO | WO 2017/197055 A1 | 11/2017 |
| WO | WO 2017/197056 A1 | 11/2017 |
| WO | WO 2017/197240 A1 | 11/2017 |
| WO | WO 2017/201069 A1 | 11/2017 |
| WO | WO 2017/201449 A1 | 11/2017 |

OTHER PUBLICATIONS

Bondeson et al. "Catalytic in vivo protein knockdown by small-molecule PROTACs" Nature Chemical Biology 2015, 11:611-617.

Burkhard et al. "Synthesis and Stability of Oxetane Analogs of Thalidomide and Lenalidomide" Organic Letters 2013, 15(7):4312-4315.

Chamberlain et al. "Structure of the human cereblon-DDB1-lenalidomide complex reveals basis for responsiveness to thalidomide analogs" Nature Structural and Molecule Biology, 2014, 21(9):803-809.

Chang, X. and Stewart, K. A. "What is the functional role of the thalidomide binding protein cereblon?" Int J Biochem Mol Bio. 2011, 2(3):287-294.

Corson et al. "Design and applications of bifunctional small molecules: Why two heads are better than one" ACS Chemical Biology 2008, 3(11): 677-692.

Crew, C. M. "Targeting the undruggable proteome: the small molecules of my dreams" Chemistry and Biology 2010, 17(6):551-555.

Cross et al. "AZD9291, an Irreversible EGFR TKI, Overcomes T790M-Mediated Resistance to EGFR Inhibitors in Lung Cancer" Cancer Discover 2014, 4:1046-61.

Deshaies et al. "Ring domain E3 ubiquitin ligases." Ann. Rev. Biochem. 2009, 78:399-434.

Faden et al. "Generic tools for conditionally altering protein abundance and phenotypes on demain" Biol. Chem. 2014, 395(7-8):737-762.

Fischer et al. "Structure of the DDB1-CRBN E3 ubiquitin ligase in complex with thalidomide" Nature 2014, 512:49-53.

Fischer et al. "The Molecular Basis of CRL4DDB2/CSA Ubiquitin Ligase Architecture, Targeting, and Activation," Cell 2011, 147:1024-1039.

Gosink et al. "Redirecting the Specificity of Ubiquitination by Modifying Ubiquitin-Conjugating Enzymes" Proc. Natl. Acad. Sci. USA 1995, 92:9117-9121.

Gustafson et al. "Small-Molecule-Mediated Degradation of the Androgen Receptor through Hydrophobic Tagging" Angewandte Chemie 2015, 54:9659-9662.

Hines et al. "Posttranslational protein knockdown couple to receptor tyrosine kinase activation with phosphoPROTACs" PNAS 2013, 110(22):8942-8947.

Ito et al. "Identification of a Primary Target of Thalidomide Teratogenicity" Science 2010, 327(5971):1345-1350.

Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16):5820-5826.

Jacques et al. "Differentiation of antiinflammatory and antitumorigenic properties of stabilized enantiomers of thalidomide analogs" PNAS 2015, 112:E1471-E1479.

Kronke et al. "Lenalidomide induces ubiquitination and degradation of CDK1[alpha] in del(5q) MDS" Nature 2015, 523(7559):183-188.

Kronke et al. "Lenalidomide Causes Selective Degradation of IKZF1 and IKZF3 in Multiple Myeloma Cells" Science 2014, 343(6168):301-305.

Lai et al. "Modular PROTAC Design for the Degradation of Oncogenic BCR-ABL" Angewandte Chemie International Edition 2016, 55:807-810.

Lee et al. "Targeted Degradation of the Aryl Hydrocarbon Receptor by the PROTAC Approach: A Useful Chemical Genetic Tool" ChemBioChem 2007, 8:2058-2062.

Li et al. "Genome-wide and functional annotation of human E3 ubiquitin ligases identifies MULAN, a mitochondrial E3 that regulates the organelle's dynamics and signaling" PLOS One 2008, 3:1487.

Liu et al. "Design and biological characterization of hybrid compounds of curcumin and thalidomide for multiple myeloma" Organic and Biomolecular Chemistry 2013, 11:4757.

Lu et al. "The myeloma drug lenalidomide promotes the cereblon-dependent destruction of Ikaros proteins" Science 2014, 343:305-309.

Lu et al. "Hijacking the E3 Ubiquitin Ligase Cereblon to Efficiently Target BRD4" Chemistry and Biology 2015, 22(6):755-763.

Lynch et al. "Activating Mutations in the Epidermal Growth Factor Receptor Underlying Responsiveness of Non-Small-Cell-Lung Cancer to Gefitinib" The New England Journal of Medicine 2004, 350(21):2129-39.

Maemondo et al. "Gefitinib or Chemotherapy for Non-Small-Cell Lung Cancer with Mutated EGFR" The New England Journal of Medicine 2010, 362(25):2380-8.

Miller et al. "Afatinib versus placebo for patients with advanced, metastatic non-small-cell lung cancer after failure of erlotinib, gefitinib, or both, and one or two lines of chemotherapy (LUX-Lung1): a phase 2b/3 randomized trial" Lancet Oncology 2012, 13:528-38.

Mok et al. "Gefitinib or Carboplatin-Paclitaxel in Pulmonary Adenocarcinoma" The New England Journal of Medicine 2009, 361(10):947-57.

Nawaz et al. "Proteasome-Dependent Degradation of the Human Estrogen Receptor" Proc. Natl. Acad. Sci. USA 1999, 96:1858-1862.

Neklesa et al. "Small-molecule hydrophobic tagging-induced degradation of HaloTag fusion proteins." Nat Chem Biol 2011, 7(8):538-543.

PubChem CID: 29021159 https://pubchem.ncbi.nlm.nih.gov/compound/29021159.

Paez et al. "EGFR Mutations in Lung Cancer: Correlation with Clinical Response to Gefitinib Therapy" Science 2004, 304(5676):1497-1500.

Raina et al. "Chemical Inducers of Targeted Protein Degradation" Journal of Biological Chemistry 2010, 285:11057-11060.

Rodriguez-Gonzalez et al. "Targeting steroid hormone receptors for ubiquitination and degradation in breast and prostate cancer" Oncogene 2008, 27:7201-7211.

Rosell et al. "Erlotinib versus standard chemotherapy as first-line treatment for European patients with advanced EGFR mutation-positive non-small-cell lung cancer (EURTAC): a multicentre, open-label, randomised phase 3 trial" Lancet Oncology 2012, 13:239-46.

Ruchelman et al. "Isosteric analogs of lenalidomide and pomalidomide: Synthesis and biological activity" Bioorganic and Medicinal Chemistry Letters 2012, 23:360-365.

Sakamoto et al. "Protacs: chimeric molecules that target proteins to the Skp1-Cullin-F box complex for ubiquitination and degradation" PNAS 2001, 98(15):8554-8559.

Sakamoto et al. "Development of Protacs to Target Cancer-Promoting Proteins for Ubiquitination and Degradation" Molecular and Cellular Proteomics 2003, 2(12):1350-1357.

(56) References Cited

OTHER PUBLICATIONS

Salomon et al. "Epidermal growth factor-related peptides and their receptors in human malignancies" Critical Reviews in Oncology/Hematology 1995, 19:182-232.
Schneekloth et al. "Targeted Intracellular Protein Degradation Induced by a Small Molecule: En Route to Chemical Proteomics" Bioorganic and Medicinal Chemisty Letters 2008, 18:5904-5908.
Schneekloth et al. "Chemical approaches to controlling intracellular protein degradation" Chembiochem 2005, 6(1):40-46.
Schneekloth et al. "Chemical Genetic Control of Protein Levels: Selective in Vivo Targeted Degradation" Journal of the American Chemical Society 2004, 126(12):3748-3754.
Sequist et al. "Phase III Study of Afatinib or Cisplatin Plus Pemetrexed in Patients With Metastatic Lung Adenocarcinoma With EGFR Mutations" Journal of Clinical Oncology 2013, 31(27):3327-34.
Smith et al. "Targeted Intracellular Protein Degradation Induced by a Small Molecule: En Route to Chemical Proteomics" Bioorg. Med. Chem. Lett. 2009, 18(22):5904-5908.
Spratt et al. "RBR E3 ubiquitin ligases: new structures, new insights, new questions." Biochem. 2014, 458:421-437.
Toure et al. "Small-Molecule PROTACs: New Approaches to Protein Degradation" Angewandte Chemie International Edition 2016, 55:1966-1973.
Vassilev et al. "In Vivo Activation of the P53 Pathway by Small-Molecule Antagonists of MDM2" Science 2004, 303:844-848.
Voldborg et al. "Epidermal growth factor receptor (EGFR) and EGFR mutations, function and possible role in clinical trials" Annals of Oncology 1997, 8:1197-1206.
Walter et al. "Discovery of a Mutant-Selective Covalent Inhibitor of EGFR that Overcomes T790M Mediated Resistance in NSCLC" Cancer Discovery 2013, 3:1404-15.
Wang et al. "Roles of F-box proteins in cancer." Nat. Rev. Cancer 2014, 14:233-347.
Winter et al. "Phthalimide conjugation as a strategy for in vivo target protein degradation" Science 2015, 348(6241):1376-1381.
Wu et al. "Afatinib versus cisplatin plus gemcitabine for first-line treatment of Asian patients with advanced non-small-cell lung cancer harbouring EGFR mutations (LUX-Lung 6): an open-label, randomised phase 3 trial" Lancet Oncology 2014, 15:213-22.
Yu et al. "Analysis of Tumor Specimens at the Time of Acquired Resistance to EGFR-TKI Therapy in 155 Patients with EGFR-Mutant Lung Cancers" Clinical Cancer Research 2013, 19:2240-7.
Yun et al. "The T790M mutation in EGFR kinase causes drug resistance by increasing the affinity for ATP" PNAS USA 2008, 105(6):2070-5.
Zengerle et al. "Selective Small Molecule Induced Degradation of the BET Bromodomain Protein BRD4" ACS Chem. Biol. 2015, 10:1770-1777.
Zhou et al. "Erlotinib versus chemotherapy as first-line treatment for patients with advanced EGFR mutation-positive non-small-cell lung cancer (Optimal, CTONG-0802): a multicentre, open-label, randomised, phase 3 trial" Lancet Oncology 2011, 12:735-42.
Zhou et al. "Harnessing the Ubiquitination Machinery to Target the Degradation of Specific Cellular Proteins" Molecular Cell 2000, 6:751-756.
Zhou et al. "Novel mutant-selective EGFR kinase inhibitors against EGFR T790M" Nature 2009, 462:1070-4.
U.S. Pat. No. 9,694,084, B2, U.S. Appl. No. 14/707,930, Bradner et al., filed Jul. 4, 2017.
U.S. Pat. No. 9,750,816, B2, U.S. Appl. No. 15/148,262, Bradner et al., filed Sep. 5, 2017.
U.S. Pat. No. 9,770,512, B2, U.S. Appl. No. 15/148,257, Bradner et al., filed Sep. 26, 2017.
U.S. Pat. No. 9,821,068, B2, U.S. Appl. No. 15/148,253, Bradner et al., filed Nov. 1, 2017.
U.S. Pat. No. 10,125,114, B2, U.S. Appl. No. 15/632,023, Bradner et al., filed Nov. 13, 2018.
U.S. Pat. No. 10,239,888, B2, U.S. Appl. No. 16/045,346, Bradner et al., filed Mar. 26, 2019.
2018/0085465, A1, U.S. Appl. No. 15/816,646, Bradner et al., filed Mar. 29, 2018.
2018/0134684, A1, U.S. Appl. No. 15/863,760, Bradner et al., filed May 17, 2018.
2018/0169109, A1, U.S. Appl. No. 15/889,963, Bradner et al., filed Jun. 21, 2018.
2018/0179522, A1, U.S. Appl. No. 15/889,990, Buckley et al., filed Jun. 28, 2018.
2019/0071415, A1, U.S. Appl. No. 16/167,091, Bradner et al., filed Mar. 7, 2019.

* cited by examiner

BIFUNCTIONAL MOLECULES FOR DEGRADATION OF EGFR AND METHODS OF USE

STATEMENT OF RELATED INVENTIONS

This application is a continuation of International Patent Application No. PCT/US2017/028950, filed with the Patent Cooperation Treaty, U.S. Receiving Office, on Apr. 21, 2017, which claims the benefit of U.S. Provisional Patent Application No. 62/326,574, filed Apr. 22, 2016. The entirety of this application is hereby incorporated by reference for all purposes.

GOVERNMENT SUPPORT

This invention was made with government support under grant number P01 CA154303 awarded by The National Institutes of Health. The government has certain rights in the invention.

BACKGROUND OF THE DISCLOSURE

Ubiquitin-Proteasome Pathway (UPP) is a critical pathway that regulates proteins and degrades misfolded or abnormal proteins. UPP is central to multiple cellular processes, and if defective or imbalanced, leads to pathogenesis of a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity. For example, cereblon (CRBN) interacts with damaged DNA binding protein 1 and forms an E3 ubiquitin ligase complex with Cullin 4 in which the proteins recognized by CRBN are ubiquitinated and degraded by proteasomes. Various immunomodulatory drugs (IMiDs), e.g. thalidomide and lenalidomide, binds to CRBN and modulate CRBN's role in the ubiquitination and degradation of protein factors involved in maintaining regular cellular function.

Harnessing the ubiquitin-proteasome pathway for therapeutic intervention has received significant interest from the scientific community. The publication by Gosink et al. (*Proc. Natl. Acad. Sci. USA* 1995, 92, 9117-9121) titled "Redirecting the Specificity of Ubiquitination by Modifying Ubiquitin-Conjugating Enzymes" showed proof of concept in vitro that engineered peptides can selectively direct ubiquitination to intracellular proteins. The publication by Nawaz et al. (*Proc. Natl. Acad. Sci. U.S.A.* 1999, 96, 1858-1862) titled "Proteasome-Dependent Degradation of the Human Estrogen Receptor" describes ER degradation as a target for the ubiquitin-proteasome pathway. The publication by Zhou et al. (*Mol. Cell* 2000, 6, 751-756) titled "Harnessing the Ubiquitination Machinery to Target the Degradation of Specific Cellular Proteins" demonstrated an engineered receptor capable of directing ubiquitination in mammalian and yeast cells.

U.S. Pat. No. 6,306,663 filed in 1999 assigned to Proteinex, Inc., titled "Controlling Protein Levels in Eucaryotic Organisms" appears to be the first patent disclosure of ubiquitinating molecules that incorporate a ubiquitination recognition element and a target protein recognition element.

U.S. Pat. No. 7,041,298 titled "Proteolysis Targeting Chimeric Pharmaceutical" was filed in September 2000 by Deshales et al. and granted in May 2006. The publication by Sakamoto et al. (*Proc. Natl. Acad. Sci. USA* 2001, 98, 8554-8559) titled "Protacs: Chimeric Molecules That Target Proteins to the Skp 1-Cullin-F Box Complex for Ubiquitination and Degradation" describes a "PROTAC" consisting of a small molecule binder of MAP-AP-2 linked to a peptide capable of binding the F-box protein (3-TRCP, the disclosure of which is also provided in the corresponding U.S. Pat. No. 7,041,298. The publication by Sakamoto et al. (*Mol. Cell. Proteomics* 2003, 2, 1350-1358) titled "Development of Protacs to Target Cancer-Promoting Proteins for Ubiquitination and Degradation" describes an analogous PROTAC (PROTAC2) that instead of degrading MAP-AP-2, degrades estrogen and androgen receptors. The publication by Schneekloth et al. (*J. Am. Chem. Soc.* 2004, 126, 3748-3754) titled "Chemical Genetic Control of Protein Levels: Selective in Vivo Targeted Degradation" describes an analogous degradation agent (PROTAC3) that targets the FK506 binding protein (FKBP12) and shows that both PROTAC2 and PROTAC3 hit their respective targets using green fluorescent protein (GFP) imaging. The publication by Schneekloth et al. (*ChemBioChem* 2005, 6, 40-46) titled "Chemical Approaches to Controlling Intracellular Protein Degradation" described the state of the field at the time. The publication by Schneekloth et al. (*Bioorg. Med. Chem. Lett.* 2008, 18, 5904-5908) titled "Targeted Intracellular Protein Degradation Induced by a Small Molecule: En Route to Chemical Proteomics" describes a degradation agent that consists of two small molecules linked by PEG that in vivo degrades the androgen receptor by concurrently binding the androgen receptor and Ubiquitin E3 ligase. WO 2013/170147 filed by Crews et al. titled "Compounds Useful for Promoting Protein Degradation and Methods Using Same" describes compounds comprising a protein degradation moiety covalently bound to a linker, wherein the C log P of the compound is equal to or higher than 1.5. A review by Buckley et al. (*Angew. Chem. Int. Ed. Engl.* 2014, 53, 2312-2330) titled "Small-Molecule Control of Intracellular Protein Levels through Modulation of the Ubiquitin Proteasome System" describes a variety of publications. WO 2015/160845 assigned to Arvinas Inc. titled "Imide Based Modulators of Proteolysis and Associated methods of Use" describes the use of degradation compounds including thalidomide to utilize cereblon as the E3 ligase protein. The publication by Lu et al. (*Chem. Biol.* 2015, 22, 755-763) titled "Hijacking the E3 Ubiquitin Ligase Cereblon to Efficiently Target Brd4" describes thalidomide based degradation compounds useful for degrading BRD4. Additional publications include Bondeson et al. (*Nat. Chem. Biol.* 2015, 11, 611-617) titled "Catalytic in Vivo Protein Knockdown by Small-Molecule Protacs"; Gustafson et al. (*Angewandte Chemie, International Edition in English* 2015, 54, 9659-9662) titled "Small-Molecule-Mediated Degradation of the Androgen Receptor through Hydrophobic Tagging"; Buckley et al. (*J. Am. Chem. Soc.* 2012, 134, 4465-4468) titled "Targeting the Von Hippel-Lindau E3 Ubiquitin Ligase Using Small Molecules to Disrupt the Vhl/Hif-1alpha Interaction"; U.S. 2016/0058872 assigned to Arvinas Inc. titled "Imide Based Modulators of Proteolysis and Associated Methods of Use"; U.S. 2016/0045607 assigned to Arvinas Inc. titled "Estrogen-related Receptor Alpha Based PROTAC Compounds and Associated Methods of Use"; U.S. 2014/0356322 assigned to Yale University, GlaxoSmithKline, and Cambridge Enterprise Limited University of Cambridge titled "Compounds and Methods for the Enhanced Degradation of Targeted Proteins & Other Polypeptides by an E3 Ubiquitin Ligase"; Lai et al. (*Angewandte Chemie, International Edition in English* 2016, 55, 807-810)

titled "Modular Protac Design for the Degradation of Oncogenic Bcr-Abl"; and Toure et al. (*Angew. Chem. Int. Ed.* 2016, 55, 1966-1973) titled "Small-Molecule Protacs: New Approaches to Protein Degradation". See also US 2016/0176916, US 2016/0235730, US 2016/0235731, US 2016/0243247, WO 2016/105518, WO 2016/077380, WO2016/105518, WO 2016/077375, WO2017/007612, and WO2017/024317.

It was discovered and reported in 2010 that thalidomide binds to cereblon (see Ito et al. (*Science* 2010, 327, 1345-1350) titled "Identification of a Primary Target of Thalidomide Teratogenicity" and Fischer et al. (*Nature* 2014, 512, 49-53) titled "Structure of the Ddb1-Crbn E3 Ubiquitin Ligase in Complex with Thalidomide"). Itoh et al. also described a small molecule linked to a peptide that utilizes E3 ubiquitin ligase to degrade retinoic acid-binding proteins. (See *J. Am. Chem. Soc.* 2010, 132, 5820-5826 titled "Protein Knockdown Using Methyl Bestatin-Ligand Hybrid Molecules: Design and Synthesis of Inducers of Ubiquitination-Mediated Degradation of Cellular Retinoic Acid-Binding Proteins").

The object of the present invention is to provide bifunctional compounds and compositions for the treatment of serious diseases, including kinase mediated disorders.

SUMMARY

The present application provides novel bifunctional compounds, which function to recruit targeted proteins to E3 ubiquitin ligase for degradation, and methods of preparation and uses thereof. The bifunctional compound is of Formula X:

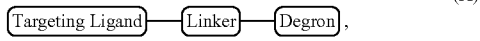

(X)

wherein:

the Targeting Ligand is capable of binding to a targeted protein, such as EGFR and/or a mutant EGFR;

the Linker is a group that covalently binds to the Targeting Ligand and the Degron; and the Degron is capable of binding to a ubiquitin ligase, such as an E3 ubiquitin ligase.

In one embodiment, the E3 ubiquitin ligase is cereblon.

The present application also provides targeted degradation of proteins through the use of bifunctional compounds, including bifunctional compounds that link an E3 ubiquitin ligase-binding moiety to a ligand that binds the targeted proteins.

The present application also describes a bifunctional compound of Formula Y:

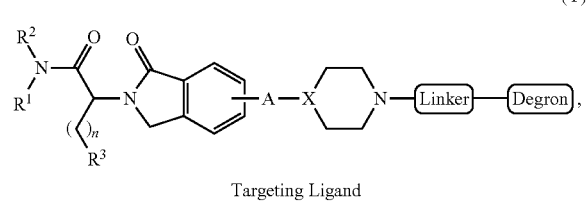

(Y)

Targeting Ligand or an enantiomer, diastereomer, stereoisomer, or pharmaceutically acceptable salt thereof optionally in a pharmaceutically acceptable carrier, wherein:

A is phenyl or pyridinyl;

X is CH, C($C_1$-$C_3$) alkyl, or N;

$R^1$ is H or ($C_1$-$C_3$) alkyl;

$R^2$ is ($C_6$-$C_{10}$) aryl, or heteroaryl comprising one or two 5- to 7-membered rings and 1-4 heteroatoms selected from N, O, and S, wherein the aryl and heteroaryl are each optionally substituted with one or more $R^4$;

each $R^4$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, CN, C(O)$R^6$, C(O)O$R^6$, C(O)N$R^6R^7$, N$R^6R^7$, ($C_3$-$C_7$) cycloalkyl, heterocyclyl comprising a 5- to 7-membered ring and 1-3 heteroatoms selected from N, O, and S, ($C_6$-$C_{10}$) aryl, and heteroaryl comprising one or two 5- to 7-membered rings and 1-4 heteroatoms selected from N, O, and S, wherein the alkyl, cycloalkyl, heterocyclyl, aryl, and heteroaryl are each optionally substituted with one or more $R^5$;

each $R^5$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, and CN;

each $R^6$ is independently H or ($C_1$-$C_3$) alkyl;

each $R^7$ is independently H or ($C_1$-$C_3$) alkyl;

$R^3$ is ($C_1$-$C_3$) alkyl or

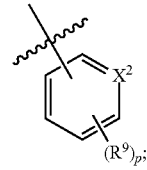

$X^2$ is N or $CR^8$;

$R^8$ is H, ($C_1$-$C_4$) alkyl, ($C_1$-$C_4$) haloalkyl, ($C_1$-$C_4$) alkoxy, ($C_1$-$C_4$) haloalkoxy, halogen, $NO_2$, $NH_2$, OH, or CN;

each $R^9$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, $NH_2$, OH, and CN;

n is 0 or 1; and p is 0, 1, 2, or 3;

the Linker is a group that covalently binds to

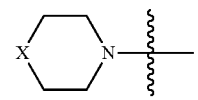

and the Degron;

the Degron is capable of binding to a ubiquitin ligase; and the Targeting Ligand is capable of binding to EGFR or a mutant EGFR.

In one embodiment, the E3 ubiquitin ligase is cereblon.

In one embodiment, the Targeting Ligand is capable of binding to EGFR.

In one embodiment, the Targeting Ligand is capable of binding to a mutant EGFR.

In a further embodiment, the Targeting Ligand is capable of binding to a T790M/L858R EGFR mutant.

In a further embodiment, the Targeting Ligand is capable of binding to a T790M/L858R/C797S EGFR mutant.

The present application describes novel bifunctional compounds, which function to recruit targeted proteins to E3 ubiquitin ligase for degradation, and methods of preparation and uses thereof.

In one embodiment the bifunctional compound is of Formula Z:

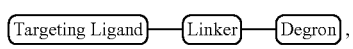
(Z)

or an enantiomer, diastereomer, stereoisomer, or pharmaceutically acceptable salt thereof optionally in a pharmaceutically acceptable carrier,
wherein:
the Targeting Ligand is selected from

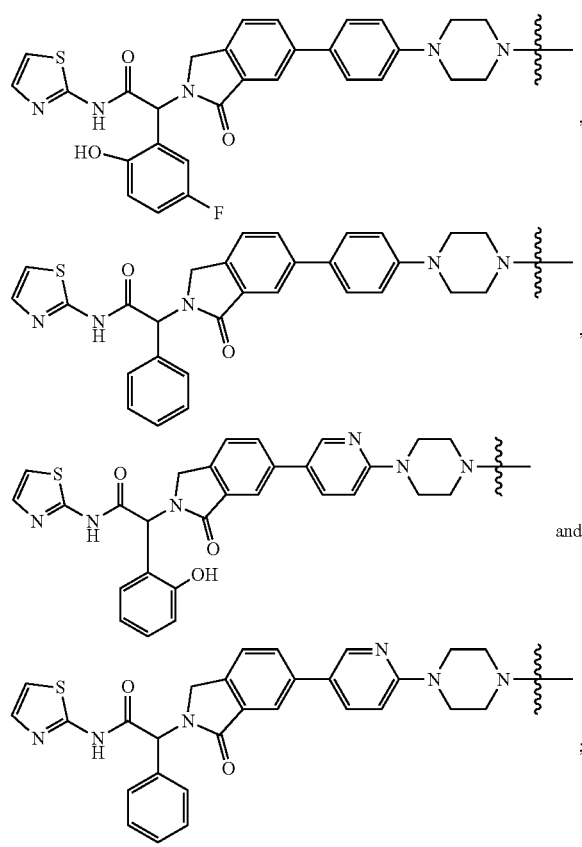

the Linker is a group that covalently binds to the Targeting Ligand and the Degron; and
the Degron is capable of binding to a ubiquitin ligase.
In one embodiment, the E3 ubiquitin ligase is cereblon.

In one embodiment the bifunctional compound is of Formula A:

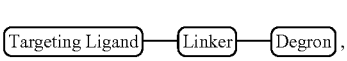
(A)

or an enantiomer, diastereomer, stereoisomer, or pharmaceutically acceptable salt thereof optionally in a pharmaceutically acceptable carrier
wherein:
the Targeting Ligand is selected from

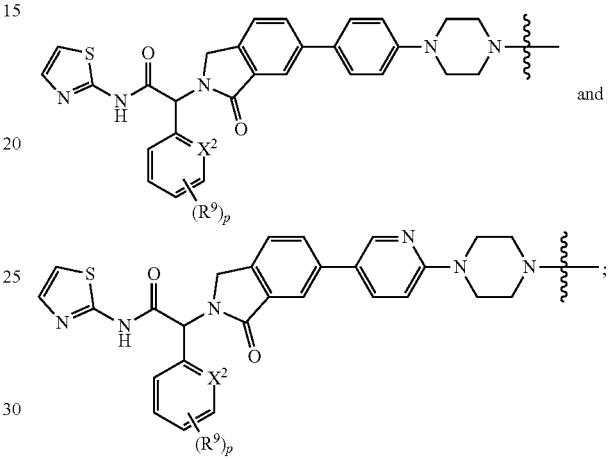

the Linker is a group that covalently binds to the Targeting Ligand and the Degron; and
the Degron is capable of binding to a ubiquitin ligase.
In one embodiment, the E3 ubiquitin ligase is cereblon.
In one embodiment the bifunctional compound is of Formula B:

(B)

or an enantiomer, diastereomer, stereoisomer, or pharmaceutically acceptable salt thereof optionally in a pharmaceutically acceptable carrier
wherein:
the Targeting Ligand-Linker is selected from

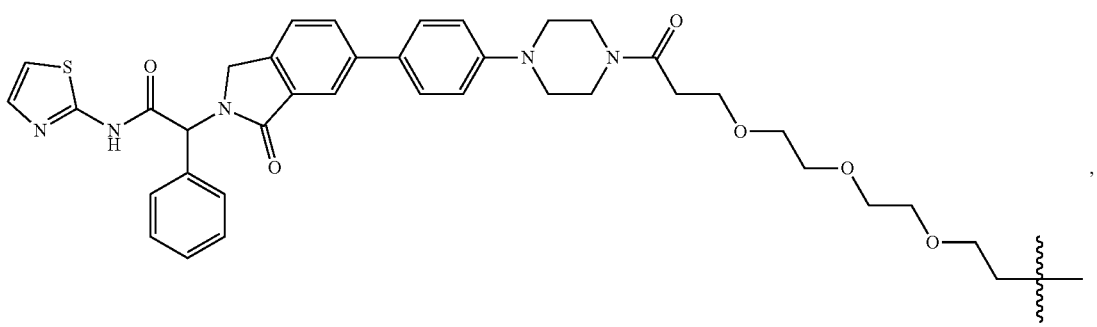

-continued
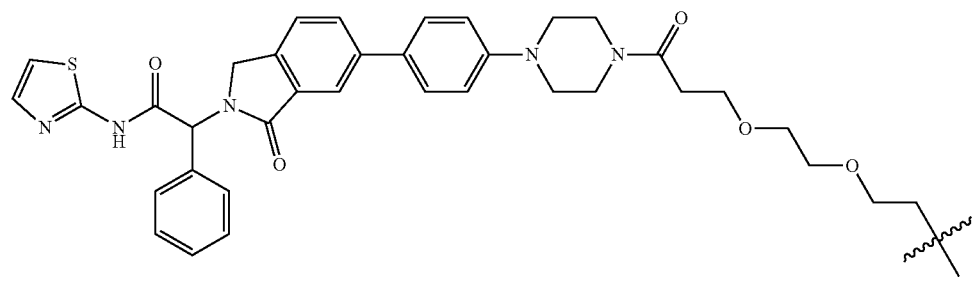
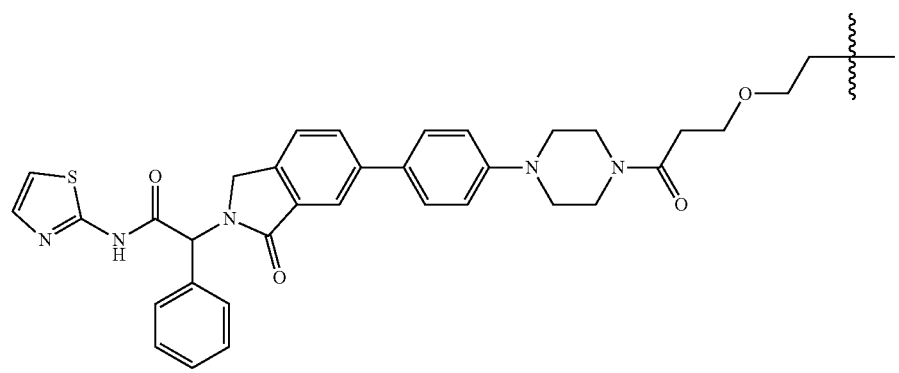
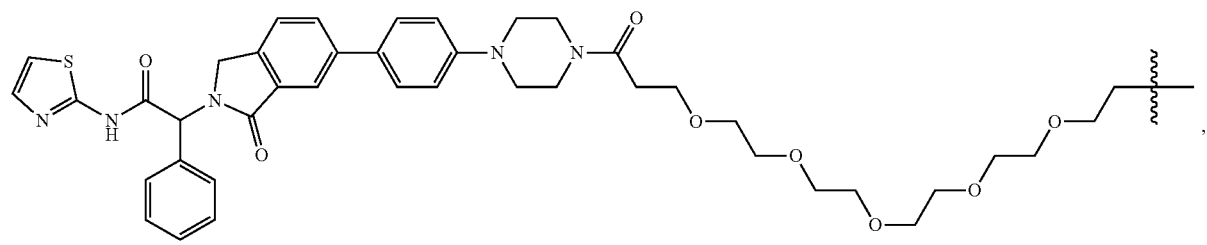
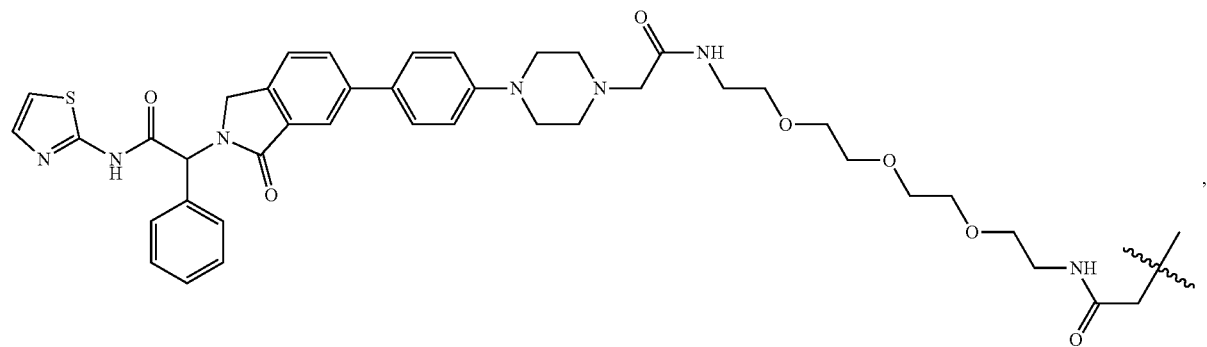
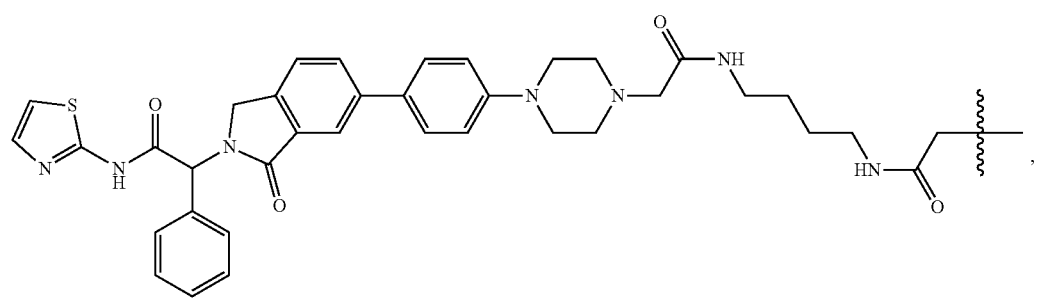

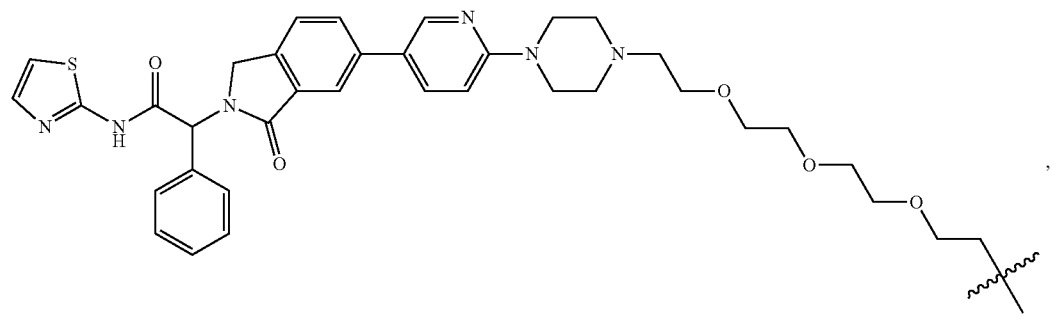
,
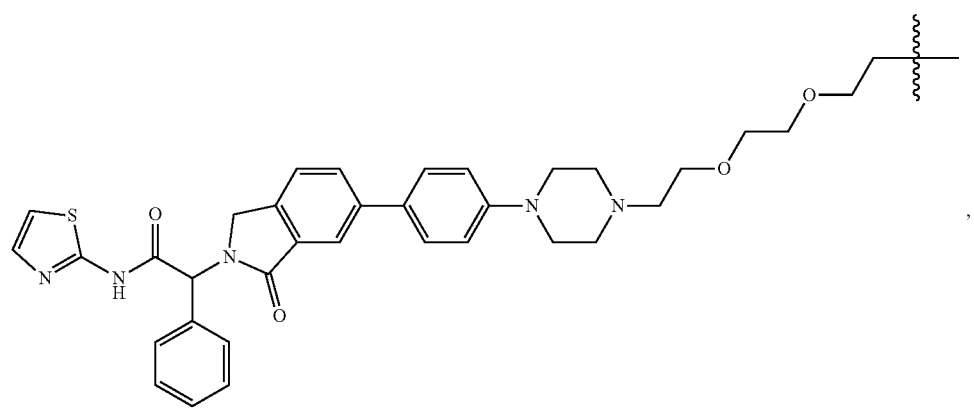 [SMILES: *CCCCCCCCN1CCN(c2ccc(-c3ccc4c(c3)C(=O)N(C(C(=O)Nc3nccs3)c3ccccc3)C4)cc2)CC1]
,
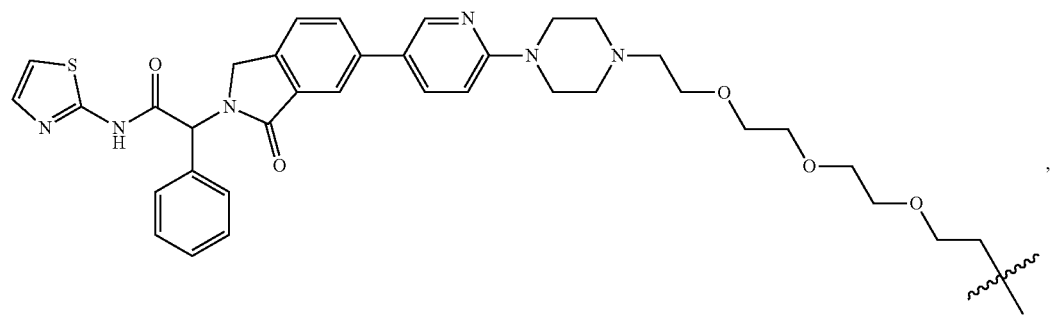
,
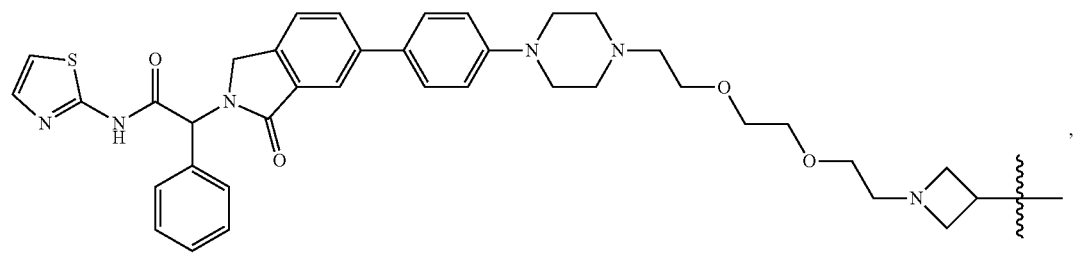
,
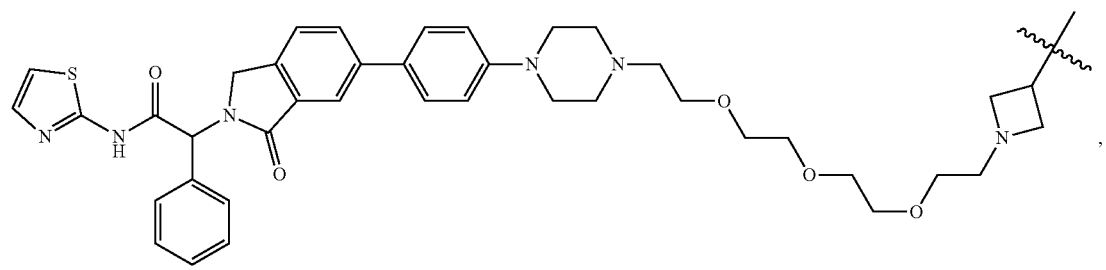
,

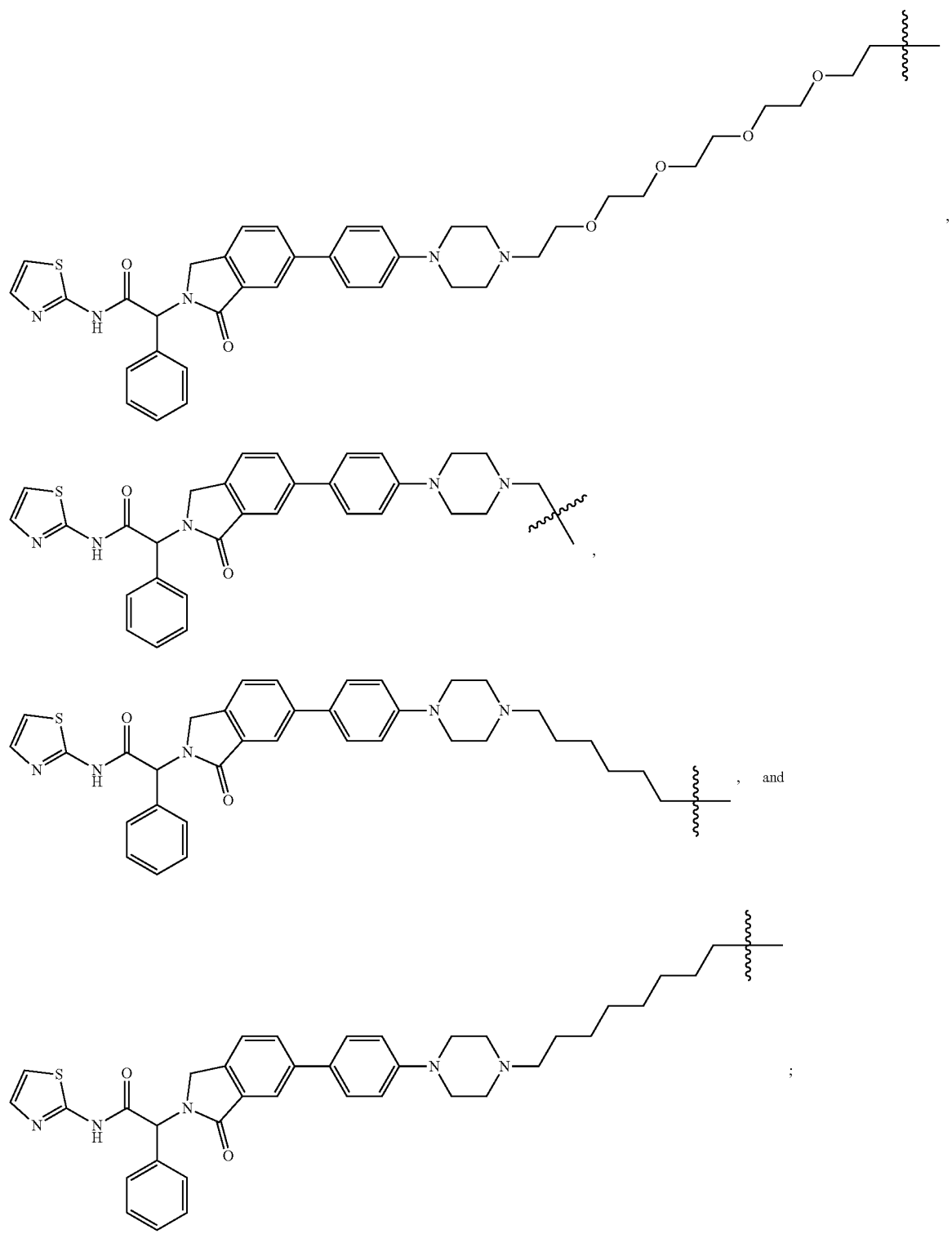
and
the Degron is capable of binding to a ubiquitin ligase.
In one embodiment, the E3 ubiquitin ligase is cereblon.
In one embodiment the bifunctional compound is of Formula C:
Targeting Ligand—Linker—Degron,  (C)

or an enantiomer, diastereomer, stereoisomer, or pharmaceutically acceptable salt thereof optionally in a pharmaceutically acceptable carrier
wherein:
the Targeting Ligand-Linker is selected from
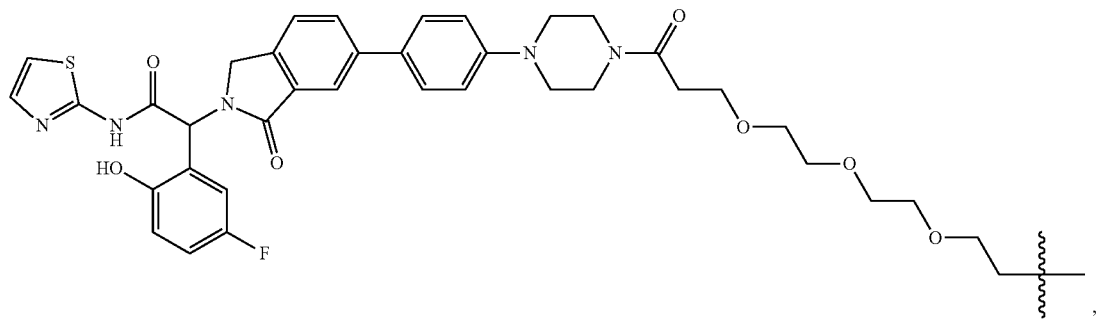
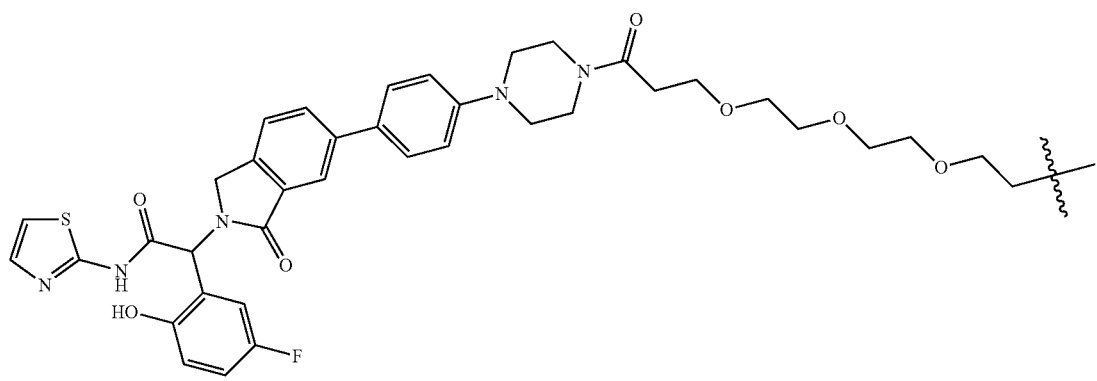
,
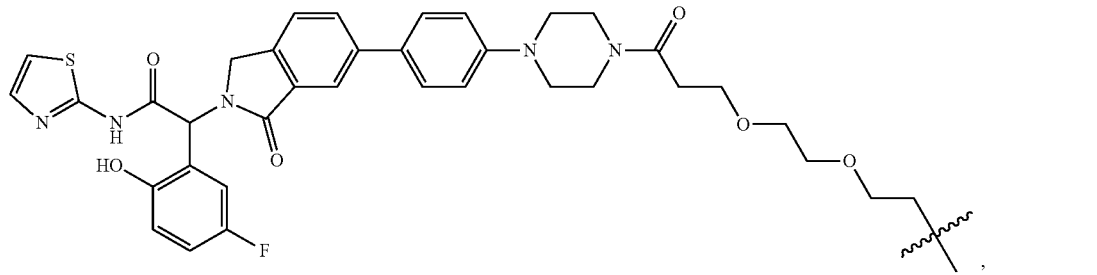
,
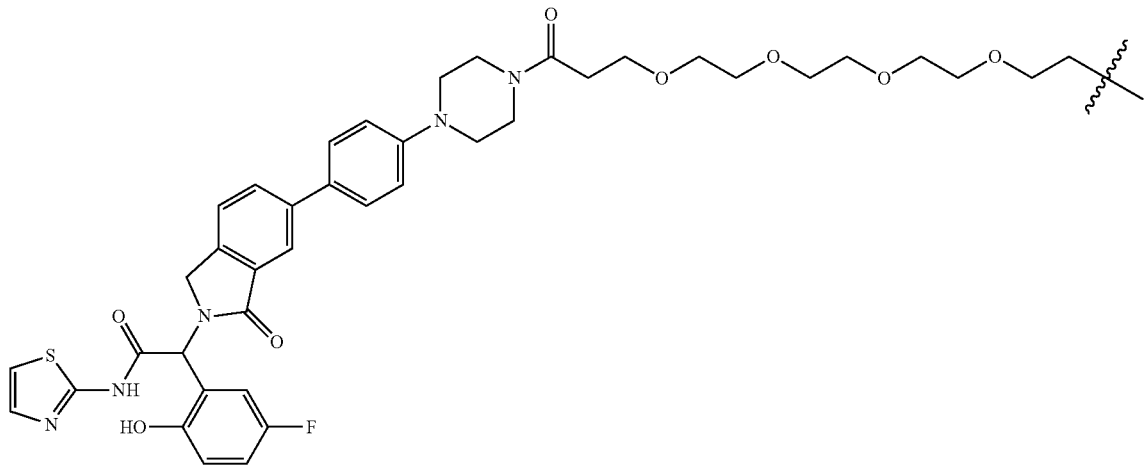

-continued
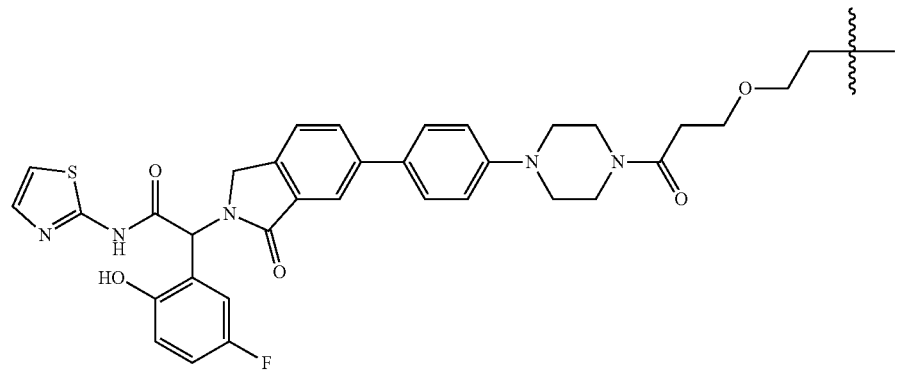
,
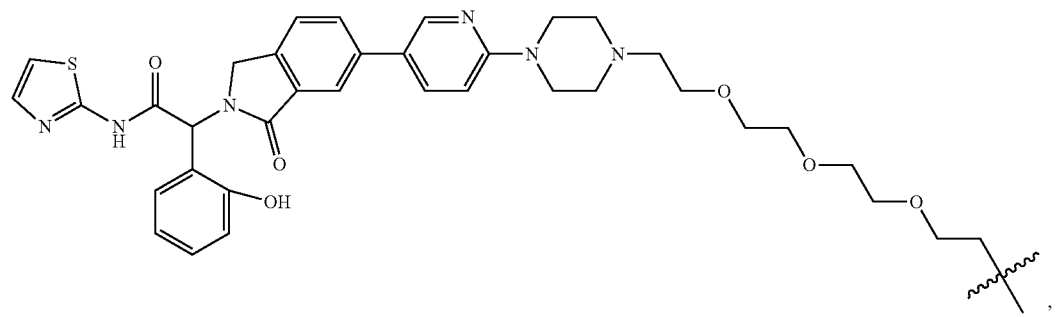
,
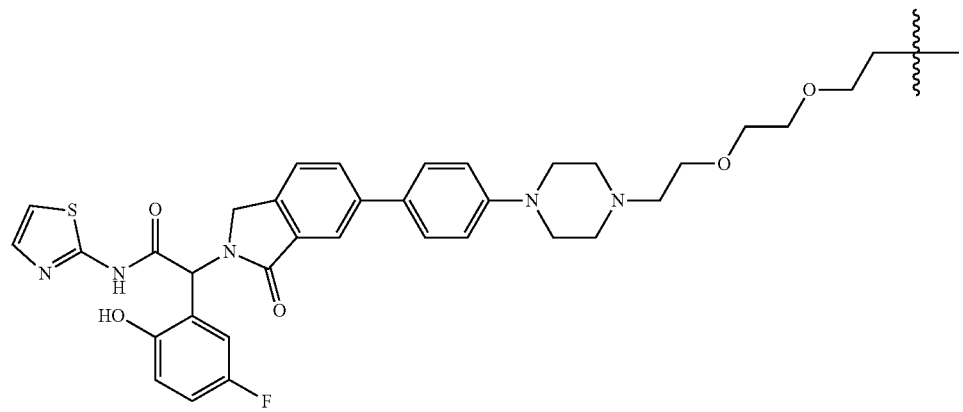
,
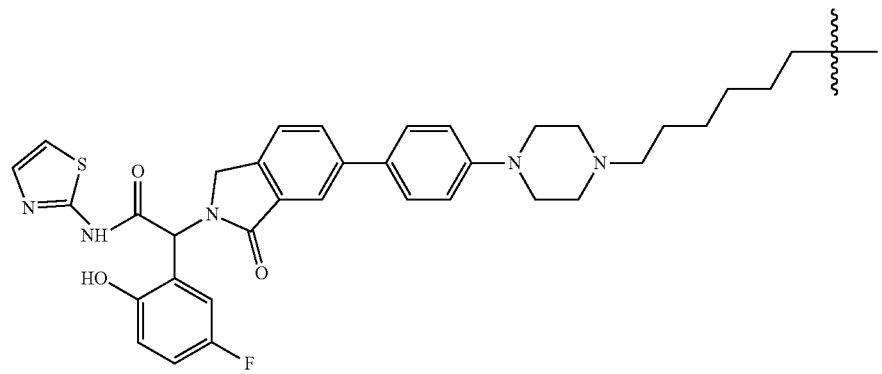
,

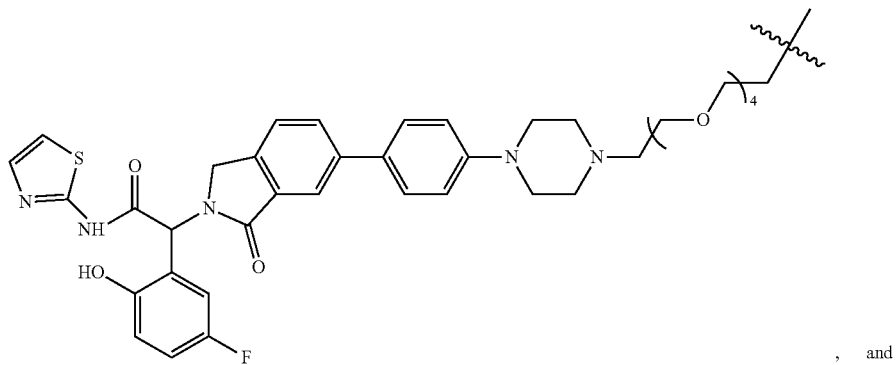

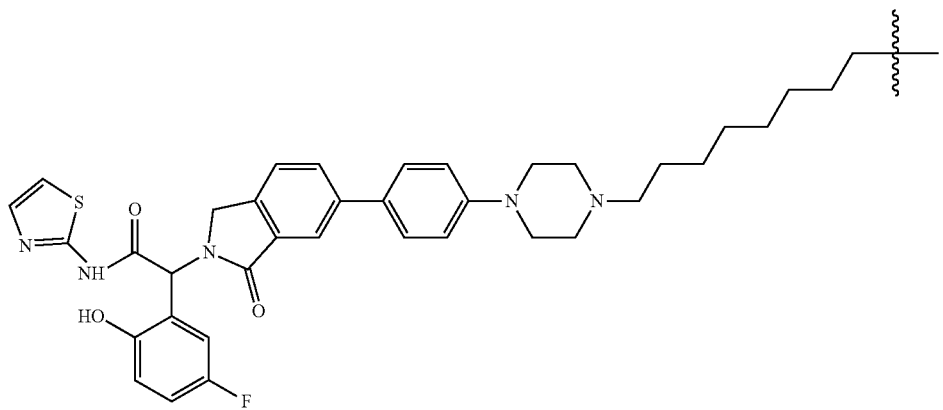 [SMILES: *CCCCCCCCN1CCN(c2ccc(-c3ccc4c(c3)C(=O)N(C(C(=O)Nc3nccs3)c3cc(F)ccc3O)C4)cc2)CC1]
, and and the Degron is capable of binding to a ubiquitin ligase.

In one embodiment, the E3 ubiquitin ligase is cereblon.

The present application also describes targeted degradation of proteins through the use of bifunctional compounds, including bifunctional compounds that link an E3 ubiquitin ligase-binding moiety to a ligand that binds the targeted proteins.

The present application also provides a bifunctional compounds of Formula D.

Formula D is a compound selected from

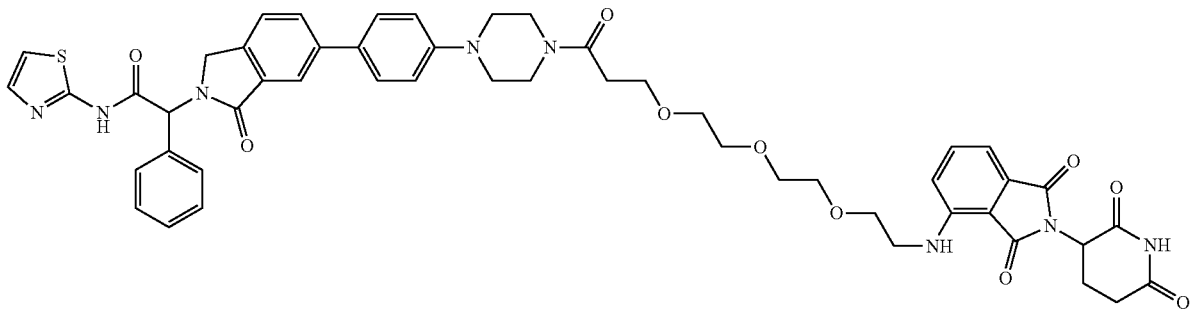

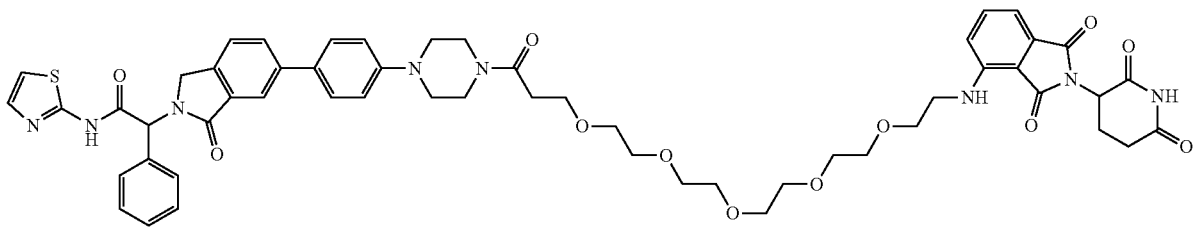

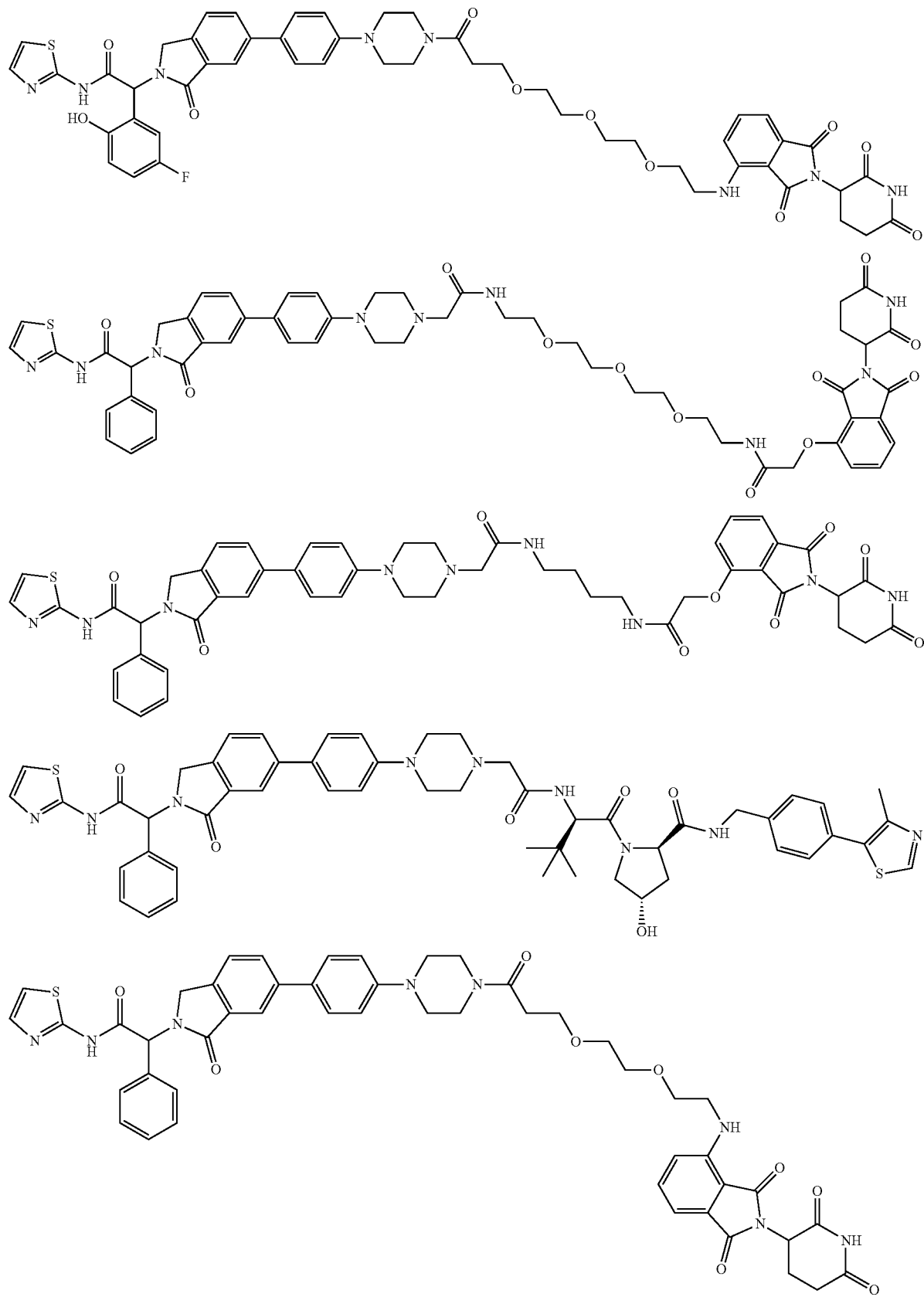

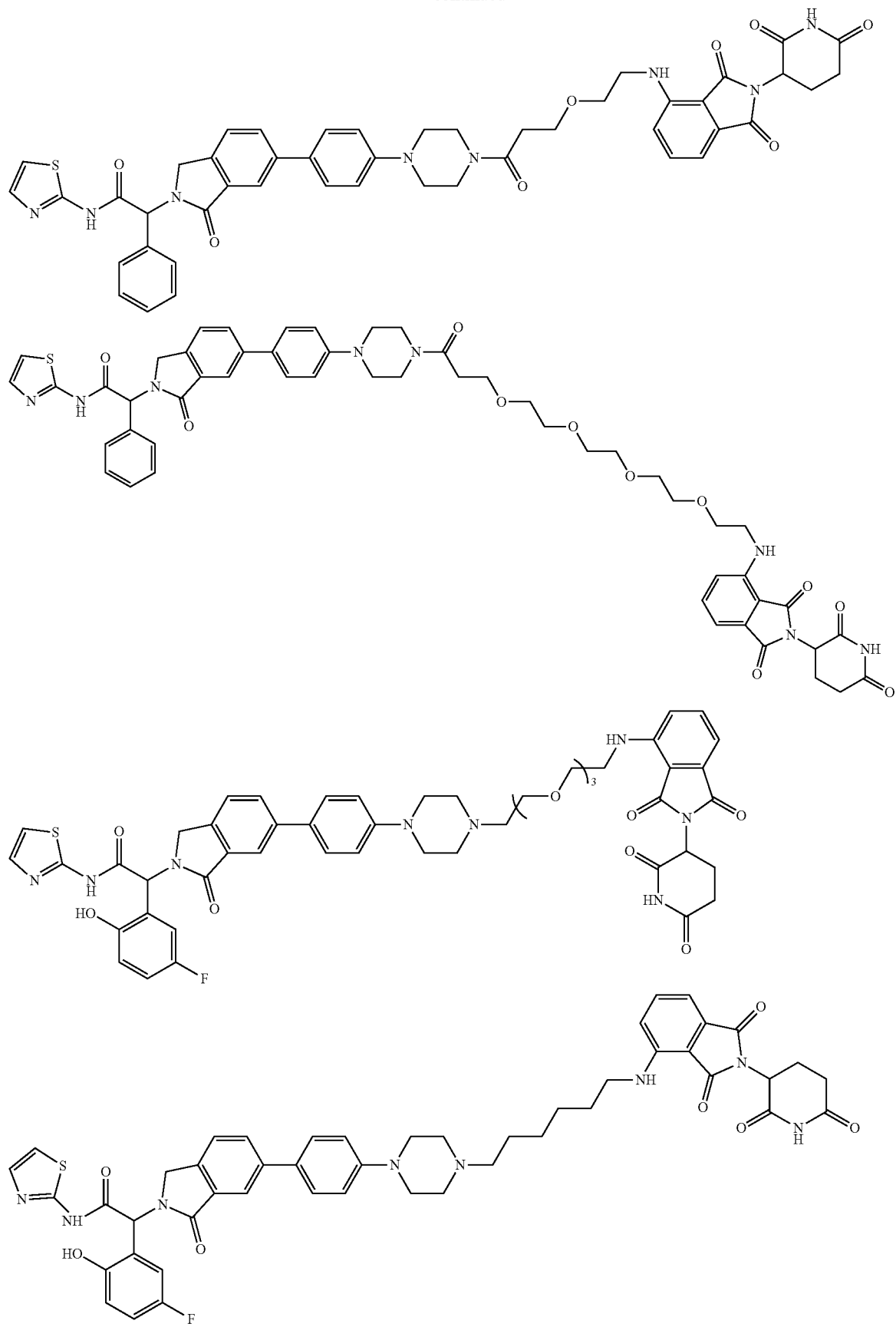

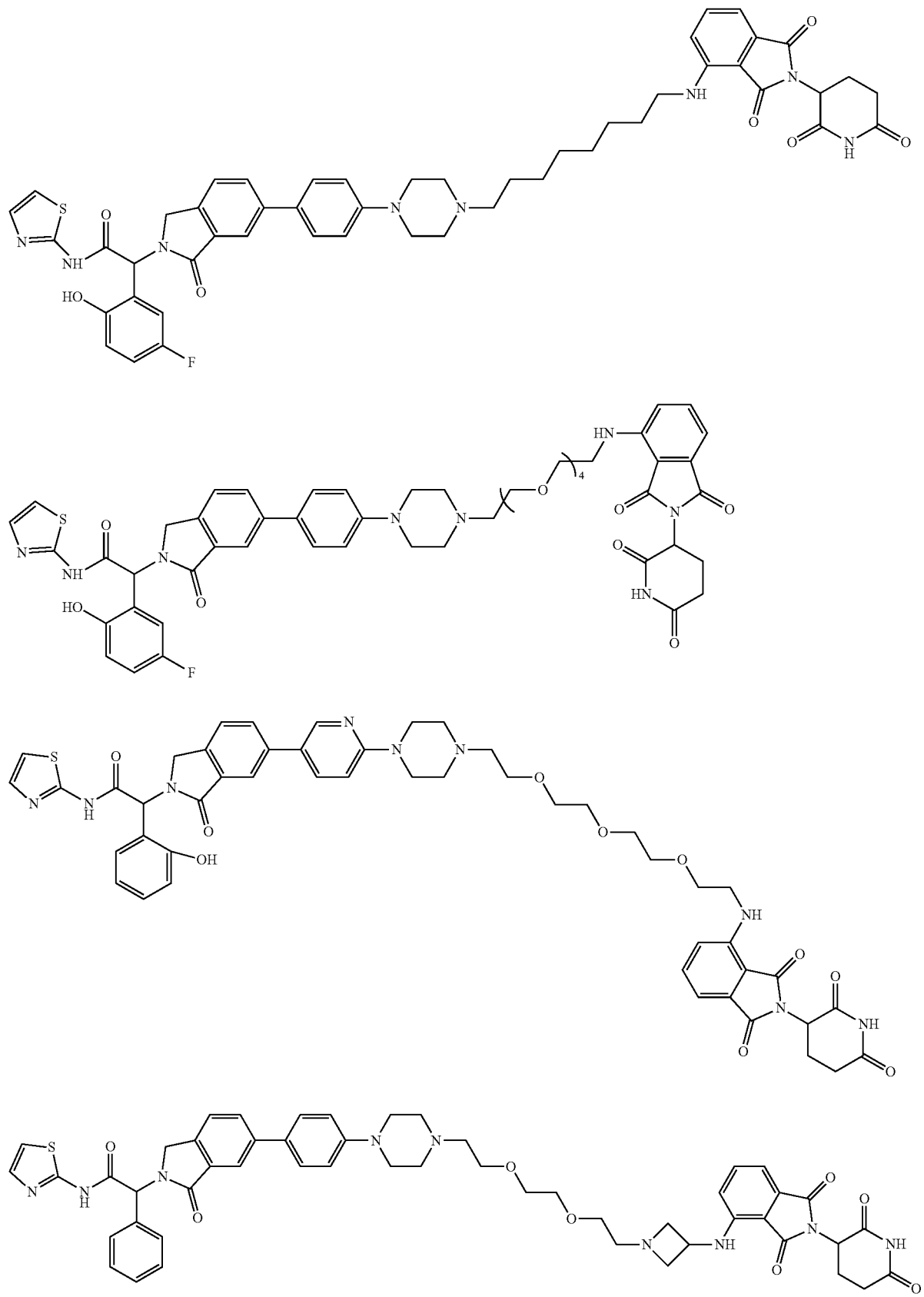

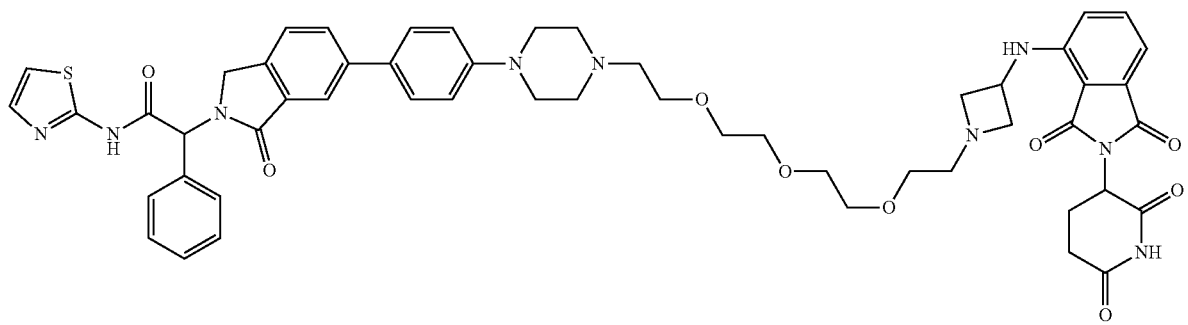
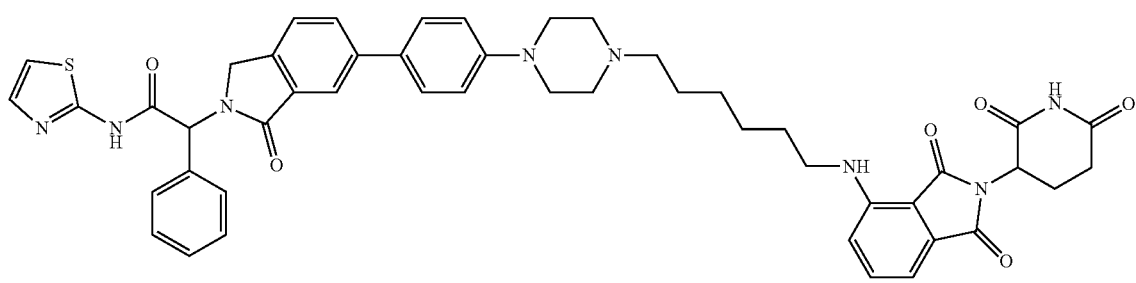
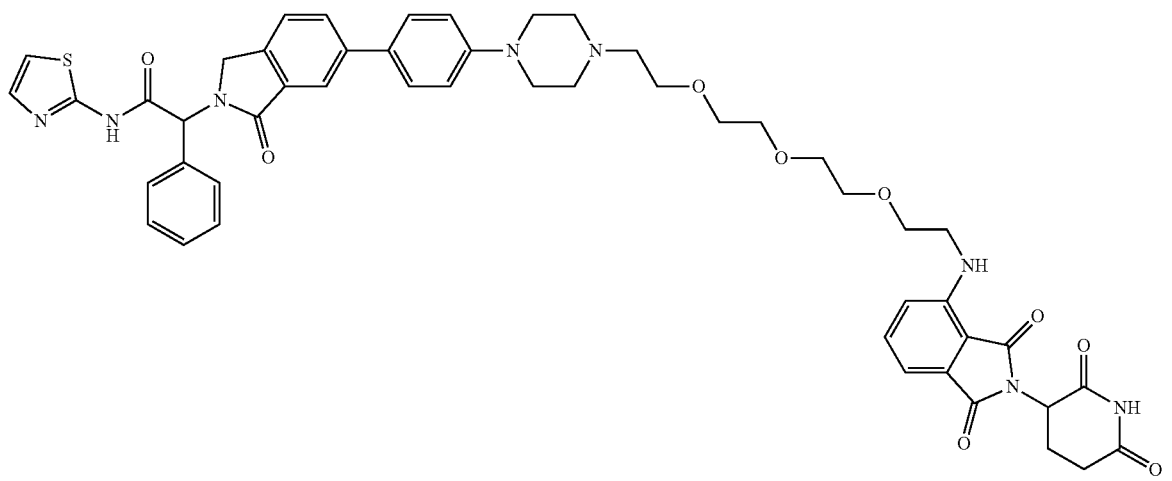
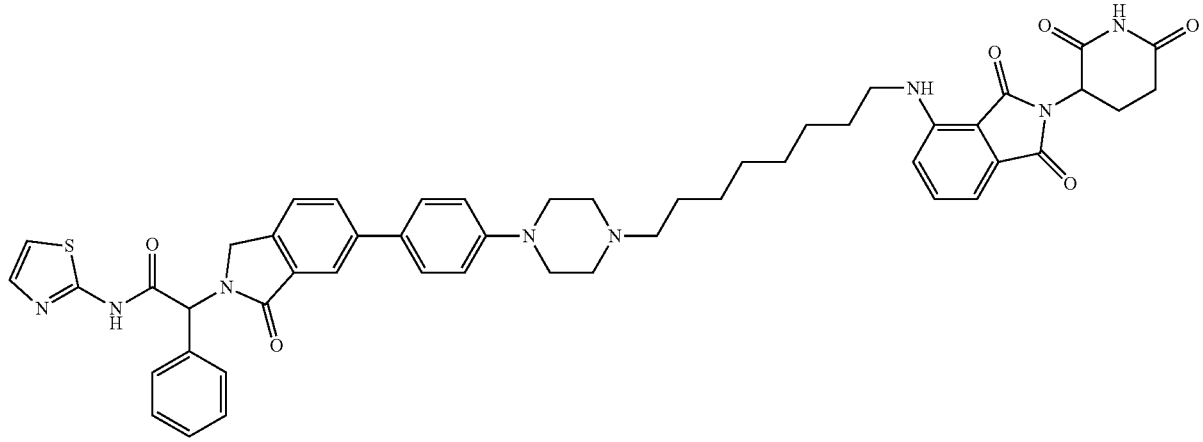

-continued
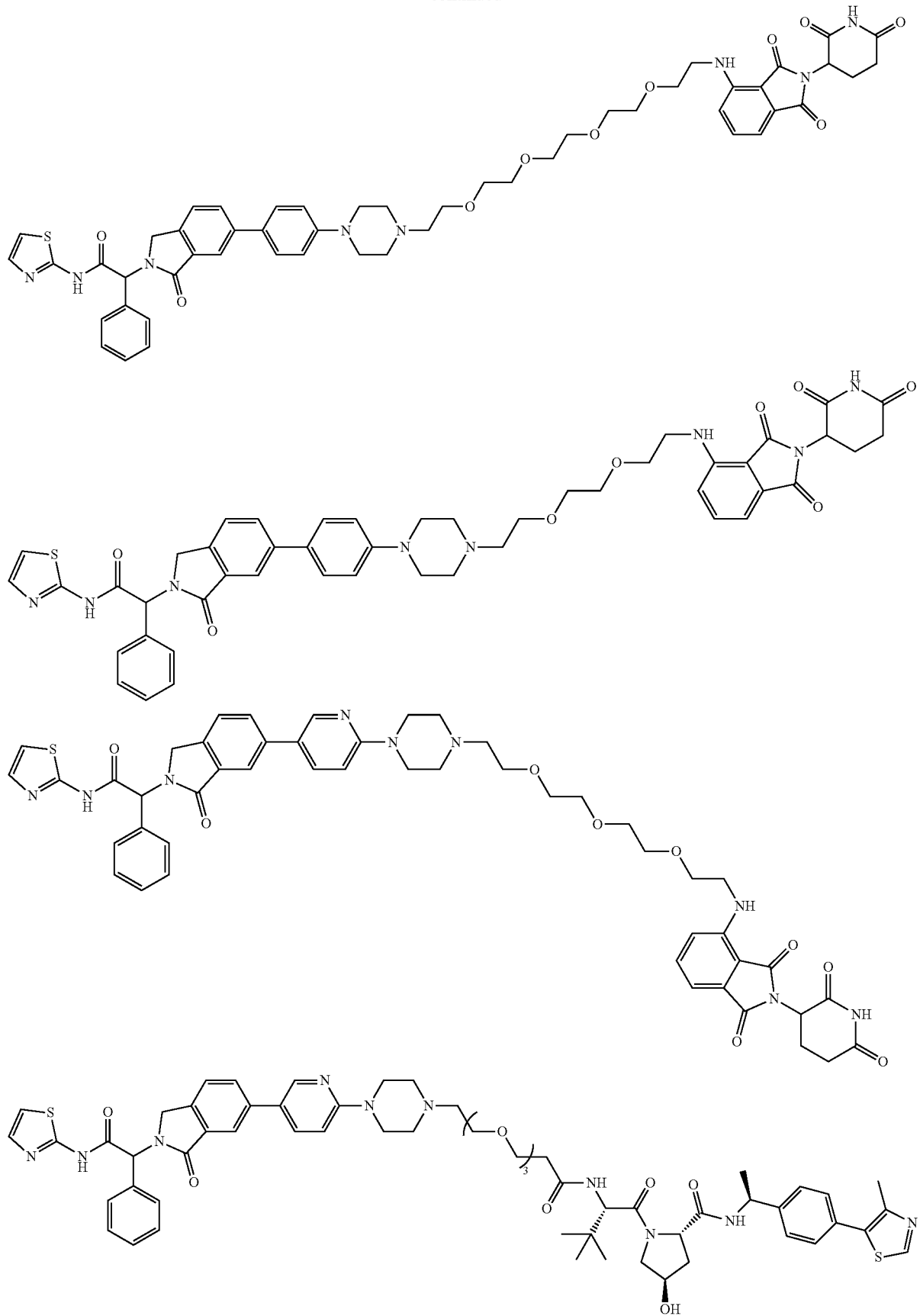

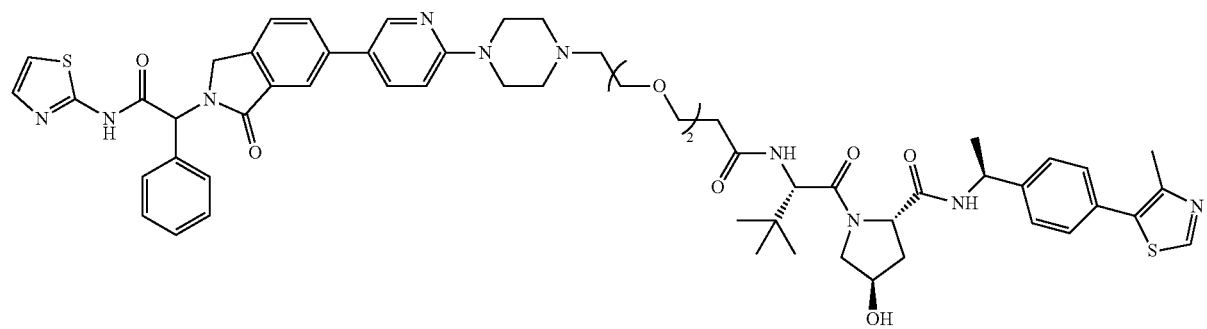
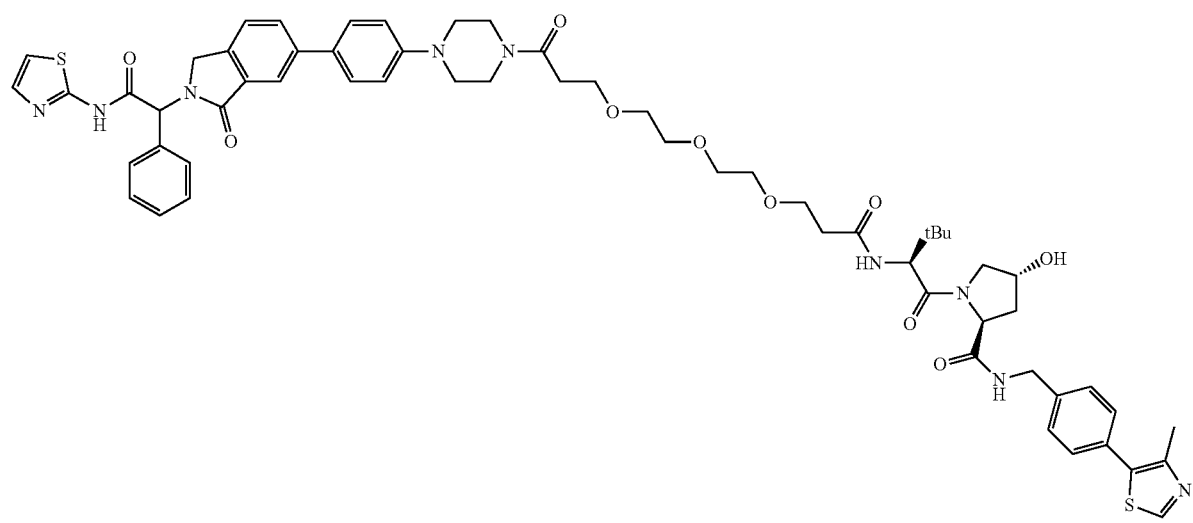
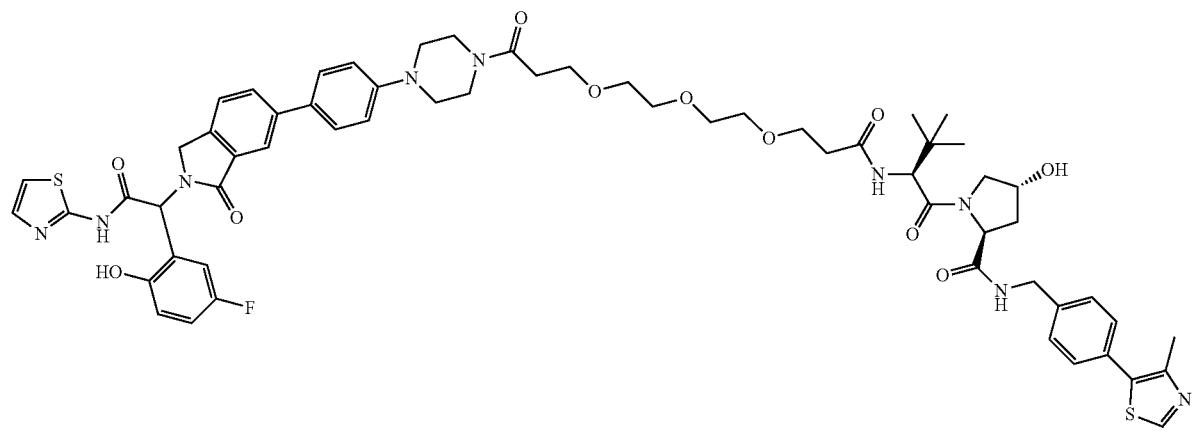
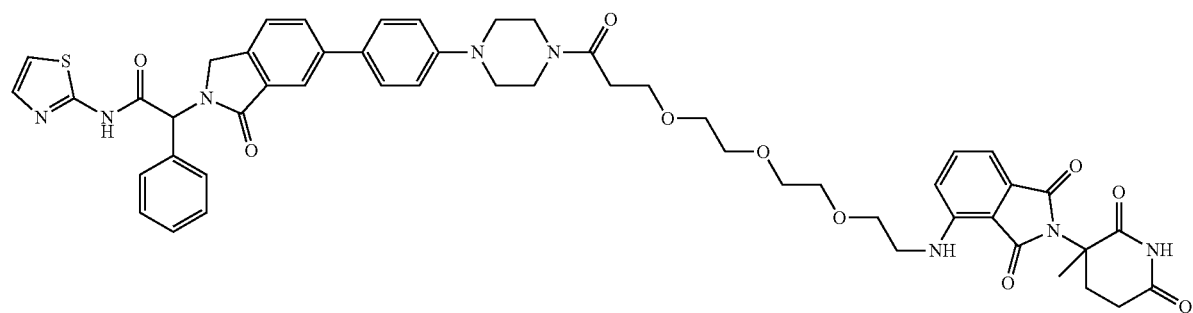

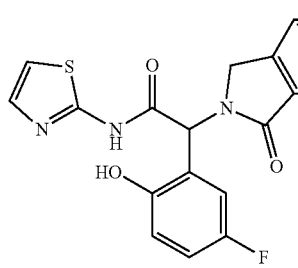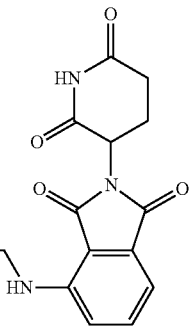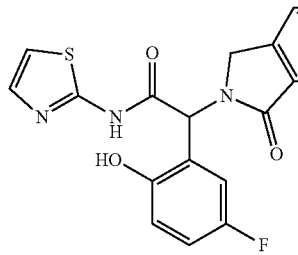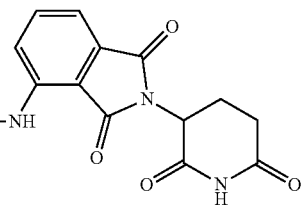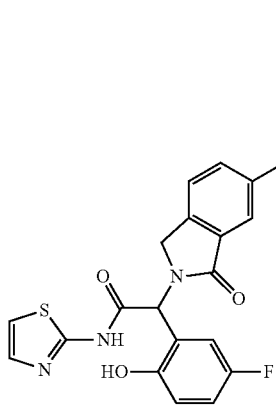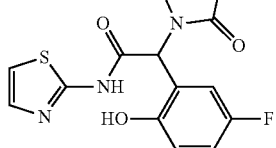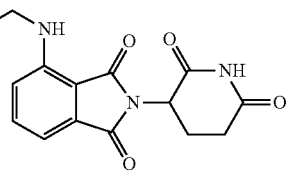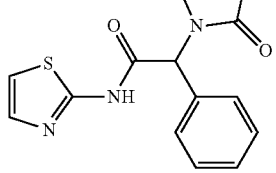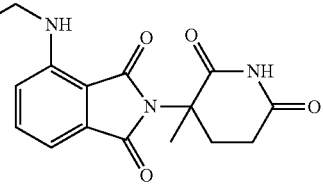

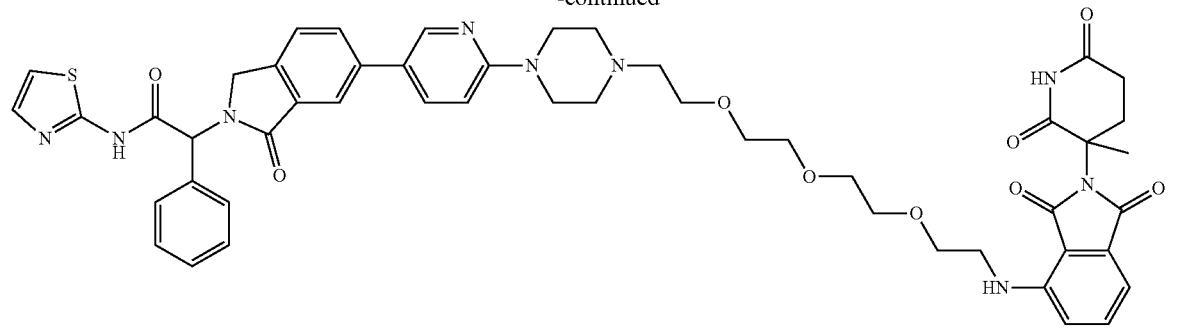

and

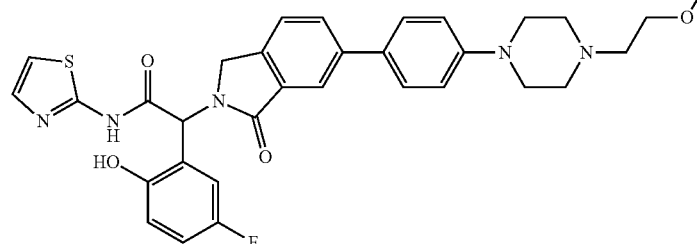

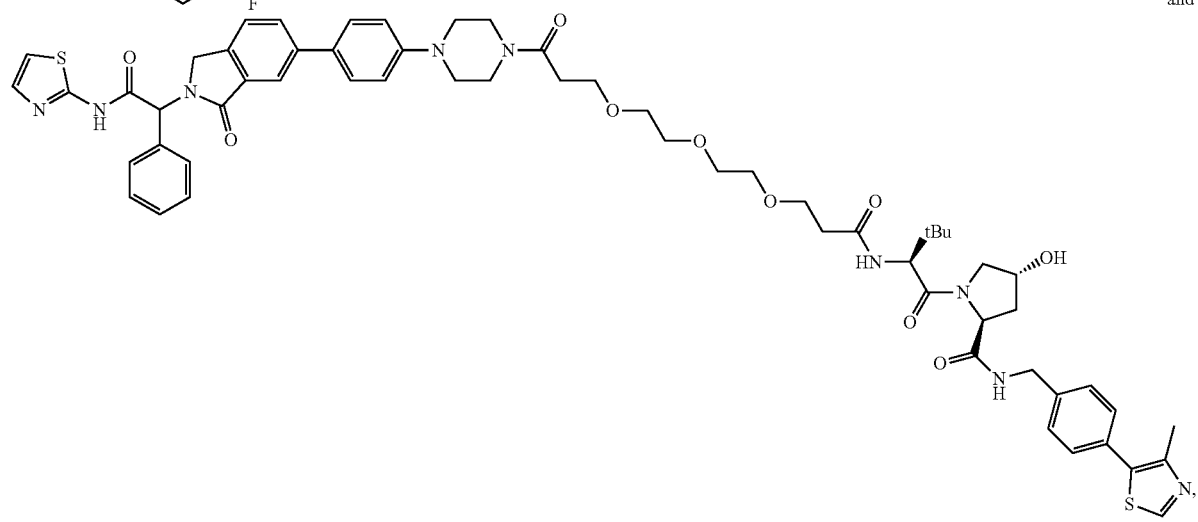

or an enantiomer, diastereomer, stereoisomer, or pharmaceutically acceptable salt thereof optionally in a pharmaceutically acceptable carrier.

The present application further includes a Degron of Formula D1:

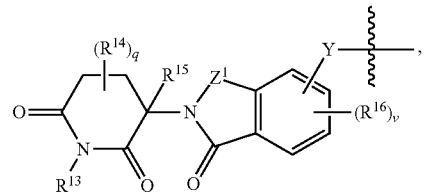

or an enantiomer, diastereomer, or stereoisomer thereof, wherein Y, $Z^1$, $R^{13}$, $R^{14}$, $R^5$, $R^{16}$, v, and q are each as defined herein.

The present application further includes a Linker of Formula L0:

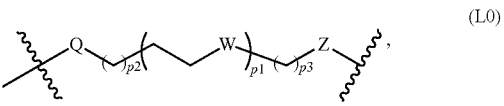

or an enantiomer, diastereomer, or stereoisomer thereof, wherein p1, p2, p3, W, Q, and Z are each as defined herein, the Linker is covalently bonded to a Degron with the

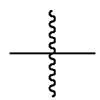

next to Q, and covalently bonded to a Targeting Ligand with the

next to Z.

The present application also describes a pharmaceutical composition comprising a therapeutically effective amount of a bifunctional compound of Formula X, Formula Y, Formula Z, Formula A, Formula B, Formula C, or Formula D or an enantiomer, diastereomer, stereoisomer, or pharmaceutically acceptable salt thereof, and a pharmaceutically acceptable carrier.

The present application provides a method of modulating or decreasing the amount of a kinase, comprising administering to a subject in need thereof a therapeutically effective amount of a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application.

The present application provides a method of modulating or decreasing the amount of epidermal growth factor receptor (EGFR) and/or a mutant thereof, comprising administering to a subject in need thereof a therapeutically effective amount of a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application.

The present application provides a method of treating or preventing a disease in which EGFR or a mutant thereof plays a role or a disease resistant to an EGFR targeted therapy, such as a therapy with gefitinib, erlotinib, AZD9291, CO-1686 or WZ4002, comprising administering to a subject in need thereof a therapeutically effective amount of a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application.

The present application provides a method of treating or preventing cancer, comprising administering to a subject in need thereof a therapeutically effective amount of a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application.

The present application provides a method of treating or preventing cancer in a subject in need thereof, wherein the cancer cell comprises an activated EGFR or a mutant thereof or wherein the subject is identified as being in need of inhibition of EGFR or a mutant thereof for the treatment or prevention of cancer, comprising administering to the subject a therapeutically effective amount of a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application.

The present application provides a method of treating or preventing cancer in a subject in need thereof, wherein the cancer cell comprises an activated ERBB2 or wherein the subject is identified as being in need of inhibition of ERBB2 for the treatment or prevention of cancer, comprising administering to a subject in need thereof a therapeutically effective amount of a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application.

The present application provides a kit comprising a compound capable of modulating or decreasing the amount of EGFR or a mutant thereof, selected from a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in modulating or decreasing the amount of a kinase.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in modulating or decreasing the amount of EGFR and/or a mutant thereof.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in treating or preventing a disease in which EGFR or a mutant thereof plays a role, or a disease resistant to an EGFR targeted therapy, such as a therapy with gefitinib, erlotinib, AZD9291, CO-1686 or WZ4002.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in treating or preventing cancer.

The present application relates a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in treating or preventing cancer in a subject, wherein the subject is identified as being in need of inhibition of EGFR or a mutant thereof for the treatment or prevention of cancer, or wherein the cancer cell comprises an activated EGFR or a mutant thereof.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in treating or preventing cancer in a subject, wherein the subject is identified as being in need of inhibition of ERBB2 for the treatment or prevention of cancer, or wherein the cancer cell comprises an activated ERBB2.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in the manufacture of a medicament for modulating or decreasing the amount of a kinase.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in the manufacture of a medicament for modulating or decreasing the amount of EGFR and/or a mutant thereof.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in the manufacture of a medicament for treating or preventing a disease in which EGFR or a mutant thereof plays a role, or a disease resistant to an EGFR targeted therapy, such as a therapy with gefitinib, erlotinib, AZD9291, CO-1686 or WZ4002.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in the manufacture of a medicament for treating or preventing cancer.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in the manufacture of a medicament for treating or preventing cancer in a subject, wherein the subject is identified as being in need of inhibition of EGFR or a mutant thereof for the treatment or prevention of cancer, or wherein the cancer cell comprises an activated EGFR or a mutant thereof.

The present application provides a bifunctional compound of Formula X, Formula Y, Formula Z, Formula A, Formula B, Formula C, or Formula D, or a pharmaceutically acceptable salt, hydrate, solvate, prodrug, stereoisomer, or tautomer thereof, or a pharmaceutical composition of the application for use in the manufacture of a medicament for treating or preventing cancer in a subject, wherein the subject is identified as being in need of inhibition of ERBB2 for the treatment or prevention of cancer, or wherein the cancer cell comprises an activated ERBB2.

The present application further provides compounds and compositions with an improved efficacy and/or safety profile relative to known EGFR inhibitors. The present application also provides agents with novel mechanisms of action toward EGFR kinases in the treatment of various types of diseases including cancer and metastasis.

The details of the disclosure are set forth in the accompanying description below. Although methods and materials similar or equivalent to those described herein can be used in the practice or testing of the present application, illustrative methods and materials are now described. Other features, objects, and advantages of the disclosure will be apparent from the description and from the claims. Unless otherwise defined, all technical and scientific terms used herein are accorded the meaning commonly known to one with ordinary skill in the art. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

DETAILED DESCRIPTION

EGFR Target Protein

Figure 1:
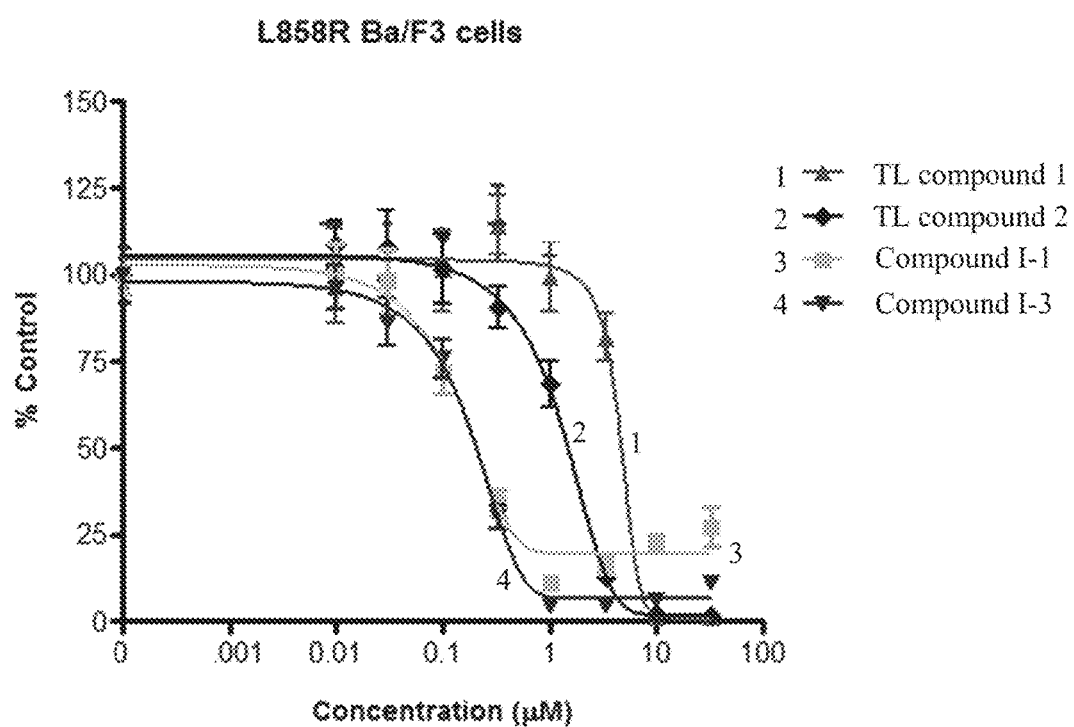
FIG. 1 is a graph showing EGFR activity in BaF3 cells expressing the EGFR/L858R mutant after the cells were treated with various concentrations of TL compound 1 (1), TL compound 2 (2), Compound I-1 (3), or Compound I-3 (4). The x-axis is concentration measured in μM and the y-axis is EGFR activity measured as a percent of the control.
Figure 2:
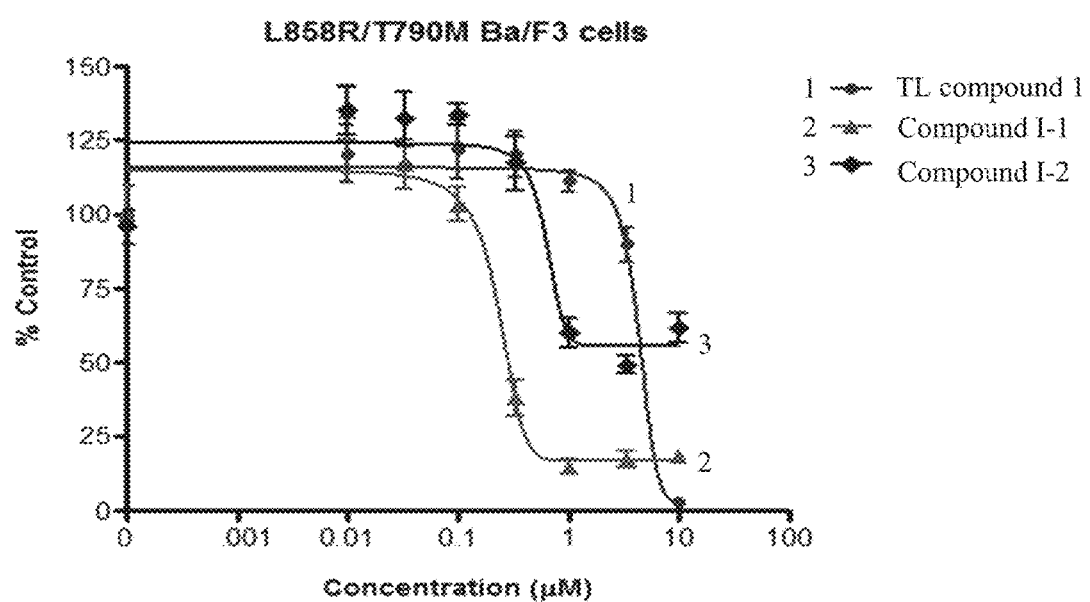
FIG. 2 is a graph showing EGFR activity in BaF3 cells expressing the EGFR L858R/T790M mutant after the cells were treated with various concentrations of TL compound 1, Compound I-1, or Compound I-2. The x-axis is concentration measured in μM and the y-axis is EGFR activity measured as a percent of the control.

The epidermal growth factor receptor (EGFR, Erb-B1) belongs to a family of proteins, involved in the proliferation of normal and malignant cells. Overexpression of Epidermal Growth Factor Receptor (EGFR) is present in at least 70% of human cancers. Epidermal growth factor receptor (EGFR) tyrosine kinase inhibitors (TKIs) are effective therapies for EGFR mutant advanced non-small cell lung cancer (NSCLC) patients. However, the vast majority of patients will develop disease progression following successful treatment with an EGFR TKI. One mechanism of acquired resistance is a substitution of leucine for arginine at position 858 (L858R) that occurs within exon 21 of the receptor. The most common mechanism of acquired resistance, detected in 60% of patients, is a secondary mutation in EGFR at position T790 (T790M). This mutation leads to an increase in ATP affinity and makes it more difficult for reversible EGFR TKIs (e.g., first-generation inhibitors gefitinib and erlotinib and second-generation inhibitors afatinib, neratinib, and dacomitinib) to bind the EGFR TKI domain.

All current EGFR TKIs target the ATP site, and while third generation irreversible inhibitors can overcome T790M, they are all rendered impotent by the C797S mutation, which is already arising in treated patients. Third-generation inhibitors include osimertinib (Tagrisso), rociletinib (CO-1686), olmutinib (Olita; BI 1482694; HM61713), naquotinib (ASP8273), nazartinib (EGF816), and PF-06747775. Cetuximab, an anti-EGFR antibody that blocks receptor dimerization, is not effective in EGFR-mutant NSCLC because mutational activation of the kinase is effectively "downstream" of receptor dimerization.

Recently, a fourth-generation inhibitor knowns as EAI045 has been discovered that is selective for drug-resistant EGFR mutants over wild-type EGFR. EAI045 is currently being developed as an inhibitor of the C797S mutation (Wang S, et al. Cancer Lett. 2017, 385:51-54).

Additionally, small molecule inhibitors of EGFR have been identified including thiazole-containing inhibitors as described in WO2017/004383 filed by Dana-Farber Cancer Institute. When tested in an EGFR T790M/L858R Ba/F3 cell line, a number of compounds were efficacious in inducing inhibition of the mutant cell line and potent compounds were reported to have an IC$_{50}$ value of less than 0.5 μM.

The present application describes bifunctional compounds having utility as modulators of ubiquitination and proteosomal degradation of targeted proteins, especially compounds comprising a moiety capable of binding to a polypeptide or a protein that is degraded and/or otherwise inhibited by the bifunctional compounds of the present invention. In particular, the present application is directed to compounds that contain a small-molecule moiety capable of binding to an E3 ubiquitin ligase, such as cereblon, and a ligand capable of binding to a target protein in such a way that the target protein is placed in proximity to the ubiquitin ligase to effect degradation (and/or inhibition) of that protein. In one embodiment, the small molecule moiety has a molecular weight below 2,000, 1,000, 500, or 200 Daltons.

In one embodiment, the small molecule moiety is a thalidomide-like moiety. In one embodiment, the E3 ubiquitin ligase is cereblon.

Compounds of the Application

The present application provides novel bifunctional compounds, which function to recruit targeted proteins to E3 ubiquitin ligase for degradation, and methods of preparation and uses thereof. The bifunctional compound is of Formula X:

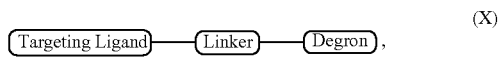
                                                                        (X)

wherein:
the Targeting Ligand is capable of binding to a targeted protein, such as EGFR and/or a mutant EGFR;
the Linker is a group that covalently binds to the Targeting Ligand and the Degron; and
the Degron is capable of binding to a ubiquitin ligase, such as an E3 ubiquitin ligase.

In one embodiment, the E3 ubiquitin ligase is cereblon.

The present application also provides targeted degradation of proteins through the use of bifunctional compounds, including bifunctional compounds that link an E3 ubiquitin ligase-binding moiety to a ligand that binds the targeted proteins.

The present application also describes a bifunctional compound of Formula Y:

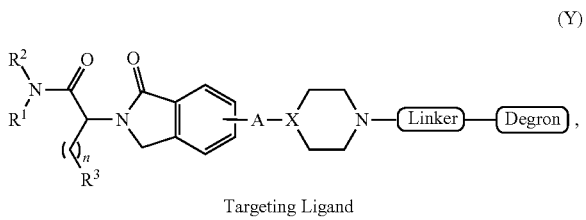
                                                                        (Y)

Targeting Ligand or an enantiomer, diastereomer, stereoisomer, or pharmaceutically acceptable salt thereof optionally in a pharmaceutically acceptable carrier,
wherein:
$R^1$, $R^2$, $R^3$, A, X, and n are each as defined herein;
the Linker is a group that covalently binds to

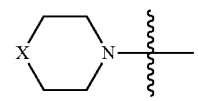

and the Degron;
the Degron is capable of binding to a ubiquitin ligase; and
the Targeting Ligand is capable of binding to EGFR or a mutant EGFR.

In one embodiment, the E3 ubiquitin ligase is cereblon.
In one embodiment, the Targeting Ligand is capable of binding to EGFR.
In one embodiment, the Targeting Ligand is capable of binding to a mutant EGFR.
In a further embodiment, the Targeting Ligand is capable of binding to a T790M/L858R EGFR mutant.

In a further embodiment, the Targeting Ligand is capable of binding to a T790M/L858R/C797S EGFR mutant.

In one embodiment the bifunctional compound is of Formula Z:

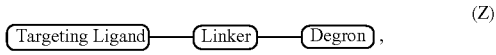
(Z)

or an enantiomer, diastereomer, stereoisomer, or pharmaceutically acceptable salt thereof optionally in a pharmaceutically acceptable carrier,
wherein:
the Targeting Ligand is selected from

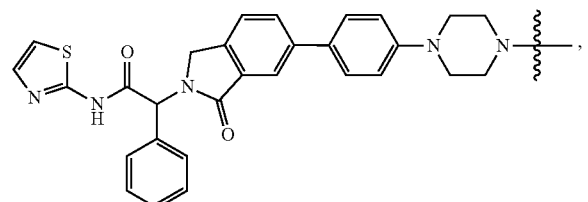

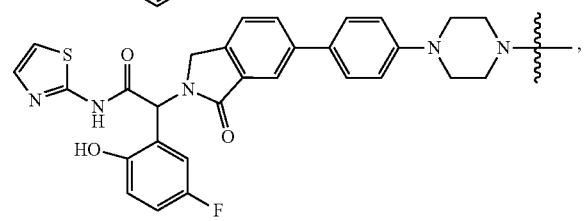

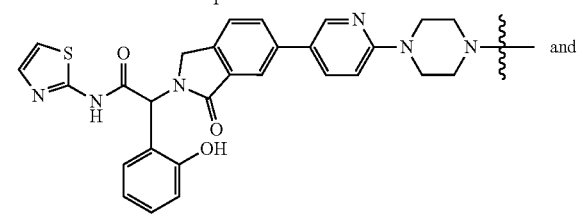

the Linker is a group that covalently binds to the Targeting Ligand and the Degron; and the Degron is capable of binding to a ubiquitin ligase.

In one embodiment, the E3 ubiquitin ligase is cereblon.

In one embodiment the bifunctional compound is of Formula A:

(A)

or an enantiomer, diastereomer, stereoisomer, or pharmaceutically acceptable salt thereof optionally in a pharmaceutically acceptable carrier,
wherein:
the Targeting Ligand is selected from

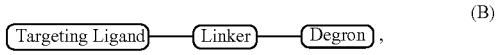

the Linker is a group that covalently binds to the Targeting Ligand and the Degron; and
the Degron is capable of binding to a ubiquitin ligase.
In one embodiment, the E3 ubiquitin ligase is cereblon.
In one embodiment the bifunctional compound is of Formula B:

(B)

or an enantiomer, diastereomer, stereoisomer, or pharmaceutically acceptable salt thereof optionally in a pharmaceutically acceptable carrier,
wherein:
the Targeting Ligand-Linker is selected from

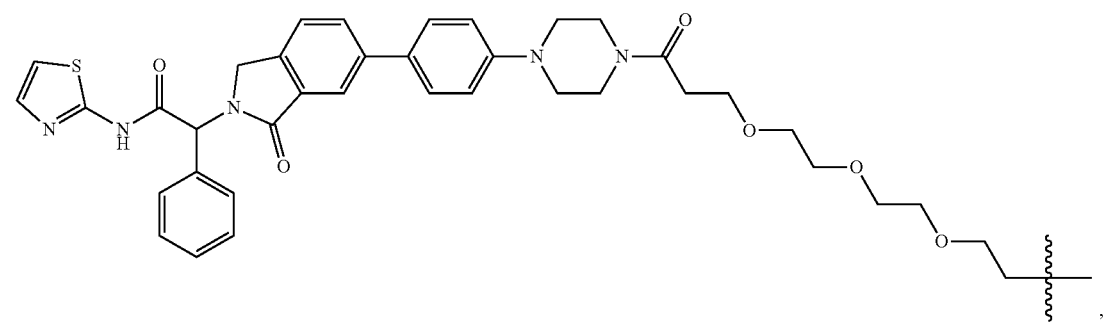

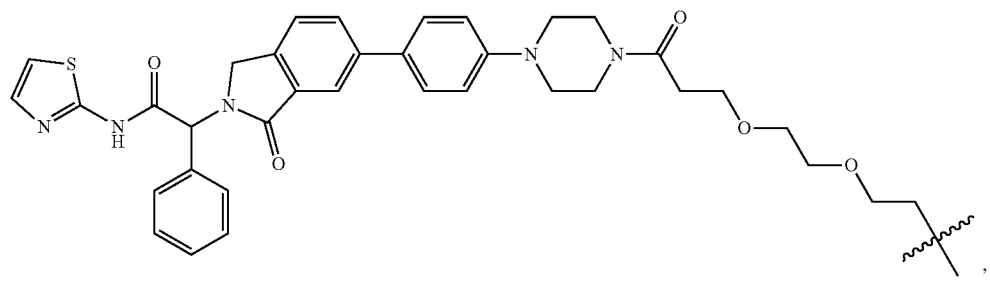
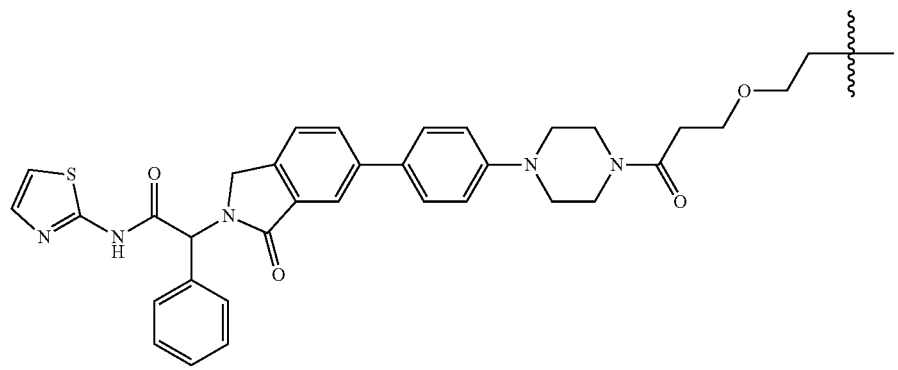
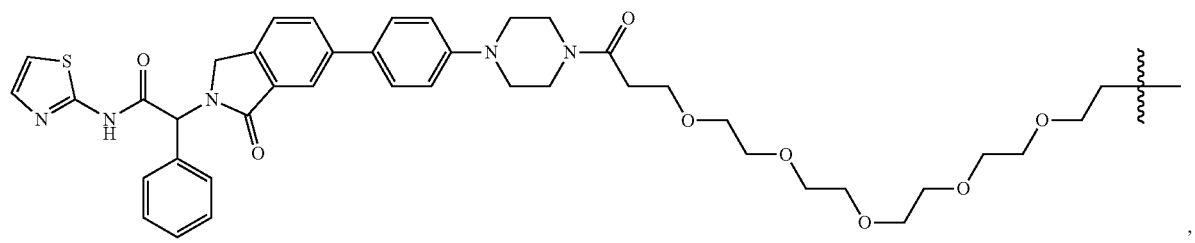
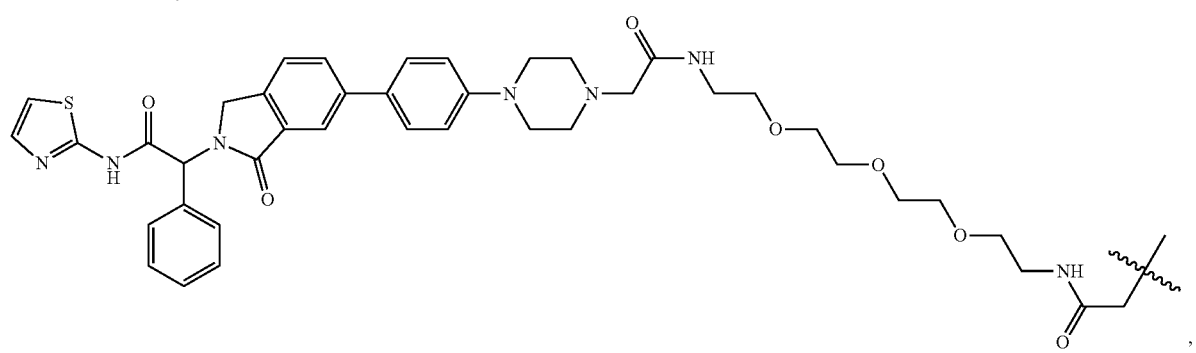
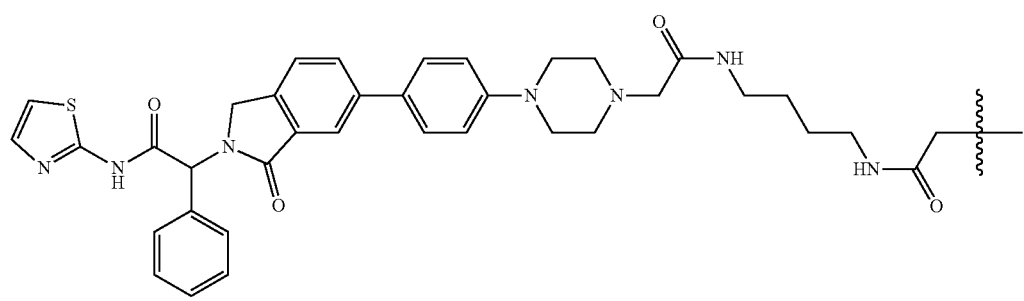

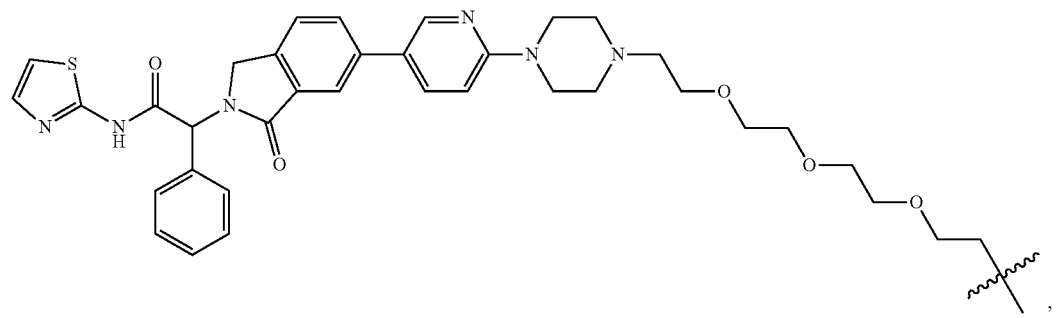,
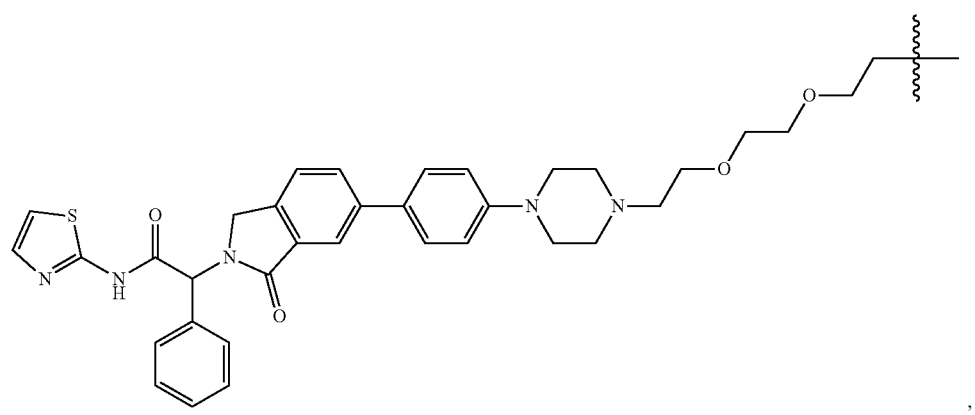,
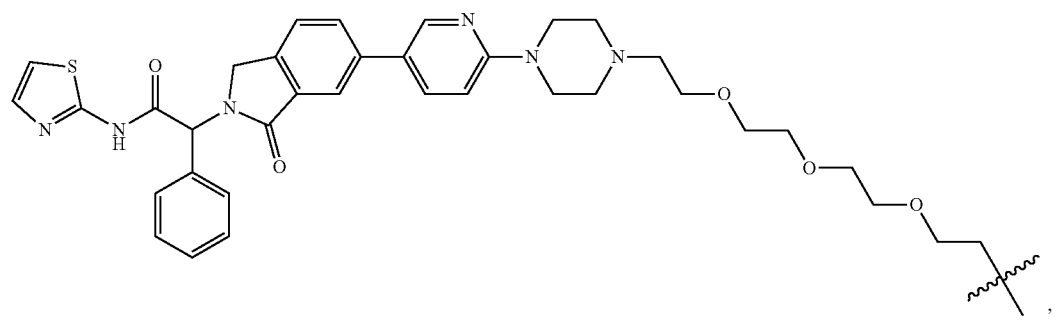,
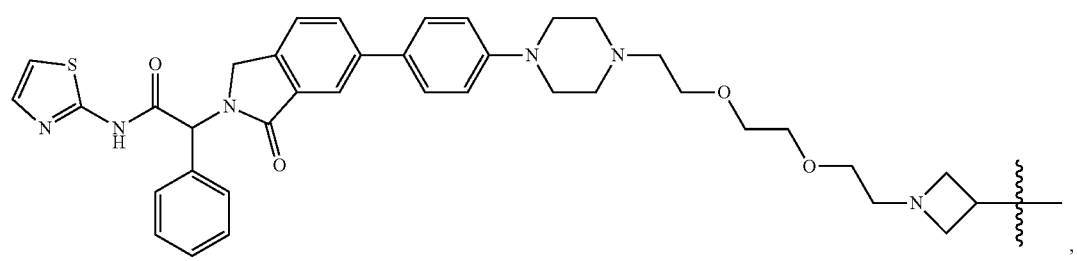,
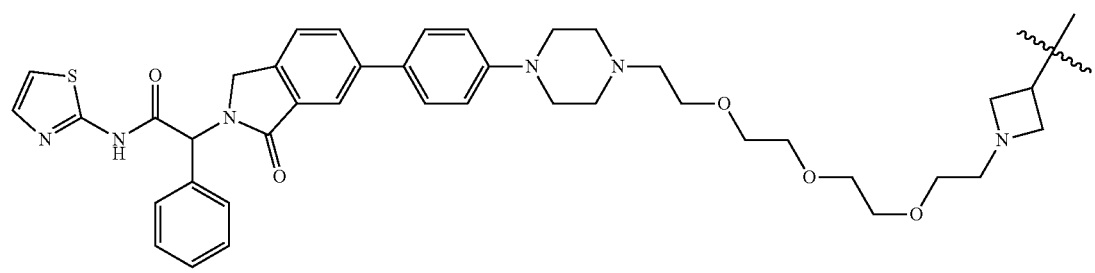,

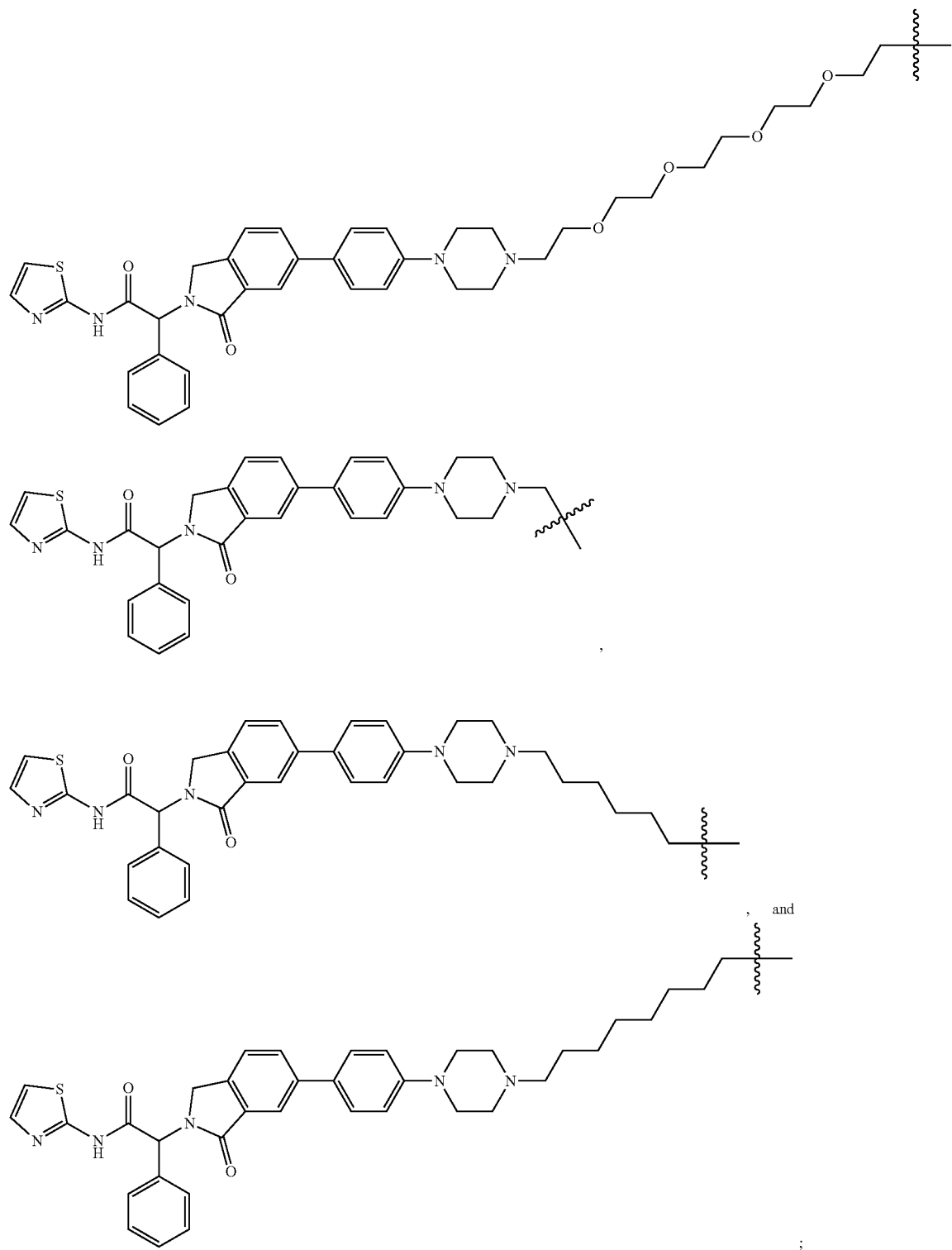
and
the Degron is capable of binding to a ubiquitin ligase.
In one embodiment, the E3 ubiquitin ligase is cereblon.
In one embodiment the bifunctional compound is of Formula C:
Targeting Ligand—Linker—Degron,  (C)

or an enantiomer, diastereomer, stereoisomer, or pharmaceutically acceptable salt thereof optionally in a pharmaceutically acceptable carrier,
wherein:
the Targeting Ligand-Linker is selected from
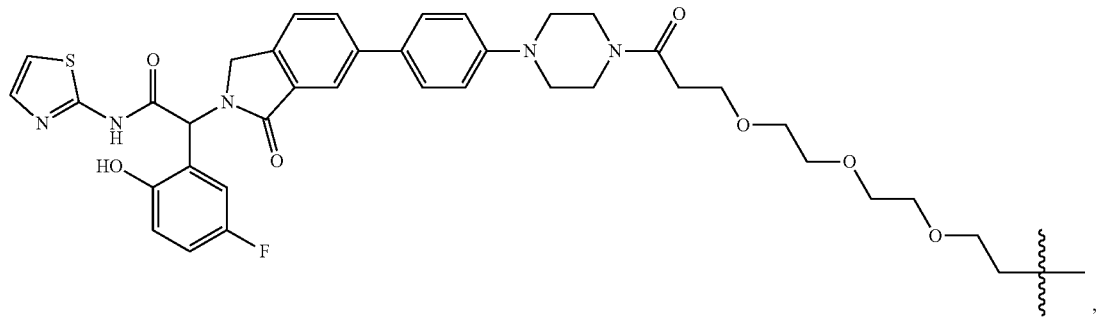
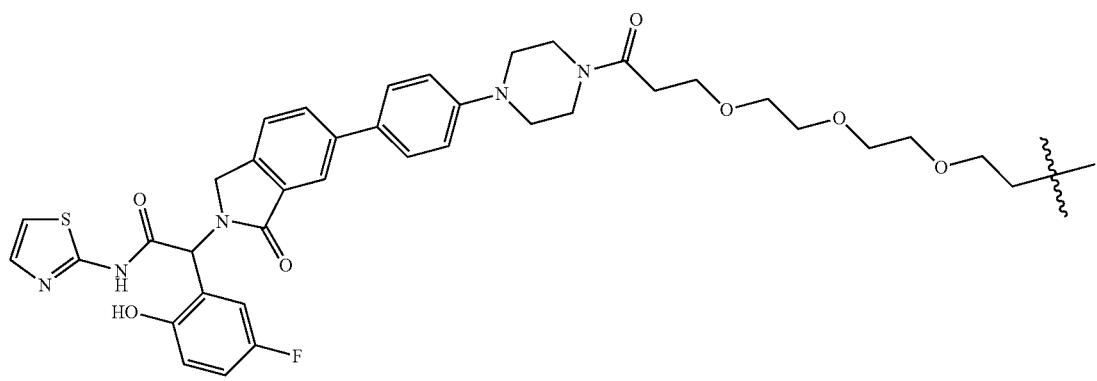
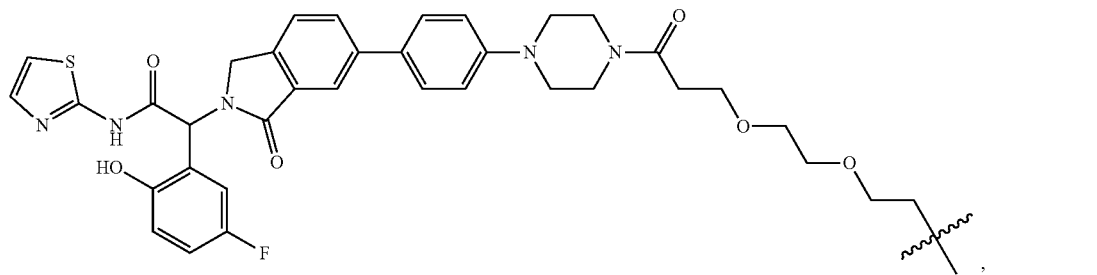
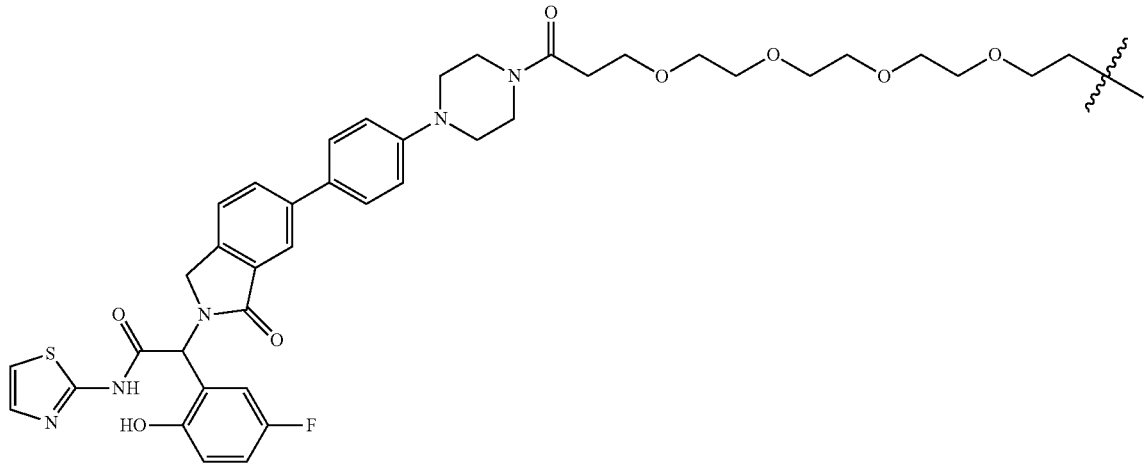

-continued
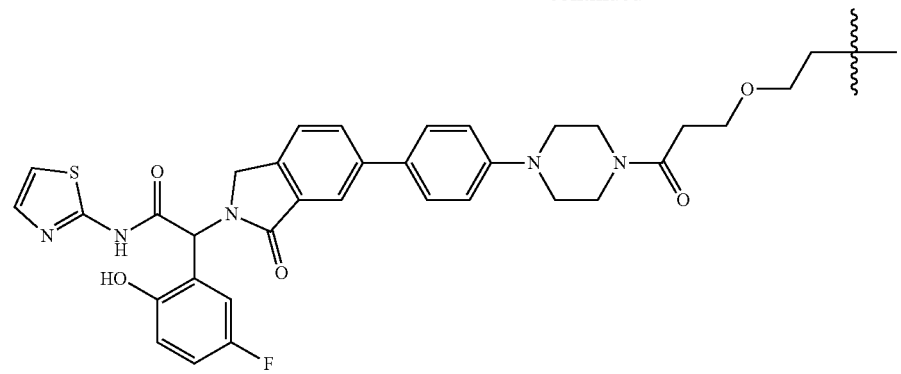
,
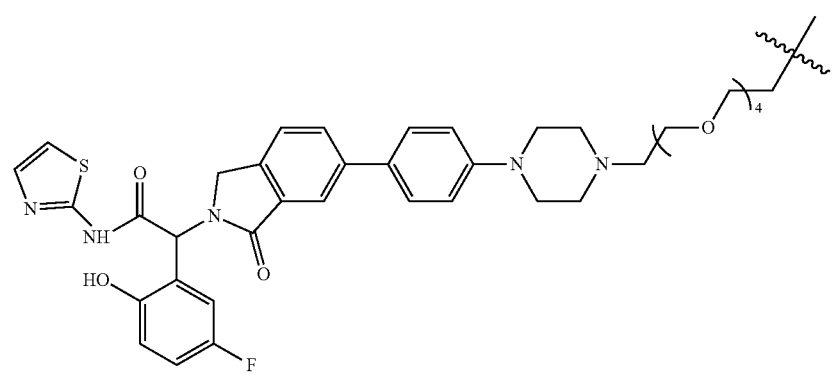
,
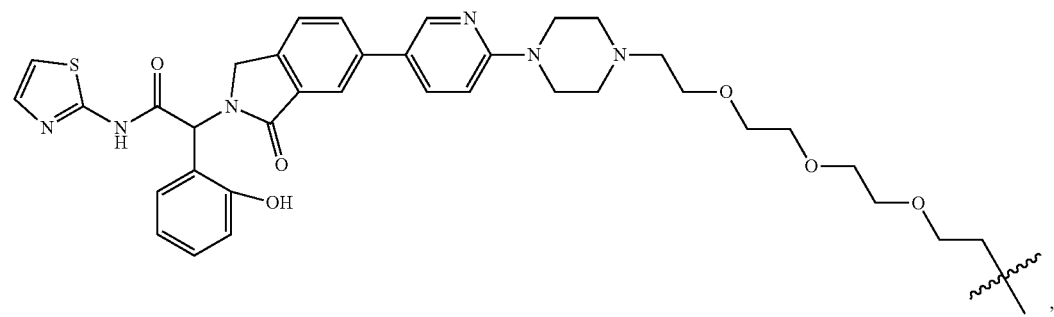
,
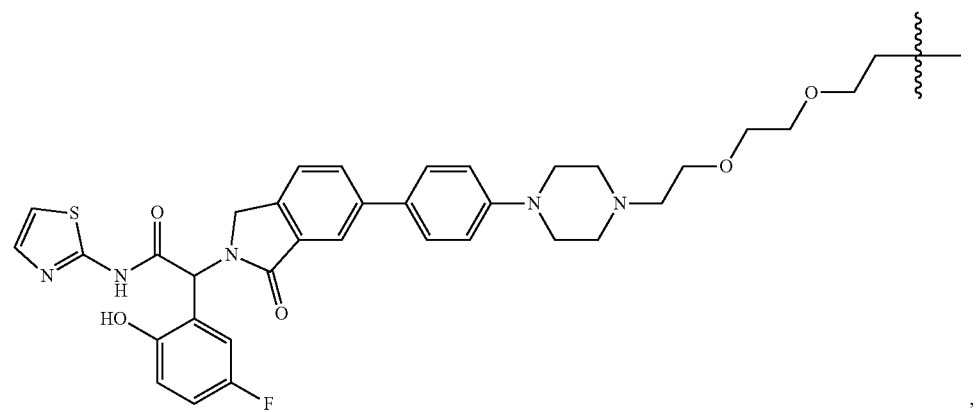
,

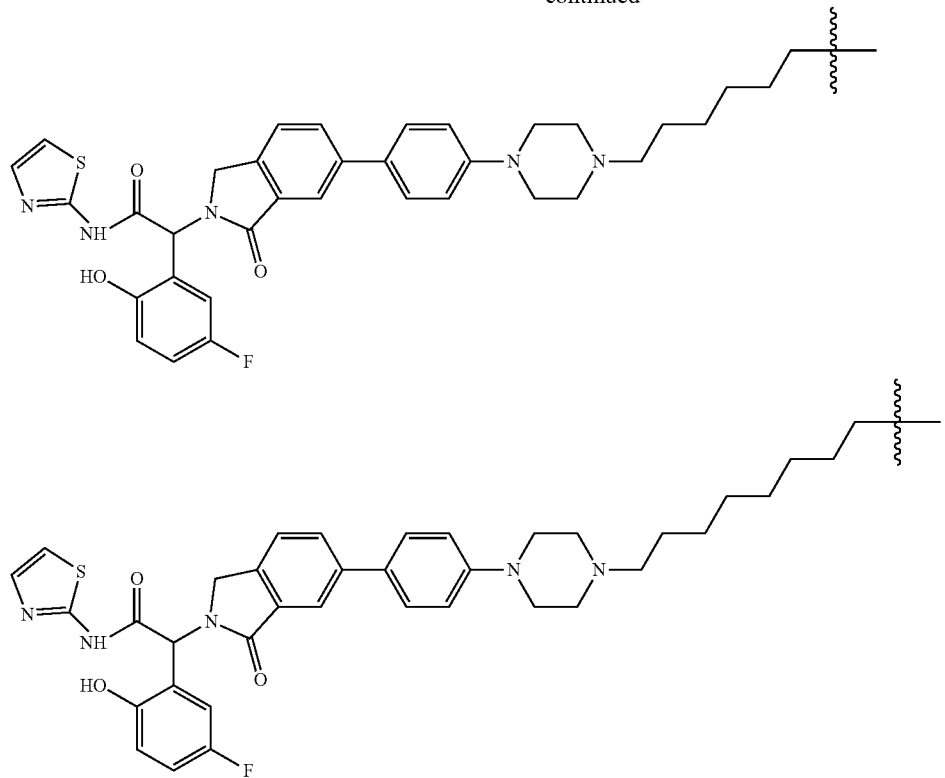

and the Degron is capable of binding to a ubiquitin ligase.

In one embodiment, the E3 ubiquitin ligase is cereblon.

The present application also describes targeted degradation of proteins through the use of bifunctional compounds, including bifunctional compounds that link an E3 ubiquitin ligase-binding moiety to a ligand that binds the targeted proteins.

Targeting Ligand

Targeting Ligand (TL) (or target protein moiety or target protein ligand or ligand) is a small molecule which is capable of binding to a target protein of interest, such as EGFR or a mutant thereof.

In one embodiment, a Targeting Ligand is a compound of Formula TL-I:

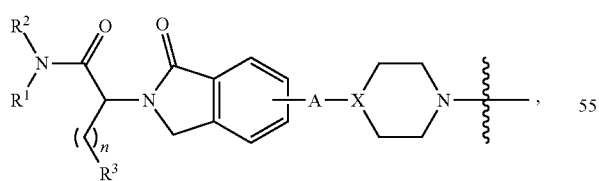

(TL-I)

or an enantiomer, diastereomer, stereoisomer, or pharmaceutically acceptable salt thereof,
wherein:
A is phenyl or pyridinyl;
X is CH, C($C_1$-$C_3$) alkyl, or N;
$R^1$ is H or ($C_1$-$C_3$) alkyl;
$R^2$ is ($C_6$-$C_{10}$) aryl, or heteroaryl comprising one or two 5- to 7-membered rings and 1-4 heteroatoms selected from N, O, and S, wherein the aryl and heteroaryl are each optionally substituted with one or more $R^4$;

each $R^4$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, CN, C(O)$R^6$, C(O)O$R^6$, C(O)N$R^6R^7$, N$R^6R^7$, ($C_3$-$C_7$) cycloalkyl, heterocyclyl comprising a 5- to 7-membered ring and 1-3 heteroatoms selected from N, O, and S, ($C_6$-$C_{10}$) aryl, and heteroaryl comprising one or two 5- to 7-membered rings and 1-4 heteroatoms selected from N, O, and S, wherein the alkyl, cycloalkyl, heterocyclyl, aryl, and heteroaryl are each optionally substituted with one or more $R^5$;

each $R^5$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, and CN;

each $R^6$ is independently H or ($C_1$-$C_3$) alkyl;
each $R^7$ is independently H or ($C_1$-$C_3$) alkyl;
$R^3$ is ($C_1$-$C_3$) alkyl or

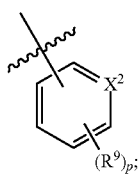

$X^2$ is N or $CR^8$;
$R^8$ is H, ($C_1$-$C_4$) alkyl, ($C_1$-$C_4$) haloalkyl, ($C_1$-$C_4$) alkoxy, ($C_1$-$C_4$) haloalkoxy, halogen, $NO_2$, $NH_2$, OH, or CN;
each $R^9$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, $NH_2$, OH, and CN;

n is 0 or 1; and
p is 0, 1, 2, or 3;
wherein the Targeting Ligand is bonded to a Linker via the

next to

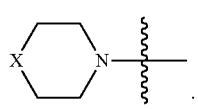

In some embodiments, X is N. In some embodiments, X is CH. In some embodiments, X is $C(CH_3)$, $C(CH_2CH_3)$, or $C(CH_2CH_2CH_3)$.

In some embodiments, A is phenyl. In some embodiments, A is pyridinyl.

In some embodiments, n is 0. In some embodiments, n is 1.

In some embodiments, $R^3$ is $(C_1-C_3)$ alkyl. In some embodiments, $R^3$ is selected from methyl, ethyl, propyl, or i-propyl. In one embodiment, $R^3$ is methyl.

In some embodiments, $R^3$ is

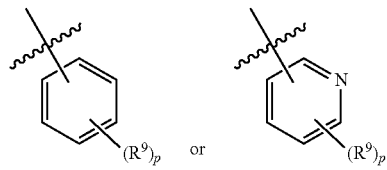

(e.g., 2-pyridinyl, 3-pyridinyl, or 4-pyridinyl). In some embodiments, $R^3$ is

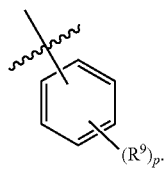

In some embodiments, $X^2$ is N. In some embodiments, $X^2$ is $CR^8$.

In some embodiments, $R^8$ is H. In some embodiments, $R^8$ is $(C_1-C_4)$ alkyl (e.g., methyl, ethyl, propyl, i-propyl, or butyl), $(C_1-C_4)$ haloalkyl (e.g., $CH_2F$, $CHF_2$, or $CF_3$), $(C_1-C_4)$ alkoxy (e.g., methoxy, ethoxy, propoxy, or butoxy), $(C_1-C_4)$ haloalkoxy (e.g., $OCH_2F$, $OCHF_2$, or $OCF_3$), halogen (e.g., F, Cl, Br, or I), $NO_2$, $NH_2$, OH, or CN. In some embodiments, $R^8$ is H, $NO_2$, $NH_2$, OH, or F. In some embodiments, $R^8$ is OH or F.

In some embodiments, p is 0. In some embodiments, p is 1. In some embodiments, p is 2. In some embodiments, p is 3. In some embodiments, p is 0, 1, or 2. In some embodiments, p is 0 or 1. In some embodiments, p is 1 or 1. In some embodiments, p is 1, 2, or 3.

In some embodiments, at least one $R^9$ is $(C_1-C_4)$ alkyl (e.g., methyl, ethyl, propyl, i-propyl, or butyl), $(C_1-C_4)$ haloalkyl (e.g., $CH_2F$, $CHF_2$, or $CF_3$), $(C_1-C_4)$ alkoxy (e.g., methoxy, ethoxy, propoxy, or butoxy), $(C_1-C_4)$ haloalkoxy (e.g., $OCH_2F$, $OCHF_2$, or $OCF_3$), halogen (e.g., F, Cl, Br or I), $NO_2$, $NH_2$, OH, or CN. In some embodiments, at least one $R^9$ is $NO_2$, $NH_2$, OH, or F. In some embodiments, at least one $R^9$ is OH or F.

In some embodiments, $R^1$ is H. In some embodiments, $R^1$ is $(C_1-C_3)$ alkyl (e.g., methyl, ethyl, propyl, or i-propyl). In some embodiments, $R^1$ is H, methyl, or ethyl. In some embodiments, $R^1$ is H or methyl. In some embodiments, $R^1$ is H.

In some embodiments, $R^2$ is (C6-C10) aryl optionally substituted with one or more $R^4$. In some embodiments, $R^2$ is phenyl optionally substituted with one or more $R^4$.

In some embodiments, $R^2$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, thiazolopyridinyl, pyrazolopyrimidinyl, etc.) optionally substituted with one or more $R^4$. In some embodiments, $R^2$ is heteroaryl comprising a 5-membered ring and 1-3 heteroatoms selected from N, O, and S, optionally substituted with one or more $R^4$. In some embodiments, $R^2$ is heteroaryl comprising a 5-membered ring and 1-2 heteroatoms selected from N, O, and S, optionally substituted with one or more $R^4$. In some embodiments, $R^2$ is heteroaryl comprising a 6-membered ring and 1-3 heteroatoms selected from N, O, and S, optionally substituted with one or more $R^4$. In some embodiments, $R^2$ is heteroaryl comprising a 6-membered ring and 1-2 heteroatoms selected from N, O, and S, optionally substituted with one or more $R^4$. In some embodiments, $R^2$ is heteroaryl comprising a 5-membered ring fused with a 6-membered ring and 1-4 heteroatoms selected from N, O, and S, optionally substituted with one or more $R^4$. In some embodiments, $R^2$ is selected from:

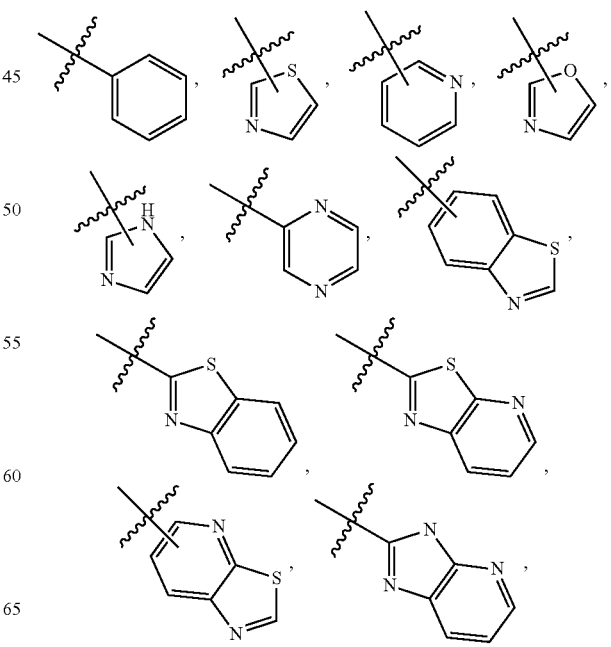

-continued

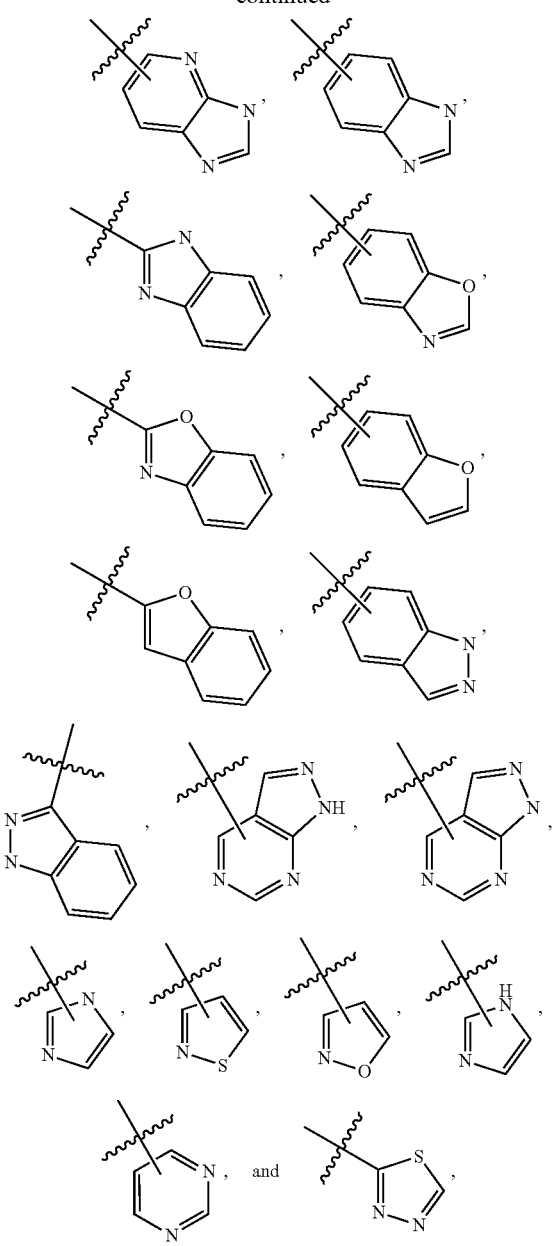

wherein each moiety is optionally substituted with one or more $R^4$. In some embodiments, $R^2$ is selected from:

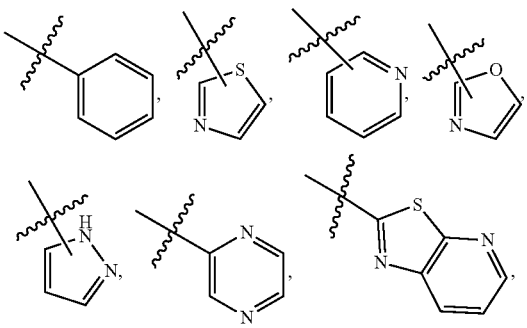

-continued

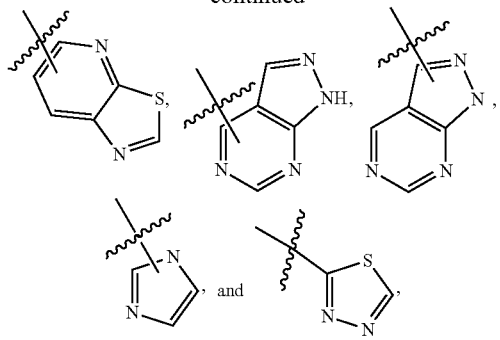

wherein each moiety is optionally substituted with one or more $R^4$. In some embodiments, $R^2$ is

optionally substituted with one or more $R^4$.

In some embodiments, at least one $R^4$ is $(C_1-C_4)$ alkyl, $(C_1-C_4)$ haloalkyl, $(C_1-C_4)$ alkoxy, $(C_1-C_4)$ haloalkoxy, halogen, $NO_2$, OH, or CN.

In some embodiments, at least one $R^4$ is $(C_1-C_4)$ alkyl (e.g., methyl, ethyl, propyl, i-propyl, or butyl) optionally substituted with one or more $R^5$. In some embodiments, at least one $R^4$ is methyl optionally substituted with one or more $R^5$. In some embodiments, at least one $R^4$ is $(C_1-C_4)$ haloalkyl (e.g., $CH_2F$, $CHF_2$, or $CF_3$). In some embodiments, at least one $R^4$ is $CF_3$.

In some embodiments, at least one $R^4$ is $(C_1-C_4)$ alkoxy (e.g., methoxy, ethoxy, propoxy, or butoxy). In some embodiments, at least one $R^4$ is $(C_1-C_4)$ haloalkoxy (e.g., $OCH_2F$, $OCHF_2$, or $OCF_3$)

In some embodiments, at least one $R^4$ is halogen (e.g., F, Cl, Br or I).

In some embodiments, at least one $R^4$ is $NO_2$, OH, or CN.

In some embodiments, at least one $R^4$ is $C(O)R^6$ or $C(O)OR^6$.

In some embodiments, at least one $R^4$ is $C(O)NR^6R^7$ or $NR^6R^7$.

In some embodiments, at least one $R^4$ is $(C_3-C_7)$ cycloalkyl (e.g., cyclopropyl, cyclobutyl, cyclopentyl, cyclohexyl, or cycloheptyl) optionally substituted with one or more $R^5$.

In some embodiments, at least one $R^4$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) optionally substituted with one or more $R^5$.

In some embodiments, at least one $R^4$ is $(C_6-C_{10})$ aryl optionally substituted with one or more $R^5$. In some embodiments, at least one $R^4$ is phenyl optionally substituted with one or more $R^5$.

In some embodiments, at least one $R^4$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, etc.) optionally substituted with one or more $R^5$. In some embodiments, at least one $R^4$ is heteroaryl comprising a 5-membered ring (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, etc.) optionally substituted with one or more $R^5$.

In some embodiments, at least one $R^4$ is heteroaryl comprising a 6-membered ring (e.g., pyridinyl, pyridazinyl, pyrimidinyl, triazinyl, etc.) optionally substituted with one or more $R^5$.

In some embodiments, at least one $R^5$ is $(C_1-C_4)$ alkyl (e.g., methyl, ethyl, propyl, i-propyl, or butyl). In some embodiments, at least one $R^5$ is $(C_1-C_4)$ haloalkyl (e.g., $CH_2F$, $CHF_2$, or $CF_3$).

In some embodiments, at least one $R^5$ is $(C_1-C_4)$ alkoxy (e.g., methoxy, ethoxy, propoxy, or butoxy). In some embodiments, at least one $R^5$ is $(C_1-C_4)$ haloalkoxy (e.g., $OCH_2F$, $OCHF_2$, or $OCF_3$).

In some embodiments, at least one $R^5$ is halogen (e.g., F, Cl, Br or I).

In some embodiments, at least one $R^5$ is $NO_2$, OH, or CN.

In some embodiments, at least one $R^6$ is H. In some embodiments, at least one $R^6$ is $(C_1-C_3)$ alkyl (e.g., methyl, ethyl, propyl, or i-propyl).

In some embodiments, at least one $R^7$ is H. In some embodiments, at least one $R^7$ is $(C_1-C_3)$ alkyl (e.g., methyl, ethyl, propyl, or i-propyl).

Any of the groups described herein for any of A, X, $X^2$, $R^1$, $R^2$, $R^3$, $R^4$, $R^5$, $R^6$, $R^7$, $R^8$, $R^9$, n, and p can be combined with any of the groups described herein for one or more of the remainder of A, X, $X^2$, $R^1$, $R^2$, $R^3$, $R^4$, $R^5$, $R^6$, $R^7$, $R^8$, $R^9$, n, and p, and may further be combined with any of the groups described herein for the Linker.

For a Targeting Ligand of Formula TL-I:

(1) In one embodiment, X is N and A is phenyl.

(2) In one embodiment, X is CH and A is phenyl.

(3) In one embodiment, X is N, A is phenyl, and n is 0.

(4) In one embodiment, X is N, A is phenyl, n is 0, and $R^1$ is H.

(5) In one embodiment, X is N, A is phenyl, n is 1, and $R^1$ is H.

(6) In one embodiment, X is N, A is phenyl, n is 0, $R^1$ is H, and $R^3$ is

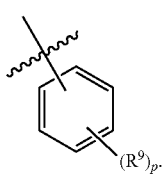

(7) In one embodiment, X is N, A is phenyl, n is 1, $R^1$ is H and $R^3$ is

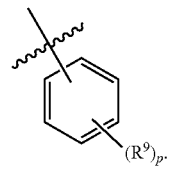

(8) In one embodiment, X is N, A is phenyl, n is 0, $R^1$ is H, and $R^3$ is phenyl.

(9) In one embodiment, X is N, A is phenyl, n is 1, $R^1$ is H, and $R^3$ is phenyl.

(10) In one embodiment, X is N, A is phenyl, n is 0, $R^1$ is H, $R^3$ is

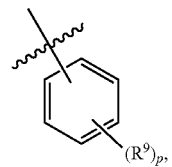

and p is 1 or 2.

(11) In one embodiment, X is N, A is phenyl, n is 1, $R^1$ is H $R^3$ is

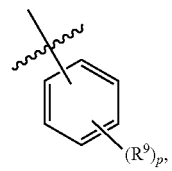

and p is 1 or 2.

(12) In one embodiment, X is N, A is phenyl, n is 0, $R^1$ is H, $R^3$ is

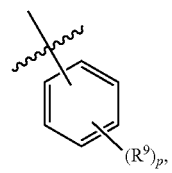

and $R^2$ is 5-membered heteroaryl comprising 1-4 heteroatoms selected from N, O, and S, optionally substituted with one or more $R^4$.

(13) In one embodiment, X is N, A is phenyl, n is 1, $R^1$ is H, $R^3$ is

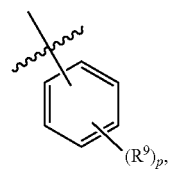

and $R^2$ is 5-membered heteroaryl comprising 1-4 heteroatoms selected from N, O, and S, optionally substituted with one or more $R^4$.

(14) In one embodiment, X is N, A is phenyl, n is 0, $R^1$ is H, $R^3$ is

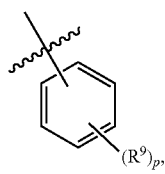

and $R^2$ is 5- or 6-membered heteroaryl comprising 1-4 heteroatoms selected from N, O, and S, optionally substituted with one or more $R^4$.

(15) In one embodiment, X is N, A is phenyl, n is 1, $R^1$ is H, $R^3$ is

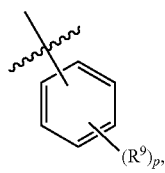

and $R^2$ is 5- or 6-membered heteroaryl comprising 1-4 heteroatoms selected from N, O, and S, optionally substituted with one or more $R^4$.

(16) In one embodiment, X is N, A is phenyl, n is 0, $R^1$ is H, $R^3$ is

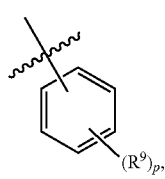

and $R^2$ is 5-membered heteroaryl comprising 1-4 heteroatoms selected from N, O, and S.

(17) In one embodiment, X is N, A is phenyl, n is 1, $R^1$ is H, $R^3$ is

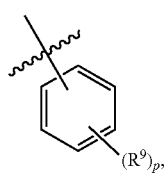

and $R^2$ is 5-membered heteroaryl comprising 1-4 heteroatoms selected from N, O, and S.

(18) In one embodiment, X is N, A is phenyl, n is 0, $R^1$ is H, $R^3$ is

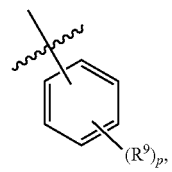

and $R^2$ is 5- or 6-membered heteroaryl comprising 1-4 heteroatoms selected from N, O, and S.

(19) In one embodiment, X is N, A is phenyl, n is 1, $R^1$ is H, $R^3$ is

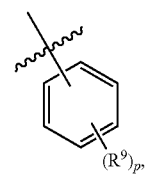

and $R^2$ is 5- or 6-membered heteroaryl comprising 1-4 heteroatoms selected from N, O, and S.

(20) In one embodiment, X is N, A is phenyl, n is 0, $R^1$ is H, $R^3$ is

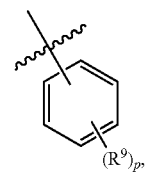

$R^2$ is 5-membered heteroaryl comprising 1-4 heteroatoms selected from N, O, and S, and at least one $R^9$ is $NO_2$, $NH_2$, OH, or F.

(21) In one embodiment, X is N, A is phenyl, n is 1, $R^1$ is H, $R^3$ is

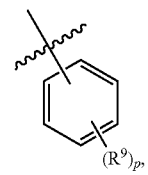

$R^2$ is 5-membered heteroaryl comprising 1-4 heteroatoms selected from N, O, and S, and at least one $R^9$ is $NO_2$, $NH_2$, OH, or F.

(22) In one embodiment, X is N, A is phenyl, n is 0, $R^1$ is H, $R^3$ is

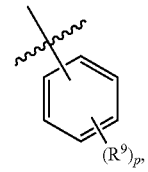

$R^2$ is 5-membered heteroaryl comprising 1-4 heteroatoms selected from N, O, and S, optionally substituted with one or more $R^4$, and at least one $R^9$ is $NO_2$, $NH_2$, OH, or F.

(23) In one embodiment, X is N, A is phenyl, n is 1, $R^1$ is H, $R^3$ is

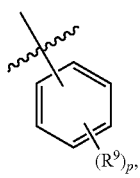

$R^2$ is 5-membered heteroaryl comprising 1-4 heteroatoms selected from N, O, and S, optionally substituted with one or more $R^4$, and at least one $R^9$ is $NO_2$, $NH_2$, OH, or F.

In one embodiment, the compound of Formula TL-I is of Formula TL-Ia or TL-Ib:

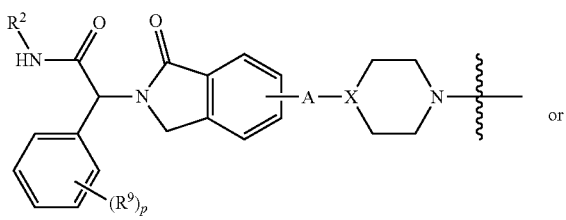

(TL-Ia)

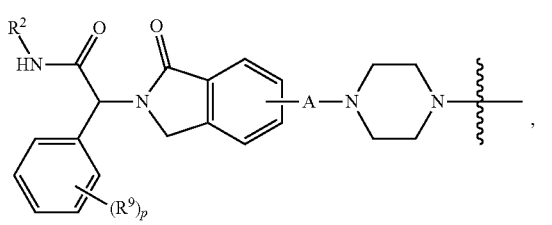

(TL-Ib)

wherein A, X, $R^2$, $R^9$, and p are each as defined above in Formula TL-I.

In one embodiment, A is phenyl.

In one embodiment, X is N.

In one embodiment, at least one $R^9$ is F or OH.

In one embodiment, p is 0, 1, or 2.

In one embodiment, $R^2$ is heteroaryl comprising one or two 5- to 7-membered rings and 1-4 heteroatoms selected from N, O, and S, optionally substituted with one or more $R^4$. In another embodiment, $R^2$ is heteroaryl comprising one 5- to 7-membered ring and 1-4 heteroatoms selected from N, O, and S, optionally substituted with one or more $R^4$. In another embodiment, $R^2$ is 5-membered heteroaryl comprising and 1-4 heteroatoms selected from N, O, and S, optionally substituted with one or more $R^4$. In another embodiment, $R^2$ is 5-membered heteroaryl comprising and 1-2 heteroatoms selected from N, O, and S, optionally substituted with one or more $R^4$.

A, X, $R^2$, $R^9$, and p can each be selected from any of the groups and combined as described above in Formula TL-I.

In another embodiment, the compound of Formula TL-I is of Formula TL-Ic or TL-Id:

(TL-Ic)

or

(TL-Id)

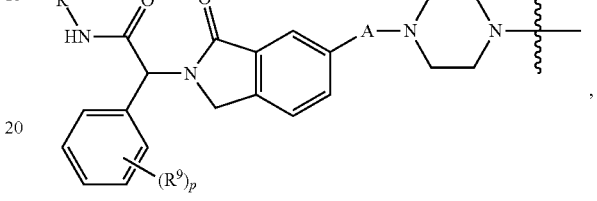

wherein A, X, $R^2$, $R^9$, and p are each as defined above in Formula TL-I.

In one embodiment, A is phenyl.

In one embodiment, X is N.

In one embodiment, at least one $R^9$ is F or OH.

In one embodiment, p is 0, 1, or 2.

In one embodiment, $R^2$ is heteroaryl comprising one or two 5- to 7-membered rings and 1-4 heteroatoms selected from N, O, and S, optionally substituted with one or more $R^4$. In another embodiment, $R^2$ is heteroaryl comprising one 5- to 7-membered ring and 1-4 heteroatoms selected from N, O, and S, optionally substituted with one or more $R^4$. In another embodiment, $R^2$ is 5-membered heteroaryl comprising and 1-4 heteroatoms selected from N, O, and S, optionally substituted with one or more $R^4$. In another embodiment, $R^2$ is 5-membered heteroaryl comprising and 1-2 heteroatoms selected from N, O, and S, optionally substituted with one or more $R^4$.

A, X, $R^2$, $R^9$, and p can each be selected from any of the groups and combined as described above in Formula TL-I.

In another embodiment, the compound of Formula TL-I is of Formula TL-Ie or TL-If:

(TL-Ie)

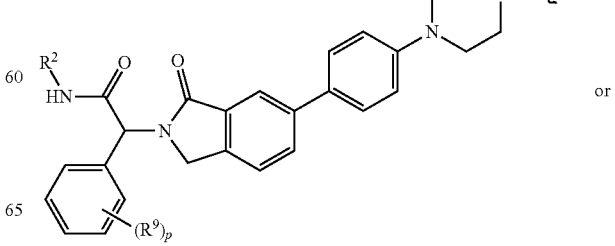

or

-continued

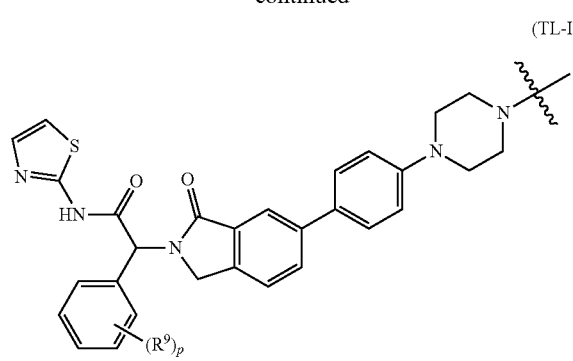

(TL-If)

wherein R², R⁹, and p are each as defined above in Formula TL-I.

In one embodiment, at least one R⁹ is F or OH.

In one embodiment, p is 0, 1 or 2.

In one embodiment, R² is heteroaryl comprising one or two 5- to 7-membered rings and 1-4 heteroatoms selected from N, O, and S, optionally substituted with one or more R⁴. In another embodiment, R² is heteroaryl comprising one 5- to 7-membered ring and 1-4 heteroatoms selected from N, O, and S, optionally substituted with one or more R⁴. In another embodiment, R² is 5-membered heteroaryl comprising and 1-4 heteroatoms selected from N, O, and S, optionally substituted with one or more R⁴.

R², R⁹, and p can each be selected from any of the groups and combined as described above in Formula TL-I.

In one embodiment, the compound of Formula TL-I is a compound of a formula selected from the group consisting of:

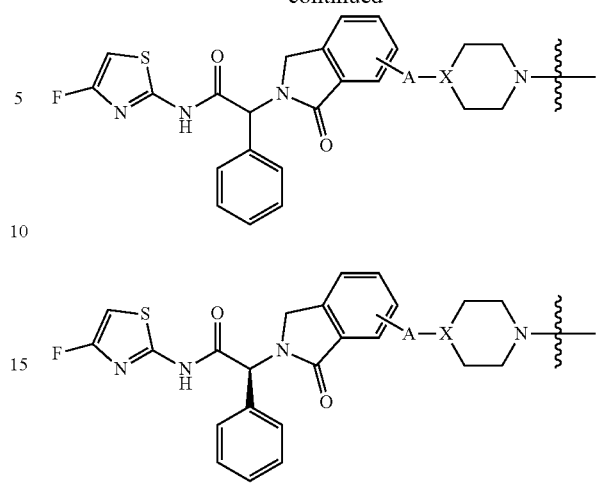

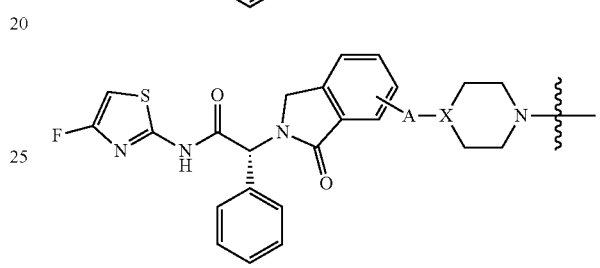

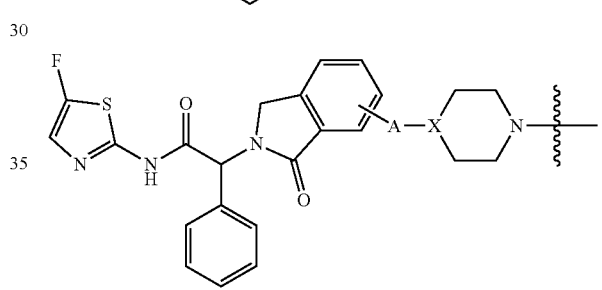

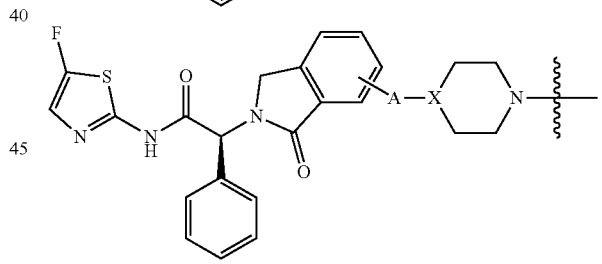

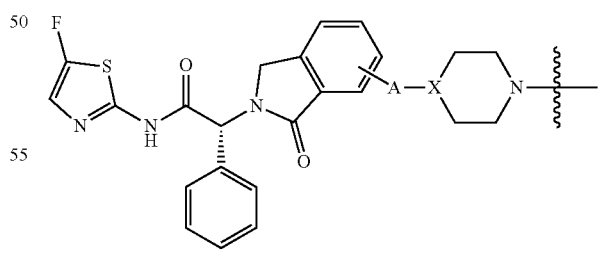

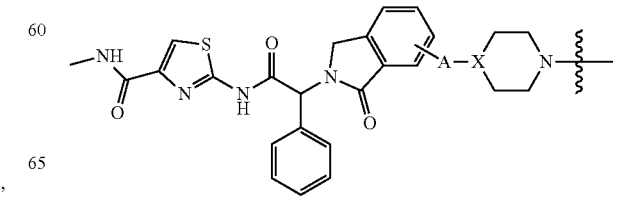

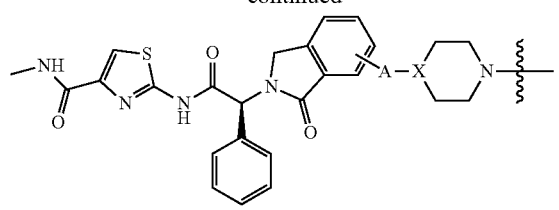,
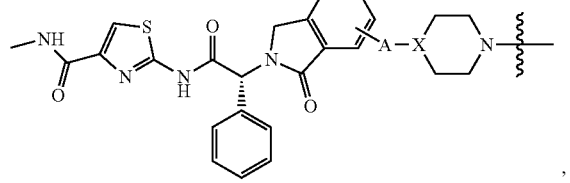,
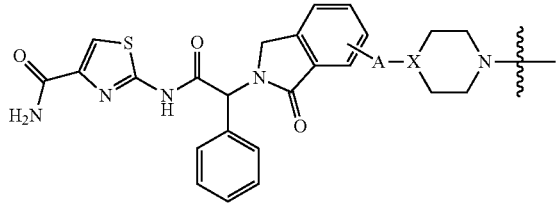,
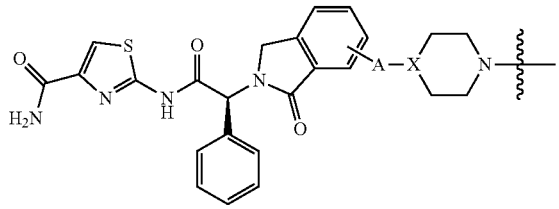,
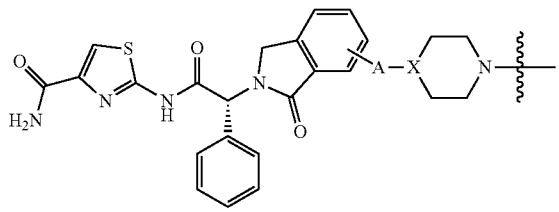,
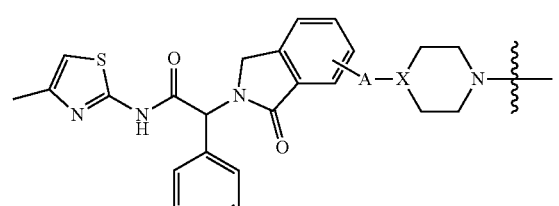,
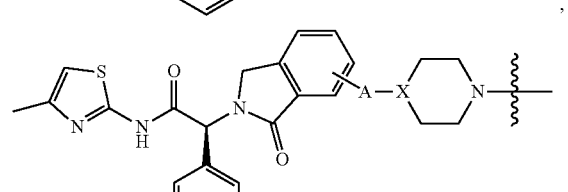,
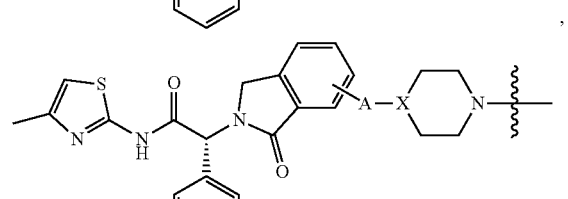,
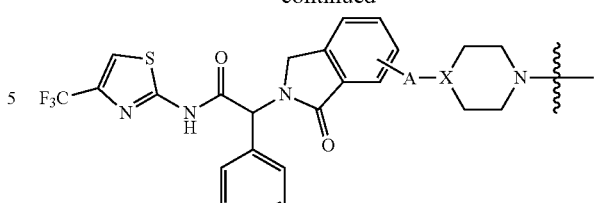,
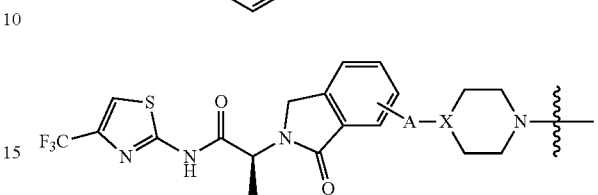,
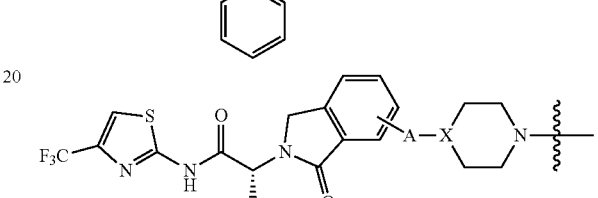,
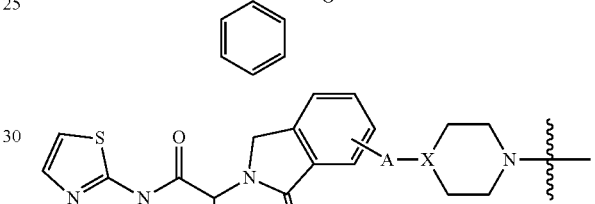,
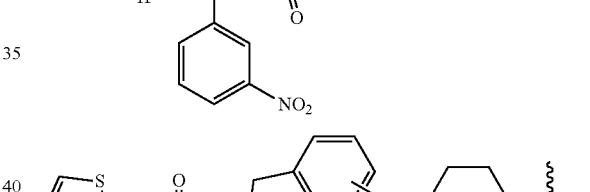,
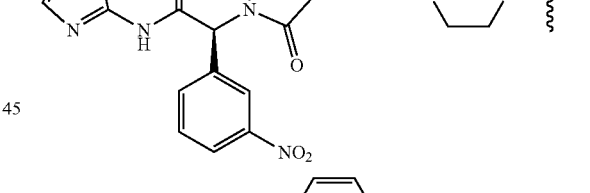,
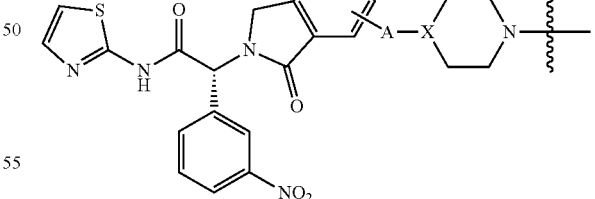,
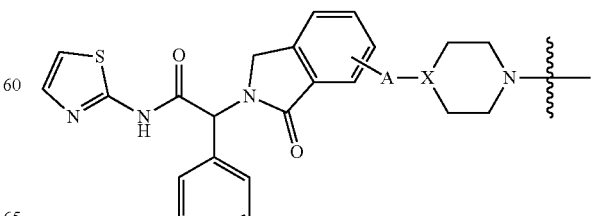,

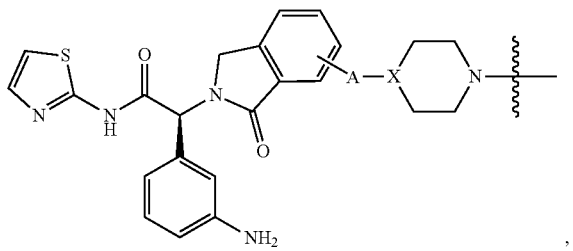
,
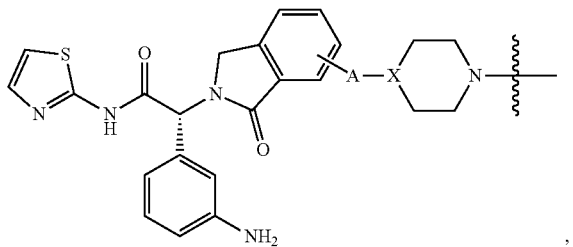
,
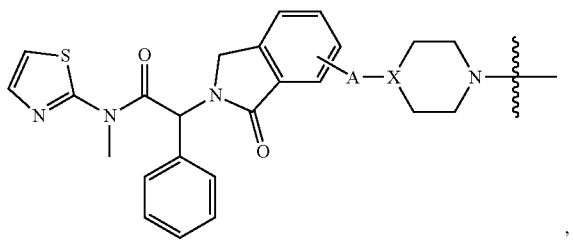
,
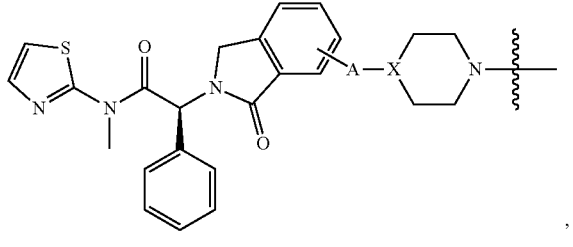
,
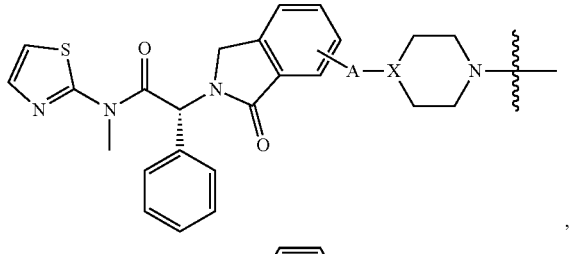
,
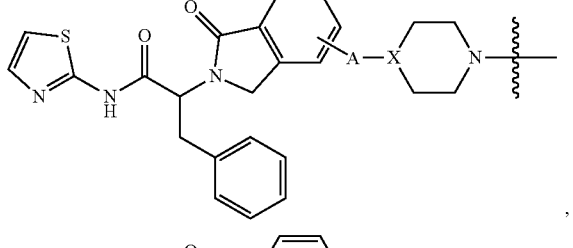
,
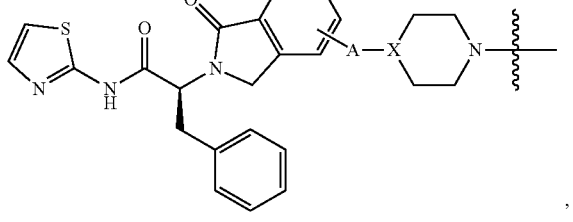
,
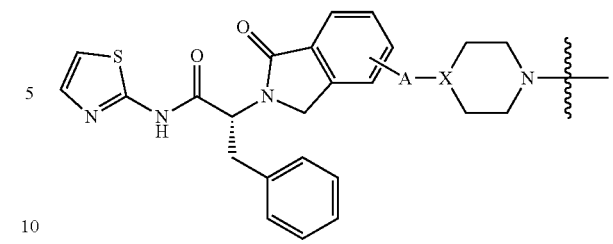
, 71
-continued
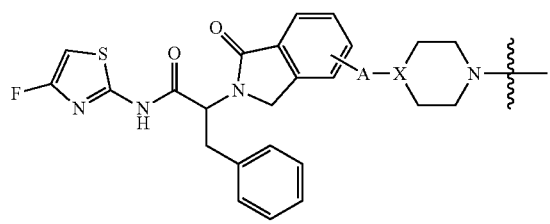
,
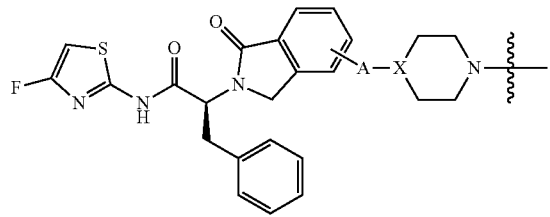
,
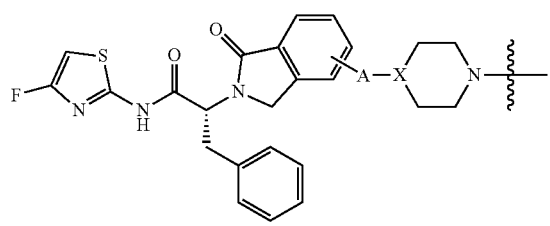
,
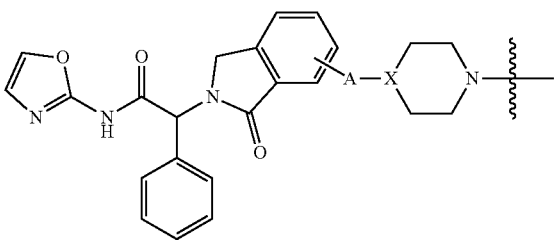
,
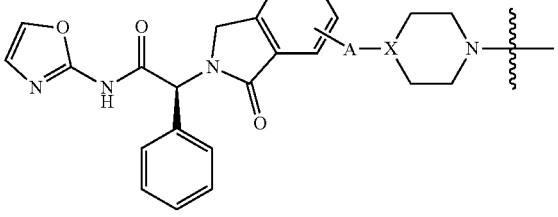
,
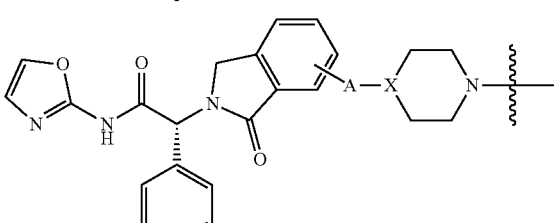
,
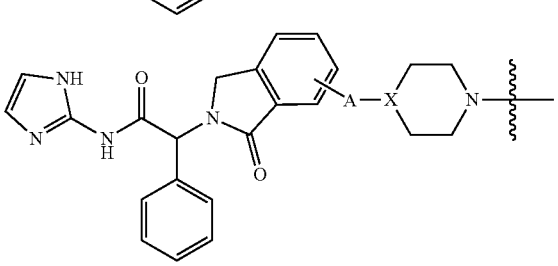
,
72
-continued
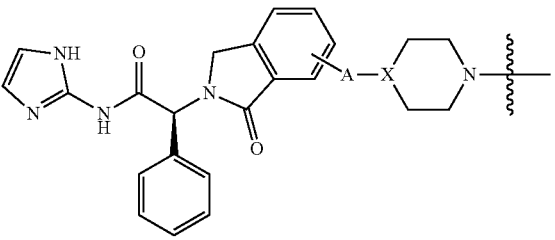
,
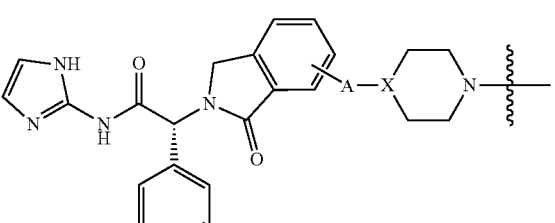
,
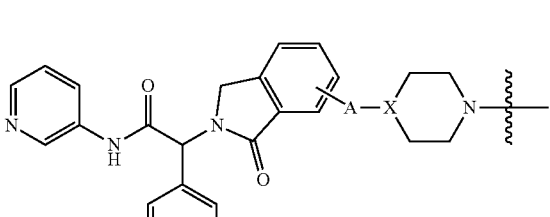
,
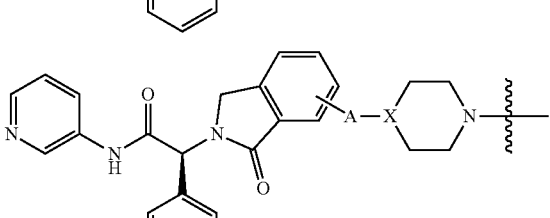
,
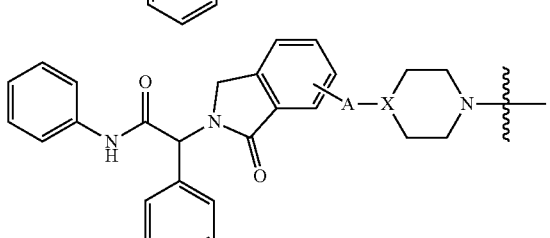
,
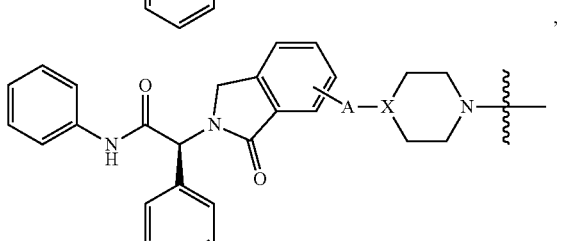
,

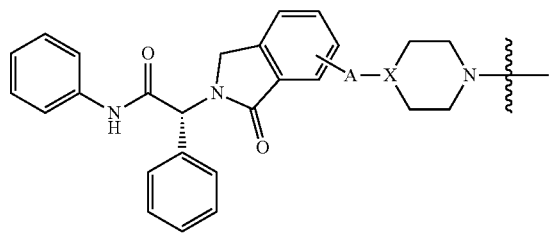
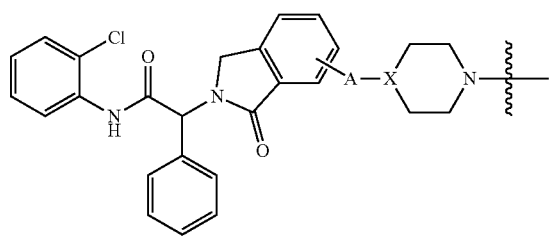
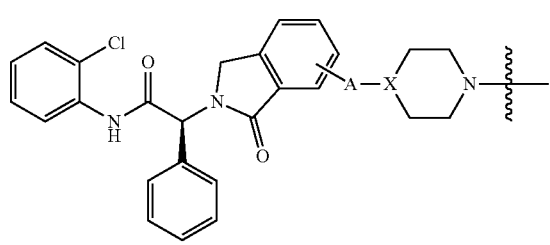
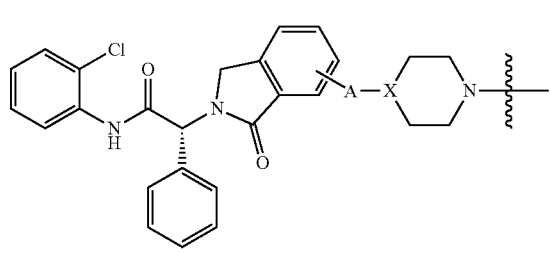
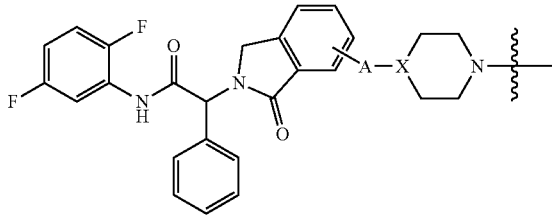
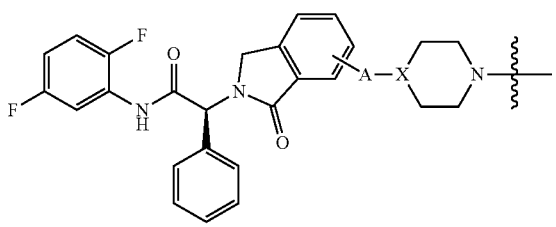
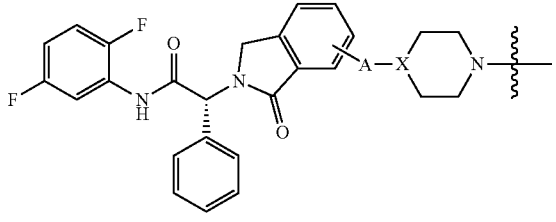
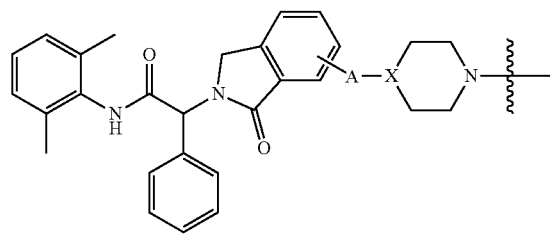
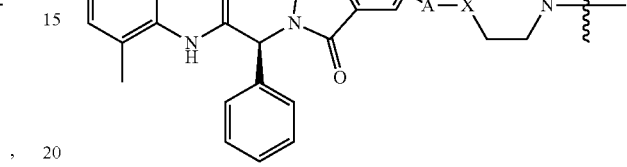
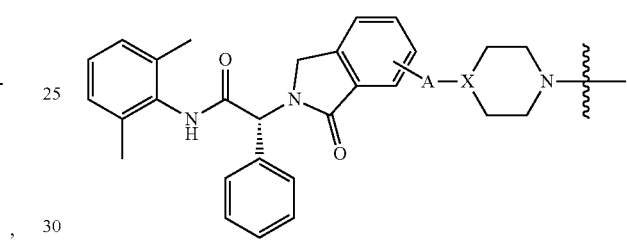
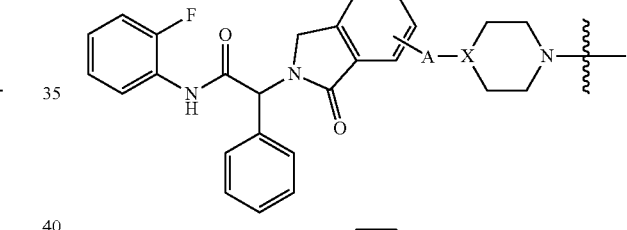
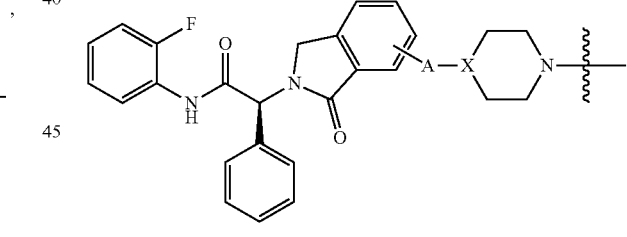
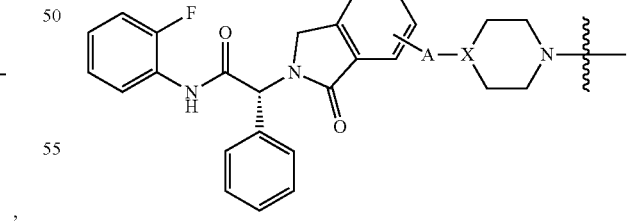
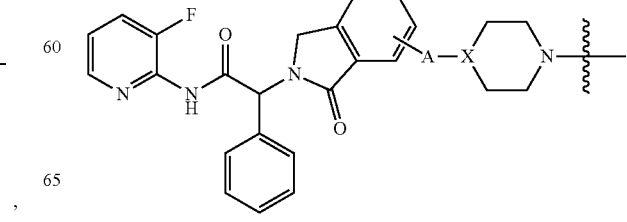

-continued
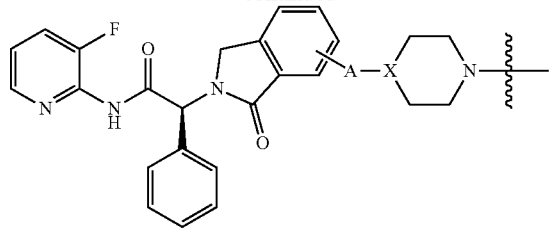
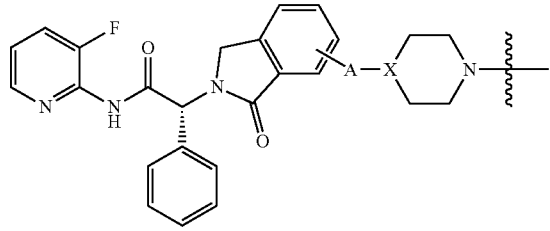
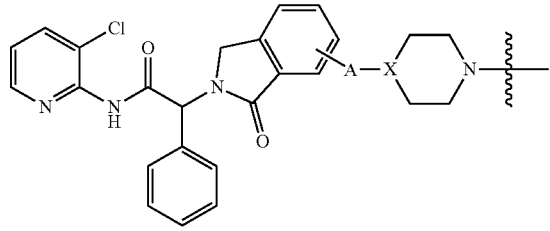
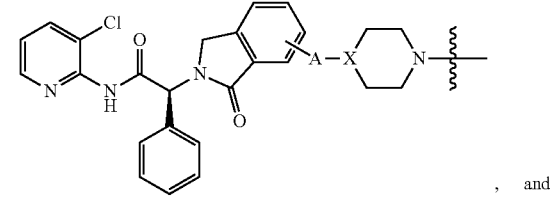
, and
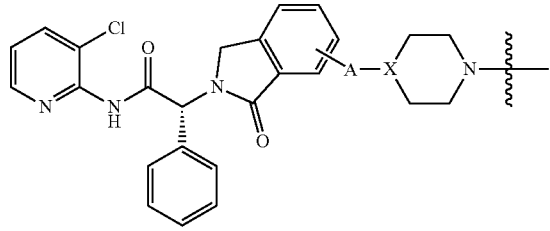
In one embodiment, the compound of Formula TL-I is a compound of a formula selected from the group consisting of:
-continued
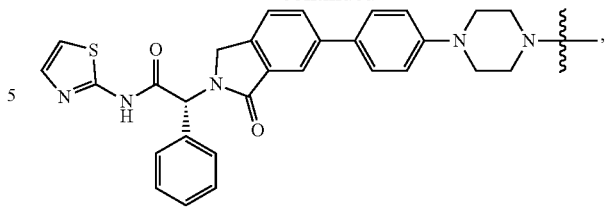
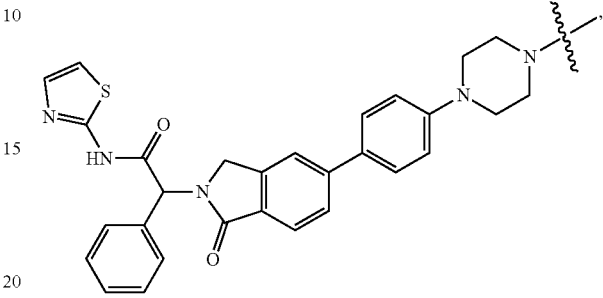
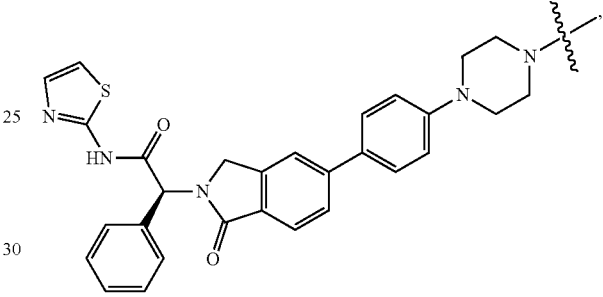
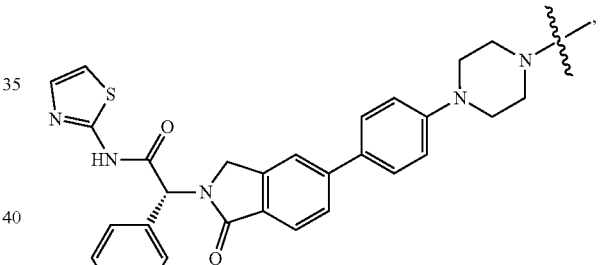
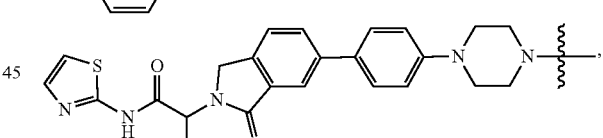
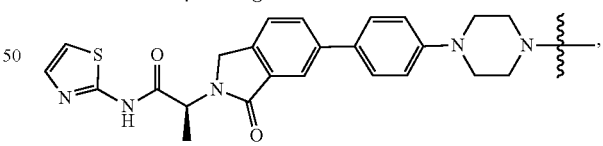
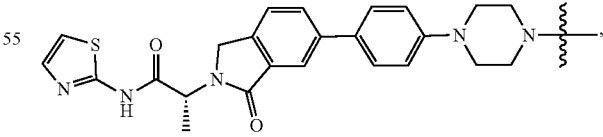
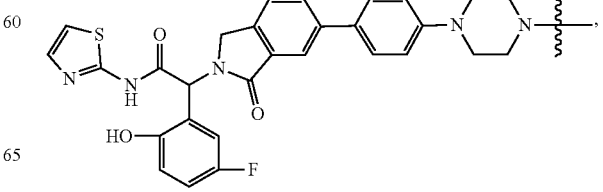

[Chemical structures shown at top of page, followed by "and"]

Targeting Ligand (TL) (or target protein moiety or target protein ligand or ligand) is a small molecule which is capable of binding to a target protein of interest, such as EGFR or a mutant thereof.

Degron

The Degron serves to link a targeted protein, through a Linker and a Targeting Ligand, to a ubiquitin ligase for proteosomal degradation. In one embodiment, the Degron is capable of binding to a ubiquitin ligase, such as an E3 ubiquitin ligase. In one embodiment, the Degron is capable of binding to cereblon.

In one embodiment, the Degron is of Formula D1:

(D1)

[Chemical structure of Formula D1]

or an enantiomer, diastereomer, or stereoisomer thereof, wherein:

Y is a bond, $(CH_2)_{1-6}$, $(CH_2)_{0-6}$—O, $(CH_2)_{0-6}$—C(O)NR$^{11}$, $(CH_2)_{0-6}$—NR$^{11}$C(O), $(CH_2)_{0-6}$—NH, or $(CH_2)_{0-6}$—NR$^{12}$;

$Z^1$ is C(O) or C(R$^{13}$)$_2$;

R$^{11}$ is H or $C_1$-$C_6$ alkyl;

R$^{12}$ is $C_1$-$C_6$ alkyl or C(O)—$C_1$-$C_6$ alkyl;

each R$^{13}$ is independently H or $C_1$-$C_3$ alkyl;

each R$^{14}$ is independently $C_1$-$C_3$ alkyl;

R$^{15}$ is H, deuterium, $C_1$-$C_3$ alkyl, F, or Cl;

each R$^{16}$ is independently halogen, OH, $C_1$-$C_6$ alkyl, or $C_1$-$C_6$ alkoxy;

q is 0, 1, or 2; and v is 0, 1, 2, or 3, wherein the Degron is covalently bonded to the Linker via

[bond symbol]

In one embodiment, $Z^1$ is C(O).

In one embodiment, $Z^1$ is C(R$^{13}$)$_2$; and each R$^{13}$ is H. In one embodiment, $Z^1$ is C(R$^{13}$)$_2$; and one of R$^{13}$ is H, and the other is $C_1$-$C_3$ alkyl selected from methyl, ethyl, and propyl. In one embodiment, $Z^1$ is C(R$^{13}$)$_2$; and each R$^{13}$ is independently selected from methyl, ethyl, and propyl.

In one embodiment, Y is a bond.

In one embodiment, Y is $(CH_2)_1$, $(CH_2)_2$, $(CH_2)_3$, $(CH_2)_4$, $(CH_2)_5$, or $(CH_2)_6$. In one embodiment, Y is $(CH_2)_1$, $(CH_2)_2$, or $(CH_2)_3$. In one embodiment, Y is $(CH_2)_1$ or $(CH_2)_2$.

In one embodiment, Y is O, CH$_2$—O, $(CH_2)_2$—O, $(CH_2)_3$—O, $(CH_2)_4$—O, $(CH_2)_5$-0, or $(CH_2)_6$—O. In one embodiment, Y is O, CH$_2$—O, $(CH_2)_{2-0}$, or $(CH_2)_{3-0}$. In one embodiment, Y is O or CH$_2$—O. In one embodiment, Y is O.

In one embodiment, Y is C(O)NR$^{11}$, CH$_2$—C(O)NR$^{11}$, $(CH_2)_2$—C(O)NR$^{11}$, $(CH_2)_3$—C(O)NR$^{11}$, $(CH_2)_4$—C(O)NR$^{11}$, $(CH_2)_5$—C(O)NR$^{11}$, or $(CH_2)_6$—C(O)NR$^{11}$. In one embodiment, Y is C(O)NR$^{11}$, CH$_2$—C(O)NR$^{11}$, $(CH_2)_2$—C(O)NR$^{11}$, or $(CH_2)_3$—C(O)NR$^{11}$. In one embodiment, Y is C(O)NR$^{11}$ or CH$_2$—C(O)NR$^{11}$. In one embodiment, Y is C(O)NR$^{11}$.

In one embodiment, Y is NR$^{11}$C(O), CH$_2$—NR$^{11}$C(O), $(CH_2)_2$—NR$^{11}$C(O), $(CH_2)_3$—NR$^{11}$C(O), $(CH_2)_4$—NR$^{11}$C(O), $(CH_2)_5$—NR$^{11}$C(O), or $(CH_2)_6$—NR$^{11}$C(O). In one embodiment, Y is NR$^{11}$C(O), CH$_2$—NR$^{11}$C(O), $(CH_2)_2$—NR$^{11}$C(O), or $(CH_2)_3$—NR$^{11}$C(O). In one embodiment, Y is NR$^{11}$C(O) or CH$_2$—NR$^{11}$C(O). In one embodiment, Y is NR$^{11}$C(O).

In one embodiment, R$^{11}$ is H. In one embodiment, R$^{11}$ is selected from methyl, ethyl, propyl, butyl, i-butyl, t-butyl, pentyl, i-pentyl, and hexyl. In one embodiment, R$^{11}$ is $C_1$-$C_3$ alkyl selected from methyl, ethyl, and propyl.

In one embodiment, Y is NH, CH$_2$—NH, $(CH_2)_2$—NH, $(CH_2)_3$—NH, $(CH_2)_4$—NH, $(CH_2)_5$—NH, or $(CH_2)_6$—NH. In one embodiment, Y is NH, CH$_2$—NH, $(CH_2)_2$—NH, or $(CH_2)_3$—NH. In one embodiment, Y is NH or CH$_2$—NH. In one embodiment, Y is NH.

In one embodiment, Y is NR$^{12}$, CH$_2$—NR$^{12}$, $(CH_2)_2$—NR$^{12}$, $(CH_2)_3$—NR$^{12}$, $(CH_2)_4$—NR$^{12}$, $(CH_2)_5$—NR$^{12}$, or $(CH_2)_6$—NR$^{12}$. In one embodiment, Y is NR$^{12}$, CH$_2$—NR$^{12}$, $(CH_2)_2$—NR$^{12}$, or $(CH_2)_3$—NR$^{12}$. In one embodiment, Y is NR$^{12}$ or CH$_2$—NR$^{12}$. In one embodiment, Y is NR$^{12}$.

In one embodiment, R$^{12}$ is selected from methyl, ethyl, propyl, butyl, i-butyl, t-butyl, pentyl, i-pentyl, and hexyl. In one embodiment, R$^{12}$ is $C_1$-$C_3$ alkyl selected from methyl, ethyl, and propyl.

In one embodiment, R$^{12}$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In one embodiment, R$^{12}$ is C(O)—$C_1$-$C_3$ alkyl selected from C(O)-methyl, C(O)-ethyl, and C(O)-propyl.

In one embodiment, R$^{13}$ is H.

In one embodiment, R$^{13}$ is $C_1$-$C_3$ alkyl selected from methyl, ethyl, and propyl. In one embodiment, R$^{13}$ is methyl.

In one embodiment, q is 0.

In one embodiment, q is 1.

In one embodiment, q is 2.

In one embodiment, each R$^{14}$ is independently $C_1$-$C_3$ alkyl selected from methyl, ethyl, and propyl.

In one embodiment, v is 0.

In one embodiment, v is 1.

In one embodiment, v is 2.

In one embodiment, v is 3.

In one embodiment, each R$^{16}$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_6$ alkoxy (e.g., methoxy, ethoxy, propoxy, butoxy, i-butoxy, t-butoxy, and pentoxy). In a further embodiment, each $R^{16}$ is independently selected from F, Cl, OH, methyl, ethyl, propyl, butyl, i-butyl, t-butyl, methoxy, and ethoxy.

In one embodiment, $R^{15}$ is H, deuterium, or $C_1$-$C_3$ alkyl. In another embodiment, $R^{15}$ is H or $C_1$-$C_3$ alkyl. In a further embodiment, $R^{15}$ is in the (S) or (R) configuration. In a further embodiment, $R^{15}$ is in the (S) configuration. In one embodiment, the compound comprises a racemic mixture of (S)—$R^{15}$ and (R)—$R^{15}$.

In one embodiment, $R^{15}$ is H.

In one embodiment, $R^{15}$ is deuterium.

In one embodiment, $R^{15}$ is $C_1$-$C_3$ alkyl selected from methyl, ethyl, and propyl. In one embodiment, $R^{15}$ is methyl.

In one embodiment, $R^{15}$ is F or Cl. In a further embodiment, $R^{15}$ is in the (S) or (R) configuration. In a further embodiment, $R^{15}$ is in the (R) configuration. In one embodiment, the compound comprises a racemic mixture of (S)—$R^{15}$ and (R)—$R^{15}$. In one embodiment, $R^{15}$ is F.

Any of the groups described herein for any of Y, $Z^1$, $R^{11}$, $R^{12}$, $R^{13}$, $R^{14}$, $R^{15}$, $R^{16}$, q, and v can be combined with any of the groups described herein for one or more of the remainder of Y, $Z^1$, $R^{11}$, $R^{12}$, $R^{13}$, $R^{14}$, $R^{15}$, $R^{16}$, q, and v, and may further be combined with any of the groups described herein for the Linker.

For a Degron of Formula D1:
(1) In one embodiment, $Z^1$ is C(O) and Y is a bond.
(2) In one embodiment, $Z^1$ is C(O) and Y is $(CH_2)_{0-6}$—O. In a further embodiment, Y is O.
(3) In one embodiment, $Z^1$ is C(O); Y is a bond; and q and v are each 0.
(4) In one embodiment, $Z^1$ is C(O); Y is a bond; and $R^{13}$ is H.
(5) In one embodiment, $Z^1$ is C(O); Y is a bond; and $R^{15}$ is H.
(6) In one embodiment, $Z^1$ is C(O); Y is a bond; and $R^{13}$ is H; and $R^{15}$ is H.
(7) In one embodiment, $Z^1$ is C(O); Y is $(CH_2)_{0-6}$—O; and $R^{13}$ is H. In a further embodiment, Y is O.
(8) In one embodiment, $Z^1$ is C(O); Y is $(CH_2)_{0-6}$—O; and $R^{15}$ is H. In a further embodiment, Y is O.
(9) In one embodiment, $Z^1$ is C(O); Y is $(CH_2)_{0-6}$—O; $R^{13}$ is H; and $R^{15}$ is H. In a further embodiment, Y is O.
(10) In one embodiment, $Z_1$ is C(O); Y is $(CH_2)_{0-6}$—NH; and $R^{13}$ is H. In a further embodiment, Y is NH.
(11) In one embodiment, $Z_1$ is C(O); Y is $(CH_2)_{0-6}$—NH; and $R^{15}$ is H. In a further embodiment, Y is NH.
(12) In one embodiment, $Z_1$ is C(O); Y is $(CH_2)_{0-6}$—NH; $R^{13}$ is H; and $R^{15}$ is H. In a further embodiment, Y is NH.
(13) In one embodiment, q and v are each 0; and Y, $Z^1$, $R^{13}$, and $R^{15}$ are each as defined in any of (1)-(12).

In one embodiment, the Degron is of Formula D1a-D1d:

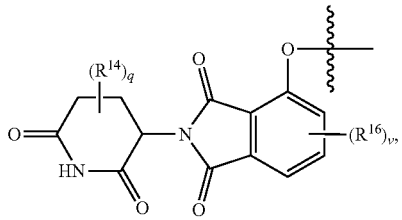
(D1a)

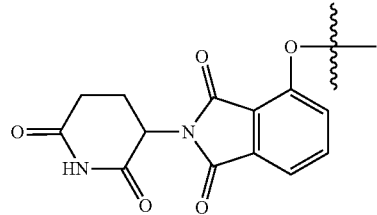
(D1b)

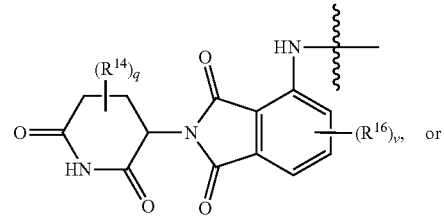
(D1c)

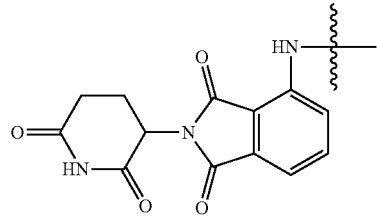
(D1d)

or an enantiomer, diastereomer, or stereoisomer thereof, wherein $R^{14}$, $R^{16}$, q, and v are each as defined above in Formula D1, and can be selected from any moieties or combinations thereof described above.

In one embodiment, the Degron is of Formula D2:

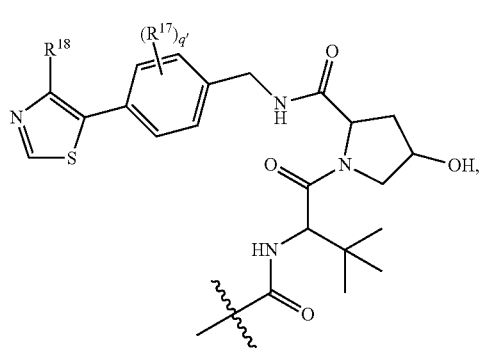
(D2)

or an enantiomer, diastereomer, or stereoisomer thereof, wherein:
each $R^{17}$ is independently $C_1$-$C_3$ alkyl;
q' is 0, 1, 2, 3 or 4; and
$R^{18}$ is H or $C_1$-$C_3$ alkyl,
wherein the Degron is covalently bonded to another moiety via

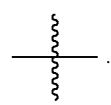

In one embodiment, the Degron is covalently bonded to a Linker via

In one embodiment, the Degron is covalently bonded to a compound via

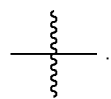

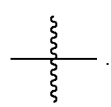

In one embodiment, q' is 0.
In one embodiment, q' is 1.
In one embodiment, q' is 2.
In one embodiment, q' is 3.
In one embodiment, each $R^{17}$ is independently $C_1$-$C_3$ alkyl selected from methyl, ethyl, and propyl.
In one embodiment, $R^{18}$ is methyl, ethyl, or propyl. In one embodiment, $R^{18}$ is methyl.
In one embodiment, the Degron is of Formula D2a or D2b:

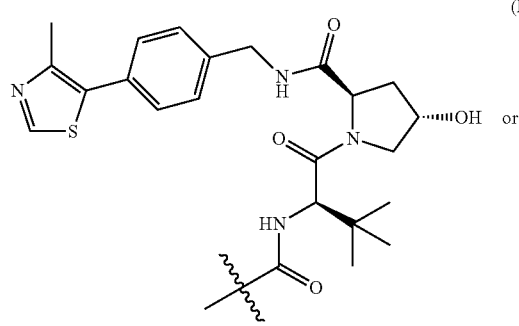

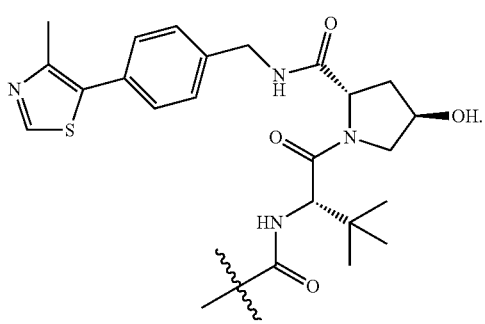

In an alternative embodiment, the Degron is of Formula D3:

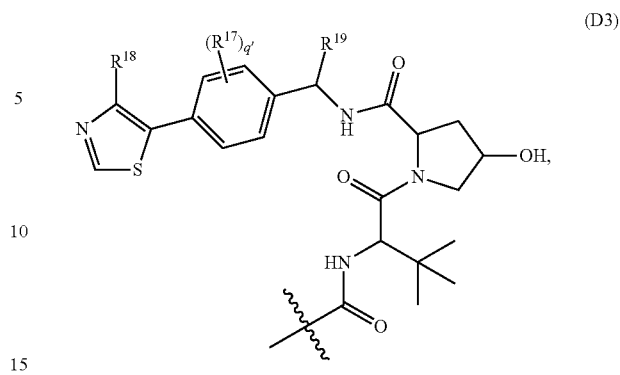

or an enantiomer, diastereomer, or stereoisomer thereof, wherein:
each $R^{17}$ is independently $C_1$-$C_3$ alkyl;
q' is 0, 1, 2, 3 or 4;
$R^{18}$ is H or $C_1$-$C_3$ alkyl; and
$R^{19}$ is $C_1$-$C_3$ alkyl,
wherein the Degron is covalently bonded to another moiety via

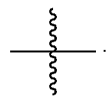

In one embodiment, the Degron is covalently bonded to a Linker via

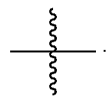

In one embodiment, the Degron is covalently bonded to a compound via

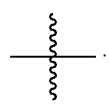

In one embodiment, q' is 0.
In one embodiment, q' is 1.
In one embodiment, q' is 2.
In one embodiment, q' is 3.
In one embodiment, each $R^{17}$ is independently $C_1$-$C_3$ alkyl selected from methyl, ethyl, and propyl.
In one embodiment, $R^{18}$ is methyl, ethyl, or propyl. In one embodiment, $R^{18}$ is methyl.
In one embodiment, $R^{19}$ is methyl, ethyl, or propyl. In one embodiment, $R^{19}$ is methyl.
In one embodiment, the Degron is of Formula D3a or D3b:

(D3a)

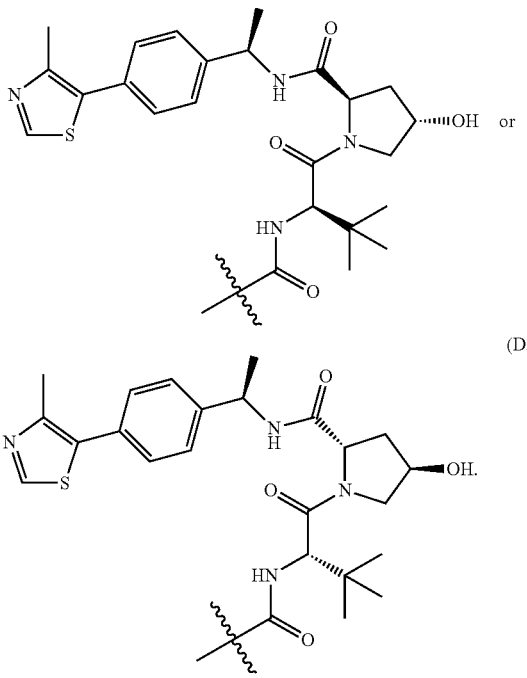

or (D3b)

Linker

The Linker is a bond or a carbon chain that serves to link a Targeting Ligand with a Degron. In one embodiment, the carbon chain optionally comprises one, two, three, or more heteroatoms selected from N, O, and S. In one embodiment, the carbon chain comprises only saturated chain carbon atoms. In one embodiment, the carbon chain optionally comprises two or more unsaturated chain carbon atoms (e.g., C=C or C≡C). In one embodiment, one or more chain carbon atoms in the carbon chain are optionally substituted with one or more substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, CN, $C_3$-$C_8$ cycloalkyl, heterocyclyl, phenyl, and heteroaryl).

In one embodiment, the Linker comprises at least 5 chain atoms (e.g., C, O, N, and S). In one embodiment, the Linker comprises less than 25 chain atoms (e.g., C, O, N, and S). In one embodiment, the Linker comprises less than 20 chain atoms (e.g., C, O, N, and S). In one embodiment, the Linker comprises 5, 6, 7, 8, 9, 10, 11, 12, 13, 14, 15, 16, 17, 18, 19, or 20, chain atoms (e.g., C, O, N, and S). In one embodiment, the Linker comprises 5, 7, 9, 11, 13, 15, 17, or 19 chain atoms (e.g., C, O, N, and S). In one embodiment, the Linker comprises 5, 7, 9, or 11 chain atoms (e.g., C, O, N, and S). In one embodiment, the Linker comprises 11, 13, 15, 17, or 19 chain atoms (e.g., C, O, N, and S). In one embodiment, the Linker comprises 6, 8, 10, 12, 14, 16, 18, or 20 chain atoms (e.g., C, O, N, and S). In one embodiment, the Linker comprises 6, 8, 10, or 12 chain atoms (e.g., C, O, N, and S). In one embodiment, the Linker comprises 12, 14, 16, 18, or 20 chain atoms (e.g., C, O, N, and S).

In one embodiment, the Linker comprises from 9 to 19 chain atoms (e.g., C, O, N, and S).

In one embodiment, the Linker is a carbon chain optionally substituted with non-bulky substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, and CN). In one embodiment, the non-bulky substitution is located on the chain carbon atom proximal to the Degron (i.e., the carbon atom is separated from the carbon atom to which the Degron is bonded by at least 3, 4, or 5 chain atoms in the Linker). In one embodiment, the non-bulky substitution is located on the chain carbon atom proximal to the Targeting Ligand (i.e., the carbon atom is separated from the carbon atom to which the Degron is bonded by at least 3, 4, or 5 chain atoms in the Linker).

In one embodiment, the Linker is of Formula L0:

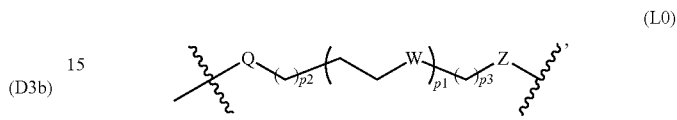

(L0)

or an enantiomer, diastereomer, or stereoisomer thereof, wherein
p1 is an integer selected from 0 to 12;
p2 is an integer selected from 0 to 12;
p3 is an integer selected from 0 to 6;
each W is independently absent, $CH_2$, O, S, NH, or $NR^{10}$;
Z is absent, $CH_2$, O, NH, $NR^{10}$, $C(O)(CH_2)_{0-3}$, or $NHC(O)(CH_2)_{0-3}$;
each $R^{10}$ is independently H or $C_1$-$C_3$ alkyl; and
Q is absent or $CH_2C(O)NH$,
wherein the Linker is covalently bonded to the Degron via the

next to Q, and covalently bonded to the Targeting Ligand via the

next to Z.

In an alternative embodiment, the Linker is of Formula L0':

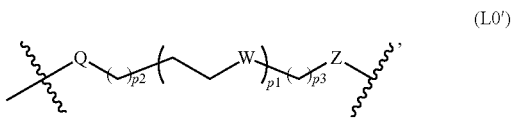

(L0')

or an enantiomer, diastereomer, or stereoisomer thereof, wherein
p1 is an integer selected from 0 to 12;
p2 is an integer selected from 0 to 12;
p3 is an integer selected from 0 to 6;
each W is independently absent, $CH_2$, O, S, NH, or $NR^{10}$;
Z is absent, $CH_2$, O, NH, $NR^{10}$, $C(O)(CH_2)_{0-3}$, or $NHC(O)(CH_2)_{0-3}$;
each $R^{10}$ is independently H or $C_1$-$C_3$ alkyl; and
Q is a heterocycle, wherein the Linker is covalently bonded to the Degron via the

next to Q, and covalently bonded to the Targeting Ligand via the

next to Z.

In one embodiment, the total number of chain atoms in the Linker is less than 30. In a further embodiment, the total number of chain atoms in the Linker is less than 20.

For a Linker of Formula L0:
In one embodiment, p1 is an integer selected from 0 to 10.
In one embodiment, p1 is an integer selected from 1 to 10.
In one embodiment, p1 is selected from 1, 2, 3, 4, 5, and 6.
In one embodiment, p1 is 0, 1, 3, or 5.
In one embodiment, p1 is 0, 1, 2, or 3.
In one embodiment, p1 is 1.
In one embodiment, p1 is 3.
In one embodiment, p1 is 5.
In one embodiment, p2 is an integer selected from 0 to 10.
In one embodiment, p2 is selected from 0, 1, 2, 3, 4, 5, and 6.
In one embodiment, p2 is 0, 1, 2, or 3.
In one embodiment, p2 is 0.
In one embodiment, p2 is 1.
In one embodiment, p3 is an integer selected from 0 to 5.
In one embodiment, p3 is 1, 2, 3, 4, or 5.
In one embodiment, p3 is 1, 2, or 3.
In one embodiment, p3 is 0.
In one embodiment, p3 is 2 or 3.
In one embodiment, p3 is 2.
In one embodiment, at least one W is $CH_2$.
In one embodiment, at least one W is O.
In one embodiment, at least one W is S.
In one embodiment, at least one W is NH.
In one embodiment, at least one W is $NR^{10}$; and $R^{10}$ is $C_1$-$C_3$ alkyl selected from methyl, ethyl, and propyl.
In one embodiment, each W is O.
In one embodiment, Q is absent.
In one embodiment, Q is $CH_2C(O)NH$.
In one embodiment, Z is $C(O)$, $C(O)(CH_2)$, $C(O)(CH_2)_2$, or $C(O)(CH_2)_3$. In one embodiment, Z is $C(O)$.
In one embodiment, Z is $NHC(O)$, $NHC(O)(CH_2)$, $NHC(O)(CH_2)_2$, or $NHC(O)(CH_2)_3$. In one embodiment, Z is $NHC(O)(CH_2)$.
In one embodiment, Z is absent.
In one embodiment, Z is $CH_2$.
In one embodiment, Z is O.
In one embodiment, Z is NH.
In one embodiment, Z is $NR^{10}$; and $R^0$ is $C_1$-$C_3$ alkyl selected from methyl, ethyl, and propyl.
In one embodiment, Z is part of the Targeting Ligand that is bonded to the Linker, namely, Z is formed from reacting a functional group of the Targeting Ligand with the Linker.

In one embodiment, the Linker-Targeting Ligand (TL) has the structure selected from Table L1:

TABLE L1

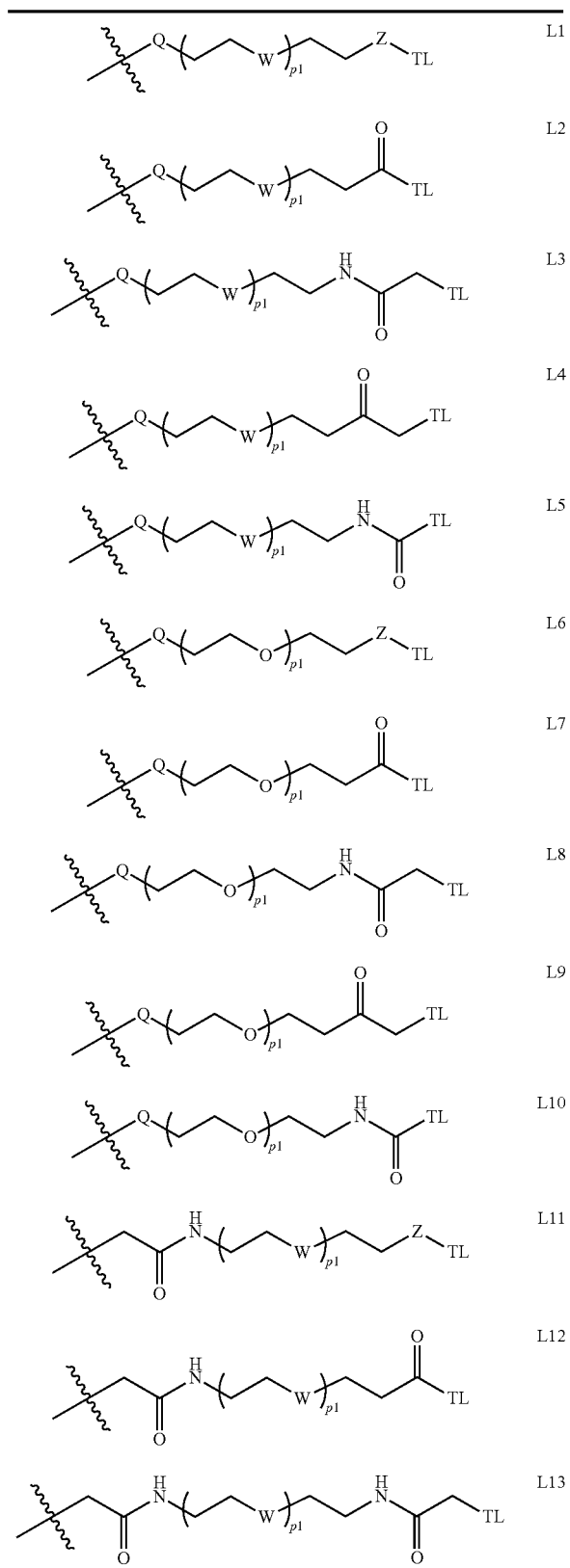

TABLE L1-continued
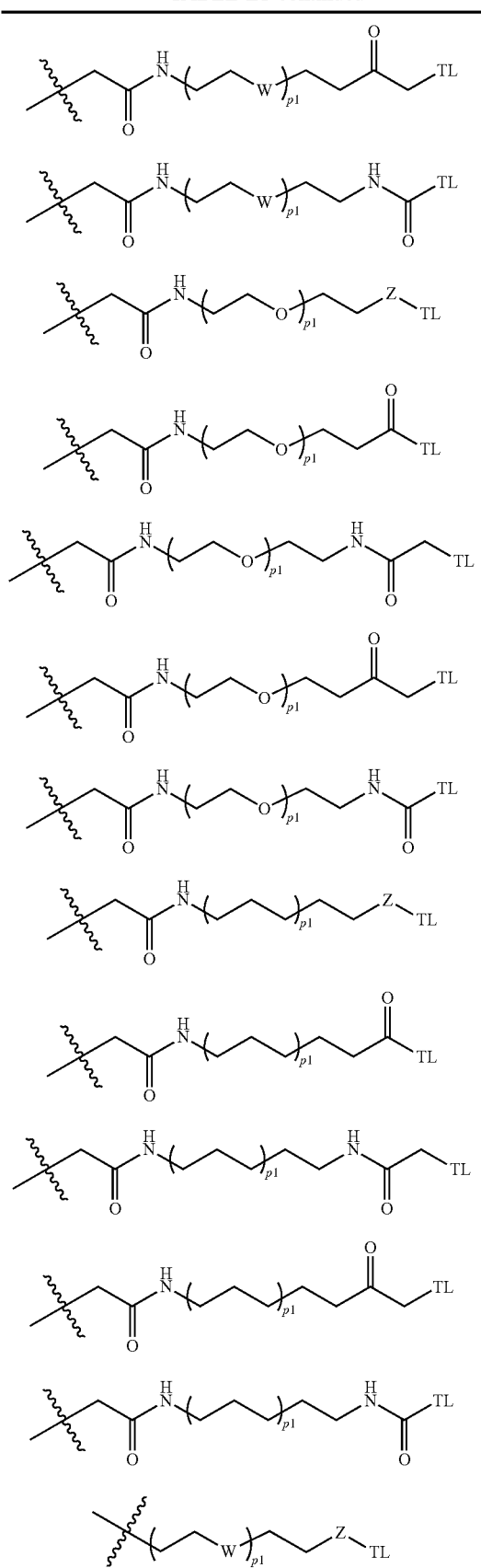
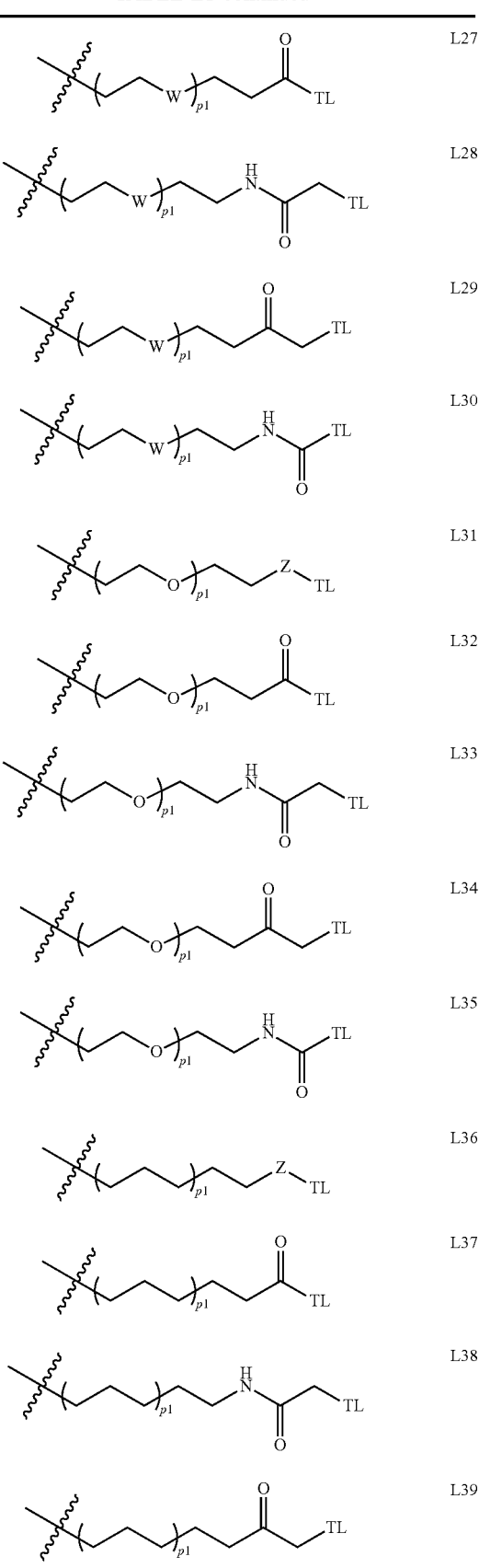

TABLE L1-continued

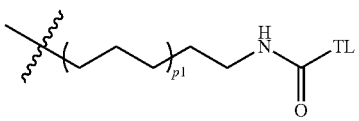
L40 wherein Q, Z, and p1 are each as described above, and TL is a Targeting Ligand.

In one embodiment, p1 is 0, 1, 2, 3, 4, or 5. In one embodiment, p1 is 0. In one embodiment, p1 is 1, 3, or 5. In one embodiment, p1 is 1. In one embodiment, p1 is 3. In one embodiment, p1 is 5.

In one embodiment, Q is $CH_2C(O)NH$.
In one embodiment, Q is absent.
In one embodiment, Z is $C(O)(CH_2)_{0-3}$. In one embodiment, Z is $C(O)$. In one embodiment, Z is $NHC(O)(CH_2)_{0-3}$. In one embodiment, Z is $NHC(O)(CH_2)$.
In one embodiment, Q is $CH_2C(O)NH$, and Z is $NHC(O)(CH_2)$.
In one embodiment, Q is $CH_2C(O)NH$, and Z is $C(O)$.
In one embodiment, Q is absent, and Z is $NHC(O)(CH_2)$.
In one embodiment, Q is absent, and Z is $C(O)$.
For a Linker of Formula L0':
In one embodiment, p1 is an integer selected from 0 to 10.
In one embodiment, p1 is an integer selected from 1 to 10.
In one embodiment, p1 is selected from 1, 2, 3, 4, 5, and 6.
In one embodiment, p1 is 0, 1, 3, or 5.
In one embodiment, p1 is 0, 1, 2, or 3.
In one embodiment, p1 is 1.
In one embodiment, p1 is 3.
In one embodiment, p1 is 5.
In one embodiment, p2 is an integer selected from 0 to 10.
In one embodiment, p2 is selected from 0, 1, 2, 3, 4, 5, and 6.
In one embodiment, p2 is 0, 1, 2, or 3.
In one embodiment, p2 is 0.
In one embodiment, p2 is 1.
In one embodiment, p3 is an integer selected from 0 to 5.
In one embodiment, p3 is 1, 2, 3, 4, or 5.
In one embodiment, p3 is 1, 2, or 3.
In one embodiment, p3 is 0.
In one embodiment, p3 is 2 or 3.
In one embodiment, p3 is 2.
In one embodiment, at least one W is $CH_2$.
In one embodiment, at least one W is O.
In one embodiment, at least one W is S.
In one embodiment, at least one W is NH.
In one embodiment, at least one W is $NR^{10}$; and $R^{10}$ is $C_1$-$C_3$ alkyl selected from methyl, ethyl, and propyl.
In one embodiment, each W is O.
In one embodiment, Q is a heterocycle.
In one embodiment, Q is azetidine.
In one embodiment, Z is $C(O)$, $C(O)(CH_2)$, $C(O)(CH_2)_2$, or $C(O)(CH_2)_3$. In one embodiment, Z is $C(O)$.
In one embodiment, Z is $NHC(O)$, $NHC(O)(CH_2)$, $NHC(O)(CH_2)_2$, or $NHC(O)(CH_2)_3$. In one embodiment, Z is $NHC(O)(CH_2)$.
In one embodiment, Z is absent.
In one embodiment, Z is $CH_2$.
In one embodiment, Z is O.
In one embodiment, Z is NH.
In one embodiment, Z is $NR^{10}$; and $R^{10}$ is $C_1$-$C_3$ alkyl selected from methyl, ethyl, and propyl.

In one embodiment, Z is part of the Targeting Ligand that is bonded to the Linker, namely, Z is formed from reacting a functional group of the Targeting Ligand with the Linker.

In an alternative embodiment, the Linker-Targeting Ligand (TL) has the structure selected from Table L2:

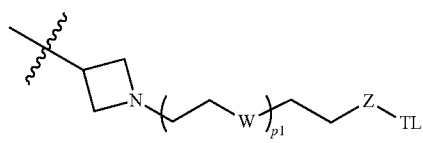
L41

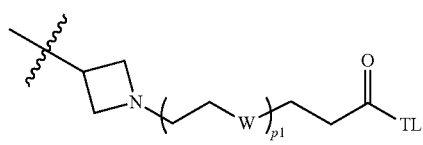
L42

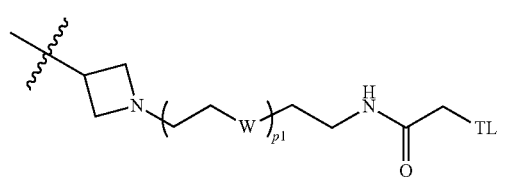
L43

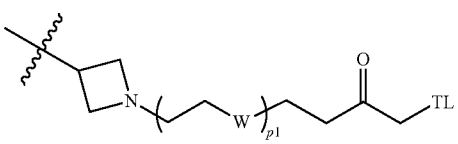
L44

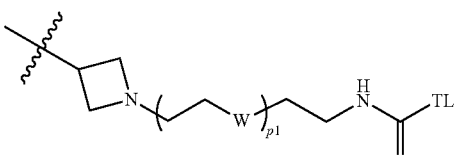
L45

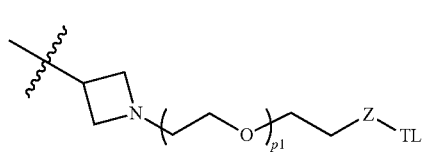
L46

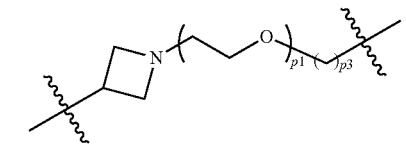
L47

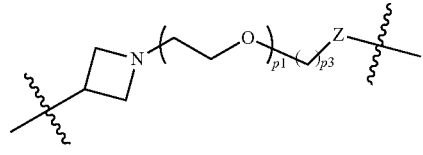
L48

In one embodiment, p1 is 0, 1, 2, 3, 4, or 5. In one embodiment, p1 is 0. In one embodiment, p1 is 1, 3, or 5. In one embodiment, p1 is 1. In one embodiment, p1 is 3. In one embodiment, p1 is 5.

In one embodiment, Q is a heterocycle.
In one embodiment, Q is azetidine.
In one embodiment, Z is $C(O)(CH_2)_{0-3}$. In one embodiment, Z is $C(O)$. In one embodiment, Z is $NHC(O)(CH_2)_{0-3}$.
In one embodiment, Z is $NHC(O)(CH_2)$.

In one embodiment, Q is a heterocycle, and Z is NHC(O)(CH$_2$).

In one embodiment, Q is a heterocycle, and Z is C(O).

In one embodiment, Q is an azetidine, and Z is NHC(O)(CH$_2$).

In one embodiment, Q is an azetidine, and Z is C(O).

In one embodiment, the Linker-Targeting Ligand has the structure selected from L2, L3, L7, L8, L12, L13, L17, L18, L22, L23, L27, L28, L32, L33, L37, L38, and L47. In one embodiment, the Linker-Targeting Ligand has the structure selected from L18, L23, L32, and L47.

Any one of the Degrons described herein can be covalently bound to any one of the Linkers described herein. Any one of the Targeting Ligands described herein can be covalently bound to any one of the Linkers described herein.

In one embodiment, the present application includes the Degron-Linker (DL), wherein the Degron is of Formula D1, and the Linker is selected from L1-L48. In one embodiment, the present application includes the Degron-Linker (DL), wherein the Degron is one of Formula D1a-D1d, and the Linker is selected from L1-L48. In one embodiment, the Degron is one of Formula D1a-D1d, and the Linker is selected from L18, L23, L32, and L47. In one embodiment, the Degron is of Formula D1a or D1b, and the Linker is L18 or L23. In one embodiment, the Degron is of Formula D1c or D1d, and the Linker is L32.

In one embodiment, the Linker is designed and optimized based on SAR (structure-activity relationship) and X-ray crystallography of the Targeting Ligand with regard to the location of attachment for the Linker.

In one embodiment, the optimal Linker length and composition vary by the Targeting Ligand and can be estimated based upon X-ray structure of the Targeting Ligand bound to its target. Linker length and composition can be also modified to modulate metabolic stability and pharmacokinetic (PK) and pharmacodynamics (PD) parameters.

Some embodiments of present application relate to the bifunctional compounds having the following structures in Table A1 and Table A2:

TABLE A1

| Cmpd No. | Structure |
|---|---|
| I-1 | 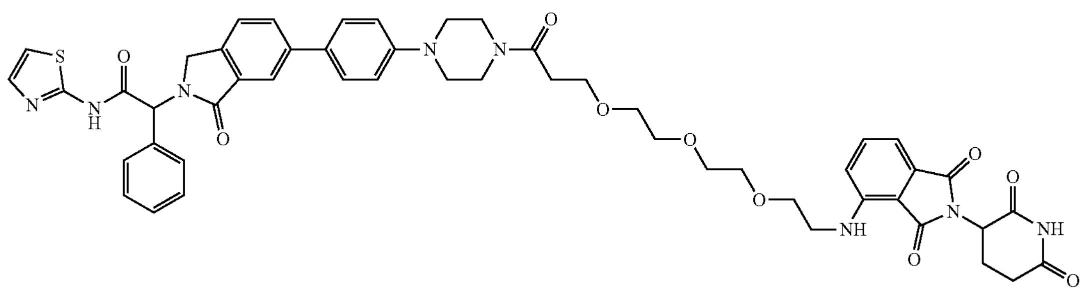 [SMILES: O=C1CCC(N2C(=O)c3cccc(NCCOCCOCCOCCC(=O)N4CCN(c5ccc(-c6ccc7c(c6)C(=O)N(C(C(=O)Nc6nccs6)c6ccccc6)C7)cc5)CC4)c3C2=O)C(=O)N1] |
| I-2 | 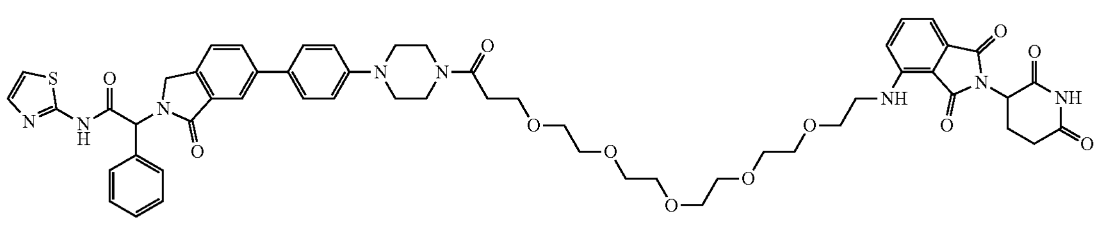 [SMILES: O=C1CCC(N2C(=O)c3cccc(NCCOCCOCCOCCOCCOCCC(=O)N4CCN(c5ccc(-c6ccc7c(c6)C(=O)N(C(C(=O)Nc6nccs6)c6ccccc6)C7)cc5)CC4)c3C2=O)C(=O)N1] |
| I-3 | 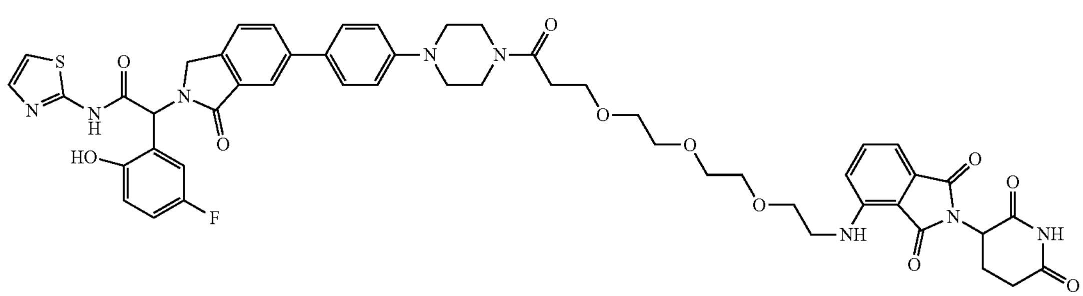 [SMILES: O=C1CCC(N2C(=O)c3cccc(NCCOCCOCCOCCC(=O)N4CCN(c5ccc(-c6ccc7c(c6)C(=O)N(C(C(=O)Nc6nccs6)c6cc(F)ccc6O)C7)cc5)CC4)c3C2=O)C(=O)N1] |

TABLE A1-continued

| Cmpd No. | Structure |
|---|---|
| I-4 | 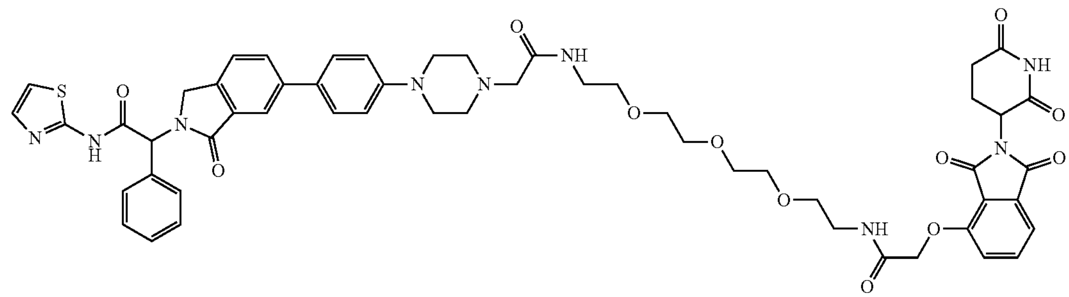 [SMILES: O=C(COc1cccc2c1C(=O)N(C1CCC(=O)NC1=O)C2=O)NCCOCCOCCOCCNC(=O)CN1CCN(c2ccc(-c3ccc4c(c3)C(=O)N(C(C(=O)Nc3nccs3)c3ccccc3)C4)cc2)CC1] |
| I-5 | 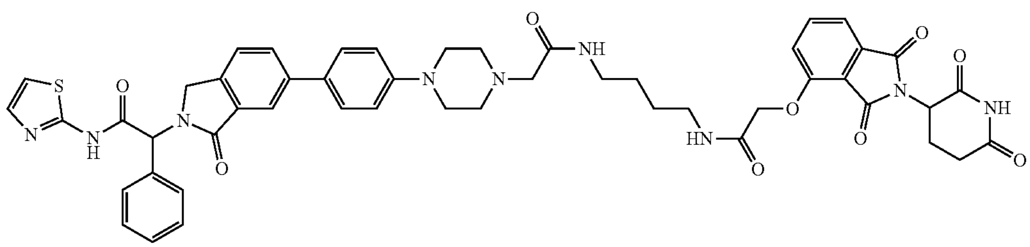 [SMILES: O=C(COc1cccc2c1C(=O)N(C1CCC(=O)NC1=O)C2=O)NCCCCNC(=O)CN1CCN(c2ccc(-c3ccc4c(c3)C(=O)N(C(C(=O)Nc3nccs3)c3ccccc3)C4)cc2)CC1] |
| I-6 | 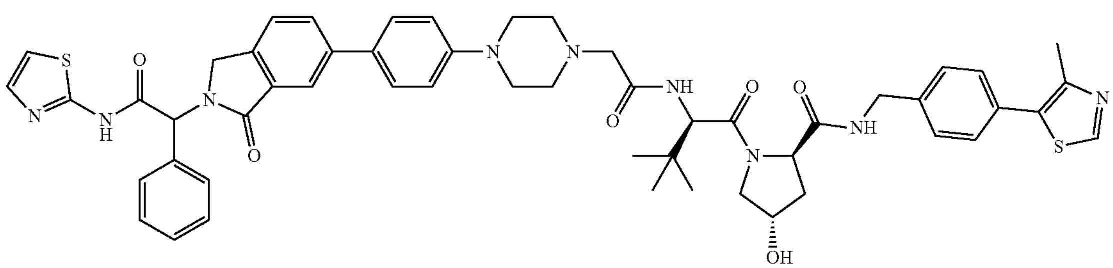 [SMILES: Cc1ncsc1-c1ccc(CNC(=O)[C@H]2C[C@H](O)CN2C(=O)[C@H](NC(=O)CN2CCN(c3ccc(-c4ccc5c(c4)C(=O)N(C(C(=O)Nc4nccs4)c4ccccc4)C5)cc3)CC2)C(C)(C)C)cc1] |

TABLE A2

| Cmpd No. | Structure |
|---|---|
| I-7 | 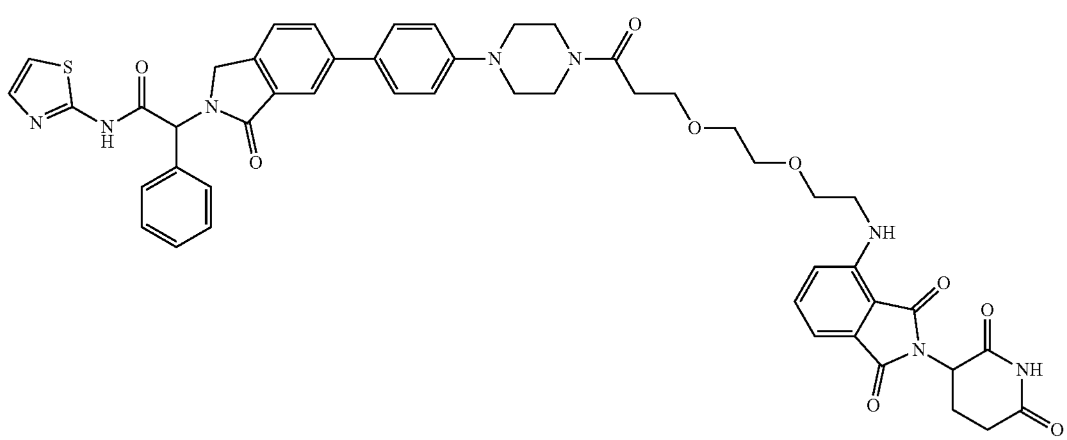 [SMILES: O=C1CCC(N2C(=O)c3cccc(NCCOCCOCCC(=O)N4CCN(c5ccc(-c6ccc7c(c6)C(=O)N(C(C(=O)Nc6nccs6)c6ccccc6)C7)cc5)CC4)c3C2=O)C(=O)N1] |

TABLE A2-continued

| Cmpd No. | Structure |
|---|---|
| I-8 | (structure) |
| I-9 | (structure) |
| I-10 | (structure) |

TABLE A2-continued

| Cmpd No. | Structure |
|---|---|
| I-11 | 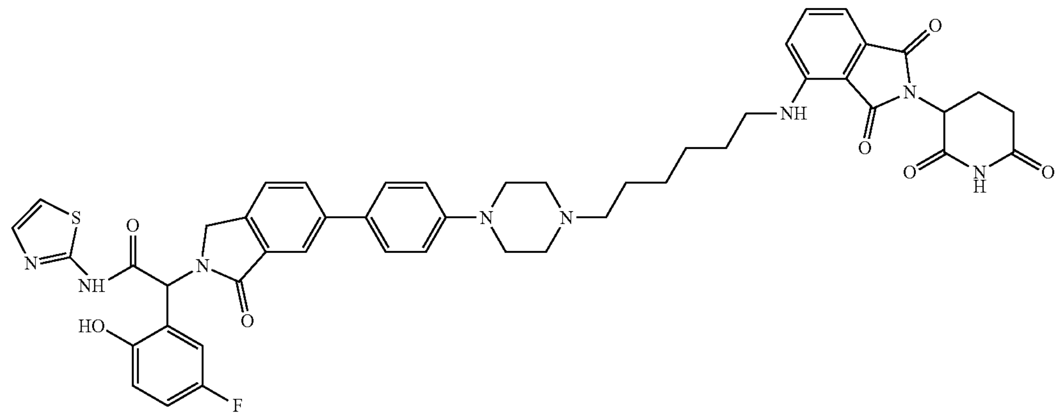 [SMILES: O=C1CCC(N2C(=O)c3cccc(NCCCCCCN4CCN(c5ccc(-c6ccc7c(c6)C(=O)N(C(C(=O)Nc6nccs6)c6cc(F)ccc6O)C7)cc5)CC4)c3C2=O)C(=O)N1] |
| I-12 | 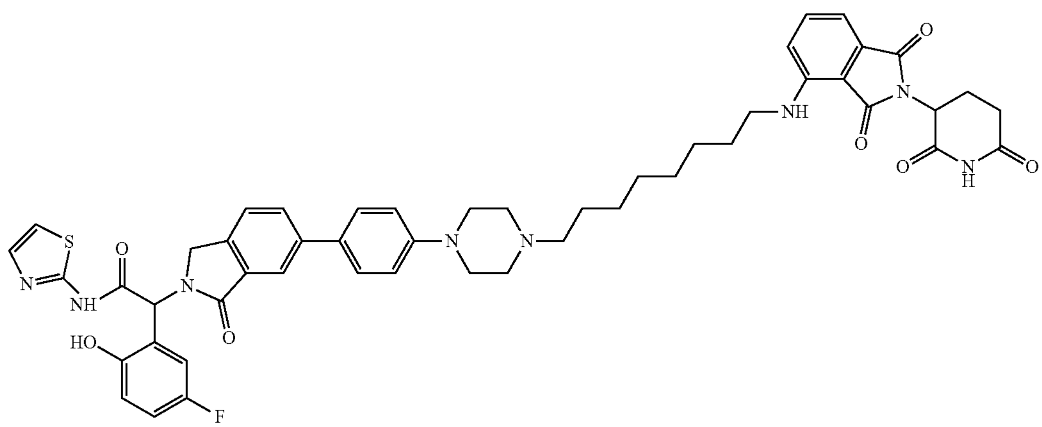 [SMILES: O=C1CCC(N2C(=O)c3cccc(NCCCCCCCCN4CCN(c5ccc(-c6ccc7c(c6)C(=O)N(C(C(=O)Nc6nccs6)c6cc(F)ccc6O)C7)cc5)CC4)c3C2=O)C(=O)N1] |
| I-13 | 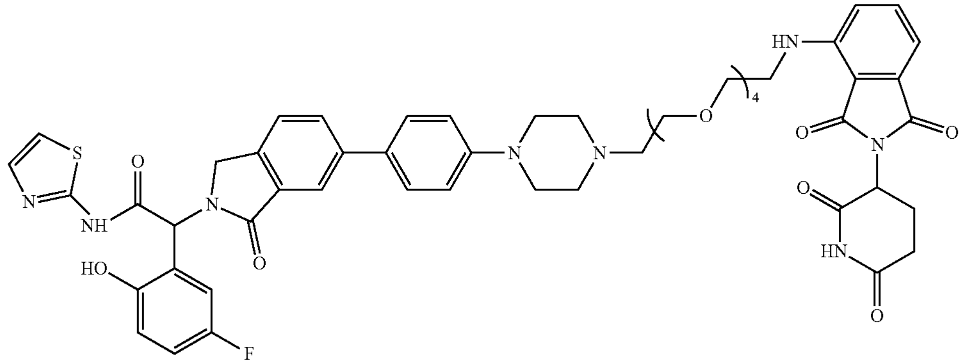 |

TABLE A2-continued
| Cmpd No. | Structure |
|---|---|
| I-14 | 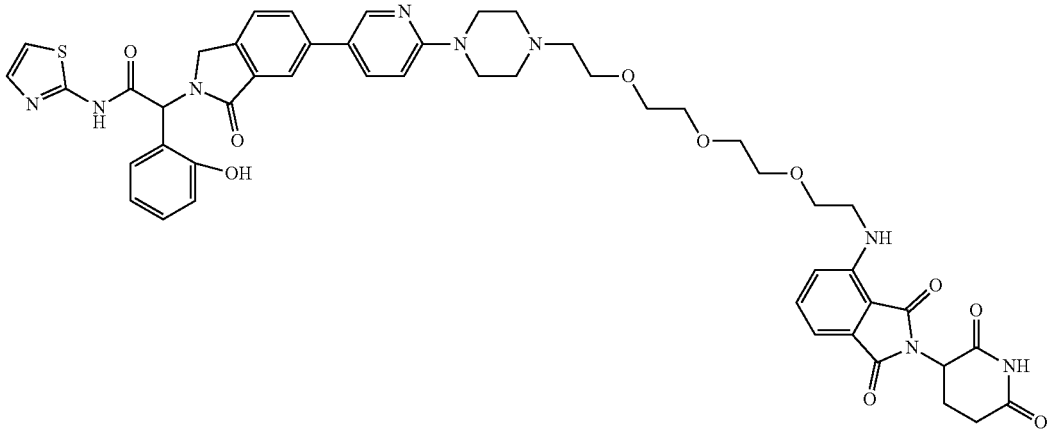 [SMILES: O=C1CCC(N2C(=O)c3cccc(NCCOCCOCCOCCN4CCN(c5ccc(-c6ccc7c(c6)C(=O)N(C(C(=O)Nc6nccs6)c6ccccc6O)C7)cn5)CC4)c3C2=O)C(=O)N1] |
| I-15 | 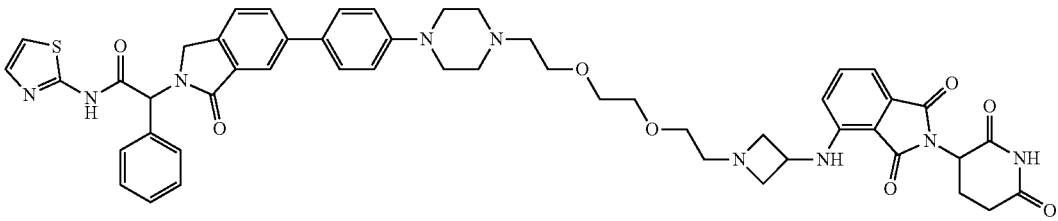 [SMILES: O=C1CCC(N2C(=O)c3cccc(NC4CN(CCOCCOCCN5CCN(c6ccc(-c7ccc8c(c7)C(=O)N(C(C(=O)Nc7nccs7)c7ccccc7)C8)cc6)CC5)C4)c3C2=O)C(=O)N1] |
| I-16 | 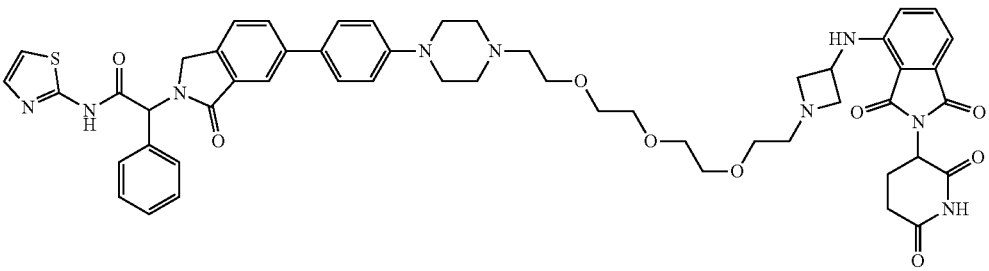 [SMILES: O=C1CCC(N2C(=O)c3cccc(NC4CN(CCOCCOCCOCCN5CCN(c6ccc(-c7ccc8c(c7)C(=O)N(C(C(=O)Nc7nccs7)c7ccccc7)C8)cc6)CC5)C4)c3C2=O)C(=O)N1] |
| I-17 | 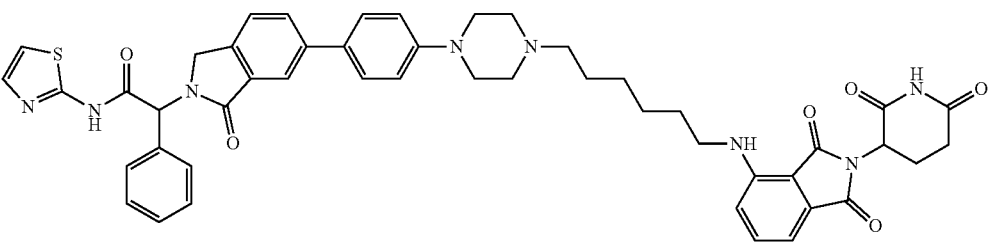 [SMILES: O=C1CCC(N2C(=O)c3cccc(NCCCCCCN4CCN(c5ccc(-c6ccc7c(c6)C(=O)N(C(C(=O)Nc6nccs6)c6ccccc6)C7)cc5)CC4)c3C2=O)C(=O)N1] |

TABLE A2-continued
| Cmpd No. | Structure |
|---|---|
| I-18 | 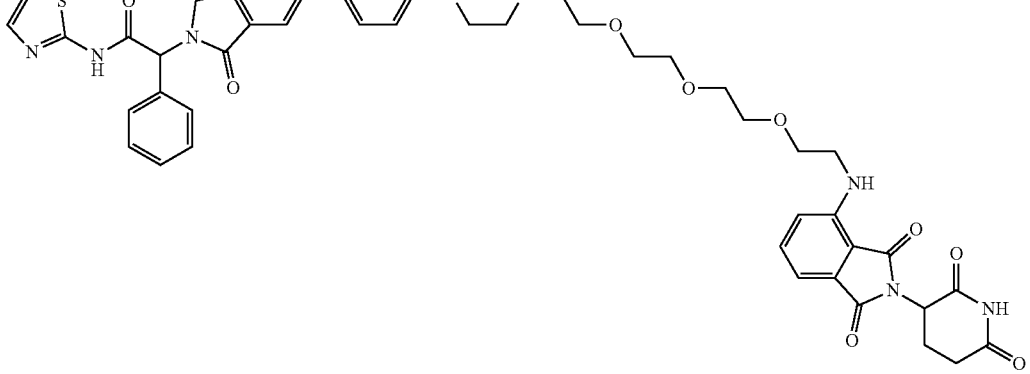 |
| I-19 | 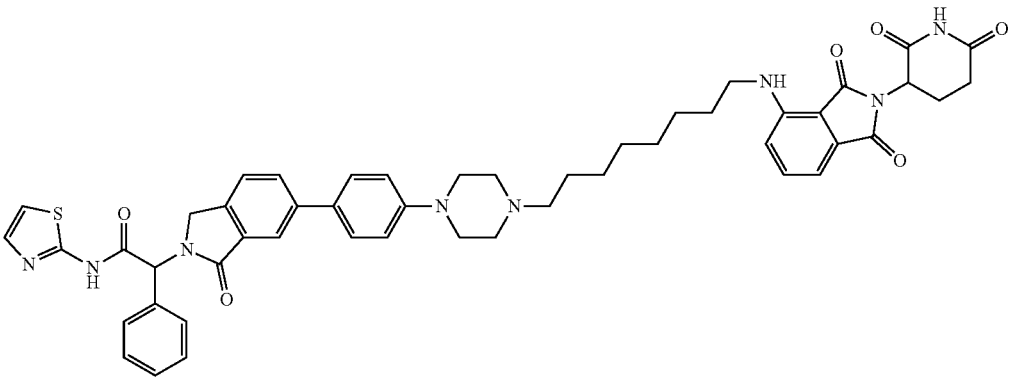 [SMILES: O=C1CCC(N2C(=O)c3cccc(NCCCCCCCCN4CCN(c5ccc(-c6ccc7c(c6)C(=O)N(C(C(=O)Nc6nccs6)c6ccccc6)C7)cc5)CC4)c3C2=O)C(=O)N1] |
| I-20 | 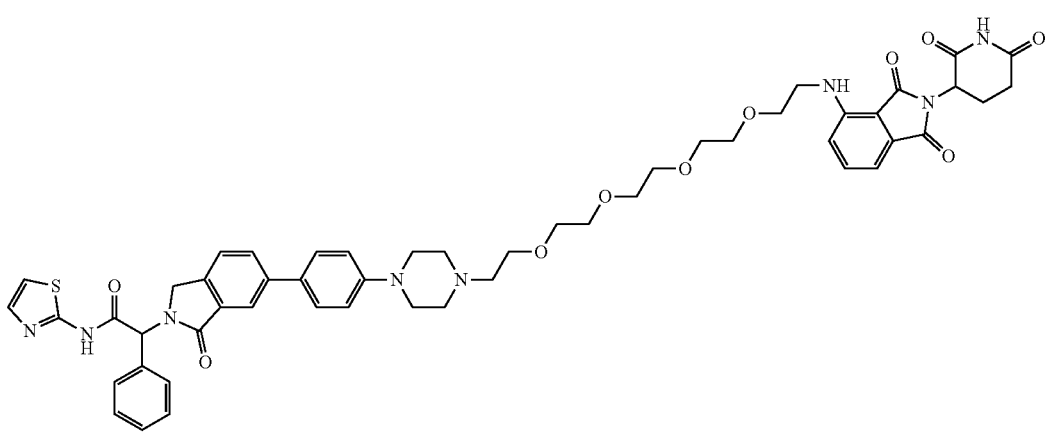 [SMILES: O=C1CCC(N2C(=O)c3cccc(NCCOCCOCCOCCOCCN4CCN(c5ccc(-c6ccc7c(c6)C(=O)N(C(C(=O)Nc6nccs6)c6ccccc6)C7)cc5)CC4)c3C2=O)C(=O)N1] |

TABLE A2-continued
| Cmpd No. | Structure |
|---|---|
| I-21 | 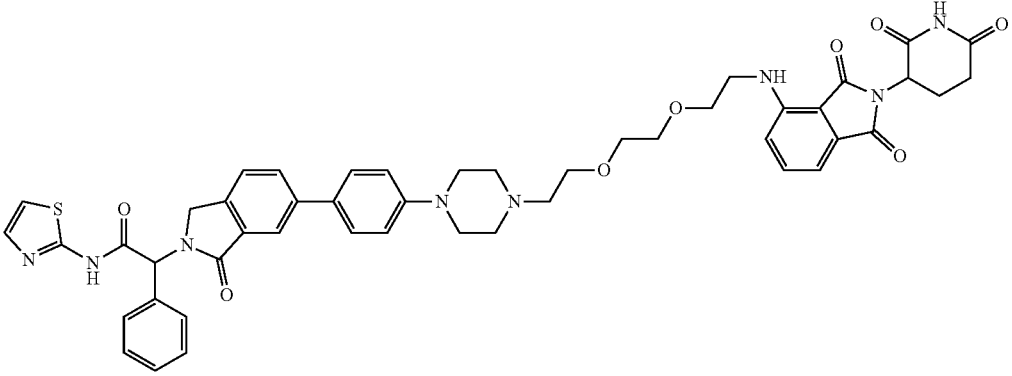 [SMILES: O=C1CCC(N2C(=O)c3cccc(NCCOCCOCCN4CCN(c5ccc(-c6ccc7c(c6)C(=O)N(C(C(=O)Nc6nccs6)c6ccccc6)C7)cc5)CC4)c3C2=O)C(=O)N1] |
| I-22 | 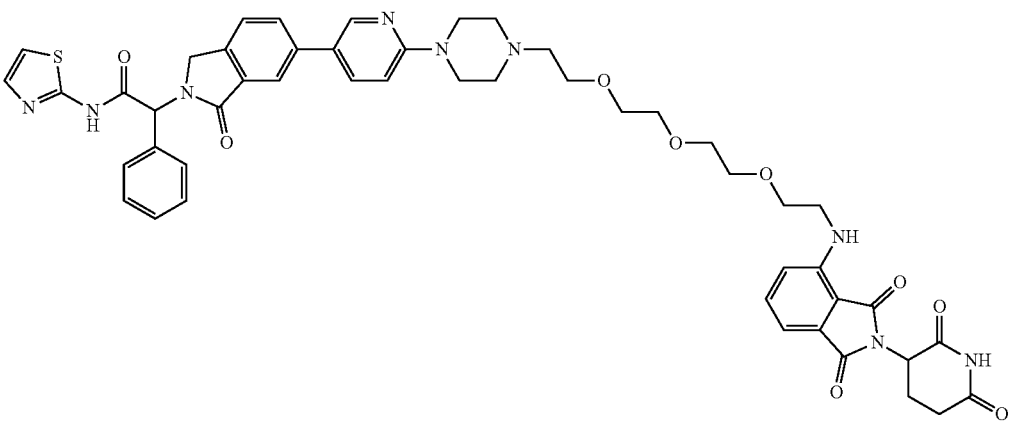 [SMILES: O=C1CCC(N2C(=O)c3cccc(NCCOCCOCCOCCN4CCN(c5ccc(-c6ccc7c(c6)C(=O)N(C(C(=O)Nc6nccs6)c6ccccc6)C7)cn5)CC4)c3C2=O)C(=O)N1] |
| I-23 | 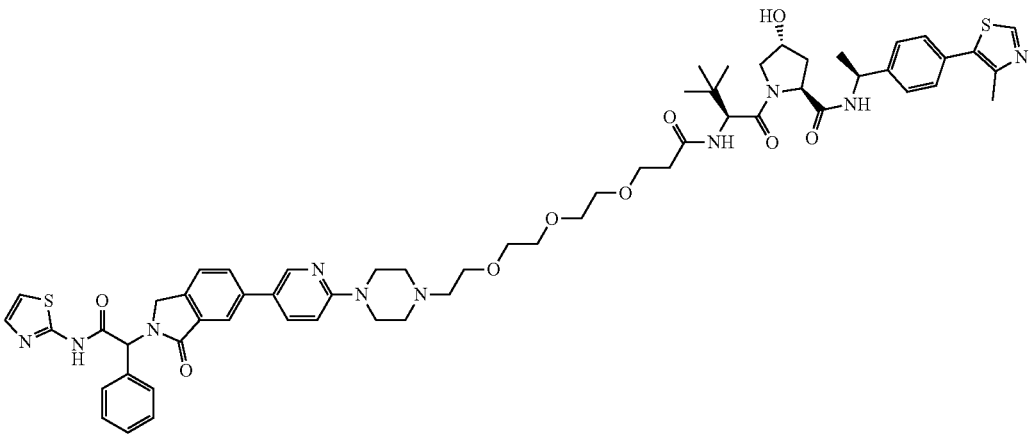 [SMILES: Cc1ncsc1-c1ccc([C@H](C)NC(=O)[C@@H]2C[C@@H](O)CN2C(=O)[C@@H](NC(=O)CCOCCOCCOCCN2CCN(c3ccc(-c4ccc5c(c4)C(=O)N(C(C(=O)Nc4nccs4)c4ccccc4)C5)cn3)CC2)C(C)(C)C)cc1] |

TABLE A2-continued

| Cmpd No. | Structure |
|---|---|
| I-24 | 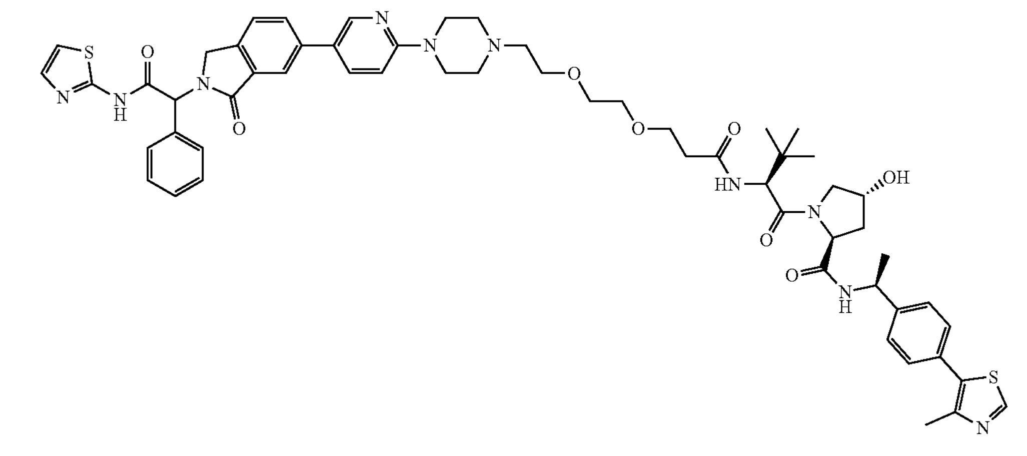 [SMILES: Cc1ncsc1-c1ccc([C@H](C)NC(=O)[C@@H]2C[C@@H](O)CN2C(=O)[C@@H](NC(=O)CCOCCOCCN2CCN(c3ccc(-c4ccc5c(c4)C(=O)N(C(C(=O)Nc4nccs4)c4ccccc4)C5)cn3)CC2)C(C)(C)C)cc1] |
| I-25 | 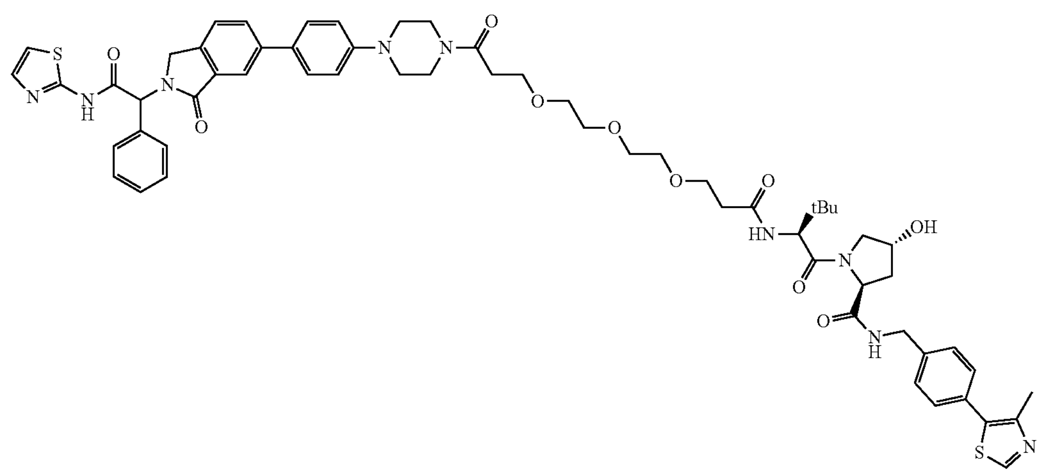 [SMILES: Cc1ncsc1-c1ccc(CNC(=O)[C@@H]2C[C@@H](O)CN2C(=O)[C@@H](NC(=O)CCOCCOCCOCCC(=O)N2CCN(c3ccc(-c4ccc5c(c4)C(=O)N(C(C(=O)Nc4nccs4)c4ccccc4)C5)cc3)CC2)C(C)(C)C)cc1] |
| I-26 | 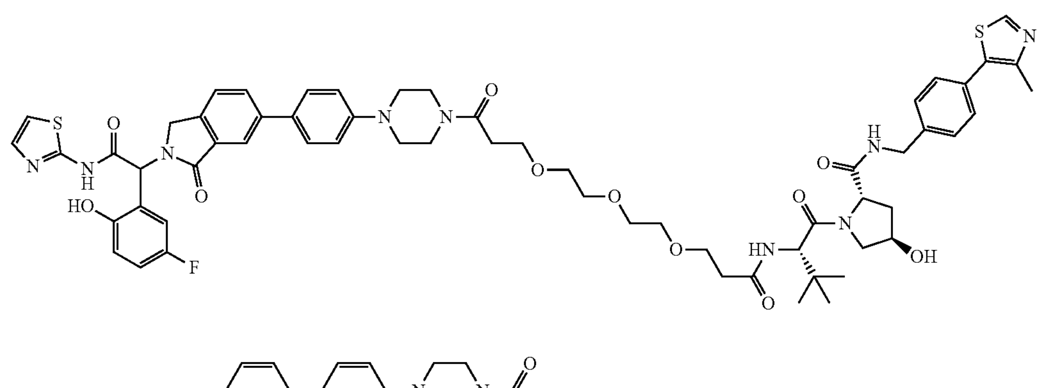 |
| I-27 | 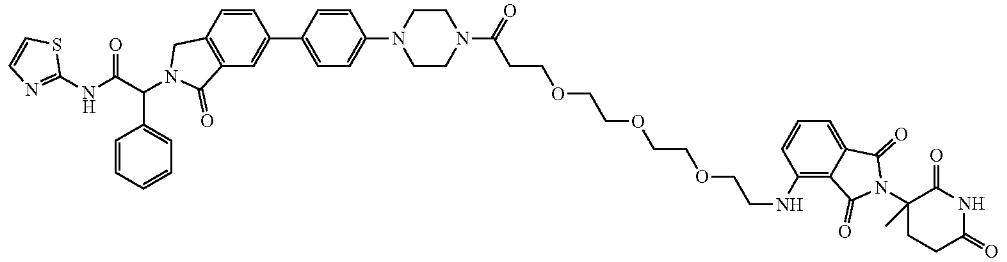 [SMILES: CC1(N2C(=O)c3cccc(NCCOCCOCCOCCC(=O)N4CCN(c5ccc(-c6ccc7c(c6)C(=O)N(C(C(=O)Nc6nccs6)c6ccccc6)C7)cc5)CC4)c3C2=O)CCC(=O)NC1=O] |

TABLE A2-continued

| Cmpd No. | Structure |
|---|---|
| I-28 | 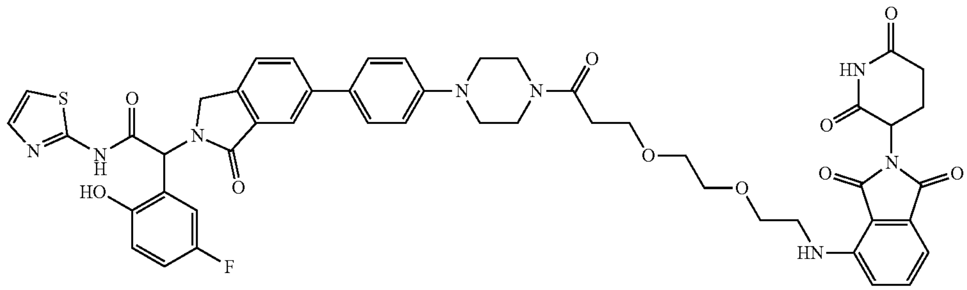 [SMILES: O=C1CCC(N2C(=O)c3cccc(NCCOCCOCCC(=O)N4CCN(c5ccc(-c6ccc7c(c6)C(=O)N(C(C(=O)Nc6nccs6)c6cc(F)ccc6O)C7)cc5)CC4)c3C2=O)C(=O)N1] |
| I-29 | 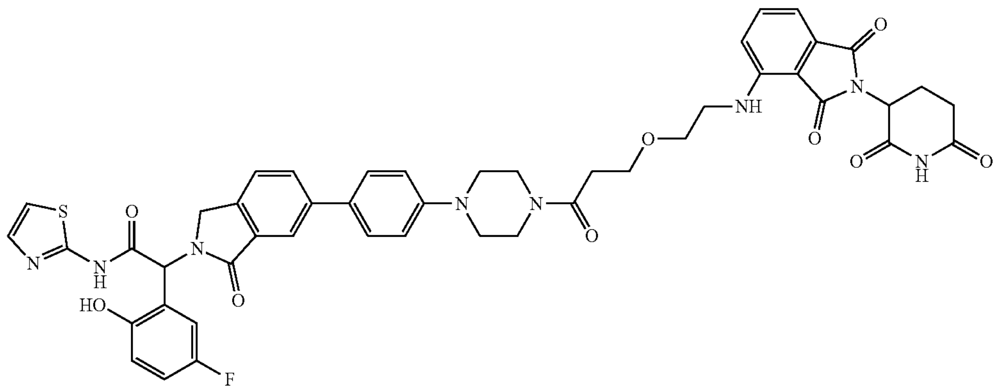 [SMILES: O=C1CCC(N2C(=O)c3cccc(NCCOCCC(=O)N4CCN(c5ccc(-c6ccc7c(c6)C(=O)N(C(C(=O)Nc6nccs6)c6cc(F)ccc6O)C7)cc5)CC4)c3C2=O)C(=O)N1] |
| I-30 | 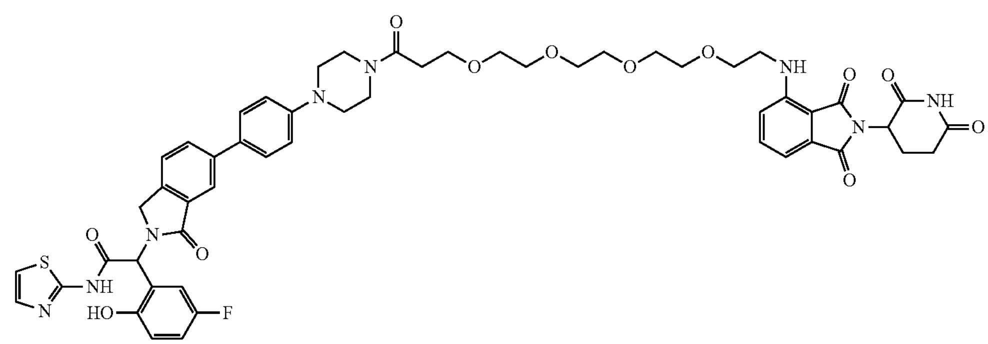 [SMILES: O=C1CCC(N2C(=O)c3cccc(NCCOCCOCCOCCOCCC(=O)N4CCN(c5ccc(-c6ccc7c(c6)C(=O)N(C(C(=O)Nc6nccs6)c6cc(F)ccc6O)C7)cc5)CC4)c3C2=O)C(=O)N1] |
| I-31 | 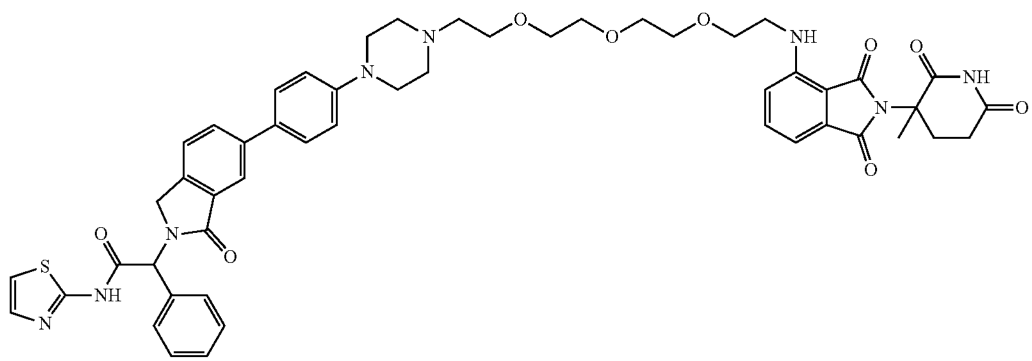 [SMILES: CC1(N2C(=O)c3cccc(NCCOCCOCCOCCN4CCN(c5ccc(-c6ccc7c(c6)C(=O)N(C(C(=O)Nc6nccs6)c6ccccc6)C7)cc5)CC4)c3C2=O)CCC(=O)NC1=O] |

TABLE A2-continued
| Cmpd No. | Structure |
|---|---|
| I-32 | 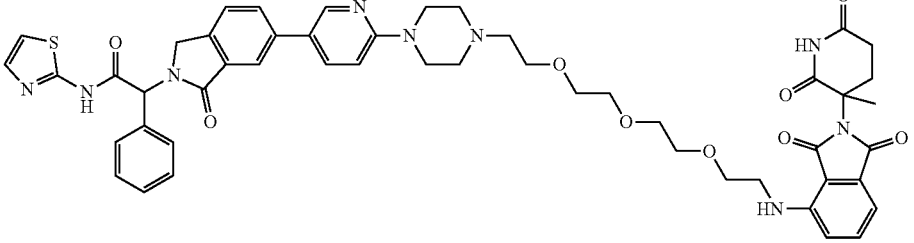 |
| I-33 | 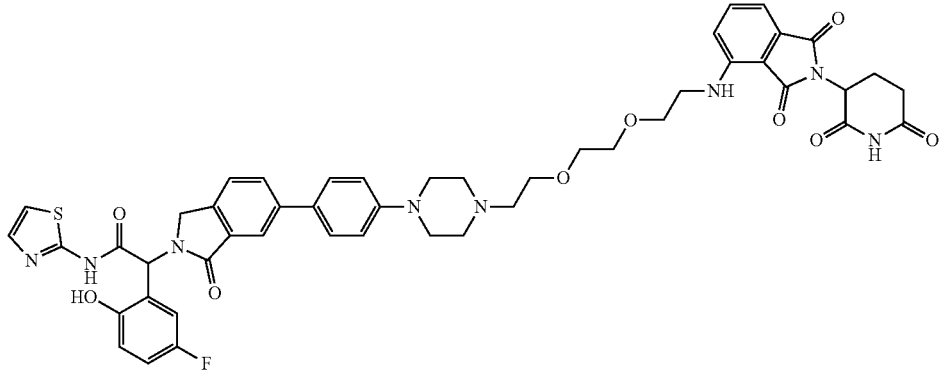 [SMILES: O=C1CCC(N2C(=O)c3cccc(NCCOCCOCCN4CCN(c5ccc(-c6ccc7c(c6)C(=O)N(C(C(=O)Nc6nccs6)c6cc(F)ccc6O)C7)cc5)CC4)c3C2=O)C(=O)N1] |
| I-34 | 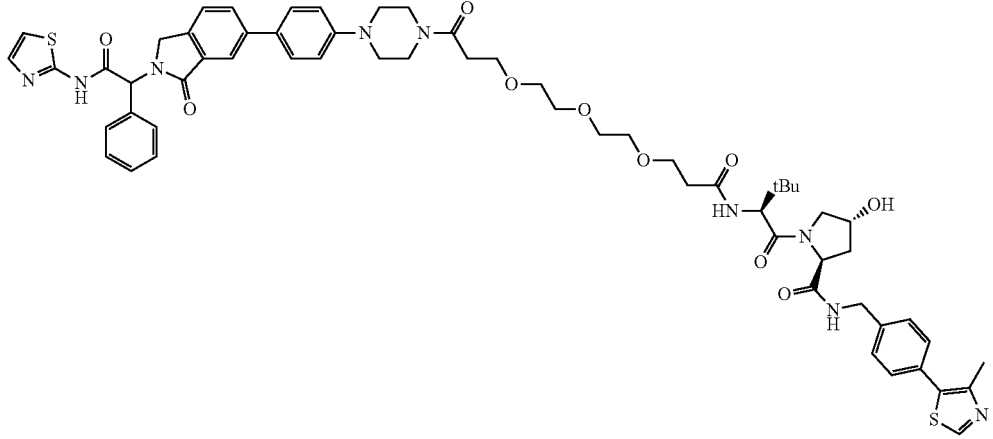 [SMILES: Cc1ncsc1-c1ccc(CNC(=O)[C@@H]2C[C@@H](O)CN2C(=O)[C@@H](NC(=O)CCOCCOCCOCCC(=O)N2CCN(c3ccc(-c4ccc5c(c4)C(=O)N(C(C(=O)Nc4nccs4)c4ccccc4)C5)cc3)CC2)C(C)(C)C)cc1] |
| I-35 | 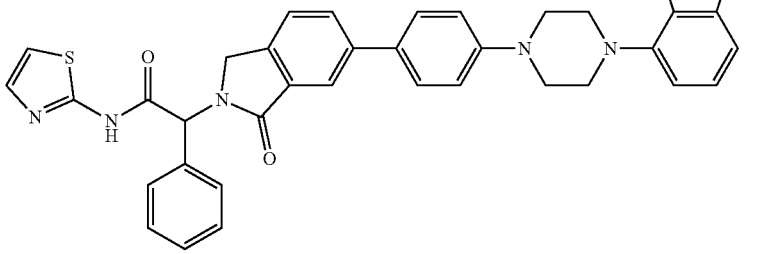 |

Some of the foregoing compounds can include one or more asymmetric centers, and thus can exist in various isomeric forms. In one embodiment, the compounds exist as stereoisomers. In one embodiment, the compounds exist as diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Furthermore, certain compounds, as described herein, may have one or more double bonds that can exist as either the Z or E isomer, unless otherwise indicated. The application additionally encompasses the compounds as individual Z/E isomers substantially free of other E/Z isomers and alternatively, as mixtures of various isomers.

In one embodiment, the present application provides compounds that target proteins, such as EGFR for degradation, which have numerous advantages over inhibitors of protein function (e.g., kinase activity) and can a) overcome resistance in certain cases; b) prolong the kinetics of drug effect by destroying the protein, thus requiring resynthesis of the protein even after the compound has been metabolized; c) target all functions of a protein at once rather than a specific catalytic activity or binding event; d) expand the number of drug targets by including all proteins that a ligand can be developed for, rather than proteins whose activity (e.g., kinase activity) can be affected by a small molecule inhibitor, antagonist or agonist; and e) have increased potency compared to inhibitors due to the possibility of the small molecule acting catalytically.

Some embodiments of the present application relate to degradation or loss of 30% to 100% of the target protein. Some embodiments relate to the loss of 50-100% of the target protein. Other embodiments relate to the loss of 75-95% of the targeted protein.

A bifunctional compound of Formula X, Formula Y, Formula Z, Formula A, Formula B, Formula C, or Formula D is capable of modulating or decreasing the amount of a targeted protein (e.g., EGFR). A bifunctional compound of Formula X, Formula Y, Formula Z, Formula A, Formula B, Formula C, or Formula D is also capable of degrading a targeted protein (e.g., EGFR) through the UPP pathway. A bifunctional compound of Formula X, Formula Y, Formula Z, Formula A, Formula B, Formula C, or Formula D is also capable of preventing EGFR dimer formation. Accordingly, a bifunctional compound of the present application (e.g., a bifunctional compound of any of the formulae described herein, or selected from any bifunctional compounds described herein) is also capable of treating or preventing a disease or disorder in which EGFR plays a role (e.g., through EGFR dimer formation) or in which EGFR is deregulated (e.g., overexpressed).

In some embodiments, the bifunctional compounds of the present application bind to an EGFR or a mutant thereof covalently. In other embodiments, the bifunctional compounds of the present application bind to an EGFR or a mutant thereof non-covalently.

In some embodiments, the bifunctional compounds of Formula X, Formula Y, Formula Z, Formula A, Formula B, Formula C, or Formula D are capable of inhibiting or decreasing the activity of EGFR containing one or more mutations. In some embodiments, the mutant EGFR contains one or more mutations selected from T790M, L718Q, L844V, V948R, L858R, I941R, C797S, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/C797S, L858R/T790M/C797S, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/C797S, Del/T790M, Del/T790M, Del/T790M/C797S, and L858R/T790M. In other embodiments, the mutant EGFR contains a combination of mutations, wherein the combination is selected from L858R/T790M, L858R/T790M/I941R, L858R/T790M/C797S, Del/T790M, Del/T790M/C797S, and L858R/T790M.

Modulation of EGFR through UPP-mediated degradation by a bifunctional compound of Formula X, Formula Y, Formula Z, Formula A, Formula B, Formula C, or Formula D provides a novel approach to the treatment, prevention, or amelioration of diseases or disorders in which EGFR plays a role including, but not limited to, cancer and metastasis, inflammation, arthritis, systemic lupus erthematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy. Further, modulation of EGFR through UPP-mediated degradation by a bifunctional compound of the application, such as those described herein, also provides a new paradigm for treating, preventing, or ameliorating diseases or disorders in which EGFR is deregulated.

In one embodiment, a bifunctional compound of the Formula X, Formula Y, Formula Z, Formula A, Formula B, Formula C, or Formula D is more efficacious in treating a disease or condition (e.g., cancer) than, or is capable of treating a disease or condition resistant to, the Targeting Ligand, when the Targeting Ligand is administered alone (i.e., not bonded to a Linker and a Degron). In one embodiment, a bifunctional compound of the present application (e.g., a bifunctional compound of any of the formulae described herein, or selected from any bifunctional compounds described herein) is capable of modulating (e.g., decreasing) the amount of EGFR, and thus is useful in treating a disease or condition (e.g., cancer) in which the EGFR plays a role.

In one embodiment, the bifunctional compound of Formula X, Formula Y, Formula Z, Formula A, Formula B, Formula C, or Formula D is more efficacious in treating a disease or condition or is capable of treating a disease or condition resistant to the Targeting Ligand, when the Targeting Ligand is administered alone (i.e., not bonded to a Linker and a Degron), is more potent in inhibiting the growth of cells (e.g., cancer cells) or decreasing the viability of cells (e.g., cancer cells), than the Targeting Ligand, when the Targeting Ligand is administered alone (i.e., not bonded to a Linker and a Degron). In one embodiment, the bifunctional compound inhibits the growth of cells (e.g., cancer cells) or decreases the viability of cells (e.g., cancer cells) at an $IC_{50}$ that is lower than the $IC_{50}$ of the Targeting Ligand (when the Targeting Ligand is administered alone (i.e., not bonded to a Linker and a Degron)) for inhibiting the growth or decreasing the viability of the cells. In one embodiment, the $IC_{50}$ of the bifunctional compound is at most 90%, 80%, 70%, 60%, 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 1%, 0.8%, 0.5%, 0.4%, 0.3%, 0.2%, or 0.1% of the $IC_{50}$ of the Targeting Ligand. In one embodiment, the bifunctional compound inhibits the growth of cells (e.g., cancer cells) or decreases the viability of cells (e.g., cancer cells) at an $E_{max}$ that is lower than the $E_{max}$ of the Targeting Ligand (when the Targeting Ligand is administered alone (i.e., not bonded to a Linker and a Degron)) for inhibiting the growth or decreasing the viability of the cells. In one embodiment, the $E_{max}$ of the bifunctional compound is at most 90%, 80%, 70%, 60%, 50%, 40%, 30%, 20%, 10%, 8%, 5%, 4%, 3%, 2%, or 1% of the $E_{max}$ of the Targeting Ligand. In one embodiment, the $E_{max}$ of the bifunctional compound is at most 50%, 40%, 30%, 20%, 10%, 8%, 5%, 4%, 3%, 2%, or 1% of the $E_{max}$ of the Targeting Ligand. In one embodiment, the $E_{max}$ of the bifunctional compound is at most 90%, 80%, 70%, 60%, 50%, 40%, 30%, 20%, or 10% of the $E_{max}$ of the Targeting Ligand.

In some embodiments, the bifunctional compounds of Formula X, Formula Y, Formula Z, Formula A, Formula B, Formula C, or Formula D can modulate EGFR containing one or more mutations, such as those described herein, but not a wild-type EGFR. In some embodiments, the compounds of the application exhibit greater inhibition of EGFR containing one or more mutations as described herein relative to a wild-type EGFR. In certain embodiments, the bifunctional compounds of the application exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the bifunctional compounds of the application exhibit up to 1000-fold greater inhibition of EGFR containing one or more mutations as described herein relative to a wild-type EGFR. In various embodiments, the bifunctional compounds of Formula X, Formula Y, Formula Z, Formula A, Formula B, Formula C, or Formula D exhibit up to 10000-fold greater inhibition of EGFR having a combination of mutations described herein (e.g., L858R/T790M, L858R/T790M/I941R, L858R/T790M/C797S, Del/T790M, Del/T790M/C797S, and L858R/T790M) relative to a wild-type EGFR.

In some embodiments, the bifunctional compounds of Formula X, Formula Y, Formula Z, Formula A, Formula B, Formula C, or Formula D exhibit from about 2-fold to about 10-fold greater inhibition of EGFR containing one or more mutations as described herein relative to a wild-type EGFR. In various embodiments, the bifunctional compounds of the application exhibit from about 10-fold to about 100-fold greater inhibition of EGFR containing one or more mutations as described herein relative to a wild-type EGFR. In various embodiments, the bifunctional compounds of the application exhibit from about 100-fold to about 1000-fold greater inhibition of EGFR containing one or more mutations as described herein relative to a wild-type EGFR. In various embodiments, the bifunctional compounds of the application exhibit from about 1000-fold to about 10000-fold greater inhibition of EGFR containing one or more mutations as described herein relative to a wild-type EGFR.

In certain embodiments, the bifunctional compounds of Formula X, Formula Y, Formula Z, Formula A, Formula B, Formula C, or Formula D exhibit at least 2-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the bifunctional compounds of the application exhibit at least 3-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the bifunctional compounds of the application exhibit at least 5-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the bifunctional compounds of the application exhibit at least 10-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the bifunctional compounds of the application exhibit at least 25-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the bifunctional compounds of the application exhibit at least 50-fold greater inhibition of EGFR having a combination of mutations selected from L L858R/T790M, L858R/T790M/I941R, L858R/T790M/C797S, Del/T790M, Del/T790M/C797S, and L858R/T790M relative to a wild-type EGFR. In certain embodiments, the bifunctional compounds of the application exhibit at least 100-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR.

In some embodiments, the inhibition of EGFR activity is measured by $IC_{50}$.

In some embodiments, the inhibition of EGFR activity is measured by $EC_{50}$.

In some embodiments, the bifunctional compounds of Formula X, Formula Y, Formula Z, Formula A, Formula B, Formula C, or Formula D bind to an allosteric site in EGFR. In some embodiments, the bifunctional compounds of the application interact with at least one amino acid residue of epidermal growth factor receptor (EGFR) selected from Lys745, Leu788, and Ala 743. In other embodiments, the bifunctional compounds of the application interact with at least one amino acid residue of epidermal growth factor receptor (EGFR) selected from Cys755, Leu777, Phe856, and Asp855. In other embodiments, the bifunctional compounds of the application interact with at least one amino acid residue of epidermal growth factor receptor (EGFR) selected from Met766, Ile759, Glu762, and Ala763. In other embodiments, the bifunctional compounds of the application interact with at least one amino acid residue of epidermal growth factor receptor (EGFR) selected from Lys745, Leu788, and Ala 743, at least one amino acid residue of epidermal growth factor receptor (EGFR) selected from Cys755, Leu777, Phe856, and Asp855, and at least one amino acid residue of epidermal growth factor receptor (EGFR) selected from Met766, Ile759, Glu762, and Ala763. In other embodiments, the bifunctional compounds of the application do not interact with the any of the amino acid residues of epidermal growth factor receptor (EGFR) selected from Met793, Gly796, and Cys797.

In some embodiments, the application provides a bifunctional compound comprising an allosteric kinase inhibitor, wherein the bifunctional compound is a more potent inhibitor of a drug-resistant EGFR mutant relative to a wild type EGFR. For example, the bifunctional compound can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002:

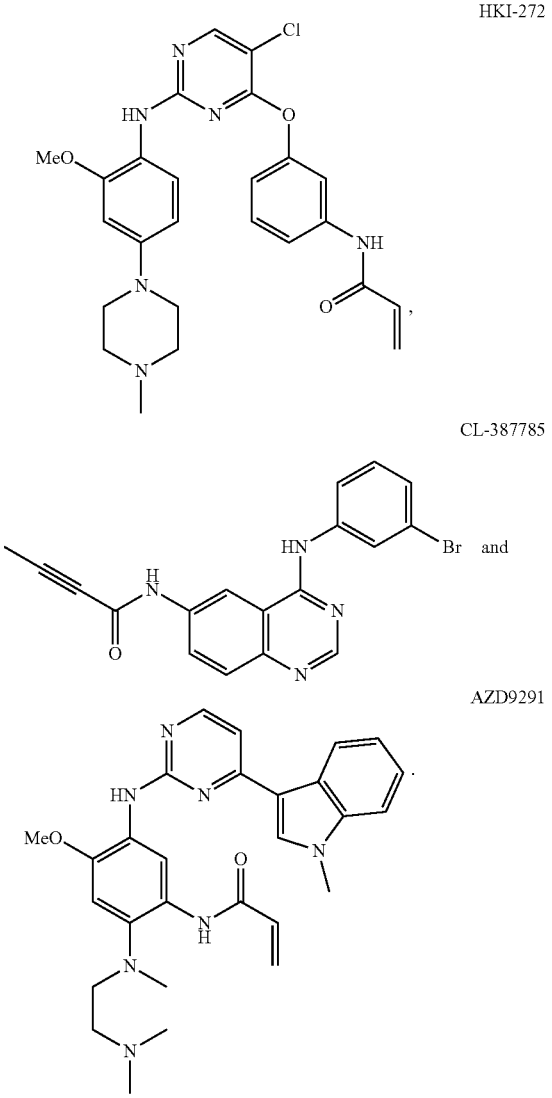

In some embodiments, the drug-resistant EGFR mutant comprises a sensitizing mutation, such as Del and L858R.

In some embodiments, the application provides a bifunctional compound comprising an allosteric kinase inhibitor, wherein the compound inhibits kinase activity of a drug-resistant EGFR mutant harboring a sensitizing mutation (e.g., Del and L858R) and a drug-resistance mutation (e.g., T790M, L718Q, C797S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold.

In some embodiments, the application provides a bifunctional compound comprising an allosteric kinase inhibitor, wherein the compound is more potent than one or more known EGFR inhibitors, including, but not limited to, gefitinib, erlotinib, lapatinib, WZ4002, HKI-272, CL-387785, and AZD9291, at inhibiting the activity of EGFR containing one or more mutations as described herein, such as T790M, L718Q, L844V, L858R, C797S, and Del. For example, the compound can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387785, and AZD9291 at inhibiting the activity of the EGFR containing one or more mutations as described herein.

In some embodiments, the application provides a bifunctional compound comprising an allosteric kinase inhibitor, wherein the bifunctional compound is less potent than one or more known EGFR inhibitors, including but not limited to gefitinib, erlotinib, lapatinib, WZ4002, HKI-272, CL-387785, and AZD9291, at inhibiting the activity of a wild-type EGFR. For example, the bifunctional compound can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and AZD9291, at inhibiting the activity of a wild-type EGFR.

Potency of the inhibitor can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining an EGFR-dependent phosphorylation level or determining cell proliferation or cell death, in vitro or in vivo (e.g., in 3T3 cells expressing a wild type EGFR, a mutant EGFR, or a fragment of any thereof).

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining an EGFR-dependent phosphorylation level or determining cell proliferation or cell death, in vitro or in vivo (e.g., in 3T3 cells expressing a wild type EGFR, a mutant EGFR, or a fragment of any thereof).

An EGFR sensitizing mutation comprises without limitation L858R, G719S, G719C, G719A, L861Q, a deletion in exon 19 and/or an insertion in exon 20. A drug-resistant EGFR mutant can have without limitation a drug resistance mutation comprising T790M, T854A, L718Q, C797S, or D761Y.

The selectivity between wild-type EGFR and EGFR containing one or more mutations as described herein can also be measured using cellular proliferation assays where cell proliferation is dependent on kinase activity. For example, murine Ba/F3 cells transfected with a suitable version of wild-type EGFR (such as VIII; containing a WT EGFR kinase domain), or Ba/F3 cells transfected with L858R/T790M, Del/T790M/L718Q, L858R/T790M/L718Q, L858R/T790M/C797S, Del/T790M/C797S, L858R/T790M/I941R, or Exon 19 deletion/T790M can be used. Proliferation assays are performed at a range of inhibitor concentrations (10 µM, 3 µM, 1.1 µM, 330 nM, 110 nM, 33 nM, 11 nM, 3 nM, I nM) and an $EC_{50}$ is calculated.

An alternative method to measure effects on EGFR activity is to assay EGFR phosphorylation. Wild type or mutant (L858R/T790M, Del/T790M, Del/T790M/L718Q, L858R/T790M/C797S, Del/T790M/C797S, L858R/T790M/I941R, or L858R/T790M/L718Q) EGFR can be transfected into NIH-3T3 cells (which do not normally express endogenous EGFR) and the ability of the inhibitor (using concentrations as above) to inhibit EGFR phosphorylation can be assayed. Cells are exposed to increasing concentrations of inhibitor for 6 hours and stimulated with EGF for 10 minutes. The effects on EGFR phosphorylation are assayed by Western Blotting using phospho-specific (Y1068) EGFR antibodies.

In another aspect, the present application provides a bifunctional compound that binds to an allosteric site in EGFR, wherein the compound exhibits greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L718Q, L858R/T790M/C797S, Del/T790M/C797S, L858R/T790M/I941R, or L858R/T790M/L718Q) relative to a wild-type EGFR.

In one embodiment, the bifunctional compounds of Formula X, Formula Y, Formula Z, Formula A, Formula B, Formula C, or Formula D are useful as anticancer agents, and thus may be useful in the treatment of cancer, by effecting tumor cell death or inhibiting the growth of tumor cells. In certain exemplary embodiments, the disclosed anticancer agents are useful in the treatment of cancers and other proliferative disorders, including, but not limited to breast cancer, cervical cancer, colon and rectal cancer, leukemia, lung cancer (e.g., non-small cell lung cancer), melanoma, multiple myeloma, non-Hodgkin's lymphoma, ovarian cancer, pancreatic cancer, prostate cancer, gastric cancer, leukemias (e.g., myeloid, lymphocytic, myelocytic and lymphoblastic leukemias), malignant melanomas, and T-cell lymphoma.

Definitions

Listed below are definitions of various terms used in this application. These definitions apply to the terms as they are used throughout this specification and claims, unless otherwise limited in specific instances, either individually or as part of a larger group.

The term "alkyl," as used herein, refers to saturated, straight or branched-chain hydrocarbon radicals containing, in certain embodiments, between one and six carbon atoms. Examples of $C_1$-$C_6$ alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl and the like.

The term "alkoxy" refers to an —O-alkyl radical.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_5$ cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a non-aromatic 3-4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl), e.g., —NH($C_1$-$C_6$ alkyl), where $C_1$-$C_{12}$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the application, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$— heterocycloalkyl, NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl, —NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NHheterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NHheterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "EGFR" herein refers to epidermal growth factor receptor kinase.

The term "HER" or "Her", herein refers to human epidermal growth factor receptor kinase.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

As used herein, the term "allosteric site" refers to a site on EGFR other than the ATP binding site, such as that characterized in a crystal structure of EGFR. An "allosteric site" can be a site that is close to the ATP binding site, such as that characterized in a crystal structure of EGFR. For example, one allosteric site includes one or more of the following amino acid residues of epidermal growth factor receptor (EGFR): Lys745, Leu788, Ala 743, Cys755, Leu777, Phe856, Asp855, Met766, Ile759, Glu762, and/or Ala763.

As used herein, the term "agent that prevents EGFR dimer formation" refers to an agent that prevents dimer formation in which the C-lobe of the "activator" subunit impinges on the N-lobe of the "receiver" subunit. Examples of agents that prevent EGFR dimer formation include, but are not limited to, cetuximab, cobimetinib, trastuzumab, panitumumab, and Mig6.

As used herein the term "GDC0973" or "Cobimetinib" refers to a compound having the chemical structure:

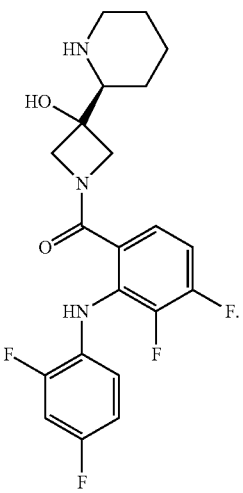 [SMILES: O=C(c1ccc(F)c(F)c1Nc1ccc(F)cc1F)N1CC(O)([C@@H]2CCCCN2)C1]

As used herein, "TL compound 1," and "TL compound 2," refers to compounds having the chemical structures:

(TL compound 1)

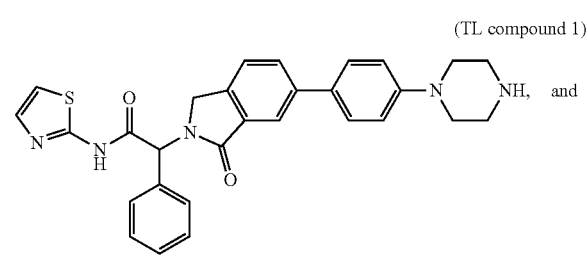

and (TL compound 2)

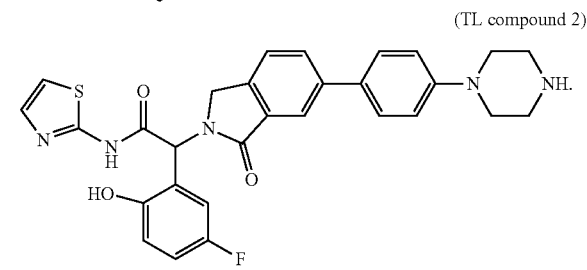

The term "targeted protein(s)" is used interchangeably with "target protein(s)", unless the context clearly dictates otherwise. In one embodiment, a "targeted protein" is EGFR.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

The terms "disease(s)", "disorder(s)", and "condition(s)" are used interchangeably, unless the context clearly dictates otherwise.

The term "therapeutically effective amount" of a bifunctional compound or pharmaceutical composition of the application, as used herein, means a sufficient amount of the bifunctional compound or pharmaceutical composition so as to decrease the symptoms of a disorder in a subject. As is well understood in the medical arts a therapeutically effective amount of a bifunctional compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, /7-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the bifunctional compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the bifunctional compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of bifunctional compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews,* 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The application also provides for a pharmaceutical composition comprising a bifunctional compound disclosed herein, or a pharmaceutically acceptable ester, salt, or prodrug thereof, together with a pharmaceutically acceptable carrier.

In another aspect, the application provides a kit comprising a bifunctional compound capable of inhibiting EGFR activity selected from one or more compounds disclosed herein, or a pharmaceutically acceptable salt, hydrate, solvate, prodrug, stereoisomer, or tautomer thereof, optionally in combination with a second agent wherein said second agent prevents EGFR dimer formation and instructions for use in treating cancer.

In another aspect, the application provides a method of synthesizing a bifunctional compound disclosed herein.

The synthesis of the bifunctional compounds of the application can be found herein and in the Examples below.

Other embodiments are a method of making a bifunctional compound of any of the formulae herein using any one, or combination of, reactions delineated herein. The method can include the use of one or more intermediates or chemical reagents delineated herein.

Another aspect is an isotopically labeled bifunctional compound of any of the formulae delineated herein. Such compounds have one or more isotope atoms which may or may not be radioactive (e.g., $^{3}$H, $^{2}$H, $^{14}$C, $^{13}$C, $^{18}$F, $^{35}$S, $^{32}$P, $^{125}$I, and $^{131}$I) introduced into the bifunctional compound. Such compounds are useful for drug metabolism studies and diagnostics, as well as therapeutic applications.

A bifunctional compound of the application can be prepared as a pharmaceutically acceptable acid addition salt by reacting the free base form of the compound with a pharmaceutically acceptable inorganic or organic acid. Alternatively, a pharmaceutically acceptable base addition salt of a bifunctional compound of the application can be prepared by reacting the free acid form of the bifunctional compound with a pharmaceutically acceptable inorganic or organic base.

Alternatively, the salt forms of the bifunctional compounds of the application can be prepared using salts of the starting materials or intermediates.

The free acid or free base forms of the bifunctional compounds of the application can be prepared from the corresponding base addition salt or acid addition salt from, respectively. For example, a bifunctional compound of the application in an acid addition salt form can be converted to the corresponding free base by treating with a suitable base (e.g., ammonium hydroxide solution, sodium hydroxide, and the like). A bifunctional compound of the application in a base addition salt form can be converted to the corresponding free acid by treating with a suitable acid (e.g., hydrochloric acid, etc.).

Prodrugs of the bifunctional compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized bifunctional compound of the application with a suitable carbamylating agent (e.g., 1,1-acyloxyalkylcarbanochloridate, para-nitrophenyl carbonate, or the like).

Protected derivatives of the bifunctional compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared, or formed during the process of the application, as solvates (e.g., hydrates). Hydrates of bifunctional compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_{14}$) occurs more than one time in any constituent or formula for a compound, its definition at each occurrence is independent of its definition at every other occurrence. Thus, for example, if a group is shown to be substituted with one or more $R_{14}$ moieties, then $R_{14}$ at each occurrence is selected independently from the definition of $R_{14}$. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the bifunctional compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the bifunctional compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The synthesized bifunctional compounds can be separated from a reaction mixture and further purified by a method such as column chromatography, high pressure liquid chromatography, or recrystallization. As can be appreciated by the skilled artisan, further methods of synthesizing the bifunctional compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Method of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester or prodrug thereof. Suitable synthetic routes are depicted in the schemes below.

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in General Schemes 1-4 which comprise different sequences of assembling intermediates 1a, 1b, 1c, 1d, 1e, 1f, 1g, 1h, 1i, 1j, 1k, 1m, 1n, 1p, 1q, and 1r. Starting materials are either commercially available or made by known procedures in the reported literature or as illustrated.

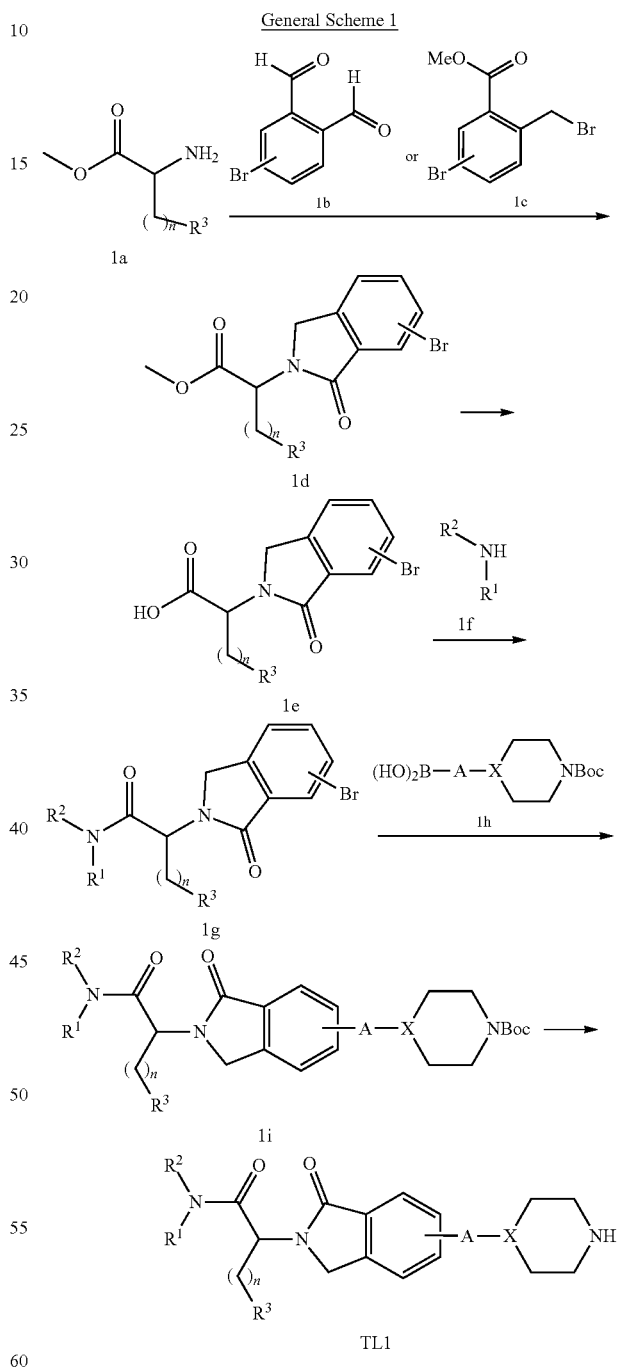

wherein R$^1$, R$^2$, R$^3$, A, X, and n are defined herein.

Target Ligand Compound of Formula TL-I can be synthesized using intermediates 1a, 1b, 1c, 1d, 1e, 1f, and 1g is outlined in General Scheme 1. Cyclization of 1a and 1b using an acid, e.g., acetic acid, in solvent, e.g., CHCl$_3$, at elevated temperatures provides intermediate 1d. Alternatively, Intermediate 1d can be obtained via cyclization of 1a and 1c using a base, e.g., N,N-diisopropylethylamine (DIEA) in a solvent, e.g., dimethylformamide (DMF) at elevated temperatures. Hydrolysis of Intermediate 1d using a base, e.g., lithium hydroxide (LiOH) in a solvent, e.g., tetrahydrofuran (THF), methanol (MeOH), and/or water ($H_2O$), provides Ie. Coupling of acid Ie and amine If under standard coupling conditions using a coupling reagent, e.g., [bis(dimethylamino)methylene]-1H-1,2,3-triazolo[4,5-b]pyridinium 3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIEA), in a solvent, e.g., dichloromethane or DMF, provides 1g. Suzuki coupling of 1g and 1h in the presence of a metal catalyst, i.e., [1,1'-Bis(diphenylphosphino)ferrocene]dichloropalladium(II) ($PdCl_2(dppf)_2$), a phosphine ligand, i.e., 2-Dicyclohexylphosphino-2',4',6'-triisopropylbiphenyl (Xphos), and a base, i.e., sodium carbonate ($Na_2CO_3$) or potassium carbonate ($K_2CO_3$), in a solvent, i.e., dioxane, provides 1i. Deprotection of 1i using a strong acid, i.e., trifluoroacetic acid (TFA) or hydrochloric acid (HCl), in a solvent, i.e., dichloromethane (DCM) or dioxane, provides the desired compound of Formula TL-I.

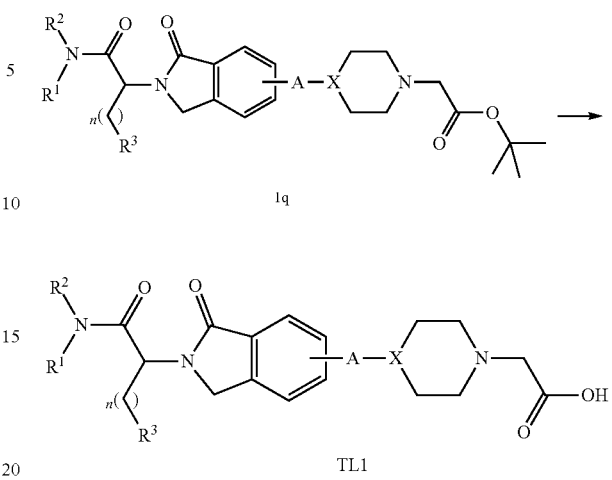

wherein $R^1$, $R^2$, $R^3$, A, X, and n are defined herein.

Target Ligand Compound of Formula TL-I can be synthesized using intermediates 1i, 1p, and 1q is outlined in General Scheme 1. Alkylation of 1i with 1p in the presence of a base, i.e., $K_2CO_3$, and in a solvent, i.e., dimethylformamide (DMF), provides intermediate 1q. Deprotection of 1q using a strong acid, i.e., trifluoroacetic acid (TFA) or hydrochloric acid (HCl), in a solvent, i.e., dichloromethane (DCM) or dioxane, provides the desired compound of Formula TL-I.

General Scheme 2

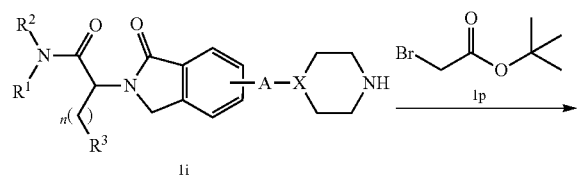

General Scheme 3

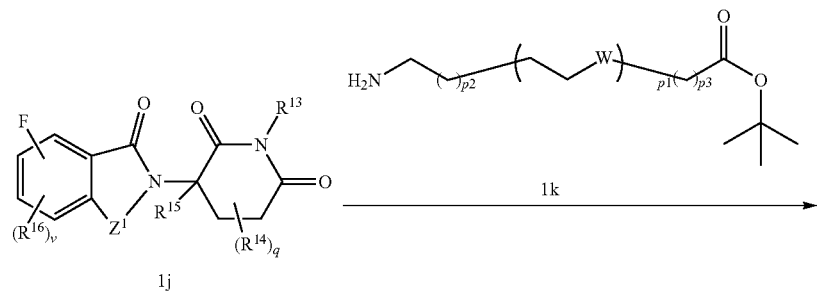

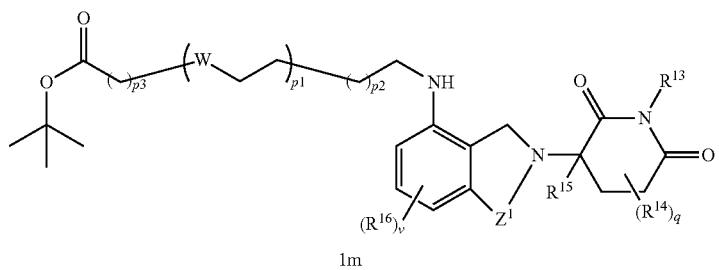

-continued

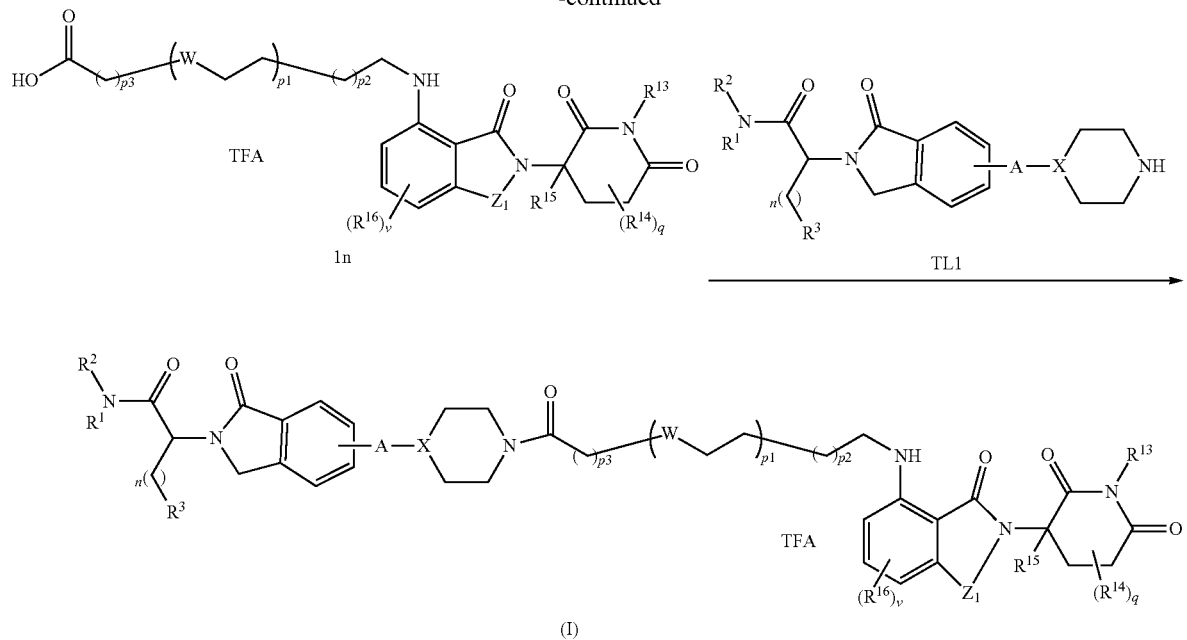

(I)

wherein $R^1$, $R^2$, $R^3$, $R^{13}$, $R^{14}$, $R^{15}$, $R^{16}$, A, X, W, $Z_1$, p1, p2, p3, n, q, and v are defined herein.

The general way of preparing representative compounds of the present application (i.e., Compound of Formula (I) shown above) using intermediates 1i, 1j, 1k, 1m, and 1n is outlined in General Scheme 3. Amination of 1j with 1k in the presence of a base, i.e., N,N-diisopropylethylamine (DIEA), in a solvent, i.e., DMF, at elevated temperatures provides intermediate 1m. Deprotection of 1m using a strong acid, i.e., trifluoroacetic acid (TFA) or hydrochloric acid (HCl), in a solvent, i.e., dichloromethane (DCM) or dioxane, provides carboxylic acid 1n. Coupling of acid 1n and amine TL-I under standard coupling conditions using a coupling reagent, e.g., 1-ethyl-3-(3-dimethylaminopropyl) carbodiimide (EDCI), and a base, e.g., DIEA, in a solvent, e.g., DCM or DMF, provides compound Formula (I).

General Scheme 4

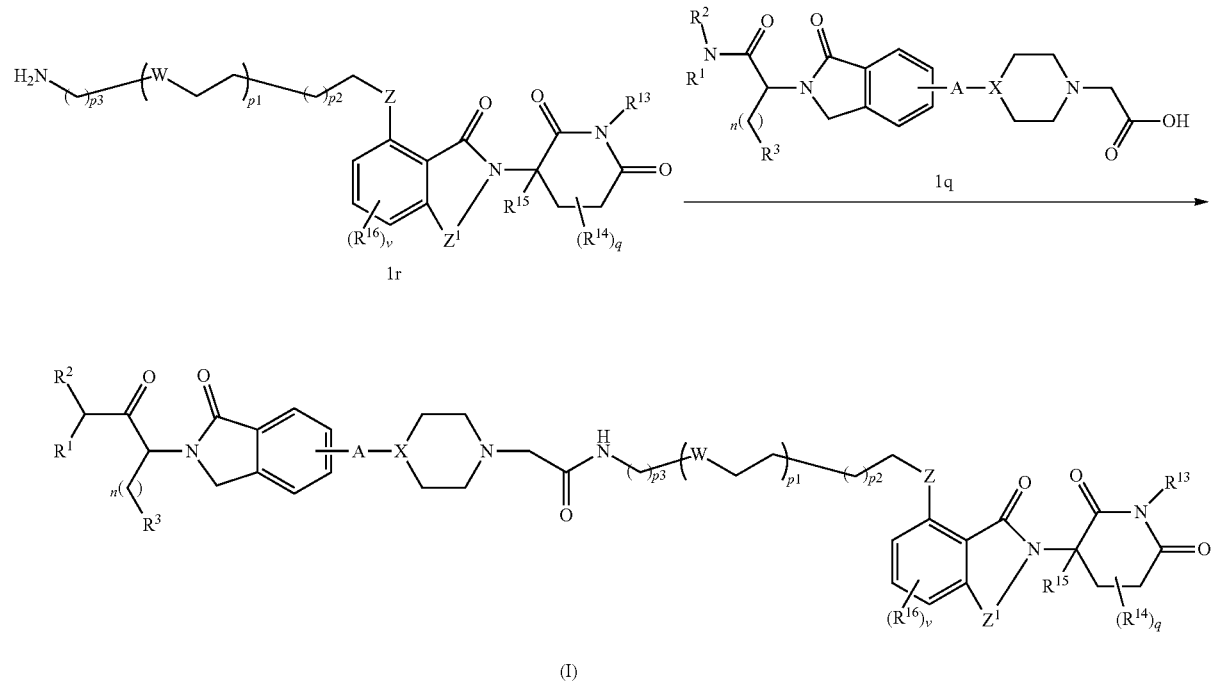

(I)

wherein $R^1$, $R^2$, $R^3$, $R^{13}$, $R^{14}$, $R^{15}$, $R^{16}$, A, X, W, Z, $Z_1$, p1, p2, p3, n, q, and v are defined herein.

Alternatively, compounds of the present application (i.e., Compound of Formula (I) shown above) can be prepared using intermediates 1r and 1a as outlined in General Scheme 4. Coupling of acid 1q and amine 1r under standard coupling conditions using a coupling reagent, e.g., [bis(dimethylamino)methylene]-1H-1,2,3-triazolo[4,5-b]pyridinium 3-oxide hexafluoro-phosphate (HATU), or O-benzotriazole-N,N,N',N'-tetramethyl-uronium-hexafluoro-phosphate (HBTU), and a base, e.g., triethylamine or DIEA, in a solvent, e.g., dichloromethane or DMF, provides desired compound of Formula (I).

Biological Assays

Biochemical Assays

EGFR biochemical assays are carried out using a homogeneous time-resolved fluorescence (HTRF) assay. The reaction mixtures contain biotin-Lck-peptide substrate, wild type, or mutant EGFR enzyme in reaction buffer. Enzyme concentrations are adjusted to accommodate varying kinase activity and ATP concentrations. Compounds of the present application are diluted into the assay mixture and $IC_{50}$ values are determined using 12-point inhibition curves.

Phospho-EGFR Target Modulation Assays and ELISA

Cells are lysed with lysis buffer containing protease and phosphatase inhibitors and the plates are shaken. An aliquot from each well is then transferred to prepared ELISA plates for analysis. Once harvested and plated, the cells are pretreated with media with or without EGF. The compounds of the present application are then added and $IC_{50}$ values are determined using an EGFR biochemical assay described above.

Solid high-binding ELISA plates are coated with goat anti-EGFR capture antibody. Plates are then blocked with BSA in a buffer, and then washed. Aliquots of lysed cell are added to each well of the ELISA plate and the plate is incubated. An anti-phospho-EGFR is then added and is followed by further incubation. After washing, anti-rabbit-HRP is added and the plate is again incubated. Chemiluminescent detection is carried out with SuperSignal ELISA Pico substrate. Signal is read on EnVision plate reader using built-in UltraLUM setting.

Western Blotting

Cell lysates are equalized to protein content and loaded onto a gel with running buffer. Membranes are probed with primary antibodies and are then washed. HRP-conjugated secondary antibodies are added and after washing. HRP is detected using a HRP substrate reagent and recorded with an imager.

EGFR protein degradation is assessed by western blotting after treatment of cell lines with a compound of the present application dose-dependently or combination with cetuximab.

Cell Proliferation Assays

Cell lines are plated in media. The compounds of the present application are then serially diluted and transferred to the cells. Cell viability is measured via a luminescent readout. Data is analyzed by non-linear regression curve-fitting.

Methods of the Application

In another aspect, the application provides a method of modulating (e.g., decreasing) the amount of a kinase, comprising contacting the kinase with a bifunctional compound disclosed herein, or a pharmaceutically acceptable salt, hydrate, solvate, prodrug, stereoisomer, or tautomer thereof. In some embodiments, the kinase comprises a mutated cysteine residue. In further embodiments, the mutated cysteine residue is located in or near the position equivalent to Cys 797 in EGFR, including such position in Jak3, Blk, Bmx, Btk, HER2 (ErbB2), HER4 (ErbB4), Itk, Tec, and Txk.

In another aspect, the application provides a method of modulating (e.g., decreasing) the amount of a kinase, comprising administering to a subject in need thereof an effective amount of a bifunctional compound disclosed herein, or a pharmaceutically acceptable salt, hydrate, solvate, prodrug, stereoisomer, or tautomer thereof. In some embodiments, the kinase is EGFR or a mutant thereof. In other embodiments, the kinase is a Her-kinase.

In still another aspect, the application provides a method of inhibiting epidermal growth factor receptor (EGFR), the method comprising administering to a subject in need thereof an effective amount of a bifunctional compound disclosed herein, or a pharmaceutically acceptable salt, hydrate, solvate, prodrug, stereoisomer, or tautomer thereof.

Another aspect of the application provides a method of treating or preventing a disease, the method comprising administering to a subject in need thereof an effective amount of a bifunctional compound disclosed herein, or a pharmaceutically acceptable salt, hydrate, solvate, prodrug, stereoisomer, or tautomer thereof. In some embodiments, the disease is mediated by a kinase. In further embodiments, the kinase comprises a mutated cysteine residue. In further embodiments, the mutated cysteine residue is located in or near the position equivalent to Cys 797 in EGFR, including such positions in Jak3, Blk, Bmx, Btk, HER2 (ErbB2), HER4 (ErbB4), Itk, Tec, and Txk.

In some embodiments, the disease is mediated by EGFR (e.g., EGFR plays a role in the initiation or development of the disease). In further embodiments, the EGFR is a Her-kinase. In further embodiments, the Her-kinase is HER1, HER2, or HER4.

In certain embodiments, the disease or disorder is cancer or a proliferation disease.

In further embodiments, the disease or disorder is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In other embodiments, the disease or disorder is inflammation, arthritis, rheumatoid arthritis, spondyiarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, or B-Cell Lymphoma.

In further embodiments, the disease or disorder is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia or lymphoma.

Another aspect of the application provides a method of treating a kinase mediated disorder, the method comprising administering to a subject in need thereof an effective amount of a bifunctional compound disclosed herein, or a pharmaceutically acceptable salt, hydrate, solvate, prodrug, stereoisomer, or tautomer thereof. In some embodiments, the bifunctional is capable of modulating (e.g., decreasing) the amount of EGFR. In other embodiments, the bifunctional compound is capable of modulating (e.g., decreasing) the amount of HER1, HER2, or HER4. In other embodiments, the subject is administered an additional therapeutic agent. In other embodiments, the bifunctional compound and the additional therapeutic agent are administered simultaneously or sequentially.

In other embodiments, the disease or disorder is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

Another aspect of the present application includes a method of modulating (e.g., decreasing) the amount of epidermal growth factor receptor (EGFR). The method comprises administering to a subject in need thereof an effective amount of a bifunctional compound of the application or a pharmaceutically acceptable salt, hydrate, solvate, prodrug, stereoisomer, or tautomer thereof, or a pharmaceutical composition of the application. In some embodiments, the bifunctional compound prevents EGFR dimer formation.

Another aspect of the present application describes a method of treating or preventing a disease, wherein the disease is resistant to an EGFR targeted therapy, such as a therapy with gefitinib, erlotinib, AZD9291, CO-1686 or WZ4002. The method comprises administering to a subject in need thereof an effective amount of a bifunctional compound of the application, or a pharmaceutically acceptable salt, hydrate, solvate, prodrug, stereoisomer, or tautomer thereof.

In another aspect, the application provides a method of treating or preventing cancer, wherein the cancer cell comprises activated EGFR, comprising administering to a subject in need thereof an effective amount of a bifunctional compound disclosed herein, or a pharmaceutically acceptable salt, hydrate, solvate, prodrug, stereoisomer, or tautomer thereof.

In certain embodiments, the EGFR activation is selected from mutation of EGFR, amplification of EGFR, expression of EGFR, and ligand mediated activation of EGFR.

In further embodiments, the mutation of EGFR is located at G719S, G719C, G719A, L858R, L861Q, an exon 19 deletion mutation, or an exon 20 insertion mutation.

Another aspect of the application provides a method of treating or preventing cancer in a subject, wherein the subject is identified as being in need of EGFR inhibition for the treatment of cancer, comprising administering to the subject an effective amount of a bifunctional compound disclosed herein, or a pharmaceutically acceptable salt, hydrate, solvate, prodrug, stereoisomer, or tautomer thereof.

In certain embodiments, the subject identified as being in need of EGFR inhibition is resistant to a known EGFR inhibitor, including but not limited to, gefitinib or erlotinib. In certain embodiments, a diagnostic test is performed to determine if the subject has an activating mutation in EGFR. In certain embodiments, a diagnostic test is performed to determine if the subject has an EGFR harboring an activating and a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, PCR, RT-PCR, or similar analysis techniques known to those of skill in the art that can detect nucleotide sequences.

In another aspect, the application provides a method of treating or preventing cancer, wherein the cancer cell comprises an activated ERBB2, comprising administering to a subject in need thereof an effective amount of a bifunctional compound disclosed herein, or a pharmaceutically acceptable salt, hydrate, solvate, prodrug, stereoisomer, or tautomer thereof. In certain embodiments, the ERBB2 activation is selected from mutation of ERBB2, expression of ERBB2, and amplification of ERBB2. In further embodiments, the mutation is a mutation in exon 20 of ERBB2.

In another aspect, the application provides a method of treating cancer in a subject, wherein the subject is identified as being in need of ERBB2 inhibition for the treatment of cancer, comprising administering to the subject in need thereof an effective amount of a bifunctional compound disclosed herein, or a pharmaceutically acceptable salt, hydrate, solvate, prodrug, stereoisomer, or tautomer thereof.

Another aspect of the application provides a method of preventing resistance to a known EGFR inhibitor, including but not limited to, gefitinib or erlotinib in a disease, comprising administering to a subject in need thereof an effective amount of a bifunctional compound disclosed herein, or a pharmaceutically acceptable salt, hydrate, solvate, prodrug, stereoisomer, or tautomer thereof.

In certain embodiments, the application provides a method of treating any of the disorders described herein, wherein the subject is a human. In certain embodiments, the application provides a method of preventing any of the disorders described herein, wherein the subject is a human.

In another aspect, the application provides a bifunctional compound disclosed herein, or a pharmaceutically acceptable salt, hydrate, solvate, prodrug, stereoisomer, or tautomer thereof, for use in the manufacture of a medicament for treating or preventing a disease in which EGFR plays a role.

In still another aspect, the application provides the a bifunctional compound of the application, or a pharmaceutically acceptable salt, hydrate, solvate, prodrug, stereoisomer, or tautomer thereof, or a pharmaceutical composition of the application for use in the treatment or prevention of a disease in which EGFR plays a role.

The bifunctional compounds and compositions of this application are particularly useful for treating or lessening the severity of a disease, condition, or disorder where a protein kinase is implicated in the disease, condition, or disorder. In one aspect, the present application provides a method for treating or lessening the severity of a disease, condition, or disorder where a protein kinase is implicated in the disease state. In another aspect, the present application provides a method for treating or lessening the severity of a kinase disease, condition, or disorder where inhibition of enzymatic activity is implicated in the treatment of the disease. In another aspect, this application provides a method for treating or lessening the severity of a disease, condition, or disorder with bifunctional compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this application provides bifunctional compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject bifunctional compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the bifunctional compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more bifunctional compounds of the application in the manufacture of a medicament for the treatment of cancer, including without limitation the various types of cancer disclosed herein.

In some embodiments, the bifunctional compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the bifunctional compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject bifunctional compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

Another aspect of this application provides a method for the treatment or lessening the severity of a disease selected from a proliferative or hyperproliferative disease, or a neurodegenerative disease, comprising administering an effective amount of a bifunctional compound, or a pharmaceutically acceptable composition comprising a bifunctional compound, to a subject in need thereof. In other embodiments, the method further comprises administering a second agent wherein said second agent prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

The bifunctional compounds and compositions of this application are also useful in biological samples. One aspect of the application is inhibiting protein kinase activity in a biological sample, which method comprises contacting said biological sample with a bifunctional compound of the application or a composition comprising said bifunctional compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this application includes the study of Her kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the bifunctional compounds and compositions of the present application as Her kinase modulators (e.g., capable of modulating or decreasing the amount of Her kinase) may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this application as an inhibitor of various kinases are set forth in the Examples below.

In accordance with the foregoing, the present application further provides a method for preventing or treating any of the diseases or disorders described above in a subject in need of such treatment, which method comprises administering to said subject a therapeutically effective amount of a bifunctional compound of the application, or a pharmaceutically acceptable salt, hydrate, solvate, prodrug, stereoisomer, or tautomer thereof, and optionally a second agent wherein said second agent prevents EGFR dimer formation. For any of the above uses, the required dosage will vary depending on the mode of administration, the particular condition to be treated and the effect desired.

Pharmaceutical Compositions

In another aspect, the application provides a pharmaceutical composition comprising a therapeutically effective amount of a bifunctional compound of the present application or an enantiomer, diastereomer, stereoisomer, or pharmaceutically acceptable salt thereof, and a pharmaceutically acceptable carrier.

Bifunctional compounds of the application can be administered as pharmaceutical compositions by any conventional route, in particular enterally, e.g., orally, e.g., in the form of tablets or capsules, or parenterally, e.g., in the form of injectable solutions or suspensions, or topically, e.g., in the form of lotions, gels, ointments or creams, or in a nasal or suppository form. Pharmaceutical compositions comprising a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds and compositions of the application can be administered in therapeutically effective amounts in a combinational therapy with one or more therapeutic agents (pharmaceutical combinations) or modalities, e.g., a second agent wherein the second agent modulates (e.g., inhibits) one or more other EGFR and/or other anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth. Compounds and compositions of the application can be administered in therapeutically effective amounts in a combinational therapy with one or more therapeutic agents (pharmaceutical combinations) or modalities, e.g., a second agent wherein said second agent prevents EGFR dimer formation, non-drug therapies, etc. For example, synergistic effects can occur with agents that prevents EGFR dimer formation, other anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with one or more other biologically active ingredients (such as, but not limited to, a second agent wherein said second agent prevents EGFR dimer formation, a second and different antineoplastic agent, a second EGFR inhibitor) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In one aspect of the application, the compounds may be administered in combination with one or more agents that prevent EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In another aspect of the application, the compounds may be administered in combination with one or more separate pharmaceutical agents, e.g., a chemotherapeutic agent, an immunotherapeutic agent, or an adjunctive therapeutic agent. In one embodiment, the chemotherapeutic agent reduces or inhibits the binding of ATP with EGFR (e.g., gefitinib, erlotinib, AZD9291, CO-1686 or WZ4002).

EXAMPLES

Analytical Methods, Materials, and Instrumentation

All reactions were monitored by Waters Acquity UPLC/MS system (Waters PDA eX Detector, QDa Detector, Sample manager—FL, Binary Solvent Manager) using Acquity UPLC® BEH C18 column (2.1×50 mm, 1.7 m particle size): solvent gradient=90% A at 0 min, 1% A at 1.8 min; solvent A=0.1% formic acid in Water; solvent B=0.1% formic acid in Acetonitrile; flow rate: 0.6 mL/min. Reaction products were purified by flash column chromatography using CombiFlash®Rf with Teledyne Isco RediSep®Rf High Performance Gold or Silicycle SiliaSep™ High Performance columns (4 g, 12 g, 24 g, 40 g, or 80 g), Waters HPLC system using SunFire™ Prep C18 column (19×100 mm, 5 m particle size): solvent gradient=80% A at 0 min, 5% A at 25 min; solvent A=0.035% TFA in Water; solvent B=0.035% TFA in MeOH; flow rate: 25 mL/min (Method A), and Waters Acquity UPLC/MS system (Waters PDA eλ Detector, QDa Detector, Sample manager—FL, Binary Solvent Manager) using Acquity UPLC® BEH C18 column (2.1×50 mm, 1.7 μm particle size): solvent gradient=80% A at 0 min, 5% A at 2 min; solvent A=0.1% formic acid in Water; solvent B=0.1% formic acid in Acetonitrile; flow rate: 0.6 mL/min (method B). The purity of all compounds was over 95% and was analyzed with Waters LC/MS system. $^1$H NMR was obtained using a 500 MHz Bruker Avance III. Chemical shifts are reported relative to dimethyl sulfoxide (δ=2.50) for $^1$H NMR. Data are reported as (br=broad, s=singlet, d=doublet, t=triplet, q=quartet, m=multiplet).

Abbreviations used in the following examples and elsewhere herein are:
atm atmosphere
br broad DCM dichloromethane
DIEA N,N-diisopropylethylamine
DMA N,N-dimethylacetamide
DMF N,N-dimethylformamide
DMSO dimethyl sulfoxide
EDCI 1-ethyl-3-(3-dimethylaminopropyl) carbodiimide
ESI electrospray ionization
EtOAc ethyl acetate
HCl hydrochloric acid
h hour(s)
HATU bis(dimethylamino)methylene]-1H-1,2,3-triazolo[4,5-b]pyridinium 3-oxide hexafluoro-phosphate
HPLC high-performance liquid chromatography
LCMS liquid chromatography-mass spectrometry
m multiplet
MeOH methanol
MHz megahertz
min minutes
MS mass spectrometry
NMR nuclear magnetic resonance
$Pd_2(dba)_3$ tris(dibenzylideneacetone)dipalladium (0)
ppm parts per million
TBAF tetra-n-butylammonium fluoride
THF tetrahydrofuran
TLC thin layer chromatography
Xphos 2-dicyclohexylphosphino-2',4',6'-triisopropylbiphenyl Example 1: Synthesis of 2-(1-Oxo-5-phenylisoindolin-2-yl)-2-phenyl-N-(thiazol-2-yl)acetamide 2-(1-oxo-6-(4-(piperazin-1-yl)phenyl)isoindolin-2-yl)-2-phenyl-N-(thiazol-2-yl)acetamide (2-6)

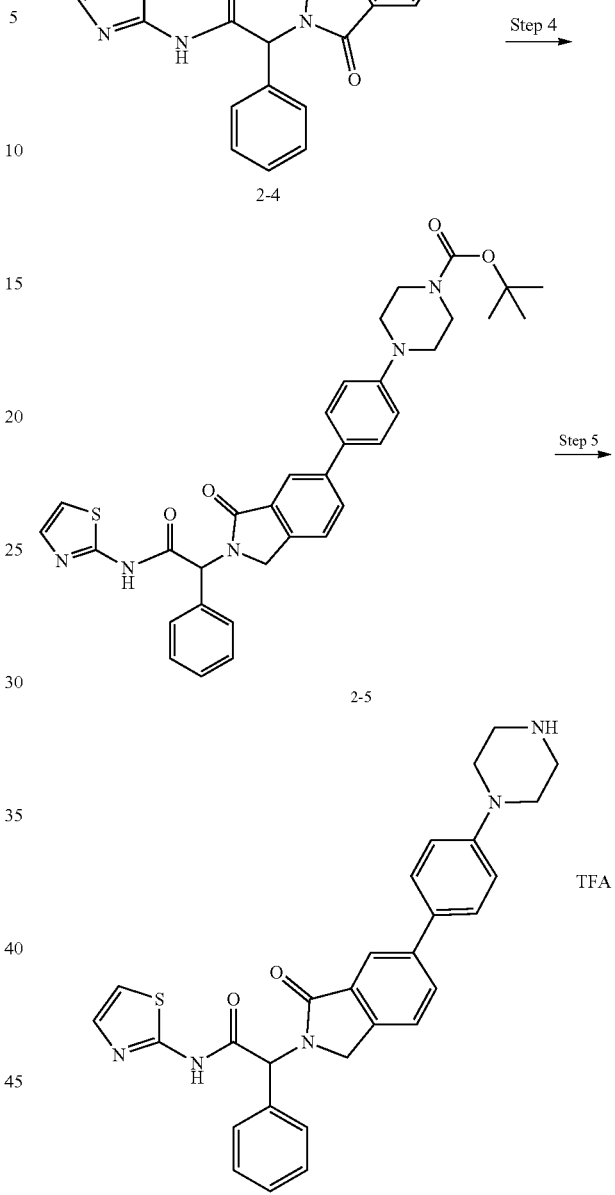

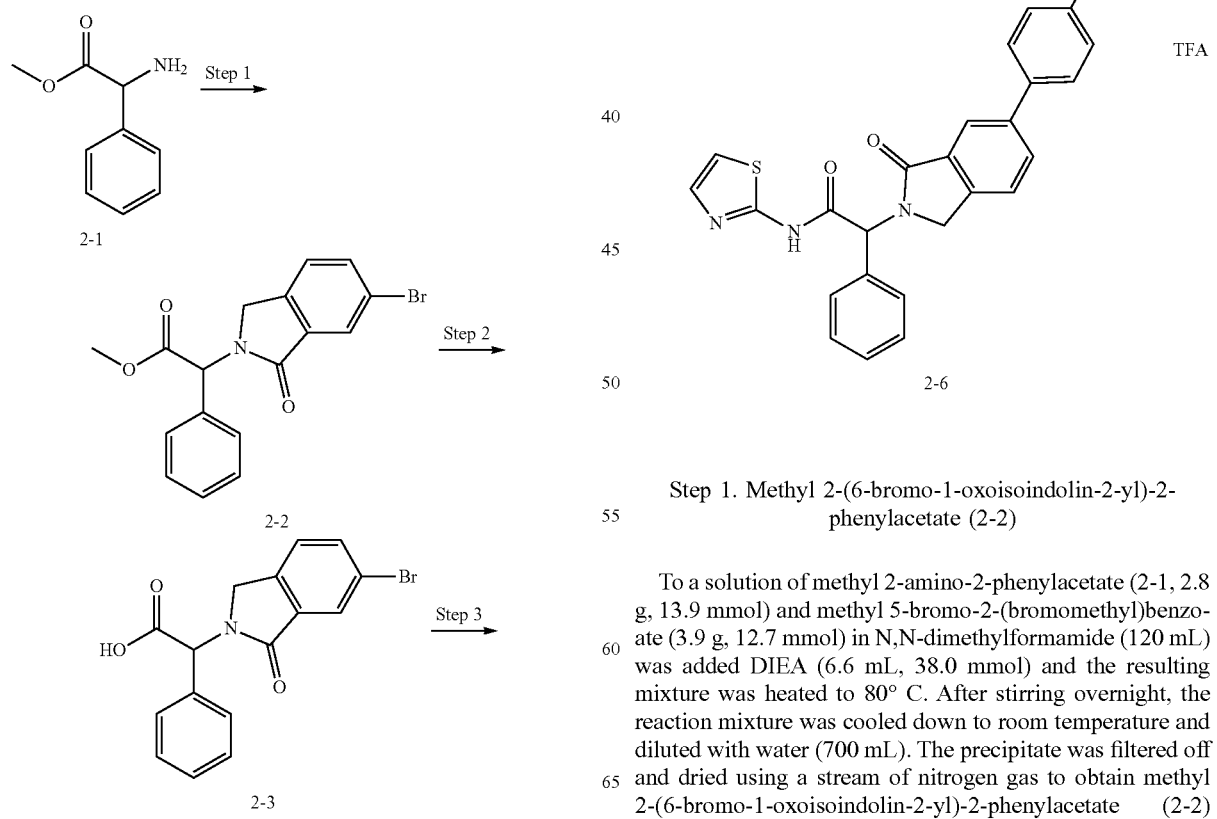

Step 1. Methyl 2-(6-bromo-1-oxoisoindolin-2-yl)-2-phenylacetate (2-2)

To a solution of methyl 2-amino-2-phenylacetate (2-1, 2.8 g, 13.9 mmol) and methyl 5-bromo-2-(bromomethyl)benzoate (3.9 g, 12.7 mmol) in N,N-dimethylformamide (120 mL) was added DIEA (6.6 mL, 38.0 mmol) and the resulting mixture was heated to 80° C. After stirring overnight, the reaction mixture was cooled down to room temperature and diluted with water (700 mL). The precipitate was filtered off and dried using a stream of nitrogen gas to obtain methyl 2-(6-bromo-1-oxoisoindolin-2-yl)-2-phenylacetate (2-2) (3.2 g, 70%) as an off-white solid.

Step 2. 2-(6-Bromo-1-oxoisoindolin-2-yl)-2-phenylacetic Acid (2-3)

To a solution of methyl 2-(6-bromo-1-oxoisoindolin-2-yl)-2-phenylacetate (2-2, 3.2 g, 8.89 mmol) in THF/MeOH/water (150 mL, 1:1:1) was added lithium hydroxide monohydrate (2.65 g, 63.3 mmol). After stirring for 1 h, the solvent was removed under reduced pressure and the resulting residue was diluted with ice water. The aqueous mixture was acidified with concentrated HCl and the resulting suspension isolated via filtration. The solid was dried using a stream of nitrogen gas to obtain 2-(6-bromo-1-oxoisoindolin-2-yl)-2-phenylacetic acid (2-3) (2.8 g, 92%) as an off-white solid.

Step 3. 2-(6-Bromo-1-oxoisoindolin-2-yl)-2-phenyl-N-(thiazol-2-yl)acetamide (2-4)

To a solution of methyl 2-(6-bromo-1-oxoisoindolin-2-yl)-2-phenylacetic acid (2-3, 2.0 g, 5.78 mmol), thiazol-2-amine (1.1 g, 11.6 mmol), and HATU (4.4 g, 11.6 mmol) in N,N-dimethylformamide (30 mL) was added DIEA (4.0 mL, 23.1 mmol). After stirring for 6 hr, the reaction mixture was diluted with EtOAc and washed with water five times. The organic layer was dried over sodium sulfate, filtered, concentrated under reduced pressure and purified by column chromatography on silica gel (DCM:EtOAc=9:1 to 4:6) to obtain 2-(6-bromo-1-oxoisoindolin-2-yl)-2-phenyl-N-(thiazol-2-yl)acetamide (2-4, 1.8 g, 73%) as an off-white solid.

Step 4. tert-Butyl 4-(4-(3-oxo-2-(2-oxo-1-phenyl-2-(thiazol-2-ylamino)ethyl)isoindolin-5-yl)phenyl)piperazine-1-carboxylate (2-5)

A mixture of 2-(6-bromo-1-oxoisoindolin-2-yl)-2-phenyl-N-(thiazol-2-yl)acetamide (50 mg, 0.117 mmol), (4-(4-(tert-butoxycarbonyl)piperazin-1-yl)phenyl)boronic acid (21 mg, 0.175 mmol) and 2 N Sodium carbonate (0.18 mL, 0.351 mmol) in dioxane (1 mL) was degassed and heated to 100° C. PdCl$_2$(dppf)$_2$ (5 mg, 0.007 mmol) and Xphos (4.5 mg, 0.011 mmol) were then added and the resulting reaction mixture was stirred for 2 hr. The reaction mixture was then cooled down to room temperature and diluted with dichloromethane. The resulting mixture was washed with water and brine, dried over sodium sulfate, filtered, and concentrated under reduced pressure. The resulting residue was purified by preparative high performance liquid chromatography (HPLC) to provide tert-butyl 4-(4-(3-oxo-2-(2-oxo-1-phenyl-2-(thiazol-2-ylamino)ethyl)isoindolin-5-yl)phenyl)piperazine-1-carboxylate (2-5, 25 mg, 50%) as a white solid.

Step 5. 2-(1-Oxo-5-phenylisoindolin-2-yl)-2-phenyl-N-(thiazol-2-yl)acetamide trifluoroacetic Acid Salt (2-6)

To a solution of tert-butyl 4-(4-(3-oxo-2-(2-oxo-1-phenyl-2-(thiazol-2-ylamino) ethyl)isoindolin-5-yl)phenyl)piperazine-1-carboxylate (2-5, 25 mg, 0.058 mmol) in DCM (1.0 mL) was added trifluoroacetic acid (0.2 mL). The resulting solution was stirred for 1 hr and then concentrated under reduced pressure. The resulting residue was purified by preparative high performance liquid chromatography (HPLC) to provide 2-6. $^1$H NMR 600 MHz (DMSO-d$_6$) δ 12.69 (bs, NH), 7.89 (d, J=1.3 Hz, 1H), 7.86 (dd, J=8.0, 1.7 Hz, 1H), 7.65 (d, J=8.9 Hz, 2H), 7.60 (d, J=8.0 Hz, 1H), 7.49-7.45 (m, 3H), 7.44-7.40 (m, 1H), 7.39-7.36 (m, 2H), 7.27 (d, J=3.5 Hz, 1H), 7.09 (d, J=8.9 Hz, 2H), 6.31 (s, 1H), 4.76 (d, J=17.5 Hz, 1H), 3.99 (d, J=17.6 Hz, 1H), 3.42-3.39 (m, 4H), 3.25 (s, 4H). MS m/z: 510.28 [M+1].

Example 2: Synthesis of 2-(2-(((tert-Butyldimethylsilyl)oxy)-5-fluorophenyl)-2-(1-oxo-6-(4-(piperazin-1-yl)phenyl)isoindolin-2-yl)-N-(thiazol-2-yl)acetamide (2-13)

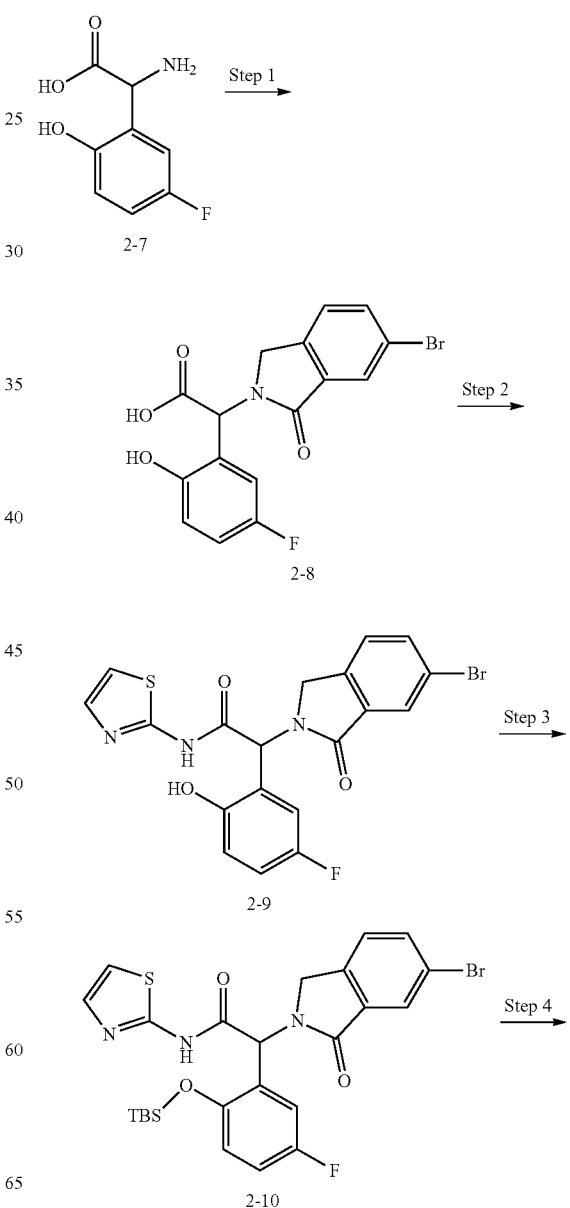

-continued

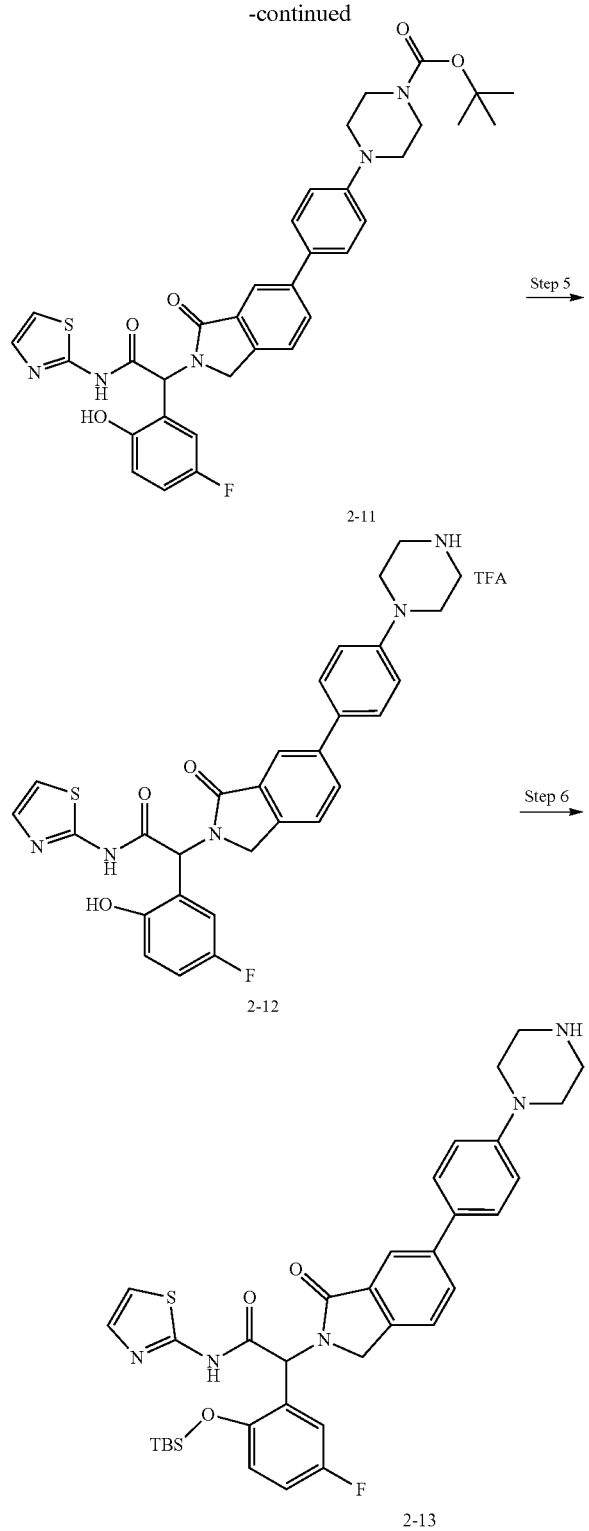

Step 1. 2-(6-Bromo-1-oxoisoindolin-2-yl)-2-(5-fluoro-2-hydroxyphenyl)acetic Acid (2-8)

To a solution of 2-amino-2-(5-fluoro-2-hydroxyphenyl) acetic acid (2-7) (250 mg, 1.13 mmol) and methyl 5-bromo-2-(bromomethyl)benzoate (331 mg, 1.07 mmol) in dioxane (5 mL) was added DIEA (0.49 mL, 2.83 mmol) and the resulting mixture was stirred at 0° C. for 2 hr and then at room temperature for 2 hr. The reaction mixture was then warmed to 30° C. and stirred for an additional 4 hr at 30° C. The mixture was cooled down to 0° C. and diluted with EtOAc. The resulting solution was washed with 1 N HCl solution and brine and the organic layer was dried over $Na_2SO_4$, filtered, and concentrated under reduced pressure to obtain 2-(6-bromo-1-oxoisoindolin-2-yl)-2-(5-fluoro-2-hydroxyphenyl)acetic acid (2-8) which was used in the next step without further purification.

Step 2. 2-(6-Bromo-1-oxoisoindolin-2-yl)-2-(5-fluoro-2-hydroxyphenyl)-N-(thiazol-2-yl)acetamide (2-9)

To a solution of 2-(6-bromo-1-oxoisoindolin-2-yl)-2-(5-fluoro-2-hydroxyphenyl)acetic acid (2-8) in DCM (15 mL) was added N-(thiazol-2-yl)-1H-imidazole-1-carboxamide (300 mg, 1.70 mmol) (N-(thiazol-2-yl)-1H-imidazole-1-carboxamide was synthesized by following the analogous method which was reported in Angew. Chem. Int. Ed. 2014, 5389-5393). After stirring for overnight, the reaction mixture was filtered and the resulting filtrate was concentrated under reduced pressure. The residue was purified by flash column chromatography (Hexane/EtOAc=70:30 to 50:50) to afford 2-(6-bromo-1-oxoisoindolin-2-yl)-2-(5-fluoro-2-hydroxyphenyl)-N-(thiazol-2-yl)acetamide (2-9) as an off-white solid. (430 mg, 50%)

Step 3. 2-(6-Bromo-1-oxoisoindolin-2-yl)-2-(2-((tert-butyldimethylsilyl)oxy)-5-fluorophenyl)-N-(thiazol-2-yl)acetamide (2-10)

To a solution of 2-(6-bromo-1-oxoisoindolin-2-yl)-2-(5-fluoro-2-hydroxyphenyl)-N-(thiazol-2-yl)acetamide (2-9) (250 mg, 0.54 mmol) in $CH_2Cl_2$ (5 mL) was added TBSCl (98 mg, 0.65 mmol) and imidazole (55 mg, 0.81 mmol). After stirring for 6 hr, the reaction mixture was diluted with $CH_2Cl_2$ and washed with water and brine. The organic layer was dried over sodium sulfate, filtered, concentrated under reduced pressure and purified by column chromatography on silica gel (DCM:MeOH=10:0 to 8:2) to obtain 2-(6-bromo-1-oxoisoindolin-2-yl)-2-(2-((tert-butyldimethylsilyl)oxy)-5-fluorophenyl)-N-(thiazol-2-yl)acetamide (2-10) (296 mg, 95%).

Step 4. tert-Butyl 4-(4-(2-(1-(5-fluoro-2-hydroxyphenyl)-2-oxo-2-(thiazol-2-ylamino)ethyl)-3-oxoisoindolin-5-yl)phenyl)piperazine-1-carboxylate (2-11)

A mixture of 2-(6-bromo-1-oxoisoindolin-2-yl)-2-(2-((tert-butyldimethylsilyl)oxy)-5-fluorophenyl)-N-(thiazol-2-yl)acetamide (2-10) (380 mg, 0.66 mmol), tert-butyl 4-(4-(4,4,5,5-tetramethyl-1,3,2-dioxaborolan-2-yl)phenyl)piperazine-1-carboxylate (333 mg, 0.857 mmol) and 2 M sodium carbonate (1.32 mL, 2.64 mmol) in dioxane (7 mL) was degassed and heated to 100° C. $PdCl_2(dppf)_2$ (48 mg, 0.066 mmol) and Xphos (47 mg, 0.099 mmol) were then added and the resulting reaction mixture was stirred for 2 hr. The reaction mixture was then cooled down to room temperature and diluted with dichloromethane. The organic layer was washed with water and brine, dried over sodium sulfate, filtered, and concentrated under reduced pressure. The resulting residue was purified by preparative high performance liquid chromatography (HPLC) to provide tert-butyl 4-(4-(2-(1-(5-fluoro-2-hydroxyphenyl)-2-oxo-2-(thiazol-2-ylamino)ethyl)-3-oxoisoindolin-5-yl)phenyl)piperazine-1-carboxylate (2-11) (42 mg, 10%).

Step 5. 2-(5-Fluoro-2-hydroxyphenyl)-2-(1-oxo-6-(4-(piperazin-1-yl)phenyl)isoindolin-2-yl)-N-(thiazol-2-yl)acetamide trifluoroacetic Acid Salt (2-12)

To a solution of tert-butyl 4-(4-(2-(1-(5-fluoro-2-hydroxyphenyl)-2-oxo-2-(thiazol-2-ylamino)ethyl)-3-oxoisoindolin-5-yl)phenyl)piperazine-1-carboxylate (2-11) in DCM (0.8 mL) was added trifluoroacetic acid (0.2 mL). The resulting solution was stirred for 2 hr and then concentrated under reduced pressure. The resulting residue was concentrated under reduced pressure to give 2-(5-fluoro-2-hydroxyphenyl)-2-(1-oxo-6-(4-(piperazin-1-yl)phenyl)isoindolin-2-yl)-N-(thiazol-2-yl)acetamide trifluoroacetic acid salt (2-12) which was used without further purification.

Step 6. 2-(2-((tert-Butyldimethylsilyl)oxy)-5-fluorophenyl)-2-(1-oxo-6-(4-(piperazin-1-yl)phenyl)isoindolin-2-yl)-N-(thiazol-2-yl)acetamide (2-13)

2-(2-((tert-butyldimethyl silyl)oxy)-5-fluorophenyl)-2-(1-oxo-6-(4-(piperazin-1-yl)phenyl)isoindolin-2-yl)-N-(thiazol-2-yl)acetamide was synthesized by following the analogous procedure of Example 2, Step 3 above (145 mg, 80%).

Example 3: Synthesis of 2-(6-(4-(4-(3-(2-(2-(2-((2-(2,6-Dioxopiperidin-3-yl)-1,3-dioxoisoindolin-4-yl)amino)ethoxy)ethoxy)ethoxy)propanoyl)piperazin-1-yl)phenyl)-1-oxoisoindolin-2-yl)-2-phenyl-N-(thiazol-2-yl)acetamide (I-1)

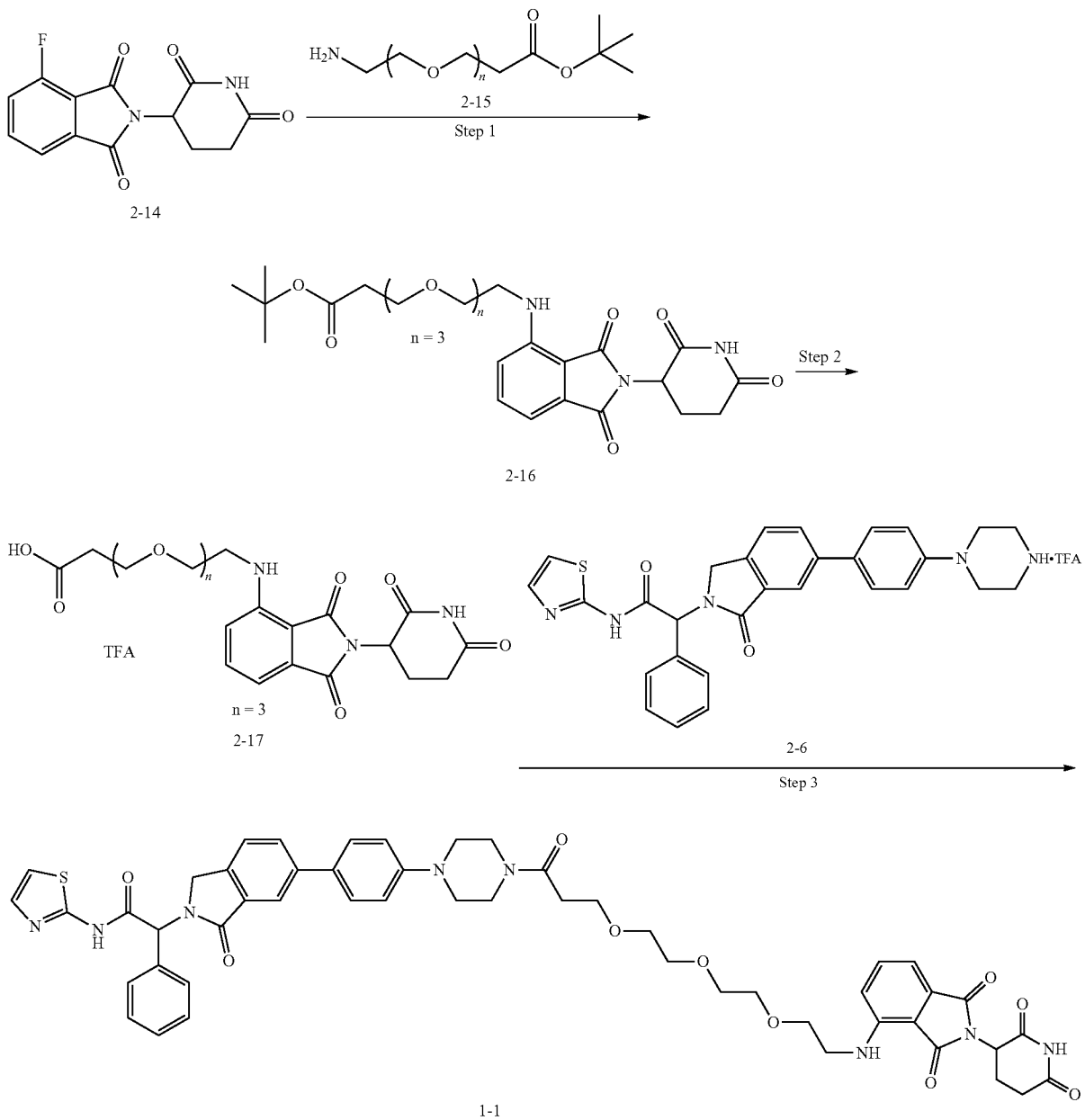

Step 1: tert-Butyl 3-(2-(2-(2-((2-(2,6-dioxopiperidin-3-yl)-1,3-dioxoisoindolin-4-yl)amino)ethoxy)ethoxy)ethoxy)propanoate (2-16)

A solution of 2-14 (280 mg, 1.01 mmol), tert-butyl 3-(2-(2-(2-aminoethoxy)ethoxy) ethoxy)propanoate (2-15 where n=3, 337 mg, 1.22 mmol) and DIEA (0.7 mL, 4.04 mmol) in DMF (5 mL) was stirred at 80° C. for overnight. The resulting mixture was diluted with EtOAc and washed with water five times. The organic layer was dried over $Na_2SO_4$, filtered, and concentrated under reduced pressure. The resulting residue was purified by flash column chromatography (DCM/EtOAc=90:10 to 50:50) to afford 2-16 where n=3.

Step 2: 3-(2-(2-(2-((2-(2,6-Dioxopiperidin-3-yl)-1,3-dioxoisoindolin-4-yl)amino)ethoxy)ethoxy)ethoxy)propanoic acid trifluoroacetic Acid Salt (2-17)

To a solution of 2-16 (n=3, 100 mg, 0.19 mmol) in DCM (1.6 mL) was added trifluoroacetic acid (0.4 mL). The resulting solution was stirred for 1 hr and then concentrated under reduced pressure. The resulting residue was purified by flash column chromatography (DCM/MeOH=100:0 to 80:20) to afford 2-17 where n=3.

Step 3: 2-(6-(4-(4-(3-(2-(2-(2-((2-(2,6-Dioxopiperidin-3-yl)-1,3-dioxoisoindolin-4-yl)amino)ethoxy)ethoxy)ethoxy)propanoyl)piperazin-1-yl)phenyl)-1-oxoisoindolin-2-yl)-2-phenyl-N-(thiazol-2-yl) acetamide (I-1)

To a solution of 2-17 (n=3, 50 mg, 0.08 mmol) and 2-6 (56 mg, 0.11 mmol) in DMF (1 mL) were added EDCI (49 mg, 0.25 mmol) and DIEA (59 μL, 0.34 mmol), and the resulting mixture was stirred for 8 hr. The reaction mixture was then diluted with DMSO and purified by preparative HPLC (Method A) to provide desired product I-1 (28 mg, 32%) as a yellow solid. $^1$H NMR 500 MHz (DMSO-$d_6$) δ 12.71 (s, 1H), 11.09 (s, 1H), 7.88 (s, 1H), 7.86 (d, J=7.9 Hz, 1H), 7.65-7.54 (m, 4H), 7.52-7.36 (m, 6H), 7.29 (d, J=3.4 Hz, 1H), 7.12 (d, J=8.5 Hz, 1H), 7.08-6.99 (m, 3H), 6.61-6.56 (m, 1H), 6.34 (s, 1H), 5.06 (dd, J=5.8, 12.8 Hz, 1H), 4.78 (d, J=17.4 Hz, 1H), 4.00 (d, J=17.4 Hz, 1H), 3.70-3.35 (m, 18H), 3.27-3.13 (m, 4H), 2.93-2.82 (m, 1H), 2.66-2.52 (m, 4H), 2.07-1.96 (m, 1H). MS m/z: 969.03 [M+1]$^+$.

Example 4: Synthesis of 2-(6-(4-(4-(1-((2-(2,6-Dioxopiperidin-3-yl)-1,3-dioxoisoindolin-4-yl)amino)-3,6,9,12,15-pentaoxaoctadecan-18-oyl)piperazin-1-yl)phenyl)-1-oxoisoindolin-2-yl)-2-phenyl-N-(thiazol-2-yl)acetamide (I-2)

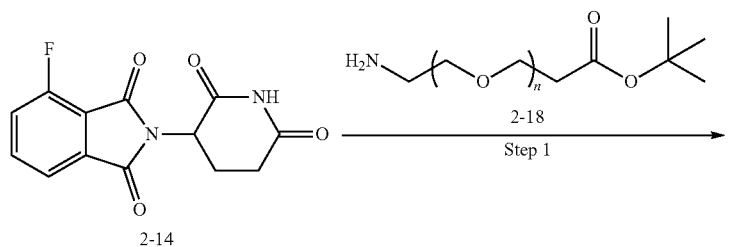

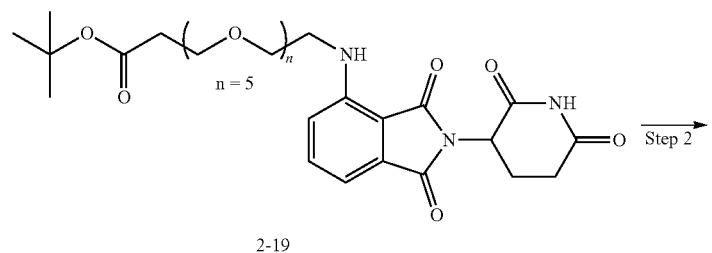

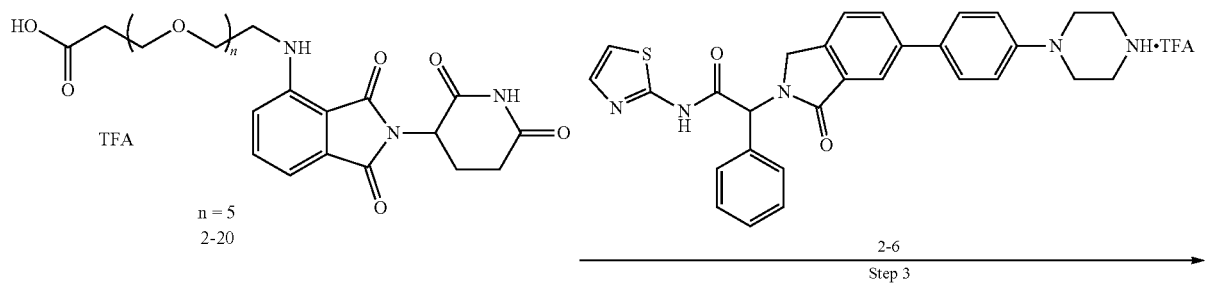

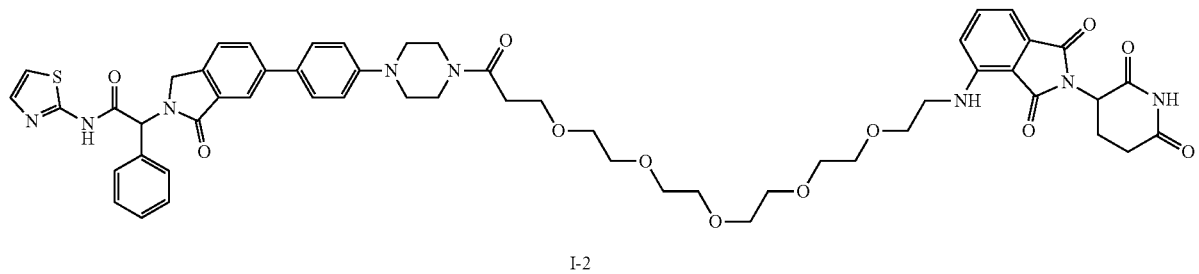

I-2

Step 1: tert-butyl 1-((2-(2,6-Dioxopiperidin-3-yl)-1,3-dioxoisoindolin-4-yl)amino)-3,6,9,12,15-pentaoxaoctadecan-18-oate (2-19)

A solution of 2-14 (280 mg, 1.01 mmol), tert-butyl 1-amino-3,6,9,12,15-pentaoxaoctadecan-18-oate (2-18 where n=5, 337 mg, 1.22 mmol) and DIEA (0.7 mL, 4.04 mmol) in DMF (5 mL) was stirred at 80° C. for overnight. The resulting mixture was diluted with EtOAc and washed with water five times. The organic layer was dried over Na$_2$SO$_4$, filtered, and concentrated under reduced pressure. The resulting residue was purified by flash column chromatography (DCM/EtOAc=90:10 to 50:50) to give 2-19 where n=5.

Step 2: 1-((2-(2,6-Dioxopiperidin-3-yl)-1,3-dioxoisoindolin-4-yl)amino)-3,6,9,12,15-pentaoxaoctadecan-18-oic acid trifluoroacetic Acid Salt (2-20)

To a solution of 2-19 (n=5, 100 mg, 0.19 mmol) in DCM (1.6 mL) was added trifluoroacetic acid (0.4 mL). The resulting solution was stirred for 1 hr and then concentrated under reduced pressure. The resulting residue was purified by flash column chromatography (DCM/MeOH=100:0 to 80:20) to afford 2-20 where n=5.

Step 3: 2-(6-(4-(4-(1-((2-(2,6-Dioxopiperidin-3-yl)-1,3-dioxoisoindolin-4-yl)amino)-3,6,9,12,15-pentaoxaoctadecan-18-oyl)piperazin-1-yl)phenyl)-1-oxoisoindolin-2-yl)-2-phenyl-N-(thiazol-2-yl)acetamide (I-2)

To a solution of 2-20 (50 mg, 0.08 mmol) and 2-6 (56 mg, 0.11 mmol) in DMF (1 mL) were added EDCI (49 mg, 0.25 mmol) and DIEA (59 µL, 0.34 mmol), and the resulting mixture was stirred for 8 hr. The reaction mixture was then diluted with DMSO and purified by preparative HPLC (Method A) to provide desired product I-2 (12 mg, 28%). $^1$H NMR 500 MHz (DMSO-d$_6$) δ 12.70 (s, 1H), 11.09 (s, 1H), 7.88 (s, 1H), 7.85 (d, J=7.6 Hz, 1H), 7.69-7.53 (m, 4H), 7.52-7.34 (m, 6H), 7.28 (s, 1H), 7.13 (d, J=8.2 Hz, 1H), 7.08-7.00 (m, 3H), 6.62-6.56 (m, 1H), 6.32 (s, 1H), 5.09-5.02 (m, 1H), 4.77 (d, J=17.7 Hz, 1H), 3.99 (d, J=17.4 Hz, 1H), 3.74-3.27 (m, 26H), 3.25-3.11 (m, 4H), 2.93-2.81 (m, 1H), 2.67-2.50 (m, 4H), 2.07-1.96 (m, 1H). MS m/z: 1057.05 [M+1]$^+$.

Example 5: Synthesis of 2-(6-(4-(4-(3-(2-(2-(2-((2-(2,6-Dioxopiperidin-3-yl)-1,3-dioxoisoindolin-4-yl)amino)ethoxy)ethoxy)ethoxy)propanoyl)piperazin-1-yl)phenyl)-1-oxoisoindolin-2-yl)-2-(5-fluoro-2-hydroxyphenyl)-N-(thiazol-2-yl)acetamide (I-3)

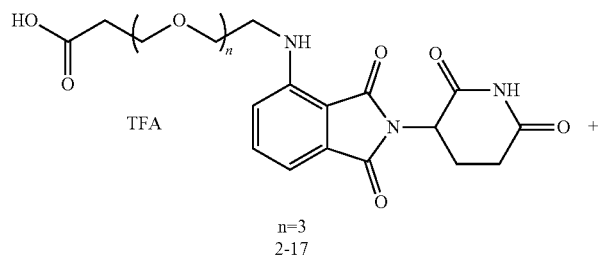

n=3
2-17

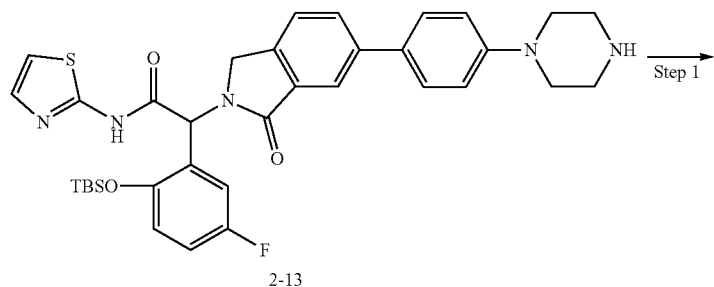

2-13

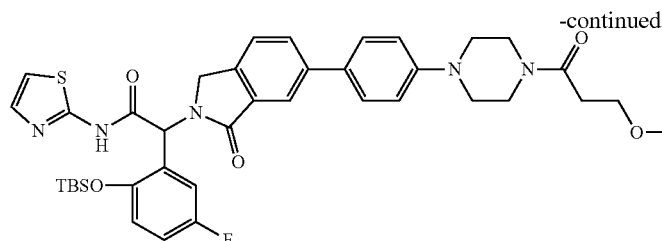

-continued

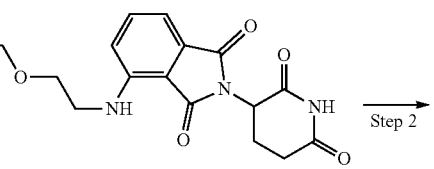

2-21

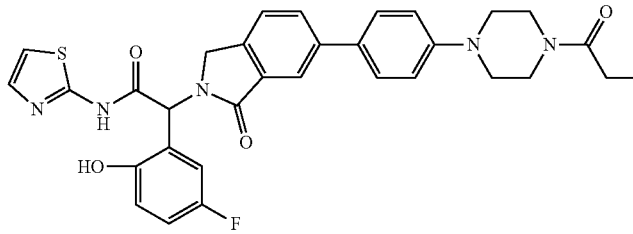

I-3

Step 1: 2-(2-(((tert-Butyldimethylsilyl)oxy)-5-fluorophenyl)-2-(6-(4-(4-(3-(2-(2-(2-((2-(2,6-dioxopiperidin-3-yl)-1,3-dioxoisoindolin-4-yl)amino)ethoxy)ethoxy)ethoxy)propanoyl) piperazin-1-yl)phenyl)-1-oxoisoindolin-2-yl)-N-(thiazol-2-yl)acetamide (2-21)

To a solution of 2-17 (n=3, 158 mg, 0.33 mmol) and 2-13 (180 mg, 0.28 mmol) in DMF (2 mL) were added HATU (160 mg, 0.414 mmol) and DIEA (0.19 mL, 1.10 mmol) at 0° C. The resulting mixture was stirred at room temperature for 6 hr. The reaction mixture was diluted with EtOAc and washed with water and brine. The organic layer was dried over Na$_2$SO$_4$, filtered, and concentrated under reduced pressure. The crude product 2-21 was used to next step without further purification.

Step 2: 2-(6-(4-(4-(3-(2-(2-(2-((2-(2,6-Dioxopiperidin-3-yl)-1,3-dioxoisoindolin-4-yl)amino) ethoxy)ethoxy)ethoxy)propanoyl)piperazin-1-yl)phenyl)-1-oxoisoindolin-2-yl)-2-(5-fluoro-2-hydroxyphenyl)-N-(thiazol-2-yl)acetamide (I-3)

To a solution of crude 2-21 in THF (1 mL) was added 1 M TBAF in THF (1 mL). After being stirred for 1 hr, the resulting mixture was diluted with DMSO and purified by preparative HPLC (Method A) to afford desired product I-3 (28 mg, 10% as two steps) as a yellow solid. $^1$H NMR 500 MHz (DMSO-d$_6$) δ 12.6 (s, 1H), 11.09 (s, 1H), 9.95 (s, 1H), 7.86 (s, 1H), 7.85 (d, J=8.2 Hz, 1H), 7.65-7.52 (m, 4H), 7.49 (d, J=3.4 Hz, 1H), 7.27 (d, J=3.4 Hz, 1H), 7.14-7.09 (m, 2H), 7.07-7.00 (m, 3H), 6.91 (dd, J=4.9, 8.9 Hz, 1H), 6.89 (dd, J=3.1, 9.2 Hz, 1H), 6.58 (t, J=5.5 Hz, 1H), 6.33 (s, 1H), 5.05 (dd, J=5.5, 12.8 Hz, 1H), 4.63 (d, J=17.4 Hz, 1H), 4.00 (d, J=17.3 Hz, 1H), 3.67-3.40 (m, 18H), 3.25-3.12 (m, 4H), 2.93-2.83 (m, 1H), 2.66-2.50 (m, 4H), 2.07-1.95 (m, 1H). MS m/z: 1002.96 [M+1]$^+$.

Example 6: Synthesis of 2-(6-(4-(4-(17-((2-(2,6-Dioxopiperidin-3-yl)-1,3-dioxoisoindolin-4-yl)oxy)-2,16-dioxo-6,9,12-trioxa-3,15-diazaheptadecyl)piperazin-1-yl)phenyl)-1-oxoisoindolin-2-yl)-2-phenyl-N-(thiazol-2-yl)acetamide (I-4)

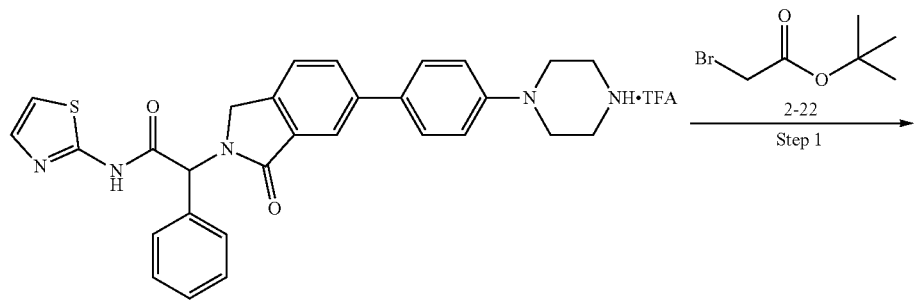

2-6

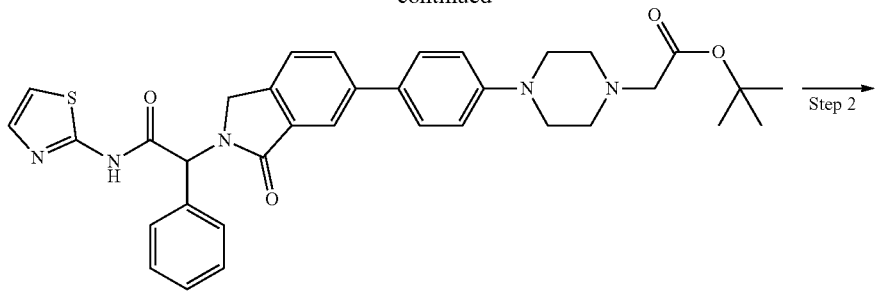

2-23

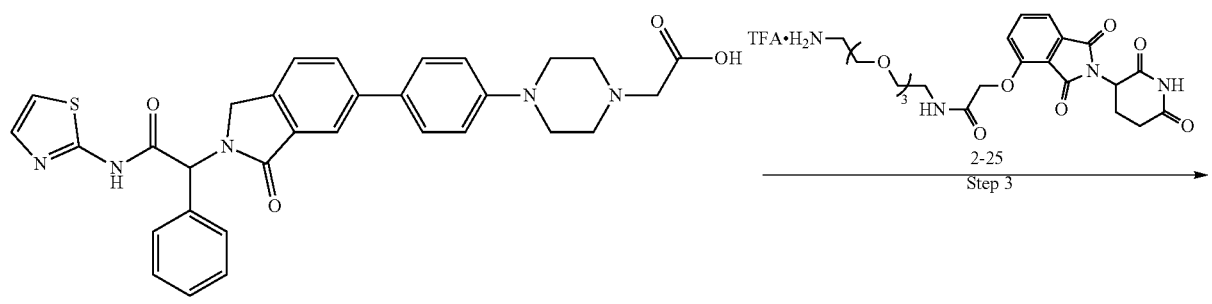

2-24

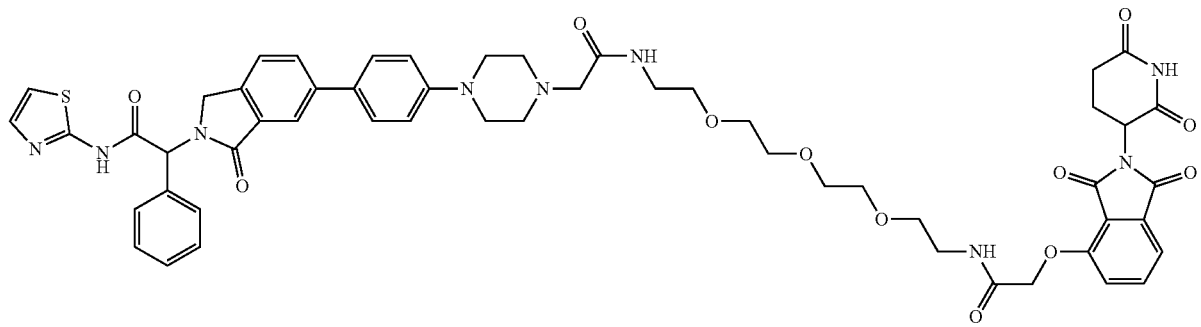

I-4

Step 1: tert-Butyl 2-(4-(4-(3-oxo-2-(2-oxo-1-phenyl-2-(thiazol-2-ylamino)ethyl)isoindolin-5-yl)phenyl)piperazin-1-yl)acetate (2-23)

A solution of 2-6 (300 mg, 0.59 mmol), tert-butyl bromoacetate (2-22, 103 µL, 0.71 mmol), and K$_2$CO$_3$ (244 mg, 1.77 mmol) in DMF (2.5 mL) was stirred at 80° C. for 8 hr. The resulting mixture was then diluted with EtOAc and washed four times with water. The organic layer was dried over Na$_2$SO$_4$, filtered, and concentrated under reduced pressure. The residue was purified by flash column chromatography (DCM/1M NH$_3$ in MeOH=100:0 to 80:20) to give product 2-23.

Step 2: 2-(4-(4-(3-Oxo-2-(2-oxo-1-phenyl-2-(thiazol-2-ylamino)ethyl)isoindolin-5-yl)phenyl)piperazin-1-yl)acetic Acid (2-24)

To a solution of the 2-23 in DCM (4 mL) was added TFA (1 mL) and the resulting mixture was stirred at room temperature. Upon reaction completion, the reaction mixture was concentrated and the crude 2-24 was used to next step without further purification.

Step 3: 2-(6-(4-(4-(17-((2-(2,6-Dioxopiperidin-3-yl)-1,3-dioxoisoindolin-4-yl)oxy)-2,16-dioxo-6,9,12-trioxa-3,15-diazaheptadecyl)piperazin-1-yl)phenyl)-1-oxoisoindolin-2-yl)-2-phenyl-N-(thiazol-2-yl)acetamide (I-4)

To a solution of 2-24 (57 mg, 0.10 mmol) and 2-25 (50 mg, 0.10 mmol) in DMF (1 mL) was added HATU (76 mg, 0.20 mmol), DIEA (122 µL, 0.70 mmol), and the resulting mixture was stirred for 3 hr. The reaction mixture was then diluted with DMSO and purified by preparative HPLC to give desired product I-4 (34 mg, 32%) as an off-white solid. $^1$H NMR 500 MHz (DMSO-d$_6$) δ 12.70 (s, 1H), 11.12 (s, 1H), 10.33-9.95 (br, 1H), 8.77-8.43 (br, 1H), 8.04-7.97 (m, 1H), 7.90 (s, 1H), 7.86 (d, J=7.9 Hz, 1H), 7.81 (t, J=7.9 Hz, 1H), 7.65 (d, J=5.8 Hz, 2H), 7.53-7.36 (m, 8H), 7.28 (d, J=3.1 Hz, 1H), 7.08 (d, J=8.2 Hz, 2H), 6.32 (s, 1H), 5.11 (dd, J=5.2, 12.5 Hz, 1H), 4.81-4.74 (m, 3H), 4.00 (d, J=17.4 Hz, 1H), 3.52 (s, 8H), 3.48-3.44 (m, 4H), 3.44-3.29 (m, 14H), 2.95-2.84 (m, 1H), 2.65-2.50 (m, 2H), 2.08-2.00 (m, 1H). MS m/z: 1055.97 [M+1]$^+$ Example 7: 2-(6-(4-(4-(2-((4-(2-((2-(2,6-Dioxopiperidin-3-yl)-1,3-dioxoisoindolin-4-yl)oxy)acetamido)butyl)amino)-2-oxoethyl)piperazin-1-yl)phenyl)-1-oxoisoindolin-2-yl)-2-phenyl-N-(thiazol-2-yl) acetamide (I-5)

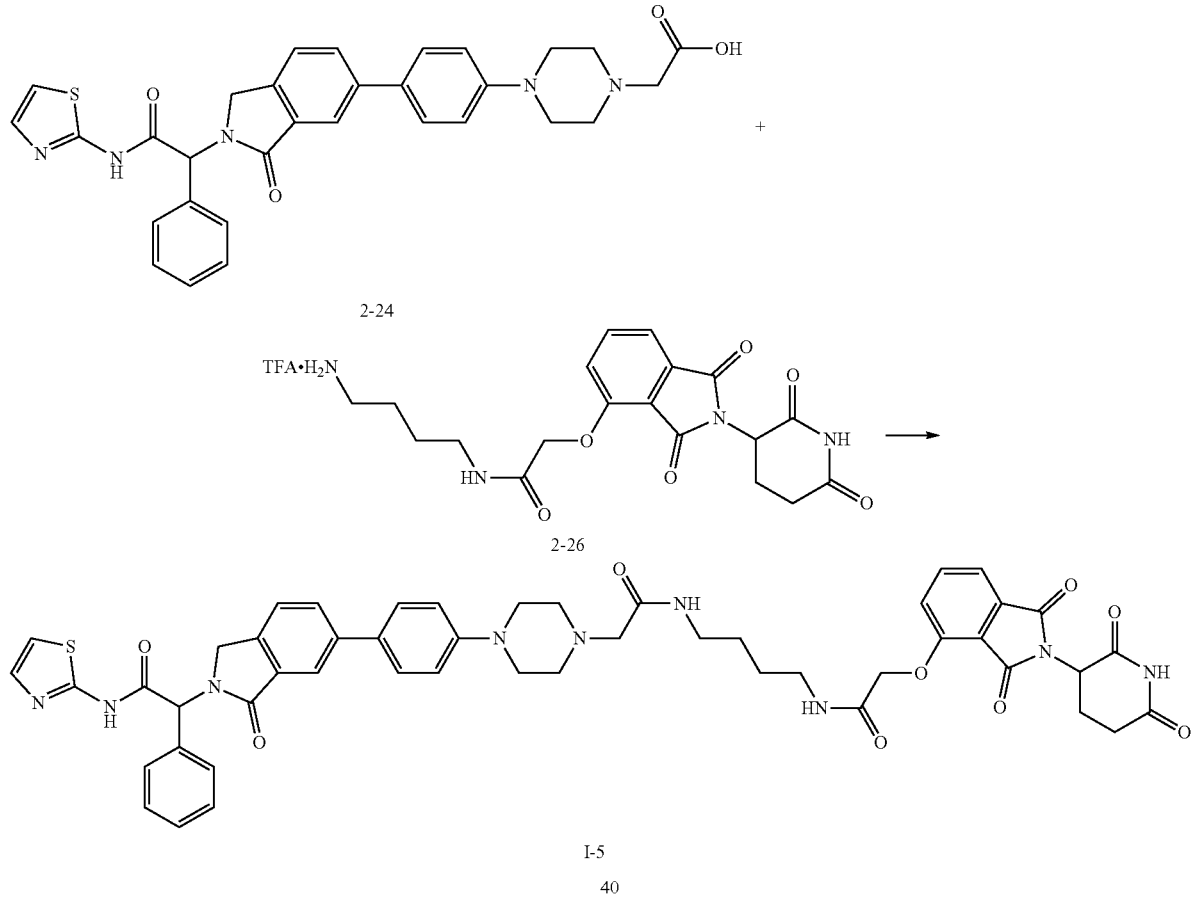

To a solution of 2-24 (57 mg, 0.10 mmol) and 2-26 (50 mg, 0.10 mmol) in DMF (1 mL) was added HATU (76 mg, 0.20 mmol), DIEA (122 μL, 0.70 mmol), and the resulting mixture was stirred for 3 hr. The reaction mixture was then diluted with DMSO and purified by preparative HPLC to give desired product I-5 (14 mg, 28%) as an off-white solid. $^1$H NMR 500 MHz (DMSO-$d_6$) δ 12.71 (s, 1H), 11.12 (s, 1H), 10.39-10.12 (br, 1H), 8.69-8.48 (br, 1H), 8.06-8.01 (m, 1H), 7.91 (s, 1H), 7.88 (d, J=7.9 Hz, 1H), 7.83 (t, J=7.9 Hz, 1H), 7.66 (d, J=8.5 Hz, 2H), 7.62 (d, J=8.5 Hz, 1H), 7.54-7.37 (m, 7H), 7.29 (d, J=3.7 Hz, 1H), 7.09 (d, J=8.9 Hz, 2H), 6.33 (s, 1H), 5.13 (dd, J=5.5, 13.1 Hz, 1H), 4.82-4.75 (m, 3H), 4.01 (d, J=17.7 Hz, 1H), 3.42-3.29 (s, 10H), 3.21-3.12 (m, 4H), 2.95-2.85 (m, 1H), 2.66-2.50 (m, 2H), 2.08-2.00 (m, 1H), 1.47 (br, 4H). MS m/z: 951.96 [M+1]$^+$.

Example 8. (2S,4R)-1-((2S)-3,3-Dimethyl-2-(2-(4-(4-(3-oxo-2-(2-oxo-1-phenyl-2-(thiazol-2-ylamino)ethyl)isoindolin-5-yl)phenyl)piperazin-1-yl)acetamido)butanoyl)-4-hydroxy-N-(4-(4-methylthiazol-5-yl)benzyl)pyrrolidine-2-carboxamide (I-6)

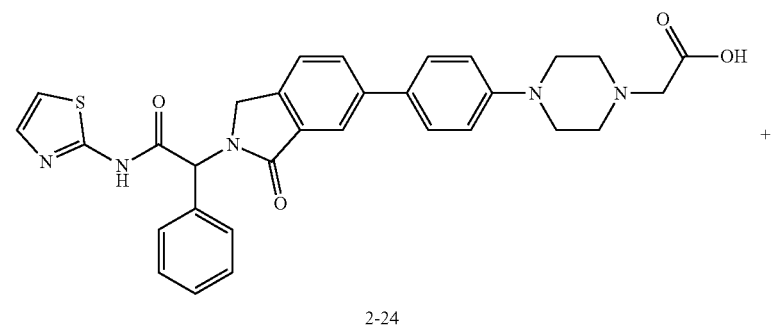

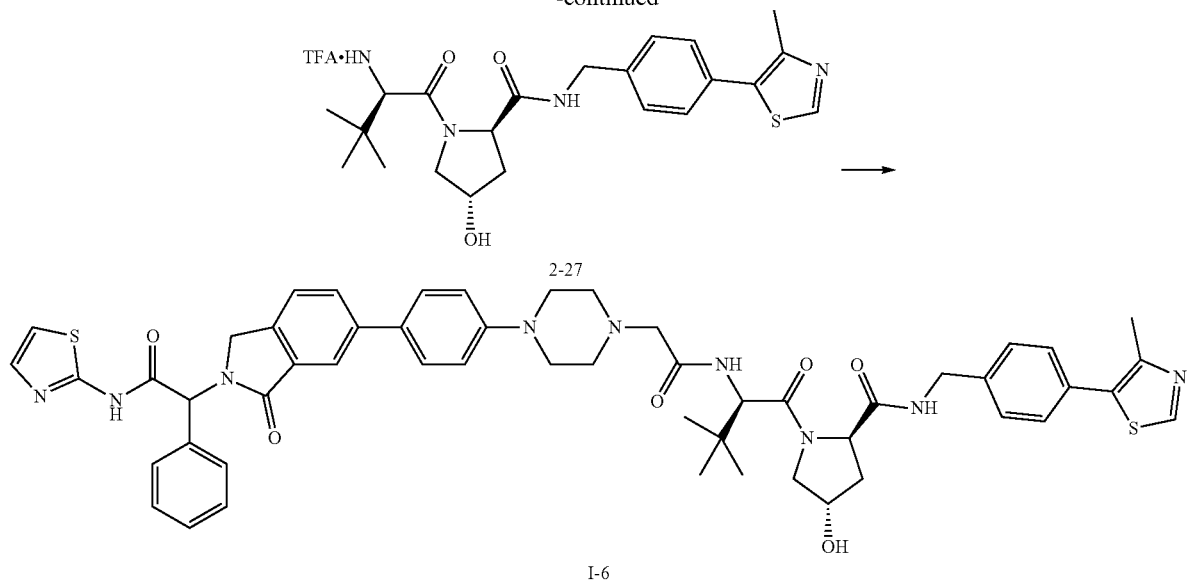

To a solution of 2-24 (1 equiv, based on tert-butyl ester) and 2-27 (24 mg, 0.055 mmol) in CH$_2$Cl$_2$ (1 mL) was added EDCI (21 mg, 0.11 mmol), DIEA (38 µL, 0.22 mmol), and the resulting mixture was stirred for 6 hr. The reaction mixture was concentrated under reduced pressure then diluted with DMSO and purified by preparative HPLC to give desired product I-6 (21 mg, 40%) as an off-white solid. MS m/z: 980.64 [M+1]$^+$.

Example 9. Alternative Synthesis of 2-(6-(4-(4-(3-(2-(2-(2-((2-(2,6-Dioxopiperidin-3-yl)-1,3-dioxoisoindolin-4-yl)amino)ethoxy)ethoxy)ethoxy)propanoyl)piperazin-1-yl)phenyl)-1-oxoisoindolin-2-yl)-2-(5-fluoro-2-hydroxyphenyl)-N-(thiazol-2-yl)acetamide (I-3)

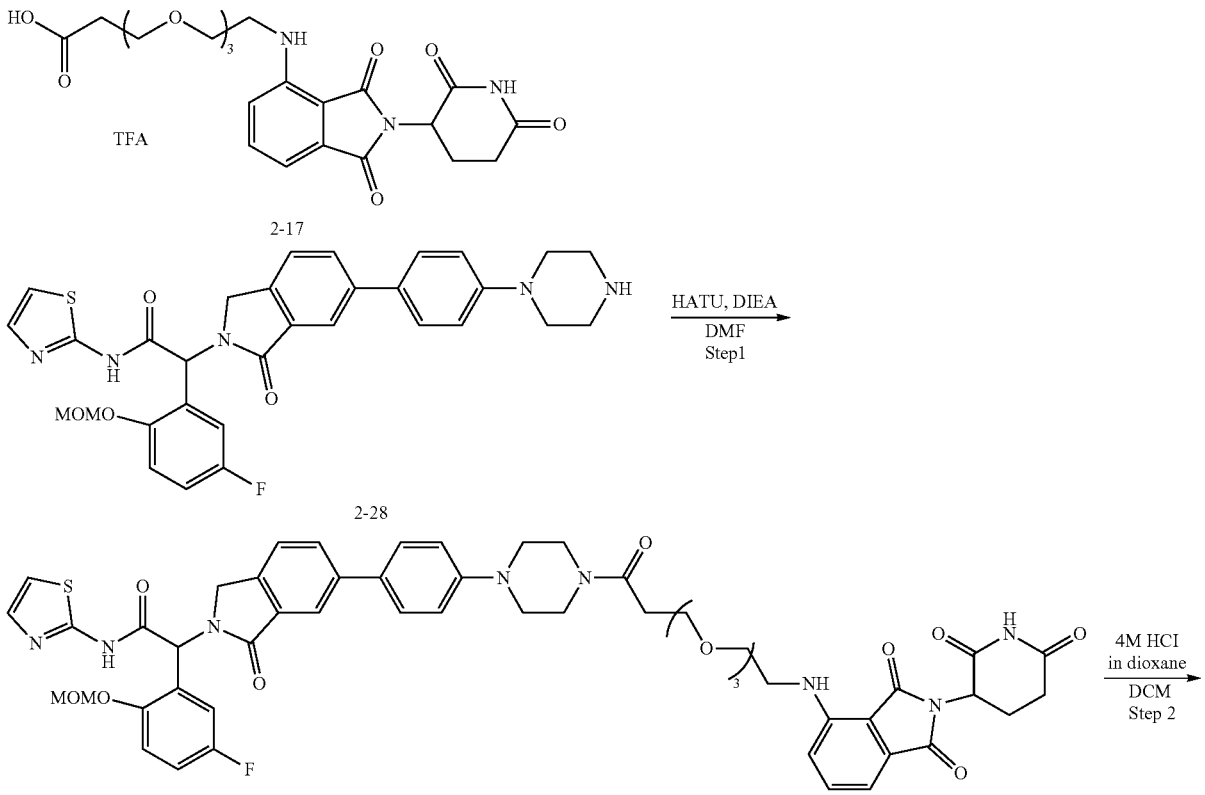

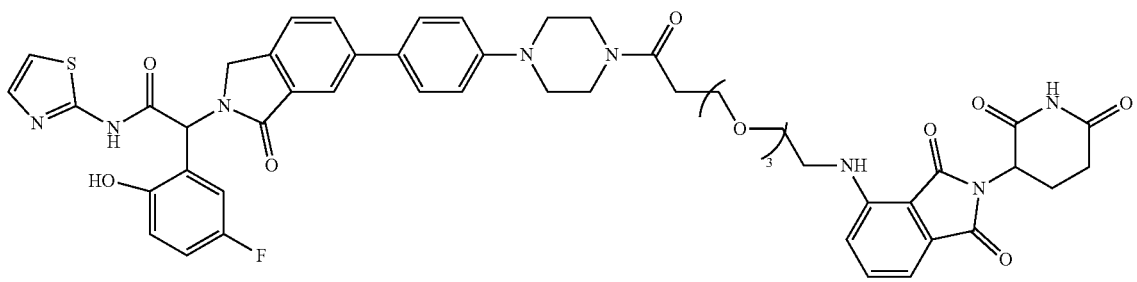

I-3

Step 1: 2-(6-(4-(4-(3-(2-((2-(2,6-Dioxopiperidin-3-yl)-1,3-dioxoisoindolin-4-yl)amino)ethoxy)propanoyl)piperazin-1-yl)phenyl)-1-oxoisoindolin-2-yl)-2-(5-fluoro-2-(methoxymethoxy)phenyl)-N-(thiazol-2-yl)acetamide (2-29)

To a solution of 2-17 (158 mg, 0.33 mmol) and 2-28 (180 mg, 0.28 mmol) in DMF (2 mL) was added HATU (160 mg, 0.414 mmol) and DIEA (0.19 mL, 1.10 mmol) at 0° C. and the resulting mixture was stirred at room temperature for 6 hours. The reaction mixture was diluted with EtOAc and washed with water and brine. The organic layer was dried over Na$_2$SO$_4$, filtered, and concentrated under reduced pressure. The residue was carried forward in the next step without further purification.

Step 2: 2-(6-(4-(4-(3-(2-(2-(2-((2-(2,6-Dioxopiperidin-3-yl)-1,3-dioxoisoindolin-4-yl)amino)ethoxy)ethoxy)ethoxy)propanoyl)piperazin-1-yl)phenyl)-1-oxoisoindolin-2-yl)-2-(5-fluoro-2-hydroxyphenyl)-N-(thiazol-2-yl)acetamide (1-3)

To a solution of crude 2-29 in THF (1 mL) was added 1 M TBAF in THF (1 mL). After stirring for 1 hour, the resulting mixture was diluted with DMSO and purified by preparative HPLC to afford desired product (28 mg, 10% as two steps) as a yellow solid. MS m/z: 1002.96 [M+1]+; $^1$H NMR 500 MHz (DMSO-d$_6$) δ 12.6 (s, 1H), 11.09 (s, 1H), 9.95 (s, 1H), 7.86 (s, 1H), 7.85 (d, J=8.2 Hz, 1H), 7.65-7.52 (m, 4H), 7.49 (d, J=3.4 Hz, 1H), 7.27 (d, J=3.4 Hz, 1H), 7.14-7.09 (m, 2H), 7.07-7.00 (m, 3H), 6.91 (dd, J=4.9, 8.9 Hz, 1H), 6.89 (dd, J=3.1, 9.2 Hz, 1H), 6.58 (t, J=5.5 Hz, 1H), 6.33 (s, 1H), 5.05 (dd, J=5.5, 12.8 Hz, 1H), 4.63 (d, J=17.4 Hz, 1H), 4.00 (d, J=17.3 Hz, 1H), 3.67-3.40 (m, 18H), 3.25-3.12 (m, 4H), 2.93-2.83 (m, 1H), 2.66-2.50 (m, 4H), 2.07-1.95 (m, 1H).

Example 10: Synthesis of 2-(6-(4-(4-(3-(2-(2-((2-(2,6-Dioxopiperidin-3-yl)-1,3-dioxoisoindolin-4-yl)amino)ethoxy)ethoxy)propanoyl)piperazin-1-yl)phenyl)-1-oxoisoindolin-2-yl)-2-phenyl-N-(thiazol-2-yl)acetamide (I-7)

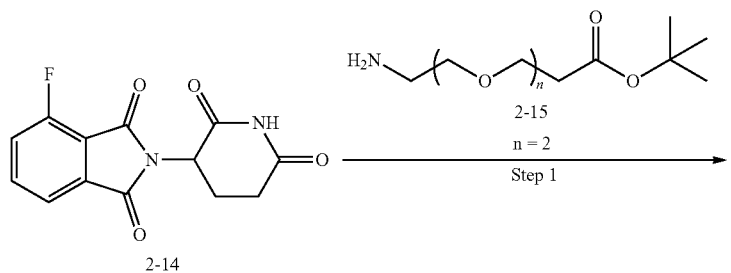

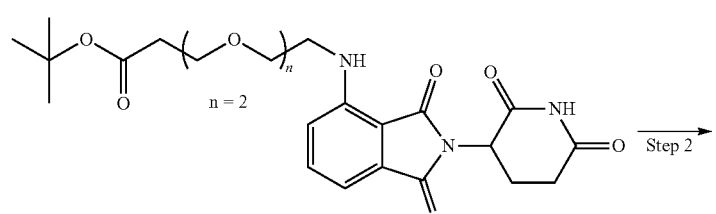

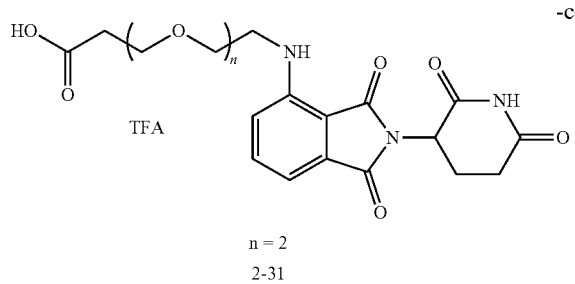
2-31
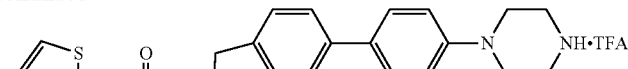
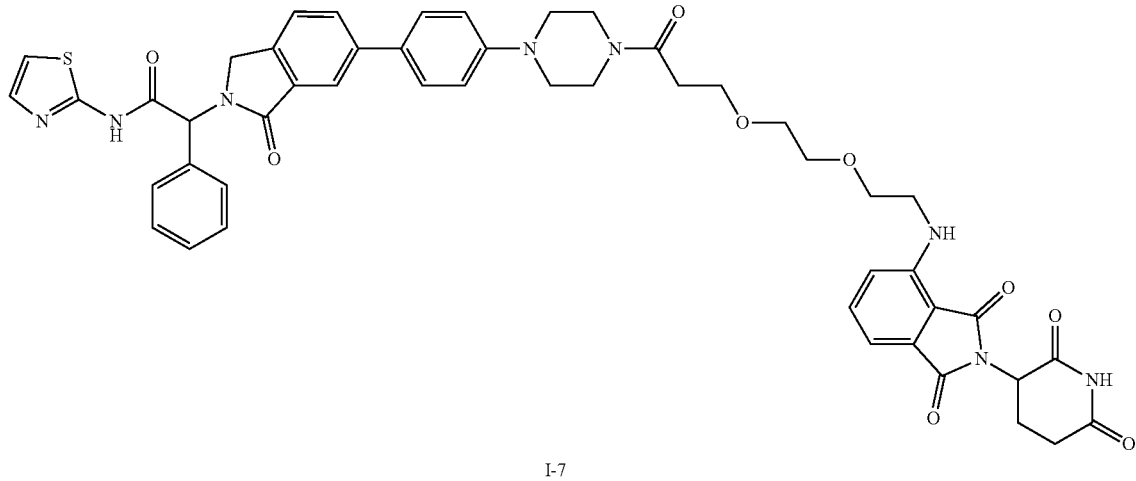
I-7
Compound I-7 was prepared according to the synthesis of Compound I-1 as shown in Example 3. MS m/z: 925.78 [M+1]$^+$; $^1$H NMR (500 MHz, DMSO-d$_6$) δ=12.70 (br s, 1H), 11.09 (br s, 1H), 7.88 (s, 1H), 7.85 (d, J=8.2 Hz, 1H), 7.66-7.54 (m, 4H), 7.52-7.36 (m, 6H), 7.31-7.25 (m, 1H), 7.13 (d, J=8.9 Hz, 1H), 7.03 (d, J=7.3 Hz, 3H), 6.64-6.55 (m, 1H), 6.33 (s, 1H), 5.05 (dd, J=5.3, 13.0 Hz, 1H), 4.77 (d, J=17.4 Hz, 1H), 4.00 (d, J=17.4 Hz, 1H), 3.71-3.48 (m, 12H), 3.48-3.40 (m, 2H), 3.25-3.09 (m, 4H), 2.92-2.81 (m, 1H), 2.63-2.51 (m, 4H), 2.07-1.96 (m, 1H).
Example 11: Synthesis of 2-(6-(4-(4-(3-(2-((2-(2,6-Dioxopiperidin-3-yl)-1,3-dioxoisoindolin-4-yl)amino)ethoxy)propanoyl)piperazin-1-yl)phenyl)-1-oxoisoindolin-2-yl)-2-phenyl-N-(thiazol-2-yl)acetamide (I-8)
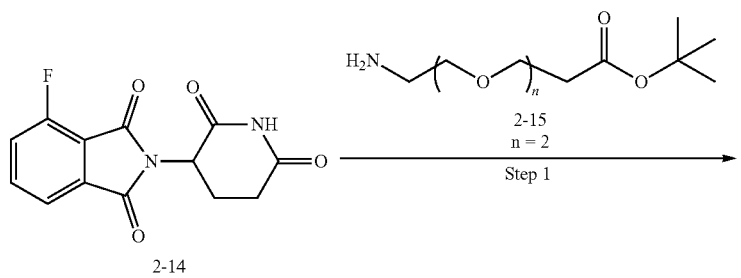
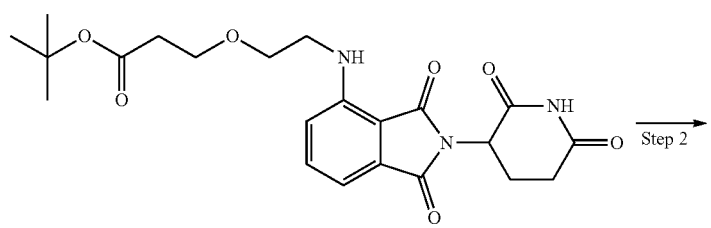
2-32

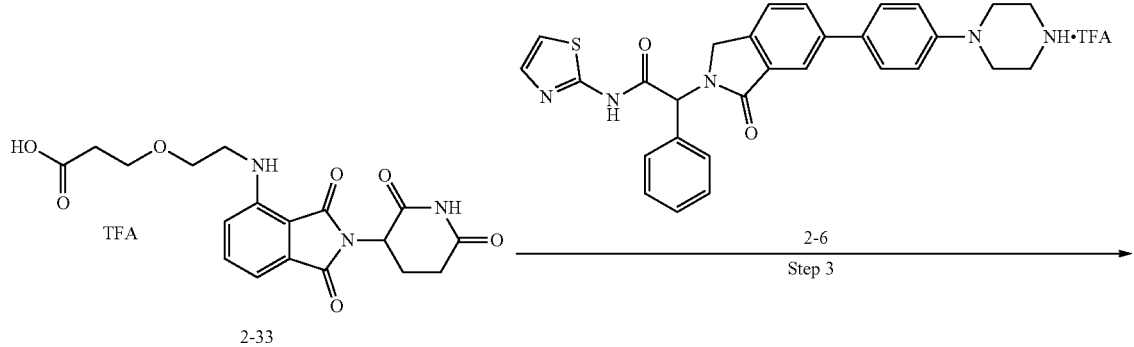

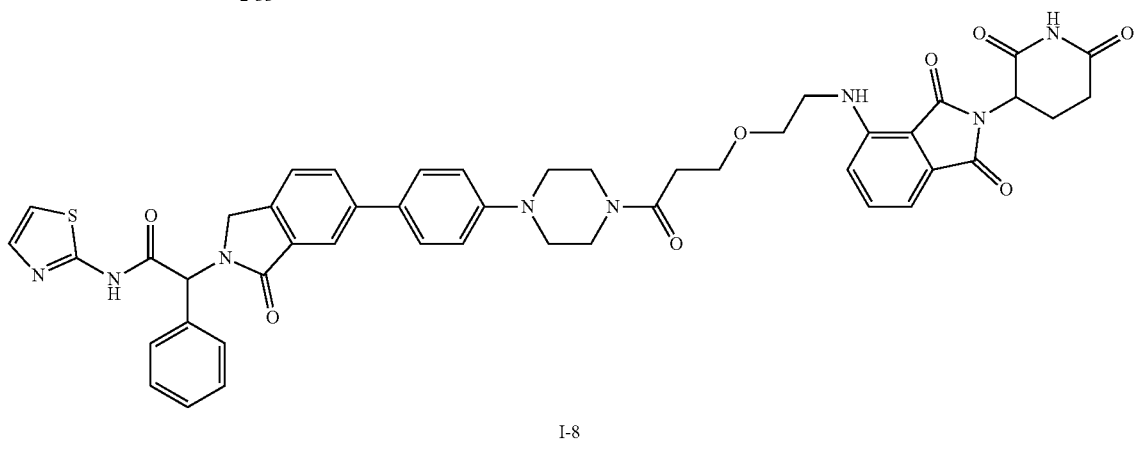

Compound 1-8 was prepared according to the synthesis of Compound I-1 as shown in Example 3. MS m/z: 881.89 [M+1]$^+$; $^1$H NMR (500 MHz, DMSO-d$_6$) δ=12.70 (br s, 1H), 11.10 (s, 1H), 7.88 (s, 1H), 7.87-7.83 (m, 1H), 7.62-7.55 (m, 4H), 7.52-7.35 (m, 6H), 7.28 (d, J=3.4 Hz, 1H), 7.13 (d, J=8.9 Hz, 1H), 7.01 (t, J=8.1 Hz, 3H), 6.58 (t, J=5.0 Hz, 1H), 6.33 (s, 1H), 5.05 (dd, J=5.5, 12.8 Hz, 1H), 4.77 (d, J=17.4 Hz, 1H), 4.00 (d, J=17.7 Hz, 1H), 3.71 (t, J=6.4 Hz, 2H), 3.64-3.59 (m, 6H), 3.48-3.44 (m, 2H), 3.20-3.13 (m, 4H), 2.90-2.82 (m, 1H), 2.64 (t, J=6.4 Hz, 2H), 2.59-2.52 (m, 2H), 2.03-1.97 (m, 1H).

Example 12: Synthesis of 2-(6-(4-(4-(1-((2-(2,6-Dioxopiperidin-3-yl)-1,3-dioxoisoindolin-4-yl)amino)-3,6,9,12-tetraoxapentadecan-15-oyl)piperazin-1-yl)phenyl)-1-oxoisoindolin-2-yl)-2-phenyl-N-(thiazol-2-yl)acetamide (I-9)

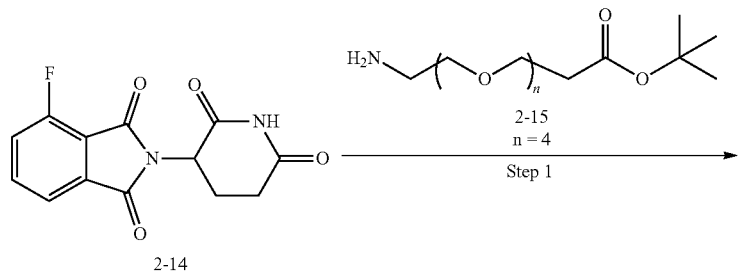

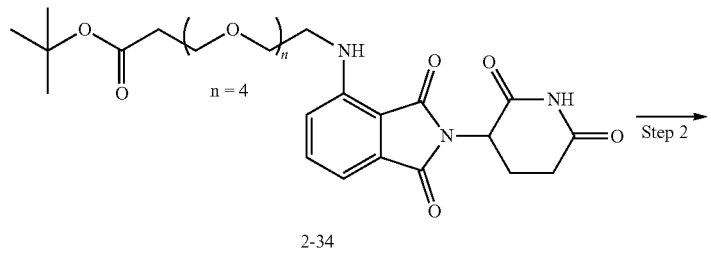

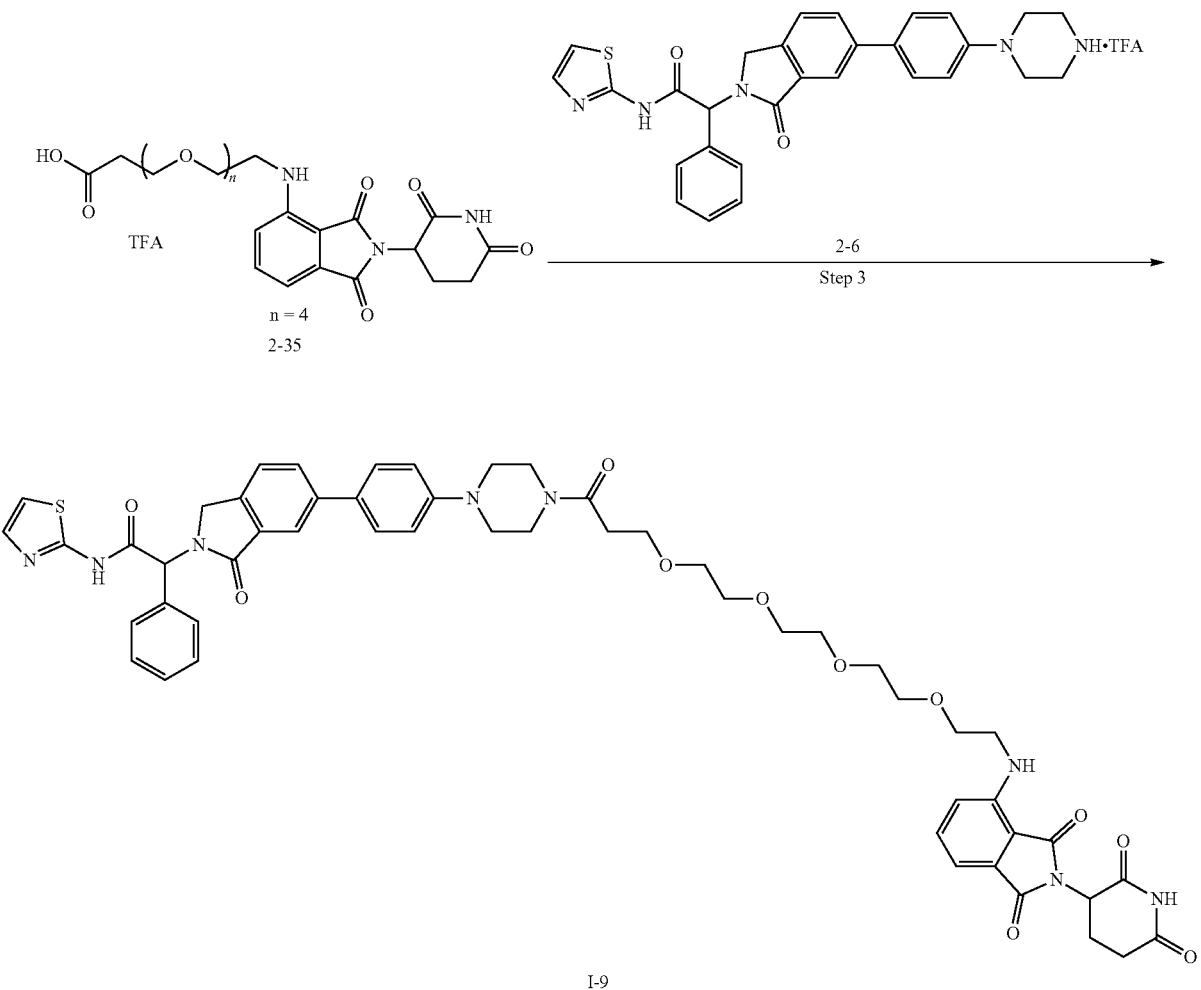

Compound 1-9 was prepared according to the synthesis of Compound I-1 as shown in Example 3. MS m/z: 1013.91 [M+1]+; 1H NMR (500 MHz, DMSO-d6) δ=12.70 (br s, 1H), 11.09 (s, 1H), 7.88 (s, 1H), 7.85 (dd, J=1.5, 7.9 Hz, 1H), 7.63-7.54 (m, 4H), 7.50-7.37 (m, 6H), 7.28 (d, J=3.4 Hz, 1H), 7.12 (d, J=8.5 Hz, 1H), 7.06-7.01 (m, 3H), 6.59 (t, J=5.8 Hz, 1H), 6.33 (s, 1H), 5.05 (dd, J=5.5, 12.8 Hz, 1H), 4.77 (d, J=17.7 Hz, 1H), 3.99 (d, J=17.7 Hz, 1H), 3.65-3.59 (m, 8H), 3.56-3.53 (m, 2H), 3.52-3.43 (m, 12H), 3.24-3.14 (m, 4H), 2.88 (ddd, J=5.5, 13.8, 17.0 Hz, 1H), 2.64-2.52 (m, 4H), 2.04-1.99 (m, 1H).

Example 13: Synthesis of 2-(6-(4-(4-(2-(2-(2-(2-((2-(2,6-Dioxopiperidin-3-yl)-1,3-dioxoisoindolin-4-yl)amino)ethoxy)ethoxy)ethoxy)ethyl)piperazin-1-yl)phenyl)-1-oxoisoindolin-2-yl)-2-(5-fluoro-2-hydroxyphenyl)-N-(thiazol-2-yl)acetamide (I-10)

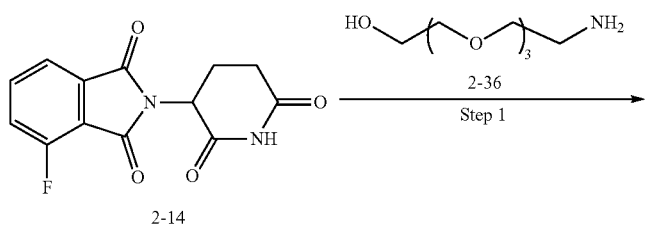

-continued
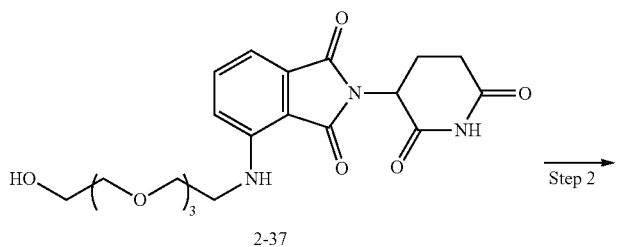
2-37 Step 2
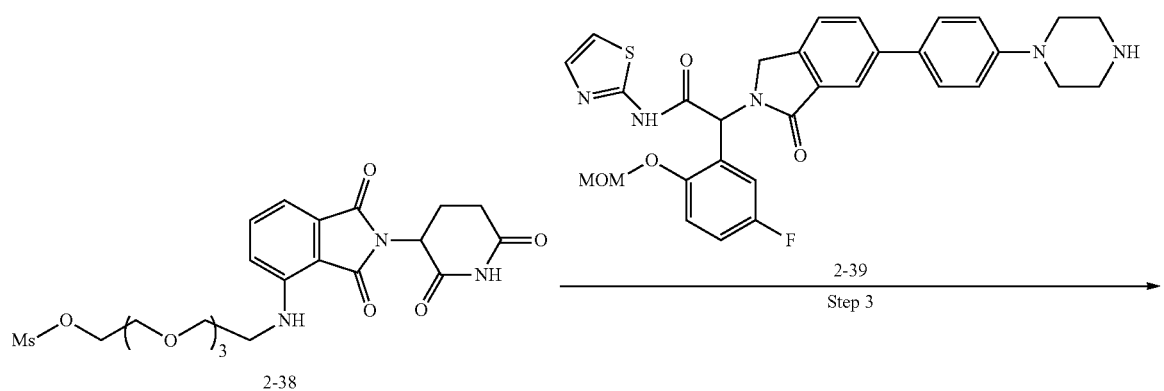
2-38 2-39 Step 3
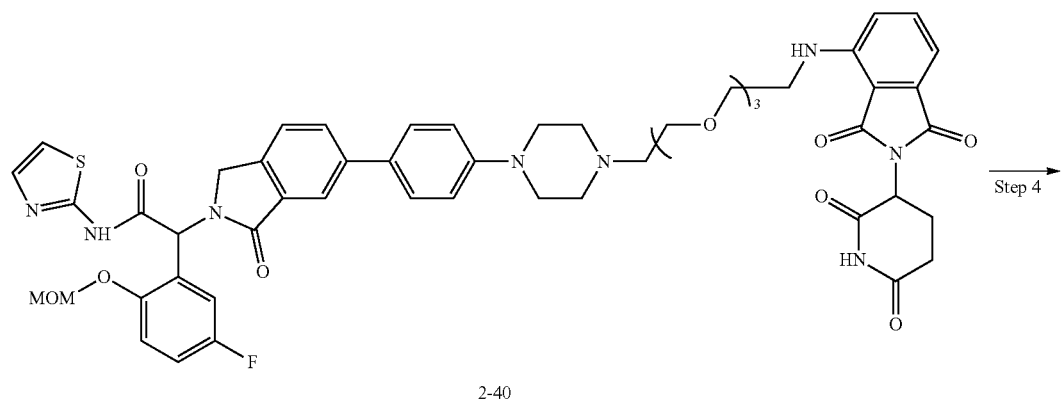
2-40 Step 4
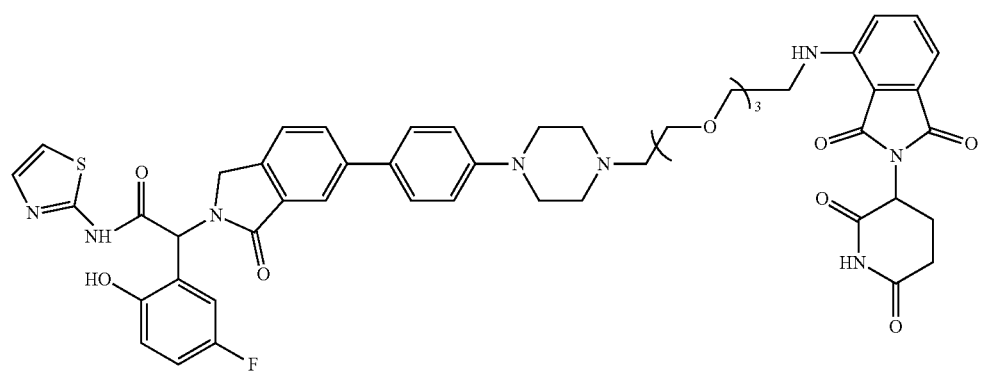
I-10

Step 1: 2-(2,6-Dioxopiperidin-3-yl)-4-((2-(2-(2-(2-hydroxyethoxy)ethoxy)ethoxy)ethyl)amino)isoindoline-1,3-dione (2-37)

To a solution of 2-(2-(2-(2-aminoethoxy)ethoxy)ethoxy)ethan-1-ol (244 mg, 1.64 mmol) in DMF (5 mL) was added DIEA (0.28 mL, 2.18 mmol). After stirring at 80° C. for overnight, the reaction mixture was cooled to room temperature and concentrated under reduced pressure. The residue was purified by flash column chromatography (DCM: MeOH=100:0 to 80:20) to afford 2-37 (284 mg, 58%) as a dark green liquid.

Step 2: 2-(2-(2-(2-((2-(2,6-Dioxopiperidin-3-yl)-1,3-dioxoisoindolin-4-yl)amino)ethoxy)ethoxy)ethoxy) ethyl methanesulfonate (2-38)

To a solution of 2-37 (225 mg, 0.50 mmol) in dry DCM was added DIEA (131 µL, 0.75 mmol) and MsCl (46 µL, 0.60 mmol) at 0° C. The mixture was gradually warmed up to room temperature for 1 hour. After completion, the reaction mixture was concentrated and purified by flash column chromatography (hexane:EtOAc=50:50 to DCM: EtOAc 50:50) to afford 2-38 (169 mg, 64%) as a yellow sticky oil.

Step 3: 2-(6-(4-(4-(2-(2-((2-(2,6-Dioxopiperidin-3-yl)-1,3-dioxoisoindolin-4-yl)amino)ethoxy)ethyl)piperazin-1-yl)phenyl)-1-oxoisoindolin-2-yl)-2-(5-fluoro-2-(methoxymethoxy)phenyl)-N-(thiazol-2-yl)acetamide (2-40)

To a solution of 2-38 (54 mg, 0.102 mmol) and 2-39 (60 mg, 0.102 mmol) in DMF (2 mL) was added DIEA (53 µL, 0.307 mmol). After stirring at 80° C. for 4 hours, the reaction mixture was diluted with DMSO and purified by preparative HPLC to obtain 2-40 (88 mg, 85%).

Step 4: 2-(6-(4-(4-(2-(2-(2-(2-((2-(2,6-Dioxopiperidin-3-yl)-1,3-dioxoisoindolin-4-yl)amino)ethoxy)ethoxy)ethoxy)ethyl)piperazin-1-yl)phenyl)-1-oxoisoindolin-2-yl)-2-(5-fluoro-2-hydroxyphenyl)-N-(thiazol-2-yl)acetamide (I-10)

To a solution of 2-40 (88 mg, 0.086 mmol) in dry DCM (4 mL) was added TFA (1 mL) at 0° C. After stirring for 5 hours, the reaction mixture was concentrated under reduced pressure and purified by flash column chromatography (DCM:1 N NH$_3$ in MeOH=100:0 to 80:20) to afford 1-10 (27 mg, 32%) as a yellowish solid. MS m/z: 975.41 [M+1]$^+$; $^1$H NMR 500 MHz (DMSO-d$_6$) δ 12.62 (bs, 1H), 11.10 (s, 1H), 9.96 (s, 1H), 7.86 (s, 1H) 7.84 (d, J=8.2 Hz, 1H), 7.62-7.54 (m, 4H), 7.49 (d, J=3.4 Hz, 1H), 7.27 (d, J=3.4 Hz, 1H), 7.17-7.09 (m, 2H), 7.06-6.99 (m, 3H), 6.94-6.89 (m, 1H), 6.89-6.85 (m, 1H), 6.62 (br t, J=5.6 Hz, 1H), 6.34 (s, 1H), 5.05 (dd, J=12.5, 5.3 Hz, 1H), 4.62 (d, J=17.4 Hz, 1H), 4.00 (d, J=17.7 Hz, 1H), 3.63 (t, J=5.3 Hz, 2H), 3.60-3.40 (m, 16H), 3.17 (br, 4H), 2.92-2.82 (m, 1H), 2.66-2.50 (m, 4H), 2.05-1.96 (m, 1H).

Example 14: Synthesis of 2-(6-(4-(4-(6-((2-(2,6-Dioxopiperidin-3-yl)-1,3-dioxoisoindolin-4-yl)amino)hexyl)piperazin-1-yl)phenyl)-1-oxoisoindolin-2-yl)-2-(5-fluoro-2-hydroxyphenyl)-N-(thiazol-2-yl)acetamide (I-11)

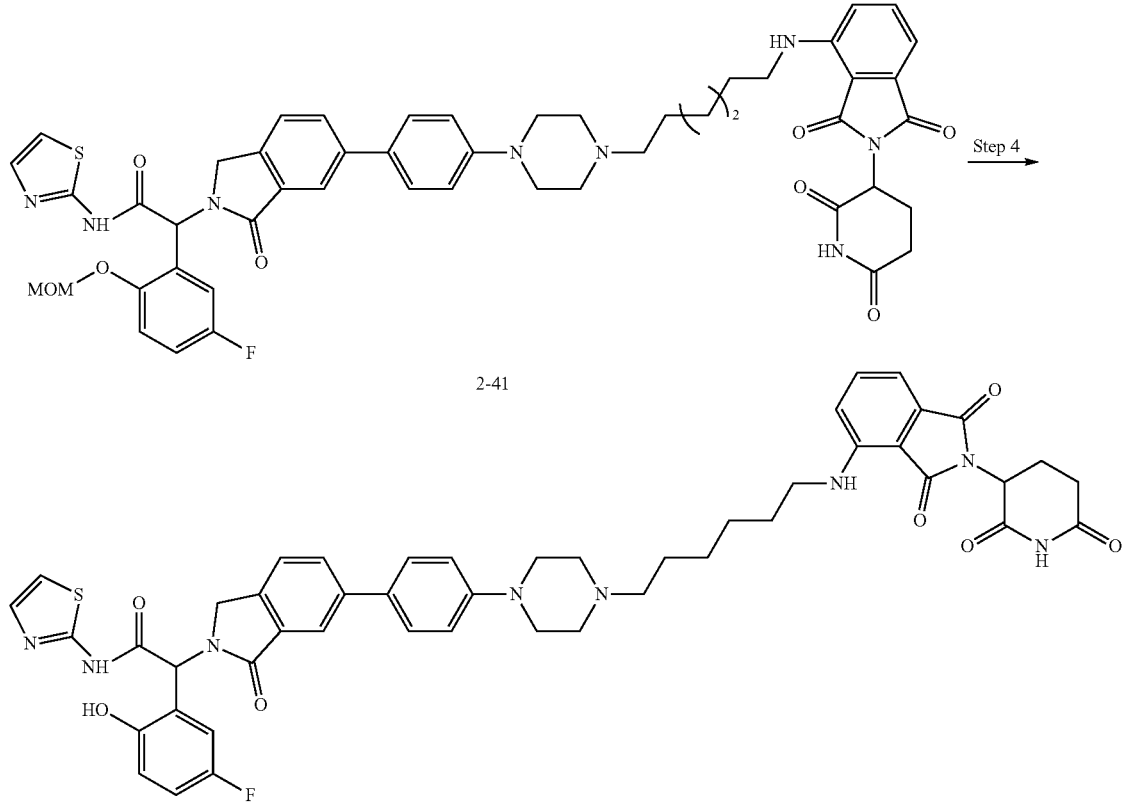

Compound I-11 was prepared in a manner similar to the synthesis of Compound I-10 as shown in Example 13. Step 4 of the synthesis of Compound I-11 is shown above in Example 14. MS m/z: 899.70 [M+1]+; 1H NMR 500 MHz (DMSO-d6) δ 12.58 (bs, 1H), 11.09 (s, 1H), 9.96 (s, 1H), 7.88-7.82 (m, 2H), 7.62-7.55 (m, 4H), 7.50-7.47 (m, 1H), 7.27-7.24 (m, 1H), 7.14-7.07 (m, 2H), 7.04-6.99 (m, 3H), 6.93-6.88 (m, 1H), 6.88-6.84 (m, 1H), 6.53 (br t, J=5.5 Hz, 1H), 6.33 (s, 1H), 5.05 (dd, J=12.6, 5.4 Hz, 1H), 4.62 (d, J=17.4 Hz, 1H), 4.00 (d, J=17.4 Hz, 1H), 3.39-3.25 (m, 4H), 3.22-3.13 (m, 4H), 2.93-2.83 (m, 1H), 2.64-2.50 (m, 4H), 2.34-2.27 (m, 2H), 2.06-1.98 (m, 1H), 1.63-1.55 (m, 2H), 1.52-1.43 (m, 2H), 1.42-1.28 (m, 4H).

Example 15: Synthesis of 2-(6-(4-(4-(8-((2-(2,6-Dioxopiperidin-3-yl)-1,3-dioxoisoindolin-4-yl)amino)octyl)piperazin-1-yl)phenyl)-1-oxoisoindolin-2-yl)-2-(5-fluoro-2-hydroxyphenyl)-N-(thiazol-2-yl)acetamide (I-12)

Compound I-12 was prepared in a manner similar to the synthesis of Compound I-10 as shown in Example 13. Step 4 of the synthesis of Compound I-12 is shown above in Example 15. MS m/z: 899.70 [M+1]+; 1H NMR 500 MHz (DMSO-d6) δ 12.58 (bs, 1H), 11.09 (s, 1H), 9.96 (s, 1H), 7.88-7.82 (m, 2H), 7.62-7.55 (m, 4H), 7.50-7.47 (m, 1H), 7.27-7.24 (m, 1H), 7.14-7.07 (m, 2H), 7.04-6.99 (m, 3H), 6.93-6.88 (m, 1H), 6.88-6.84 (m, 1H), 6.53 (br t, J=5.5 Hz, 1H), 6.33 (s, 1H), 5.05 (dd, J=12.6, 5.4 Hz, 1H), 4.62 (d, J=17.4 Hz, 1H), 4.00 (d, J=17.4 Hz, 1H), 3.39-3.25 (m, 4H), 3.22-3.13 (m, 4H), 2.93-2.83 (m, 1H), 2.64-2.50 (m, 4H), 2.34-2.27 (m, 2H), 2.06-1.98 (m, 1H), 1.63-1.55 (m, 2H), 1.52-1.43 (m, 2H), 1.42-1.28 (m, 4H).

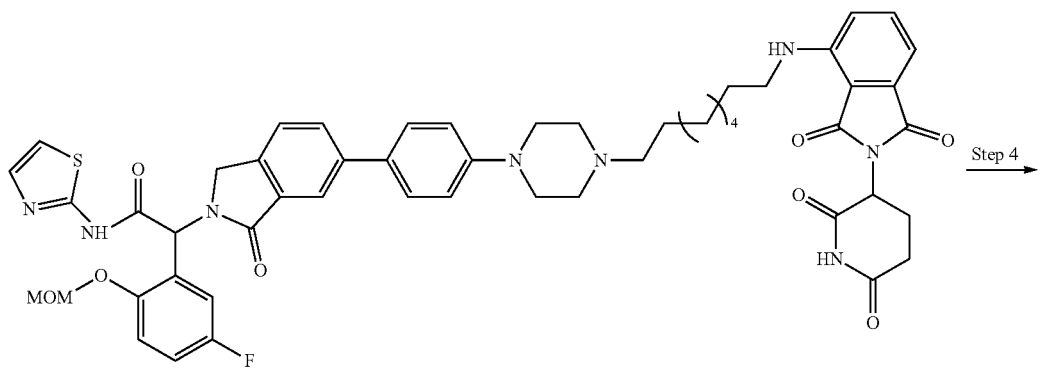

2-42

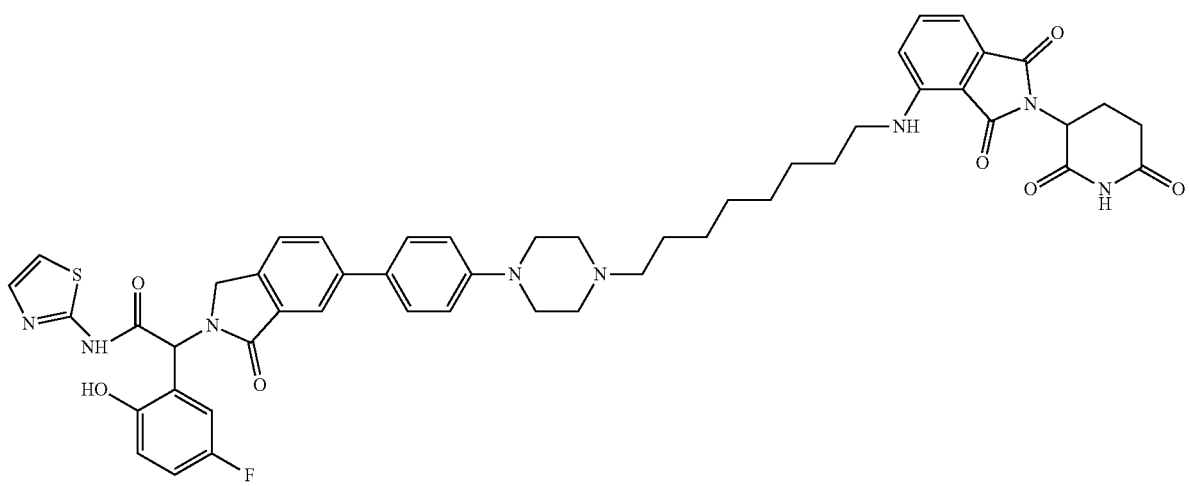

I-12

Example 16: Synthesis of 2-(6-(4-(4-(8-((2-(2,6-Dioxopiperidin-3-yl)-1,3-dioxoisoindolin-4-yl)amino)octyl)piperazin-1-yl)phenyl)-1-oxoisoindolin-2-yl)-2-(5-fluoro-2-hydroxyphenyl)-N-(thiazol-2-yl)acetamide (I-13)

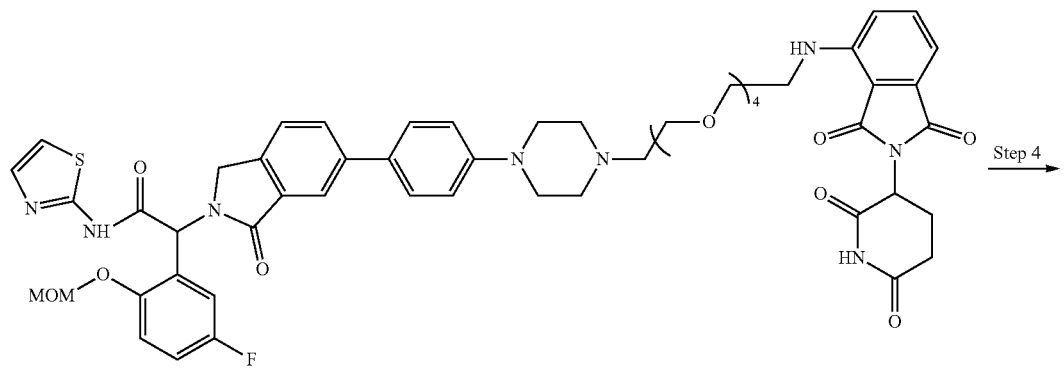

2-43

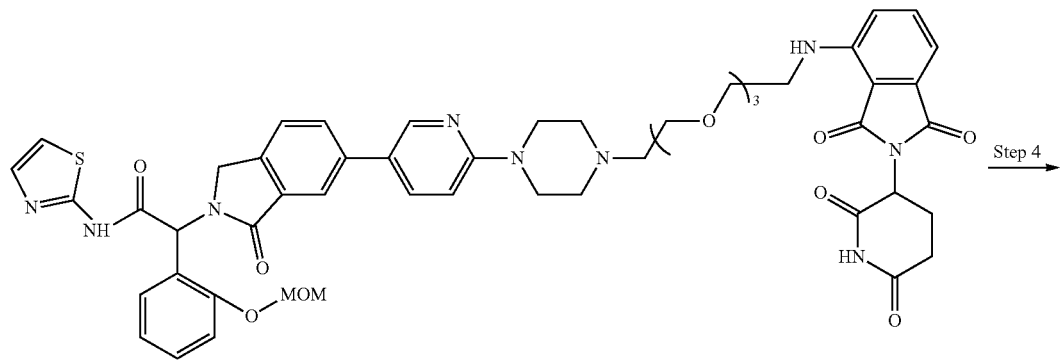

I-13

Compound I-13 was prepared in a manner similar to the synthesis of Compound I-10 as shown in Example 13. Step 4 of the synthesis of Compound 1-13 is shown in Example 16. MS m/z: 1019.50 [M+1]$^+$.

Example 17: Synthesis of 2-(6-(6-(4-(2-(2-(2-(2-((2-(2,6-Dioxopiperidin-3-yl)-1,3-dioxoisoindolin-4-yl)amino)ethoxy)ethoxy)ethoxy)ethyl)piperazin-1-yl)pyridin-3-yl)-1-oxoisoindolin-2-yl)-2-(2-hydroxyphenyl)-N-(thiazol-2-yl)acetamide (I-14)

2-44

-continued
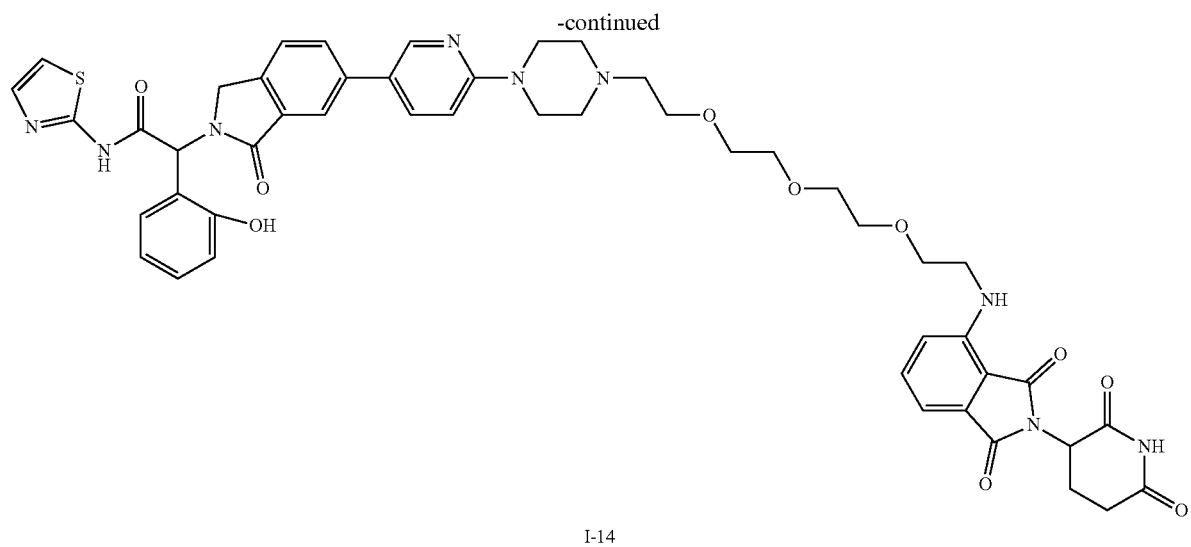
I-14
Compound I-14 was prepared according to the synthesis of Compound I-10 as shown in Example 13. Step 4 of the synthesis of Compound I-14 is shown in Example 17. MS m/z: 959.09 [M+1]$^+$.
Example 18: Synthesis of 2-(6-(4-(4-(2-(2-(2-(3-((2-(2,6-Dioxopiperidin-3-yl)-1,3-dioxoisoindolin-4-yl)amino)azetidin-1-yl)ethoxy)ethoxy)ethyl)piperazin-1-yl)phenyl)-1-oxoisoindolin-2-yl)-2-phenyl-N-(thiazol-2-yl)acetamide (I-15)
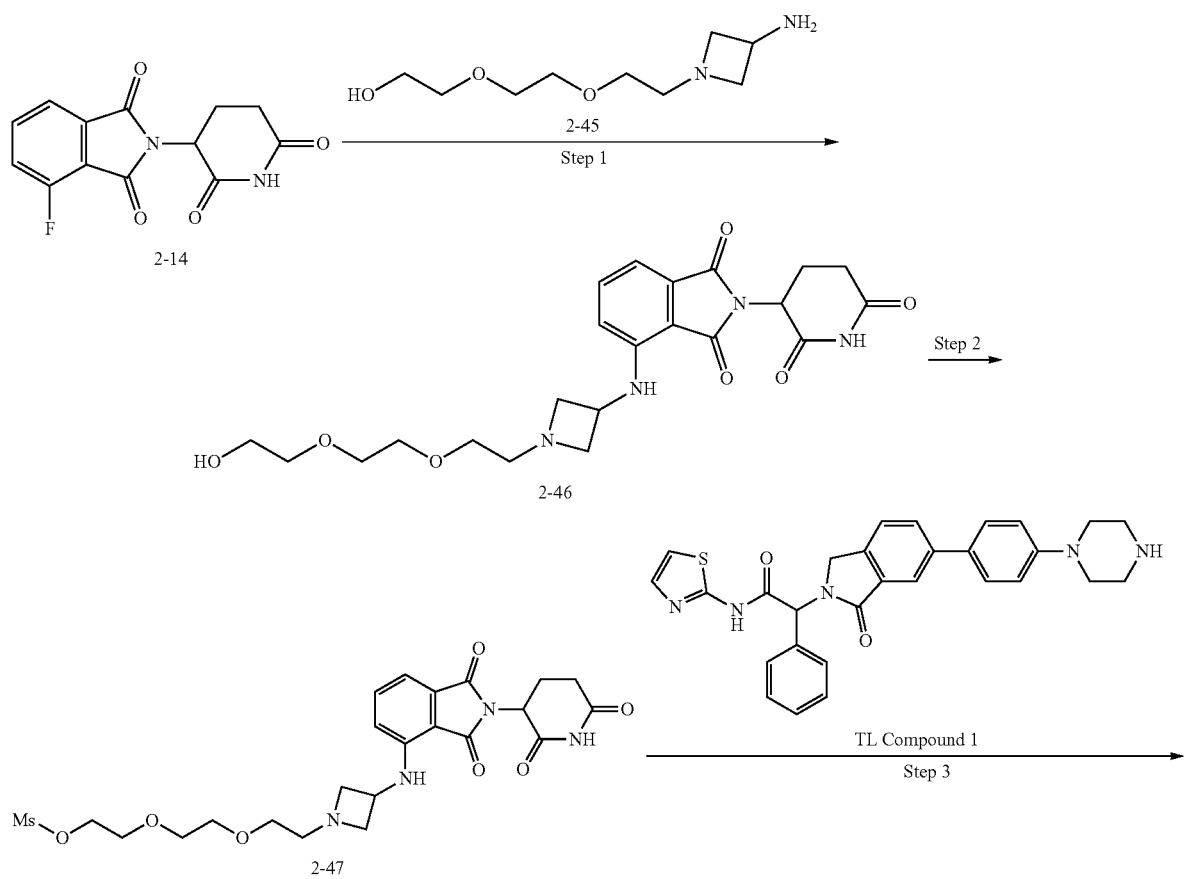

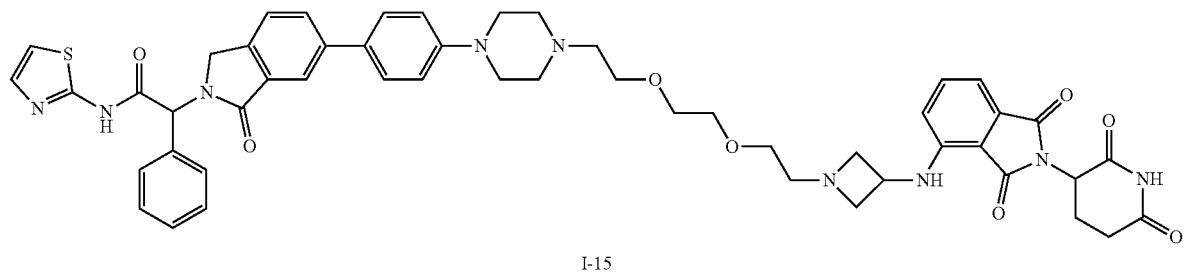

I-15

Compound I-15 was prepared in a manner similar to the synthesis of Compound I-10 as shown in Example 13. MS m/z: 952.54 [M+1]+; 1H NMR 500 MHz (DMSO-d6) δ 12.31 (bs s, 1H), 11.10 (s, 1H), 7.87-7.85 (m, 1H) 7.83 (dd, J=7.9, 1.8 Hz, 1H), 7.60-7.53 (m, 4H), 7.51-7.37 (m, 6H), 7.28 (d, J=3.7 Hz, 1H), 7.06 (d, J=7.0 Hz, 1H), 7.04-7.00 (m, 1H), 6.99 (d, J=8.5 Hz, 2H), 6.59 (d, J=6.7 Hz, 1H), 6.32 (s, 1H), 5.05 (dd, J=12.8, 5.5 Hz, 1H), 4.77 (d, J=17.4 Hz, 1H), 4.27-4.20 (m, 1H), 3.99 (d, J=17.7 Hz, 1H), 3.69 (t, J=7.0 Hz, 2H), 3.55 (t, J=5.8 Hz, 2H), 3.53-3.42 (m, 4H), 3.40 (t, J=5.8 Hz, 2H), 3.22-3.15 (m, 4H), 2.97 (t, J=6.7 Hz, 2H), 2.93-2.83 (m, 1H), 2.65-2.47 (m, 10H), 2.04-1.96 (m, 1H).

Example 19: Synthesis of 2-(6-(4-(4-(2-(2-(2-(2-(3-((2-(2,6-Dioxopiperidin-3-yl)-1,3-dioxoisoindolin-4-yl)amino)azetidin-1-yl)ethoxy)ethoxy)ethoxy)ethyl)piperazin-1-yl)phenyl)-1-oxoisoindolin-2-yl)-2-phenyl-N-(thiazol-2-yl)acetamide (I-16)

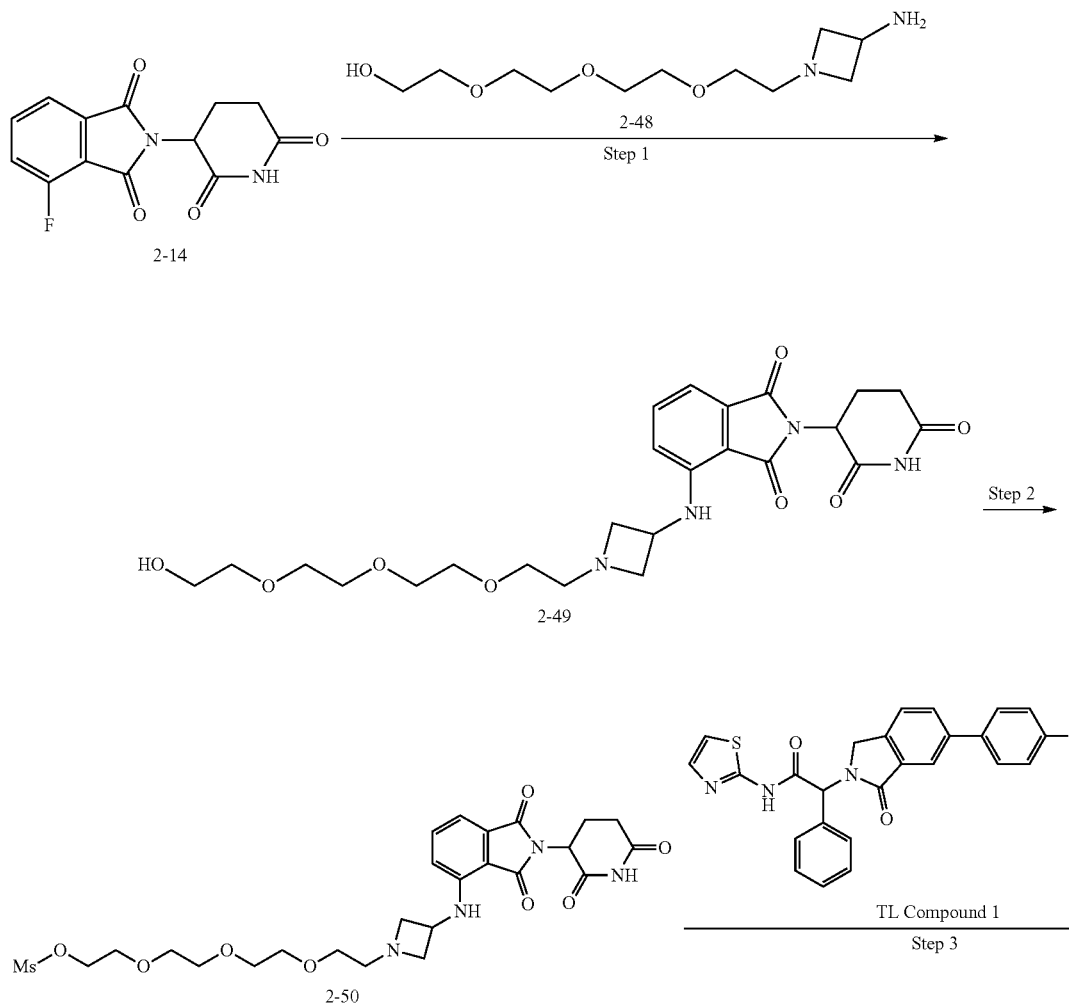

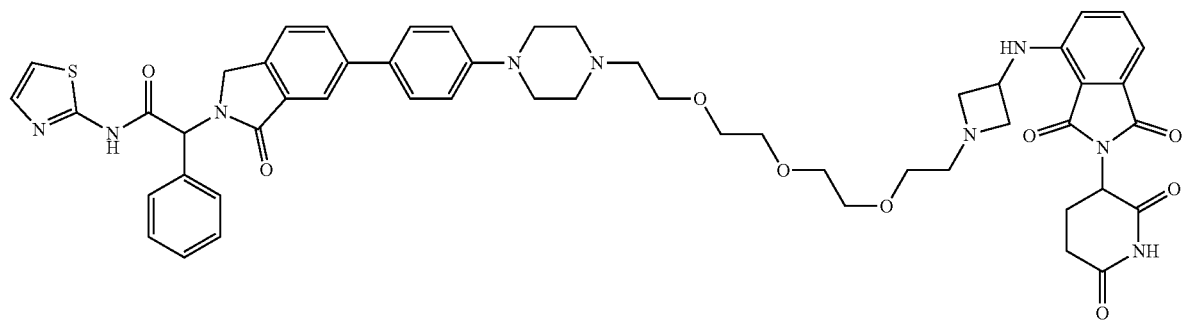

I-16

Compound I-16 was prepared according to the synthesis of Compound I-10 as shown in Example 13. MS m/z: 996.80 [M+1]⁺; ¹H NMR 500 MHz (DMSO-$d_6$) δ 12.50 (bs s, 1H), 11.10 (s, 1H), 7.86 (s, 1H) 7.83 (dd, J=7.9, 1.5 Hz, 1H), 7.62-7.53 (m, 4H), 7.52-7.36 (m, 6H), 7.27 (d, J=3.4 Hz, 1H), 7.06 (d, J=7.0 Hz, 1H), 7.04-6.93 (m, 3H), 6.58 (d, J=7.0 Hz, 1H), 6.32 (s, 1H), 5.05 (dd, J=12.8, 5.5 Hz, 1H), 4.76 (d, J=17.4 Hz, 1H), 4.27-4.16 (m, 1H), 3.98 (d, J=17.7 Hz, 1H), 3.67 (t, J=7.0 Hz, 2H), 3.58-3.43 (m, 10H), 3.38 (t, J=5.8 Hz, 2H), 3.21-3.10 (m, 4H), 2.97 (t, J=6.7 Hz, 2H), 2.92-2.80 (m, 1H), 2.73-2.45 (m, 10H), 2.07-1.95 (m, 1H).

Example 20: Synthesis of 2-(6-(4-(4-(6-((2-(2,6-Dioxopiperidin-3-yl)-1,3-dioxoisoindolin-4-yl)amino)hexyl)piperazin-1-yl)phenyl)-1-oxoisoindolin-2-yl)-2-phenyl-N-(thiazol-2-yl)acetamide (I-17)

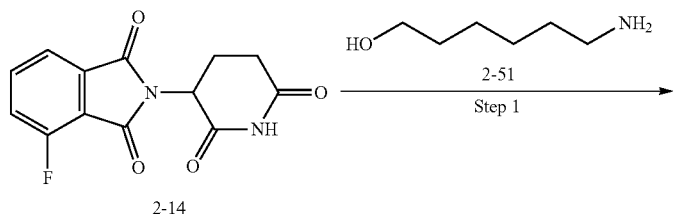

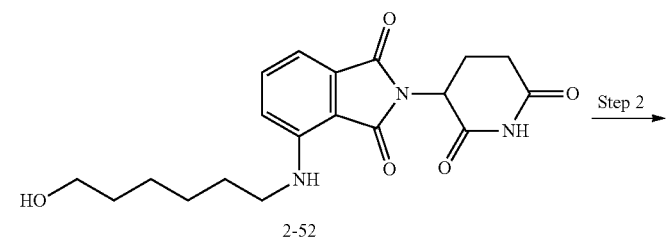

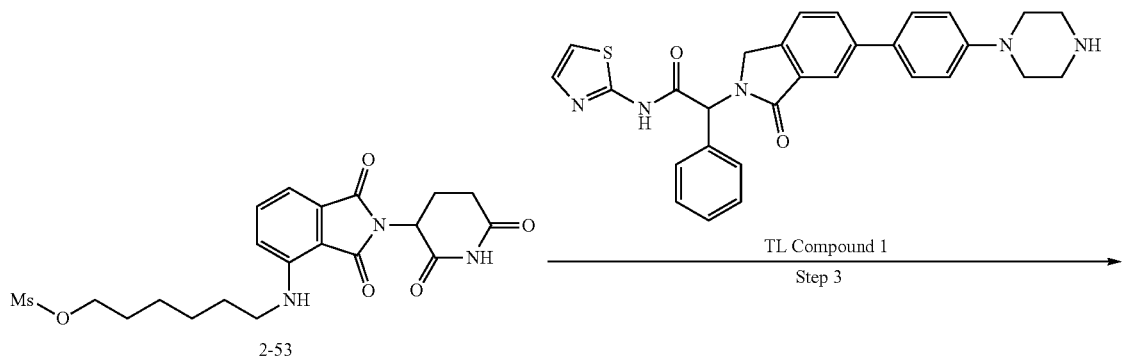

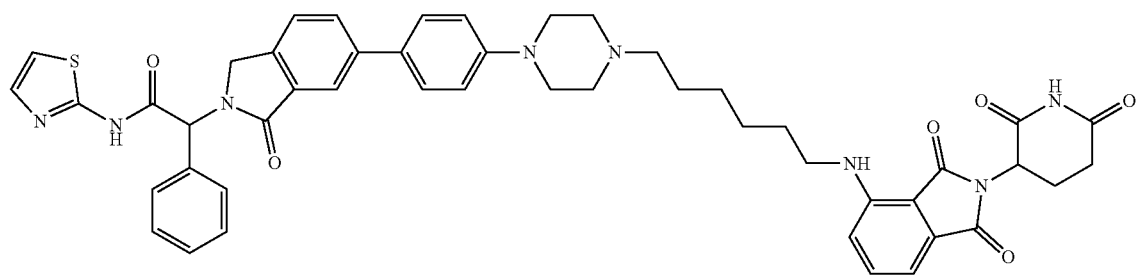

I-17

Compound I-17 was prepared in a manner similar to the synthesis of Compound I-10 as shown in Example 13. MS m/z: 865.92 [M+1]$^+$; $^1$H NMR (500 MHz, DMSO-d$_6$) δ=12.70 (br s, 1H), 11.09 (s, 1H), 7.88 (s, 1H), 7.85 (d, J=7.9 Hz, 1H), 7.66-7.54 (m, 4H), 7.50-7.37 (m, 6H), 7.28 (d, J=3.1 Hz, 1H), 7.10 (d, J=8.5 Hz, 1H), 7.02 (d, J=6.7 Hz, 3H), 6.56-6.51 (m, 1H), 6.32 (s, 1H), 5.05 (dd, J=5.5, 12.8 Hz, 1H), 4.77 (d, J=17.7 Hz, 1H), 3.99 (d, J=17.4 Hz, 1H), 3.31-3.28 (m, 3H), 3.26-3.10 (m, 4H), 2.92-2.84 (m, 1H), 2.65-2.52 (m, 4H), 2.42-2.16 (m, 3H), 2.05-1.99 (m, 1H), 1.63-1.56 (m, 2H), 1.53-1.45 (m, 2H), 1.41-1.32 (m, 4H).

Example 21: Synthesis of 2-(6-(4-(4-(2-(2-(2-(2-((2-(2,6-Dioxopiperidin-3-yl)-1,3-dioxoisoindolin-4-yl)amino)ethoxy)ethoxy)ethoxy)ethyl)piperazin-1-yl)phenyl)-1-oxoisoindolin-2-yl)-2-phenyl-N-(thiazol-2-yl)acetamide (I-18)

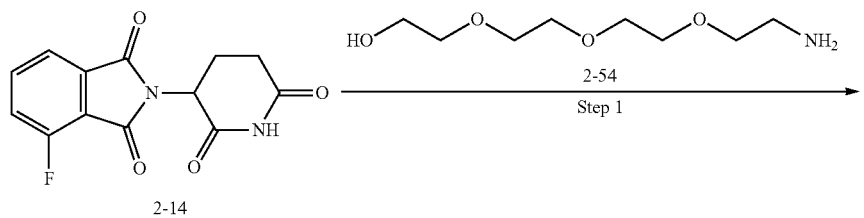

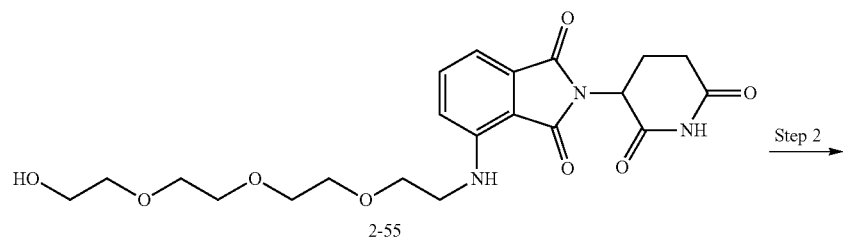

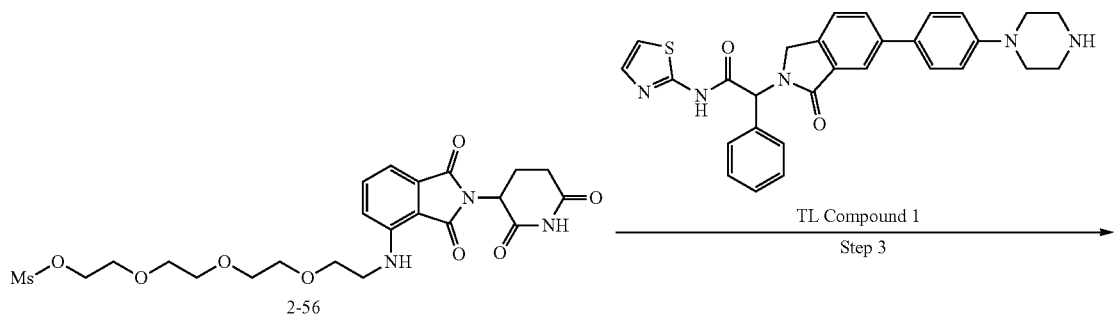

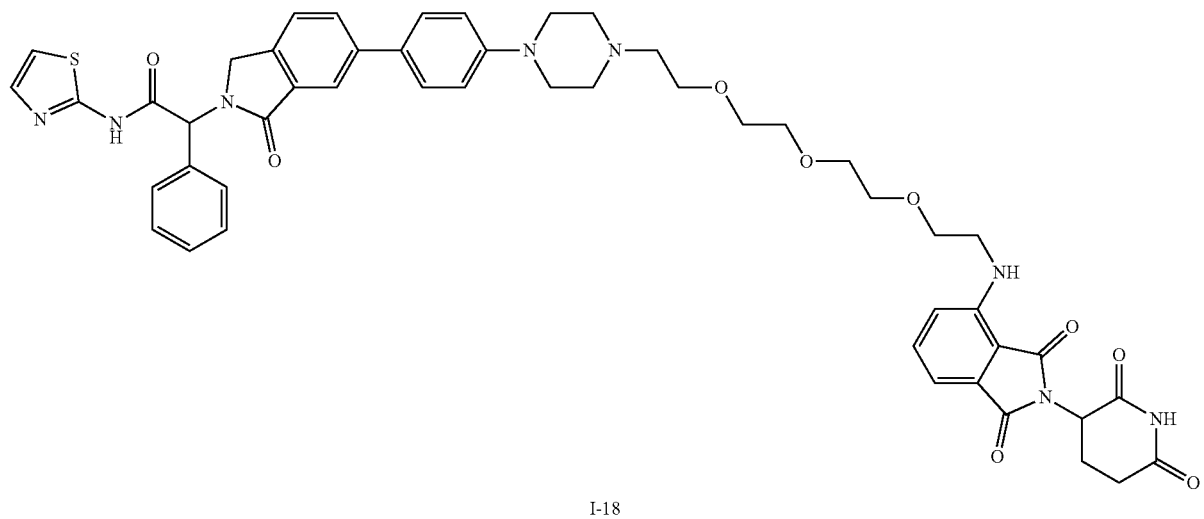

I-18

Compound I-18 was prepared in a manner similar to the synthesis of Compound I-10 as shown in Example 13. MS m/z: 941.90 [M+1]$^+$; $^1$H NMR (500 MHz, DMSO-d$_6$) δ=12.67 (br s, 1H), 11.10 (br s, 1H), 7.87 (s, 1H), 7.84 (d, J=8.5 Hz, 1H), 7.63-7.54 (m, 4H), 7.50-7.36 (m, 6H), 7.26 (br s, 1H), 7.14 (d, J=8.5 Hz, 1H), 7.02 (dd, J=7.9, 15.9 Hz, 3H), 6.61 (t, J=5.6 Hz, 1H), 6.31 (s, 1H), 5.05 (dd, J=5.3, 12.7 Hz, 1H), 4.78 (d, J=17.1 Hz, 1H), 3.99 (d, J=17.4 Hz, 1H), 3.65-3.61 (m, 2H), 3.58-3.45 (m, 12H), 3.21-3.12 (m, 4H), 2.92-2.83 (m, 1H), 2.65-2.51 (m, 8H), 2.04-1.99 (m, 1H).

Example 22: Synthesis of 2-(6-(4-(4-(8-((2-(2,6-Dioxopiperidin-3-yl)-1,3-dioxoisoindolin-4-yl)amino)octyl)piperazin-1-yl)phenyl)-1-oxoisoindolin-2-yl)-2-phenyl-N-(thiazol-2-yl)acetamide (I-19)

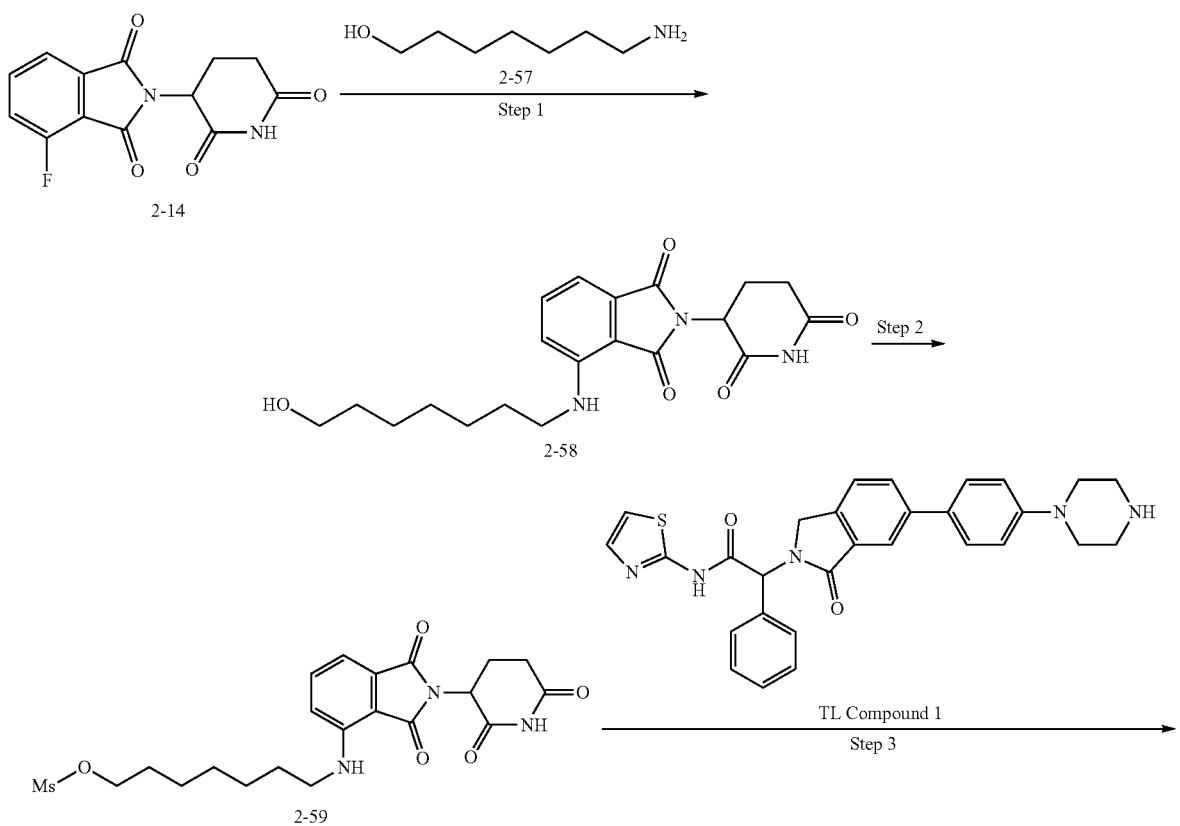

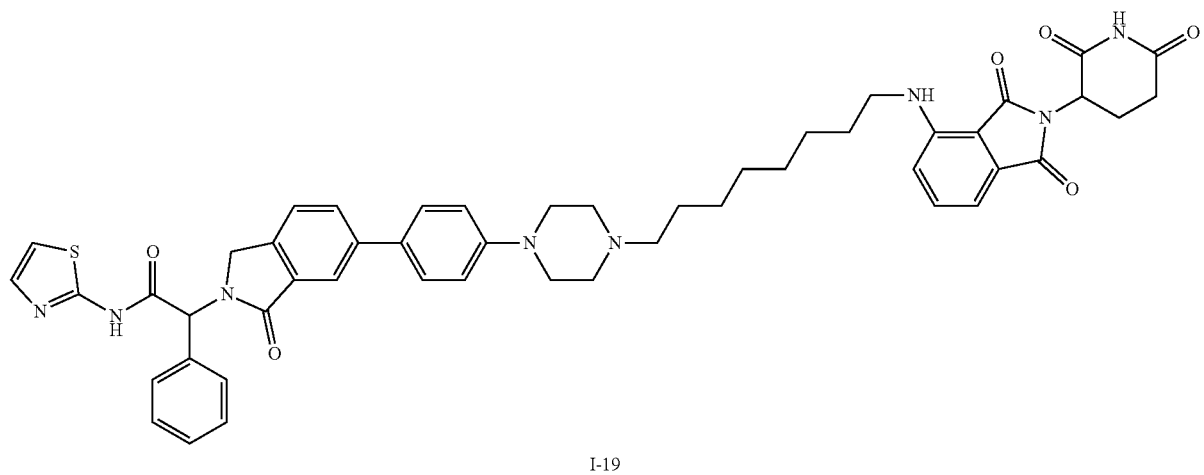

I-19

Compound I-19 was prepared in a manner similar to the synthesis of Compound I-10 as shown in Example 13. MS m/z: 893.72 [M+1]+; $^1$H NMR (500 MHz, DMSO-$d_6$) δ=12.70 (br s, 1H), 11.09 (s, 1H), 7.88 (s, 1H), 7.85 (d, J=7.9 Hz, 1H), 7.62-7.55 (m, 4H), 7.50-7.37 (m, 6H), 7.28 (d, J=3.4 Hz, 1H), 7.09 (d, J=8.5 Hz, 1H), 7.04-7.00 (m, 3H), 6.52 (t, J=5.6 Hz, 1H), 6.32 (s, 1H), 5.05 (dd, J=5.3, 12.7 Hz, 1H), 4.77 (d, J=17.7 Hz, 1H), 3.99 (d, J=17.4 Hz, 1H), 3.31-3.27 (m, 3H), 3.24-3.11 (m, 4H), 2.92-2.84 (m, 1H), 2.64-2.52 (m, 4H), 2.43-2.21 (m, 3H), 2.05-1.99 (m, 1H), 1.61-1.55 (m, 2H), 1.51-1.43 (m, 2H), 1.38-1.28 (m, 8H).

Example 23: Synthesis of 2-(6-(4-(4-(14-((2-(2,6-Dioxopiperidin-3-yl)-1,3-dioxoisoindolin-4-yl)amino)-3,6,9,12-tetraoxatetradecyl)piperazin-1-yl)phenyl)-1-oxoisoindolin-2-yl)-2-phenyl-N-(thiazol-2-yl)acetamide (I-20)

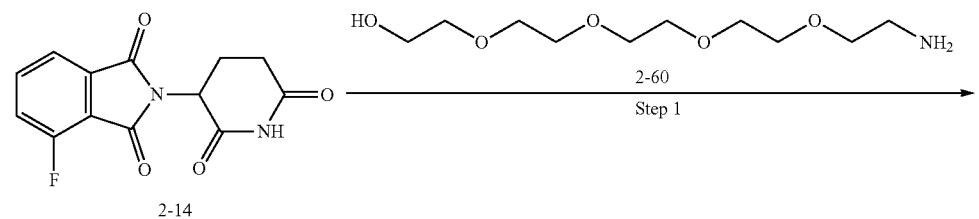

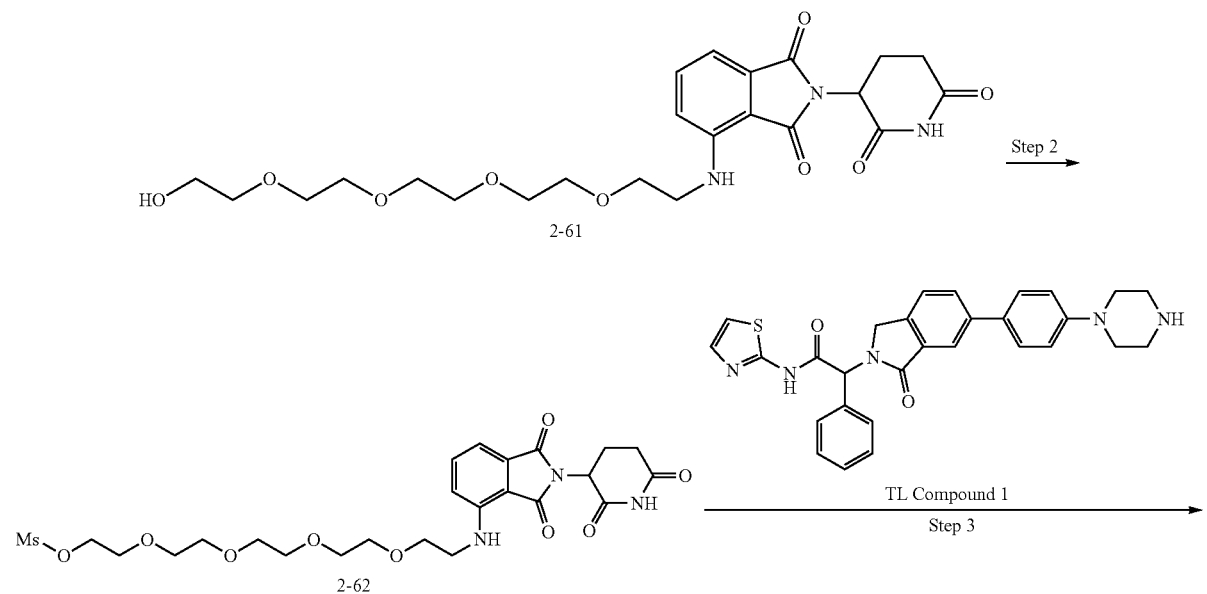

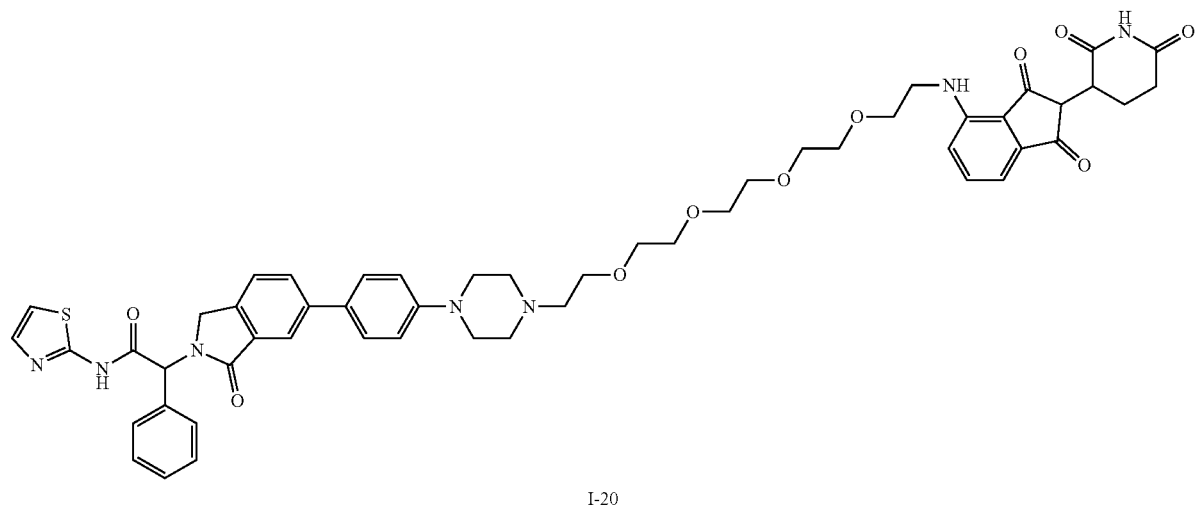

I-20

Compound I-20 was prepared in a manner similar to the synthesis of Compound I-10 as shown in Example 13. MS m/z: 985.93 [M+1]$^+$; $^1$H NMR (500 MHz, DMSO-d$_6$) δ=12.70 (br s, 1H), 11.10 (s, 1H), 7.87 (d, J=0.9 Hz, 1H), 7.84 (dd, J=1.7, 8.1 Hz, 1H), 7.60-7.55 (m, 4H), 7.50-7.37 (m, 6H), 7.28 (d, J=3.7 Hz, 1H), 7.13 (d, J=8.5 Hz, 1H), 7.04-6.99 (m, 3H), 6.59 (t, J=5.8 Hz, 1H), 6.32 (s, 1H), 5.05 (dd, J=5.5, 12.8 Hz, 1H), 4.77 (d, J=17.7 Hz, 1H), 3.99 (d, J=17.7 Hz, 1H), 3.63-3.59 (m, 2H), 3.58-3.49 (m, 14H), 3.46 (q, J=5.7 Hz, 2H), 3.21-3.14 (m, 4H), 2.92-2.84 (m, 1H), 2.65-2.51 (m, 8H), 2.04-1.98 (m, 1H).

Example 24: Synthesis of 2-(6-(4-(4-(2-(2-(2-((2-(2,6-Dioxopiperidin-3-yl)-1,3-dioxoisoindolin-4-yl)amino)ethoxy)ethoxy)ethyl)piperazin-1-yl)phenyl)-1-oxoisoindolin-2-yl)-2-phenyl-N-(thiazol-2-yl)acetamide (I-21)

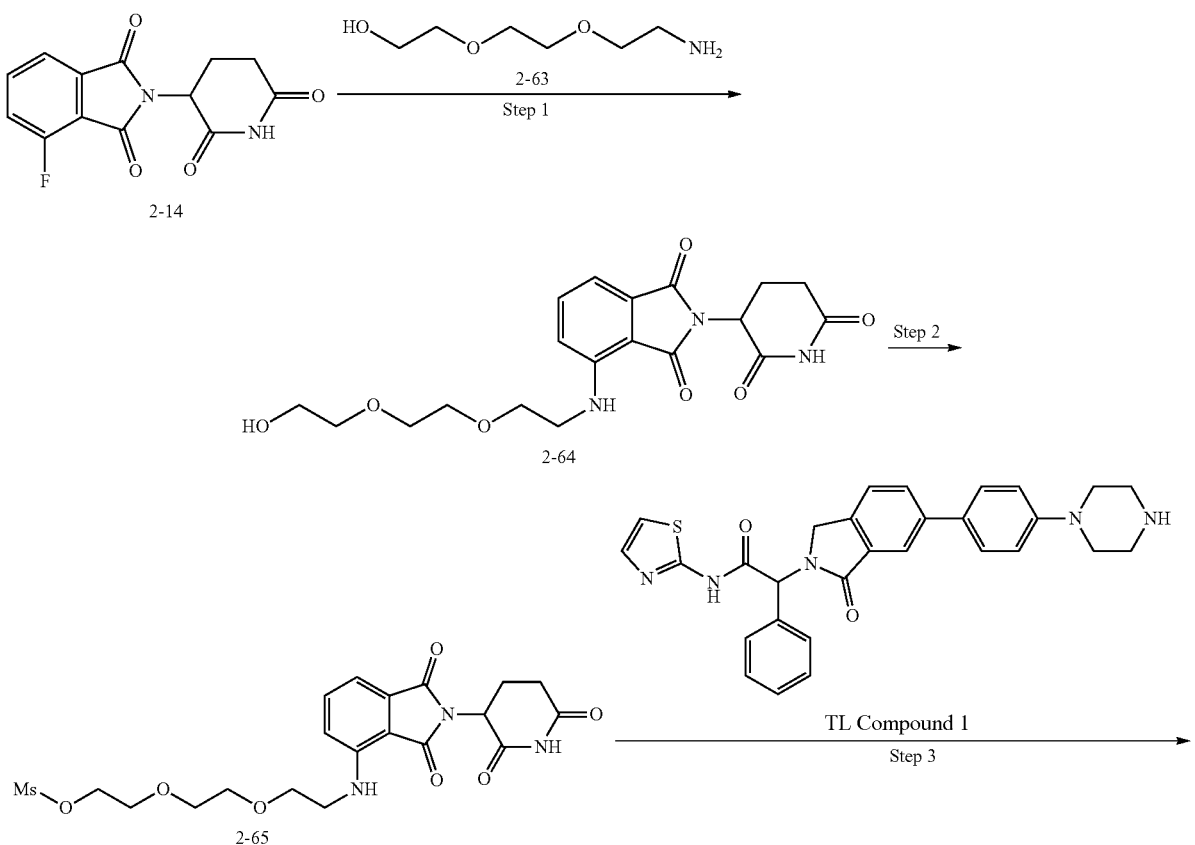

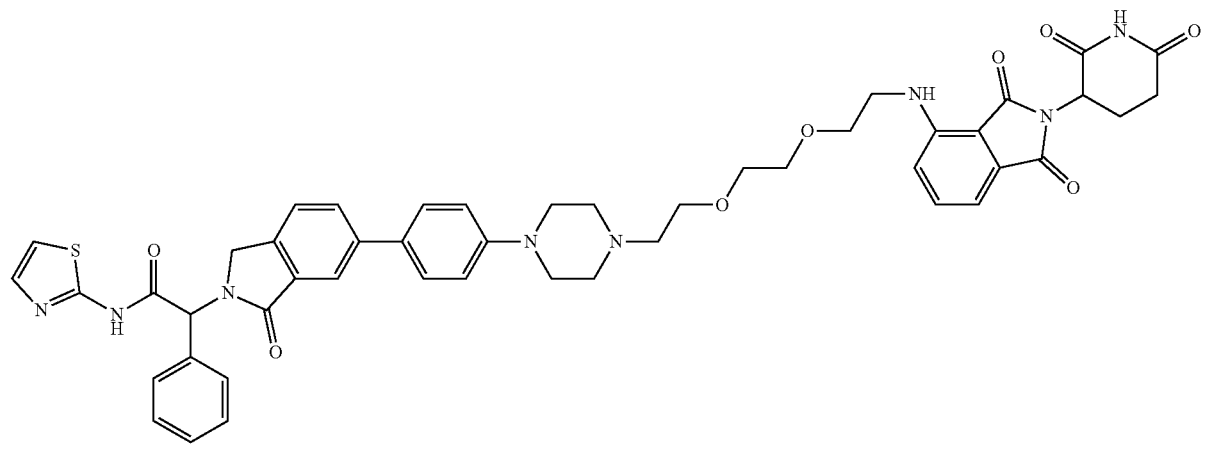

I-21

Compound I-21 was prepared in a manner similar to the synthesis of Compound I-10 as shown in Example 13. MS m/z: 897.95 [M+1]$^+$; $^1$H NMR (500 MHz, DMSO-d$_6$) δ=12.70 (br s, 1H), 11.10 (s, 1H), 7.89 (s, 1H), 7.88-7.84 (m, 1H), 7.66-7.55 (m, 4H), 7.51-7.36 (m, 6H), 7.28 (d, J=3.7 Hz, 1H), 7.15 (d, J=8.5 Hz, 1H), 7.05 (d, J=7.3 Hz, 3H), 6.60 (t, J=5.6 Hz, 1H), 6.32 (s, 1H), 5.05 (dd, J=5.3, 12.7 Hz, 1H), 4.78 (d, J=17.7 Hz, 1H), 4.00 (d, J=17.7 Hz, 1H), 3.80-3.76 (m, 2H), 3.68-3.57 (m, 8H), 3.51-3.47 (m, 4H), 3.21-3.06 (m, 4H), 2.90-2.80 (m, 1H), 2.61-2.50 (m, 4H), 2.04-1.97 (m, 1H).

Example 25: Synthesis of 2-(6-(6-(4-(2-(2-(2-(2-((2-(2,6-Dioxopiperidin-3-yl)-1,3-dioxoisoindolin-4-yl)amino)ethoxy)ethoxy)ethoxy)ethyl)piperazin-1-yl)pyridin-3-yl)-1-oxoisoindolin-2-yl)-2-phenyl-N-(thiazol-2-yl)acetamide (I-22)

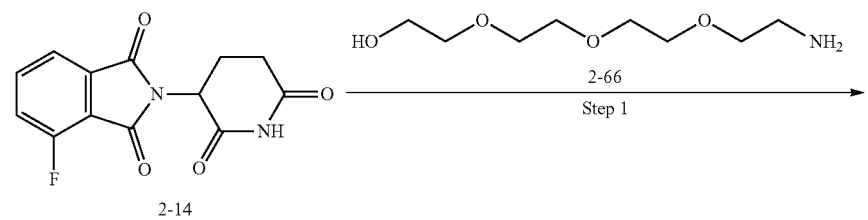

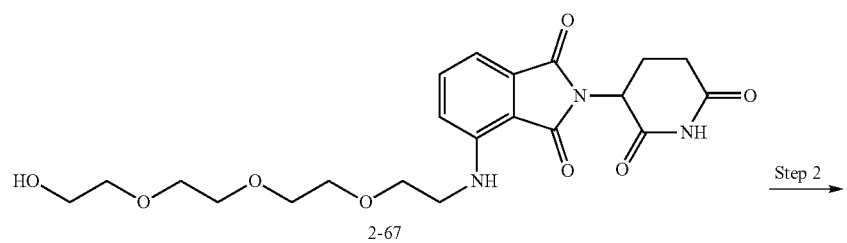

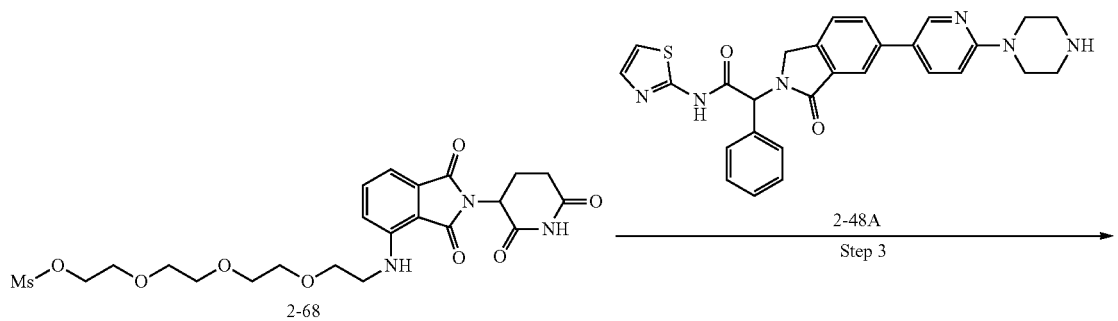

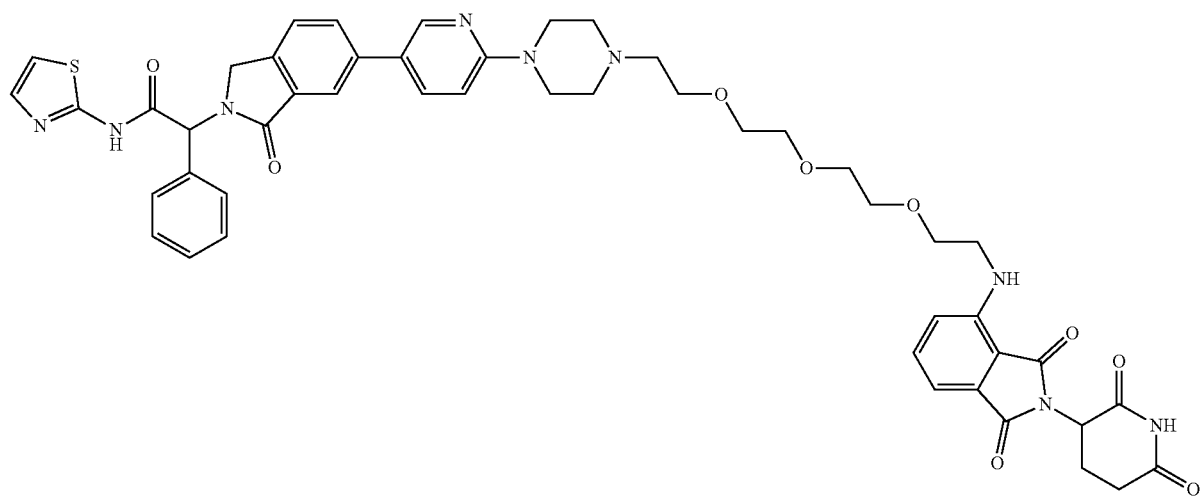

I-22

Compound I-22 was prepared in a manner similar to the synthesis of Compound I-10 as shown in Example 13. MS m/z: 942.95 [M+1]$^+$; $^1$H NMR (500 MHz, DMSO-d$_6$) δ=12.70 (s, 1H), 11.10 (s, 1H), 8.49 (br s, 1H), 7.99-7.91 (m, 1H), 7.90 (s, 1H), 7.86 (dd, J=1.7, 8.1 Hz, 1H), 7.63-7.55 (m, 2H), 7.50-7.37 (m, 6H), 7.28 (d, J=3.7 Hz, 1H), 7.14 (d, J=8.5 Hz, 1H), 7.03 (d, J=7.0 Hz, 1H), 6.92 (br s, 1H), 6.60 (t, J=5.8 Hz, 1H), 6.33 (s, 1H), 5.05 (dd, J=5.3, 12.7 Hz, 1H), 4.78 (d, J=17.7 Hz, 1H), 4.00 (d, J=17.7 Hz, 1H), 3.69-3.40 (m, 18H), 2.88 (ddd, J=5.3, 13.9, 17.1 Hz, 1H), 2.66-2.50 (m, 8H), 2.05-1.98 (m, 1H).

Example 26: Synthesis of (2S,4R)-1-((14S)-14-(tert-Butyl)-12-oxo-1-(4-(5-(3-oxo-2-(2-oxo-1-phenyl-2-(thiazol-2-ylamino)ethyl)isoindolin-5-yl)pyridin-2-yl)piperazin-1-yl)-3,6,9-trioxa-13-azapentadecan-15-oyl)-4-hydroxy-N—((S)-1-(4-(4-methylthiazol-5-yl)phenyl)ethyl)pyrrolidine-2-carboxamide (I-23)

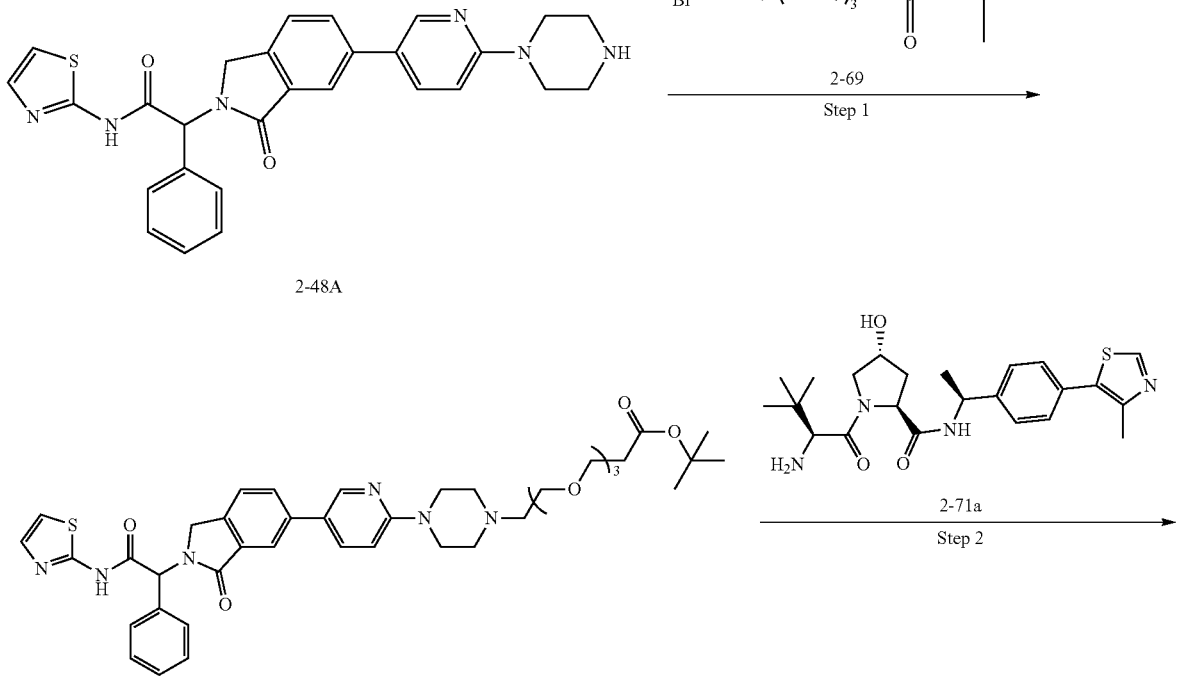

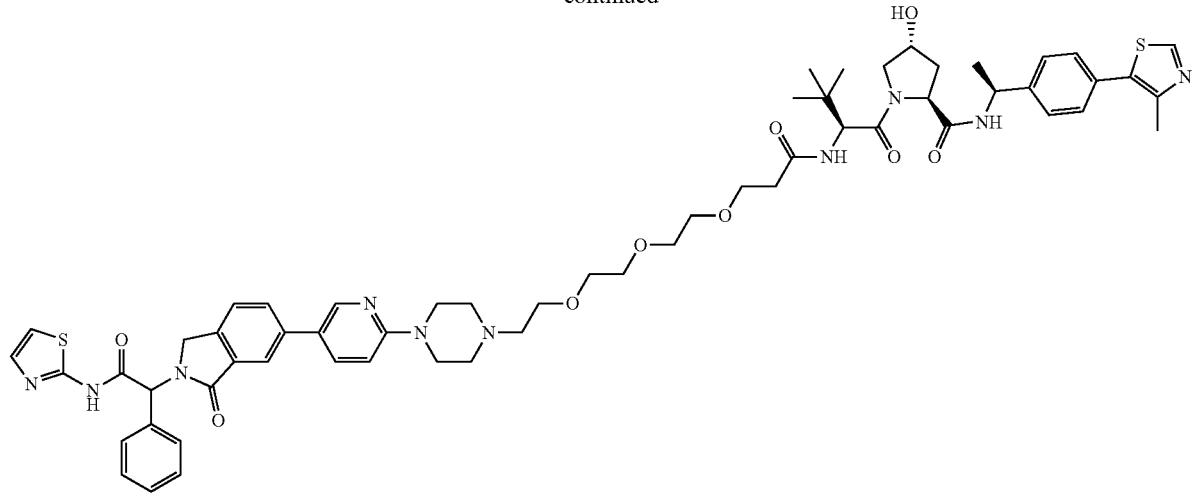

I-23

Step 1: tert-Butyl 3-(2-(4-(5-(3-oxo-2-(2-oxo-1-phenyl-2-(thiazol-2-ylamino)ethyl)isoindolin-5-yl)pyridin-2-yl)piperazin-1-yl)ethoxy)propanoate (2-70)

To a solution of 2-48A (204 mg, 0.40 mmol) in DMF (1.5 mL) was added tert-butyl 3-(2-(2-(2-bromoethoxy)ethoxy)ethoxy)propanoate (2-69, 136 mg, 0.40 mmol) and DIEA (0.14 mL, 0.80 mmol). The resulting mixture was stirred at 80° C. for 8 hours. After cooling to room temperature, the reaction mixture was diluted with EtOAc and washed with water five times. The organic layer was dried over $Na_2SO_4$, filtered and concentrated under reduced pressure. The residue was purified by flash column chromatography (hexane:EtOAc=100:0 to 0:100 then, DCM:MeOH=100:0 to 80:20) to afford 2-70 (191 mg, 62%) as an off-white solid.

Step 2: (2S,4R)-1-((14S)-14-(tert-Butyl)-12-oxo-1-(4-(5-(3-oxo-2-(2-oxo-1-phenyl-2-(thiazol-2-ylamino)ethyl)isoindolin-5-yl)pyridin-2-yl)piperazin-1-yl)-3,6,9-trioxa-13-azapentadecan-15-oyl)-4-hydroxy-N—((S)-1-(4-(4-methylthiazol-5-yl)phenyl)ethyl)pyrrolidine-2-carboxamide (I-23)

To a solution of 2-70 (150 mg, 0.19 mmol) in DCM (3.5 mL) was added TFA (1.5 mL). After stirring for 1 hour, the reaction mixture was concentrated under reduced pressure and the residue was purified by preparative HPLC to afford 3-(2-(2-(2-(4-(5-(3-oxo-2-(2-oxo-1-phenyl-2-(thiazol-2-ylamino)ethyl)isoindolin-5-yl)pyridin-2-yl)piperazin-1-yl)ethoxy)ethoxy)ethoxy)propanoic acid (114 mg, 82%) as an off-white solid. Then, to a solution of 2-71 (31 mg, 0.07 mmol) and 3-(2-(2-(2-(4-(5-(3-oxo-2-(2-oxo-1-phenyl-2-(thiazol-2-ylamino)ethyl)isoindolin-5-yl)pyridin-2-yl)piperazin-1-yl)ethoxy)ethoxy)ethoxy)propanoic acid (63 mg, 0.088 mmol) in DMF (1.0 mL) was added EDCI (20 mg, 0.11 mmol), HOBt (9 mg, 0.07 mmol) and DIEA (0.05 mL, 0.28 mmol). After stirring overnight, the reaction mixture was diluted with DMSO and purified by preparative HPLC to afford I-23 (34 mg, 43%) as an off-white solid. MS m/z: 1141.74 [M+1]$^+$; $^1$H NMR (500 MHz, DMSO-$d_6$) δ=12.69 (br s, 1H), 8.97 (s, 1H), 8.50 (d, J=2.4 Hz, 1H), 8.37 (d, J=7.6 Hz, 1H), 7.94-7.90 (m, 2H), 7.86 (dd, J=1.7, 8.1 Hz, 2H), 7.61 (d, J=7.9 Hz, 1H), 7.52-7.31 (m, 10H), 7.28 (d, J=3.4 Hz, 1H), 6.92 (d, J=8.9 Hz, 1H), 6.32 (s, 1H), 5.10 (d, J=3.7 Hz, 1H), 4.95-4.87 (m, 1H), 4.78 (d, J=17.4 Hz, 1H), 4.53 (d, J=9.5 Hz, 1H), 4.42 (t, J=8.1 Hz, 1H), 4.27 (br s, 1H), 4.00 (d, J=17.7 Hz, 1H), 3.65-3.42 (m, 18H), 2.58-2.51 (m, 7H), 2.45 (s, 3H), 2.35 (dt, J=6.1, 14.6 Hz, 1H), 2.04-1.97 (m, 1H), 1.79 (ddd, J=4.7, 8.4, 12.8 Hz, 1H), 1.37 (d, J=7.0 Hz, 3H), 0.93 (s, 9H).

Example 27: Synthesis of (2S,4R)-1-((2S)-3,3-Dimethyl-2-(3-(2-(2-(4-(5-(3-oxo-2-(2-oxo-1-phenyl-2-(thiazol-2-ylamino)ethyl)isoindolin-5-yl)pyridin-2-yl)piperazin-1-yl)ethoxy)ethoxy)propanamido)butanoyl)-4-hydroxy-N—((S)-1-(4-(4-methylthiazol-5-yl)phenyl)ethyl)pyrrolidine-2-carboxamide (I-24)

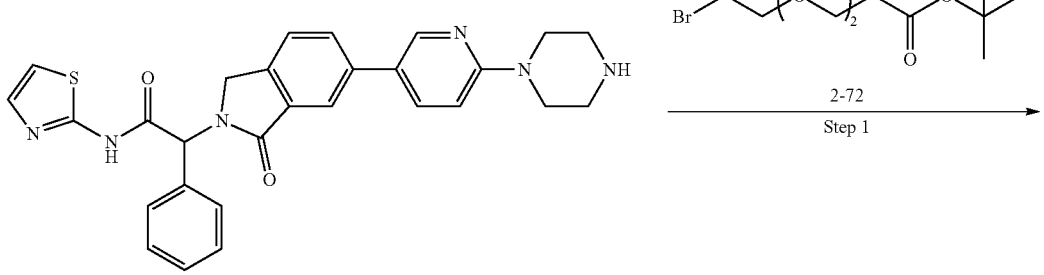

-continued

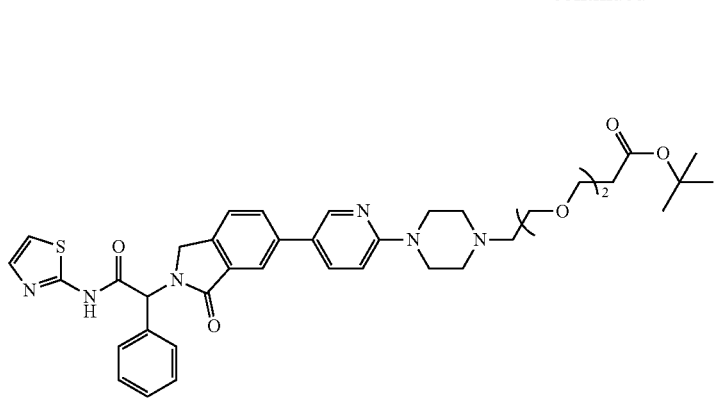

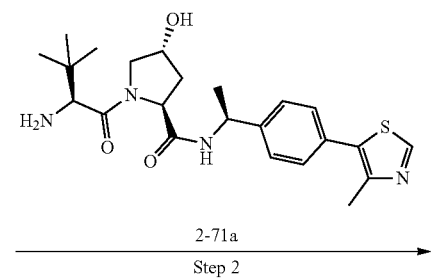

2-71a
Step 2

2-73

I-24

Compound I-24 was prepared in a manner similar to the synthesis of Compound I-23 as shown in Example 26. MS m/z: 1097.92 [M+1]$^+$; $^1$H NMR (500 MHz, DMSO-d$_6$) δ=12.70 (br s, 1H), 8.98 (s, 1H), 8.50 (d, J=2.7 Hz, 1H), 8.37 (d, J=7.6 Hz, 1H), 7.94-7.90 (m, 2H), 7.88-7.84 (m, 2H), 7.61 (d, J=8.2 Hz, 1H), 7.51-7.35 (m, 10H), 7.28 (d, J=3.7 Hz, 1H), 6.92 (d, J=9.2 Hz, 1H), 6.33 (s, 1H), 5.10 (d, J=3.4 Hz, 1H), 4.96-4.88 (m, 1H), 4.78 (d, J=17.7 Hz, 1H), 4.53 (d, J=9.5 Hz, 1H), 4.43 (t, J=8.1 Hz, 1H), 4.28 (br s, 1H), 4.00 (d, J=17.7 Hz, 1H), 3.67-3.45 (m, 15H), 2.58-2.51 (m, 6H), 2.45 (s, 3H), 2.38-2.32 (m, 1H), 2.04-1.98 (m, 1H), 1.79 (ddd, J=4.6, 8.2, 12.8 Hz, 1H), 1.37 (d, J=7.0 Hz, 3H), 0.94 (s, 9H).

Example 28: Alternative Synthesis of (2S,4R)-1-((2S)-3,3-Dimethyl-2-(2-(4-(4-(3-oxo-2-(2-oxo-1-phenyl-2-(thiazol-2-ylamino)ethyl)isoindolin-5-yl)phenyl)piperazin-1-yl)acetamido)butanoyl)-4-hydroxy-N-(4-(4-methylthiazol-5-yl)benzyl)pyrrolidine-2-carboxamide (I-6)

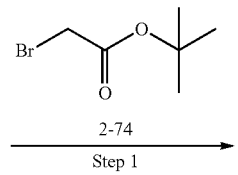

2-74
Step 1

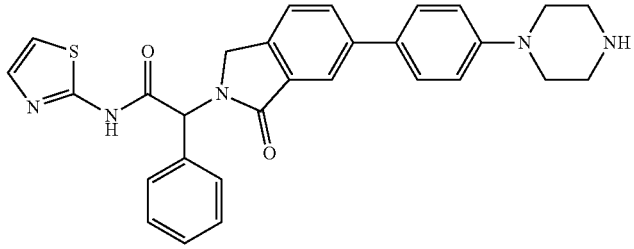

TL compound 1

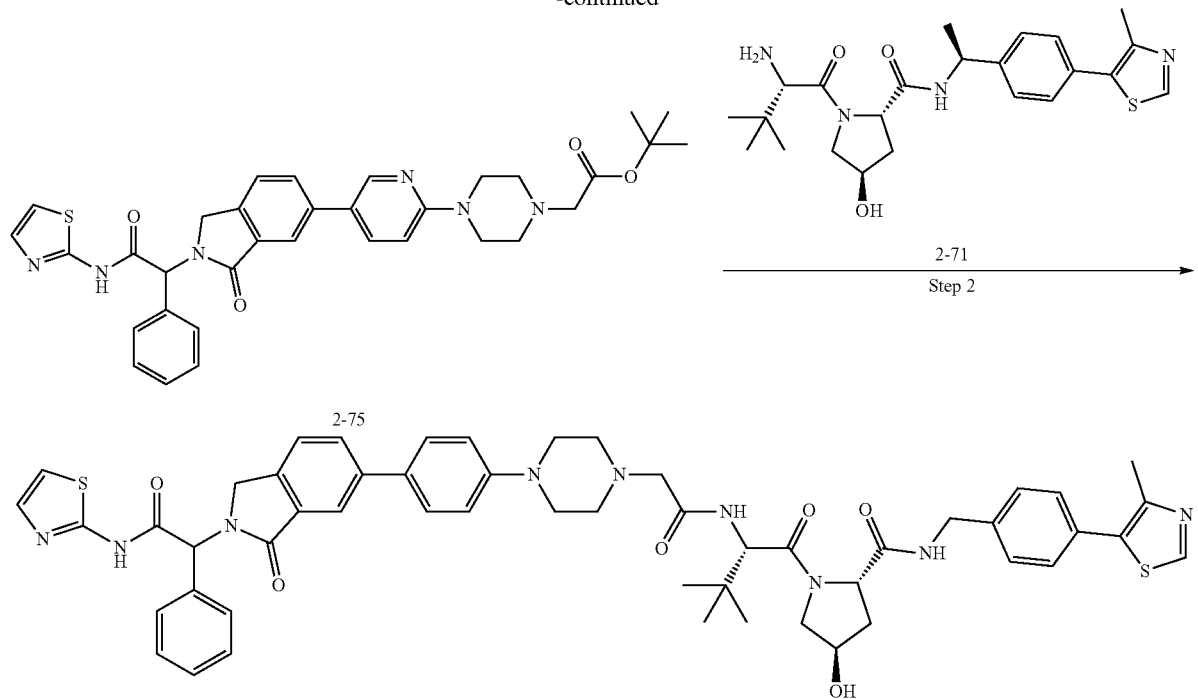
Compound I-6 was prepared in a manner similar to the synthesis of Compound I-23 as shown in Example 26. MS m/z: 980.55 [M+1]⁺.
Example 29: Synthesis of (2S,4R)-1-((2S)-2-(tert-Butyl)-4,16-dioxo-16-(4-(4-(3-oxo-2-(2-oxo-1-phenyl-2-(thiazol-2-ylamino)ethyl)isoindolin-5-yl)phenyl)piperazin-1-yl)-7,10,13-trioxa-3-azahexadecanoyl)-4-hydroxy-N-(4-(4-methylthiazol-5-yl)benzyl)pyrrolidine-2-carboxamide (I-25)
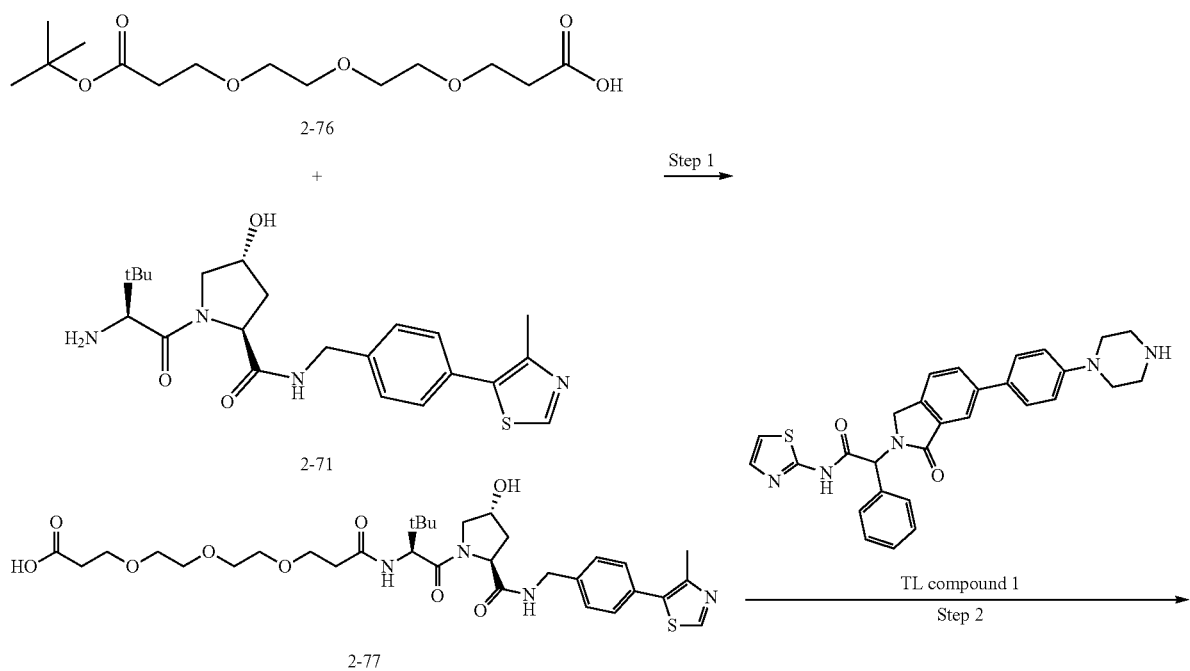

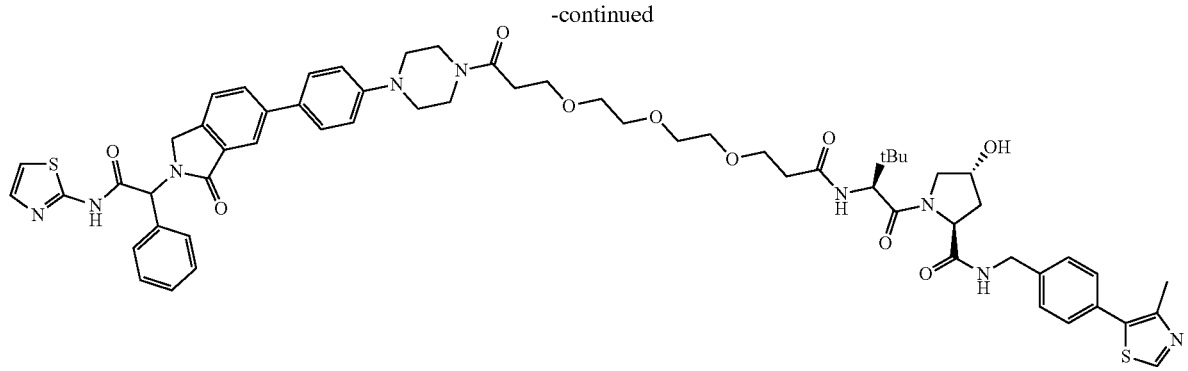

I-25

Step 1. (S)-15-((2S,4R)-4-Hydroxy-2-((4-(4-methyl-thiazol-5-yl)benzyl)carbamoyl)pyrrolidine-1-carbonyl)-16,16-dimethyl-13-oxo-4,7,10-trioxa-14-azaheptadecanoic Acid (2-77)

2,2-dimethyl-4-oxo-3,7,10,13-tetraoxahexadecan-16-oic acid (107 mg, 0.35 mmol), 2-71 (100 mg, 0.23 mmol) and HATU (175 mg, 0.46 mmol) were dissolved in DMF (2.5 mL), and DIEA (160 μL, 0.92 mmol) was added to the mixture. After stirring for 30 minutes, the reaction mixture was diluted with EtOAc and washed with water five times. The organic layer was dried over Na$_2$SO$_4$, filtered and concentrated. The residue was purified by preparative HPLC to afford tert-butyl (S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoate as an off-white solid.

To a solution of tert-butyl (S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoate in DCM (7 mL) was added TFA (3 mL). After stirring for 1.5 hours, the reaction mixture was concentrated and purified by flash column chromatography (DCM:1.75 N NH$_3$ in MeOH=100:0 to 80:20) to afford 2-77 (108 mg, 70%) as a white solid.

Step 2: (2S,4R)-1-((2S)-2-(tert-Butyl)-4,16-dioxo-16-(4-(4-(3-oxo-2-(2-oxo-1-phenyl-2-(thiazol-2-ylamino)ethyl)isoindolin-5-yl)phenyl)piperazin-1-yl)-7,10,13-trioxa-3-azahexadecanoyl)-4-hydroxy-N-(4-(4-methylthiazol-5-yl)benzyl)pyrrolidine-2-carboxamide (I-25)

To a solution of TL compound 1 (61 mg, 0.12 mmol) and 2-77 (53 mg, 0.08 mmol) in DMF (1 mL) was added HATU (61 mg, 0.16 mmol) and DIEA (56 μL, 0.32 mmol). After stirring overnight, the reaction mixture was purified by preparative HPLC to afford 1-25 (50 mg, 52%) as a white solid. MS m/z: 1154.84 [M+1]$^+$; $^1$H NMR (500 MHz, DMSO-d$_6$) δ=12.70 (br s, 1H), 8.98 (s, 1H), 8.56 (t, J=6.3 Hz, 1H), 7.95-7.81 (m, 3H), 7.65-7.55 (m, 3H), 7.54-7.31 (m, 10H), 7.28 (d, J=3.4 Hz, 1H), 7.05 (d, J=8.5 Hz, 2H), 6.33 (s, 1H), 5.12 (d, J=3.7 Hz, 1H), 4.77 (d, J=17.7 Hz, 1H), 4.55 (d, J=9.5 Hz, 1H), 4.46-4.39 (m, 2H), 4.37-4.32 (m, 1H), 4.21 (dd, J=5.5, 15.6 Hz, 1H), 3.99 (d, J=17.7 Hz, 1H), 3.69-3.53 (m, 10H), 3.51-3.43 (m, 8H), 3.25-3.20 (m, 2H), 3.19-3.14 (m, 2H), 2.62 (t, J=6.6 Hz, 2H), 2.57-2.53 (m, 1H), 2.44 (s, 3H), 2.39-2.32 (m, 1H), 2.07-2.00 (m, 1H), 1.90 (ddd, J=4.3, 8.5, 12.9 Hz, 1H), 0.92 (s, 9H).

Example 30: Synthesis of (2S,4R)-1-((2S)-2-(tert-Butyl)-16-(4-(4-(2-(1-(5-fluoro-2-hydroxyphenyl)-2-oxo-2-(thiazol-2-ylamino)ethyl)-3-oxoisoindolin-5-yl)phenyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide (I-26)

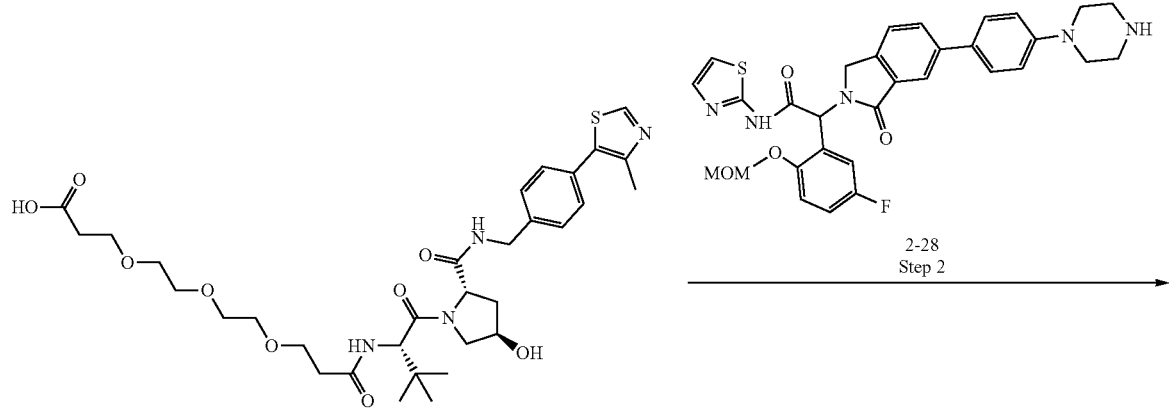

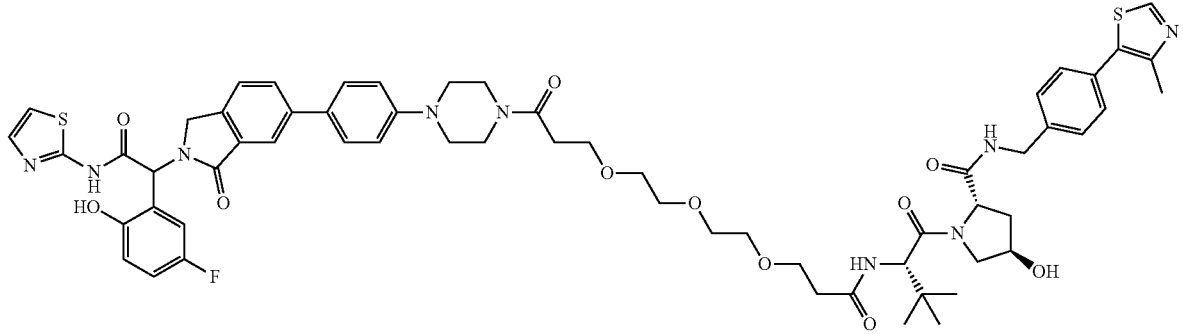

I-26

Compound I-26 was prepared in a manner similar to the synthesis of Compound I-25 as shown in Example 29. Step 2 of the synthesis of Compound I-26 is shown above in Example 30. MS m/z: 1189.12 [M+1]$^+$; $^1$H NMR (500 MHz, DMSO-d$_6$) δ=9.96 (s, 1H), 8.98 (s, 1H), 8.56 (t, J=5.6 Hz, 1H), 7.93-7.83 (m, 3H), 7.65-7.57 (m, 3H), 7.49 (d, J=3.4 Hz, 1H), 7.44-7.35 (m, 4H), 7.27 (d, J=3.1 Hz, 1H), 7.14-7.06 (m, 1H), 7.05 (d, J=8.5 Hz, 2H), 6.91 (dd, J=8.7, 4.7 Hz, 1H), 6.86 (dd, J=9.0, 2.6 Hz, 1H), 6.33 (s, 1H), 5.12 (br s, 1H), 4.63 (d, J=17.1 Hz, 1H), 4.55 (d, J=9.5 Hz, 1H), 4.47-4.39 (m, 2H), 4.35 (br s, 1H), 4.21 (dd, J=15.7, 5.3 Hz, 1H), 3.99 (d, J=17.4 Hz, 1H), 3.73-3.53 (m, 10H), 3.53-3.40 (m, 8H), 3.23 (br s, 2H), 3.17 (br s, 2H), 2.62 (t, J=6.6 Hz, 2H), 2.57-2.53 (m, 1H), 2.44 (s, 3H), 2.39-2.29 (m, 1H), 2.08-1.98 (m, 1H), 1.96-1.83 (m, 1H), 0.93 (s, 9H).

Example 31. Synthesis of 4-Fluoro-2-(3-methyl-2,6-dioxopiperidin-3-yl)isoindoline-1,3-dione (2-81)

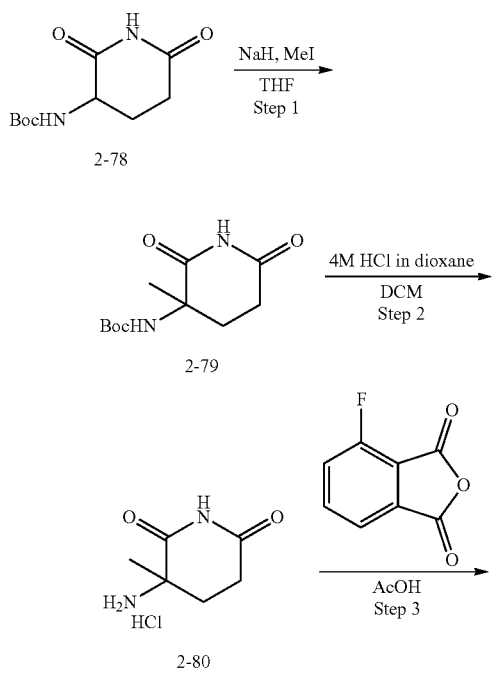

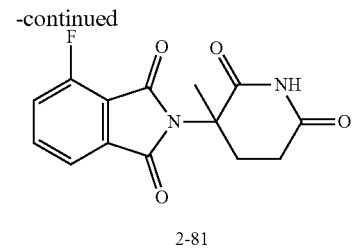

2-81

Step 1: tert-Butyl (3-methyl-2,6-dioxopiperidin-3-yl)carbamate (2-79)

To a solution of tert-butyl (2-78, 2,6-dioxopiperidin-3-yl) carbamate (1.0 g, 4.38 mmol) in THF (15 mL) was added NaH (263 mg, 6.57 mmol) at 0° C. After stirring for 20 minutes at room temperature, iodomethane (327 μL, 5.26 mmol) was added to the reaction mixture. After stirring for 2 hours, the mixture was diluted with EtOAc and quenched with water. The organic layer was collected and the aqueous layer was washed with EtOAc. The combined organic layers were dried over Na$_2$SO$_4$, filtered and concentrated. The crude compound 2-79 was carried forward in the next step without additional purification.

Step 2: 3-Amino-3-methylpiperidine-2,6-dione HCl salt (2-80)

Compound 2-79 was dissolved in dioxane and 4M HCl in dioxane was added to the resulting solution. After stirring for 2 hours, the reaction mixture was concentrated under reduced pressure to afford crude product which was carried forward in the next step without additional purification.

Step 3: 4-Fluoro-2-(3-methyl-2,6-dioxopiperidin-3-yl)isoindoline-1,3-dione (2-81)

Compound 2-80 and 4-fluoroisobenzofuran-1,3-dione were dissolved in acetic acid. The resulting mixture was stirred at 100° C. for overnight and the reaction mixture was concentrated under reduced pressure. The residue was re-dissolved in DCM and basified with saturated NaHCO$_3$. The aqueous layer was washed with DCM three times. Combined organic layer was dried over Na$_2$SO$_4$, filtered and concentrated under reduced pressure. The residue was purified by flash column chromatography to afford compound 2-81 (432 mg, 34%, three steps) as a white solid. $^1$H NMR (500 MHz, DMSO-d$_6$) δ=10.97 (s, 1H), 7.88-7.81 (m, 1H), 7.69-7.59 (m, 1H), 2.69-2.45 (m, 3H), 2.04-1.95 (m, 1H).

Example 32. Synthesis of 2-(6-(4-(4-(3-(2-(2-(2-((2-(3-Methyl-2,6-dioxopiperidin-3-yl)-1,3-dioxoisoindolin-4-yl)amino)ethoxy)ethoxy)ethoxy)propanoyl)piperazin-1-yl)phenyl)-1-oxoisoindolin-2-yl)-2-phenyl-N-(thiazol-2-yl)acetamide (1-27)

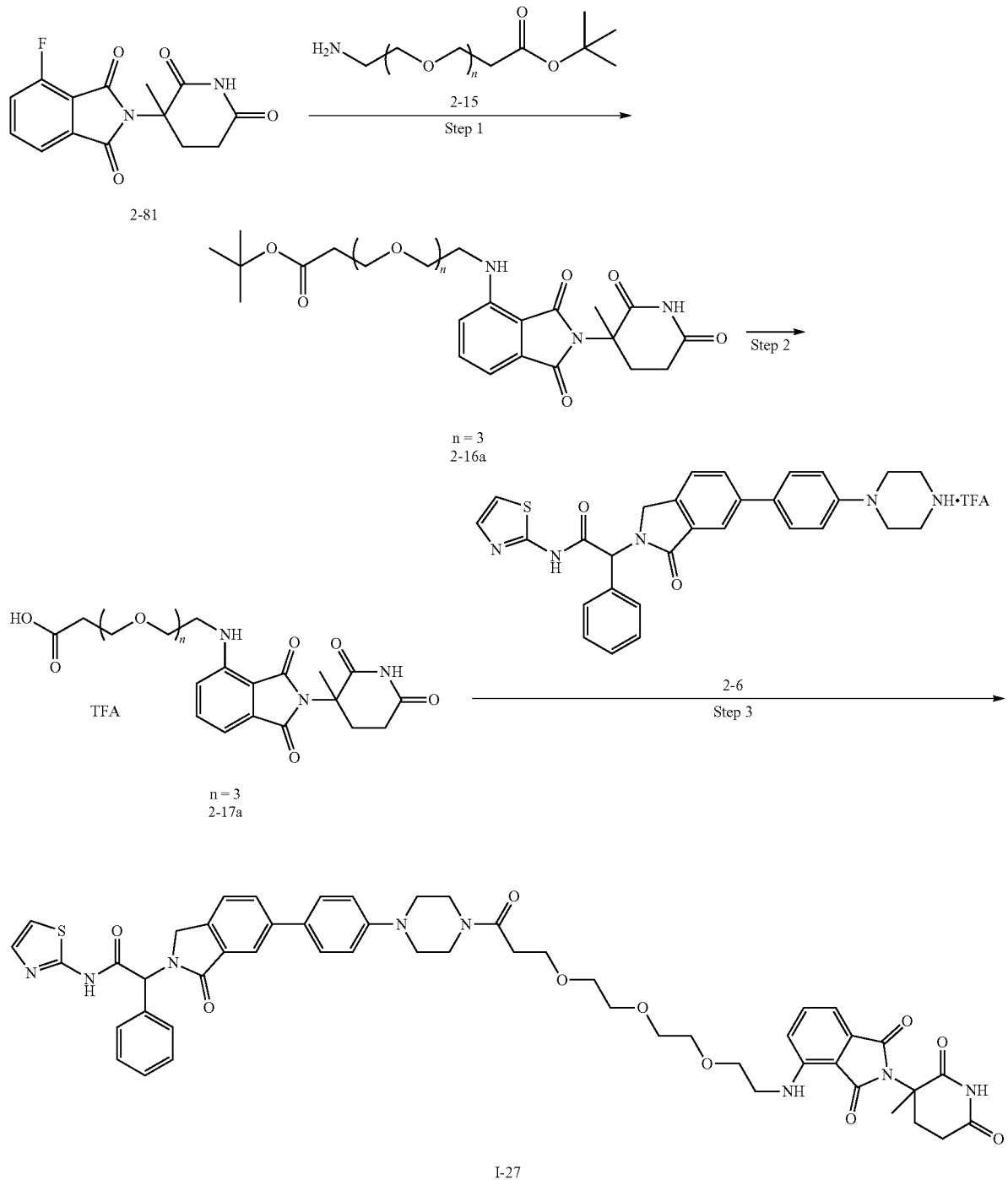

Compound I-27 was prepared according to the synthesis of Compound I-1 as shown in Example 3. MS m/z: 983.48 [M+1]$^+$; $^1$H NMR (500 MHz, DMSO-d$_6$) δ=12.70 (s, 1H), 10.97 (s, 1H), 7.91-7.82 (m, 2H), 7.67-7.57 (m, 3H), 7.55-7.41 (m, 5H), 7.39 (d, J=7.3 Hz, 2H), 7.28 (d, J=3.1 Hz, 1H), 7.07 (d, J=8.5 Hz, 1H), 7.04 (d, J=8.5 Hz, 2H), 6.94 (d, J=7.0 Hz, 1H), 6.60 (t, J=5.5 Hz, 1H), 6.33 (s, 1H), 4.77 (d, J=17.4 Hz, 1H), 3.99 (d, J=17.4 Hz, 1H), 3.69-3.55 (m, 8H), 3.55-3.47 (m, 6H), 3.44-3.39 (m, 2H), 3.22 (br s, 2H), 3.16 (br s, 2H), 2.74-2.45 (m, 7H), 2.06-1.95 (m, 1H), 1.87 (s, 3H).

Example 33. Synthesis of 2-(6-(4-(4-(3-(2-(2-((2-(2,6-dioxopiperidin-3-yl)-1,3-dioxoisoindolin-4-yl)amino)ethoxy)ethoxy)propanoyl)piperazin-1-yl)phenyl)-1-oxoisoindolin-2-yl)-2-(5-fluoro-2-hydroxyphenyl)-N-(thiazol-2-yl)acetamide (I-28)

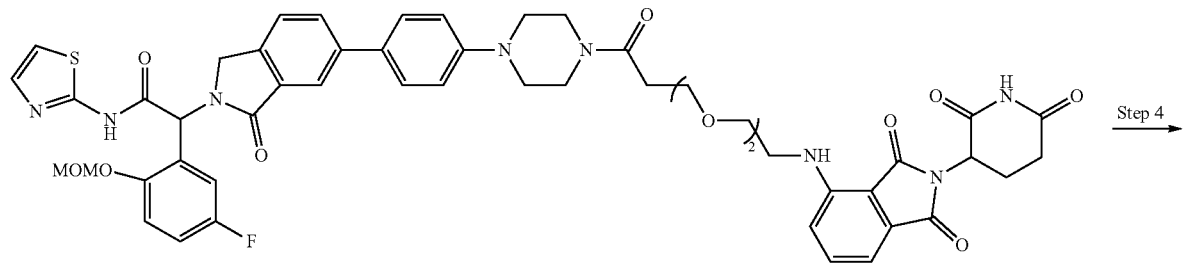

2-82

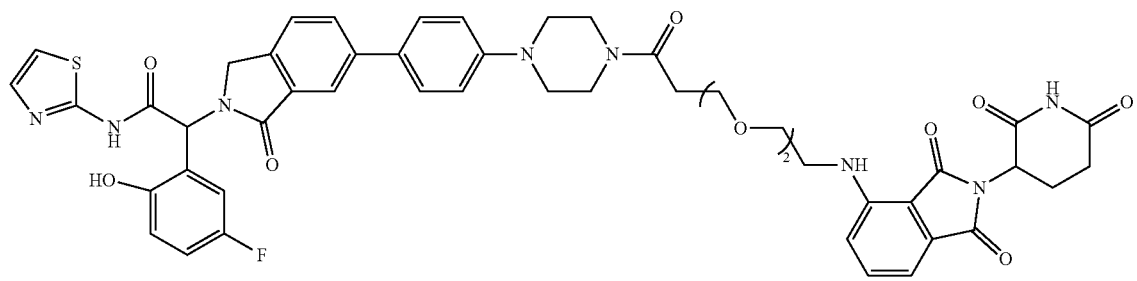

I-28

Compound I-28 was prepared in a manner similar to the synthesis of Compound I-3 as shown in Example 9. Step 4 of the synthesis of Compound I-28 is shown above in Example 33. MS m/z: 959.43 [M+1]$^+$; $^1$H NMR 500 MHz (DMSO-d$_6$) δ 11.10 (s, 1H), 7.88-7.81 (m, 2H), 7.63-7.54 (m, 4H), 7.38 (d, J=3.1 Hz, 1H), 7.13 (d, J=8.5 Hz, 1H), 7.10-7.01 (m, 4H), 6.89-6.82 (m, 2H), 6.60 (br t, J=5.3 Hz, 1H), 6.20 (s, 1H), 5.05 (dd, J=12.6, 5.2 Hz, 1H), 4.80 (d, J=17.7 Hz, 1H), 4.22 (d, J=17.7 Hz, 1H), 3.68-3.40 (m, 10H), 3.22-3.12 (m, 4H), 2.92-2.82 (m, 1H), 2.65-2.50 (m, 4H), 2.06-1.97 (m, 1H).

Example 34. Synthesis of 2-(6-(4-(4-(3-(2-((2-(2,6-dioxopiperidin-3-yl)-1,3-dioxoisoindolin-4-yl)amino)ethoxy)propanoyl)piperazin-1-yl)phenyl)-1-oxoisoindolin-2-yl)-2-(5-fluoro-2-hydroxyphenyl)-N-(thiazol-2-yl)acetamide (I-29)

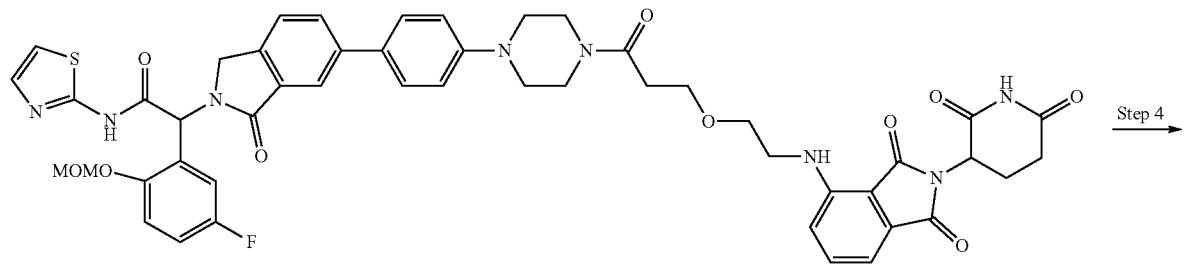

2-83

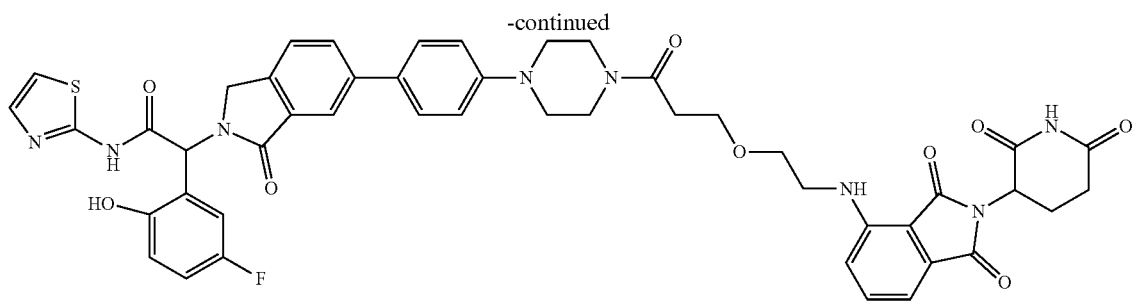

I-29

Compound I-29 was prepared according to the synthesis of Compound I-3 as shown in Example 9. Step 4 of the synthesis of Compound I-29 is shown above in Example 34. MS m/z: 915.45 [M+1]$^+$; $^1$H NMR 500 MHz (DMSO-d$_6$) δ 11.10 (bs, 1H), 7.83 (bs, 2H) 7.64 (d, J=8.9 Hz, 1H), 7.69-7.53 (m, 3H), 7.23 (d, J=3.4 Hz, 1H), 7.13 (d, J=8.9 Hz, 1H), 7.05-6.97 (m, 3H), 6.94-6.88 (m, 1H), 6.85-6.80 (m, 1H), 6.79-6.72 (m, 2H), 6.58 (br t, J=5.0 Hz, 1H), 6.02 (s, 1H), 5.12-5.00 (m, 2H), 4.54 (d, J=18.3 Hz, 1H), 3.71 (t, J=6.6 Hz, 2H), 3.65-3.57 (m, 6H), 3.49-3.43 (m, 4H), 2.92-2.82 (m, 1H), 2.64 (t, J=6.3 Hz, 2H), 2.60-2.50 (m, 2H), 2.05-1.96 (m, 1H).

Example 35. Synthesis of 2-(6-(4-(4-(1-((2-(2,6-dioxopiperidin-3-yl)-1,3-dioxoisoindolin-4-yl)amino)-3,6,9,12-tetraoxapentadecan-15-oyl)piperazin-1-yl)phenyl)-1-oxoisoindolin-2-yl)-2-(5-fluoro-2-hydroxyphenyl)-N-(thiazol-2-yl)acetamide (I-30)

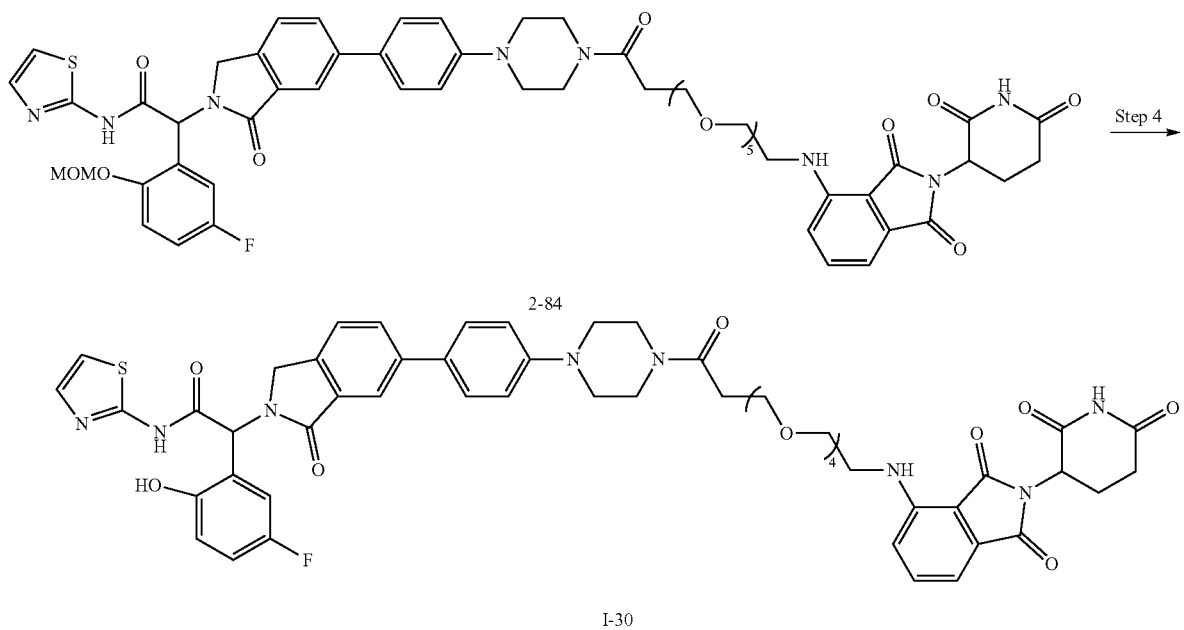

I-30

Compound I-30 was prepared according to the synthesis of Compound I-3 as shown in Example 9. Step 4 of the synthesis of Compound I-30 is shown above in Example 35. MS m/z: 1047.45 [M+1]$^+$; $^1$H NMR 500 MHz (DMSO-d$_6$) δ 12.61 (bs, 1H), 11.09 (s, 1H), 10.02 (bs, 1H), 7.88-7.87 (m, 1H), 7.86 (dd, J=7.9, 1.5 Hz, 1H), 7.65 (d, J=8.9 Hz, 2H), 7.62-7.54 (m, 2H), 7.49 (d, J=3.7 Hz, 1H), 7.27 (d, J=3.7 Hz, 1H), 7.17-7.08 (m, 4H), 7.03 (d, J=7.0 Hz, 1H), 6.94 (dd, J=9.2, 4.9 Hz, 1H), 6.86 (dd, J=9.2, 3.7 Hz, 1H), 6.59 (br, 1H), 6.33 (s, 1H), 5.05 (dd, J=12.8, 5.5 Hz, 1H), 4.63 (d, J=17.4 Hz, 1H), 4.00 (d, J=17.4 Hz, 1H), 3.68-3.42 (m, 22H), 3.28-3.17 (m, 4H), 2.92-2.83 (m, 1H), 2.65-2.50 (m, 4H), 2.34-2.27 (m, 2H), 2.05-1.98 (m, 1H).

Example 36. Synthesis of 2-(6-(4-(4-(2-(2-(2-(2-((2-(3-methyl-2,6-dioxopiperidin-3-yl)-1,3-dioxoisoindolin-4-yl)amino)ethoxy)ethoxy)ethoxy)ethyl)piperazin-1-yl)phenyl)-1-oxoisoindolin-2-yl)-2-phenyl-N-(thiazol-2-yl)acetamide (I-31)

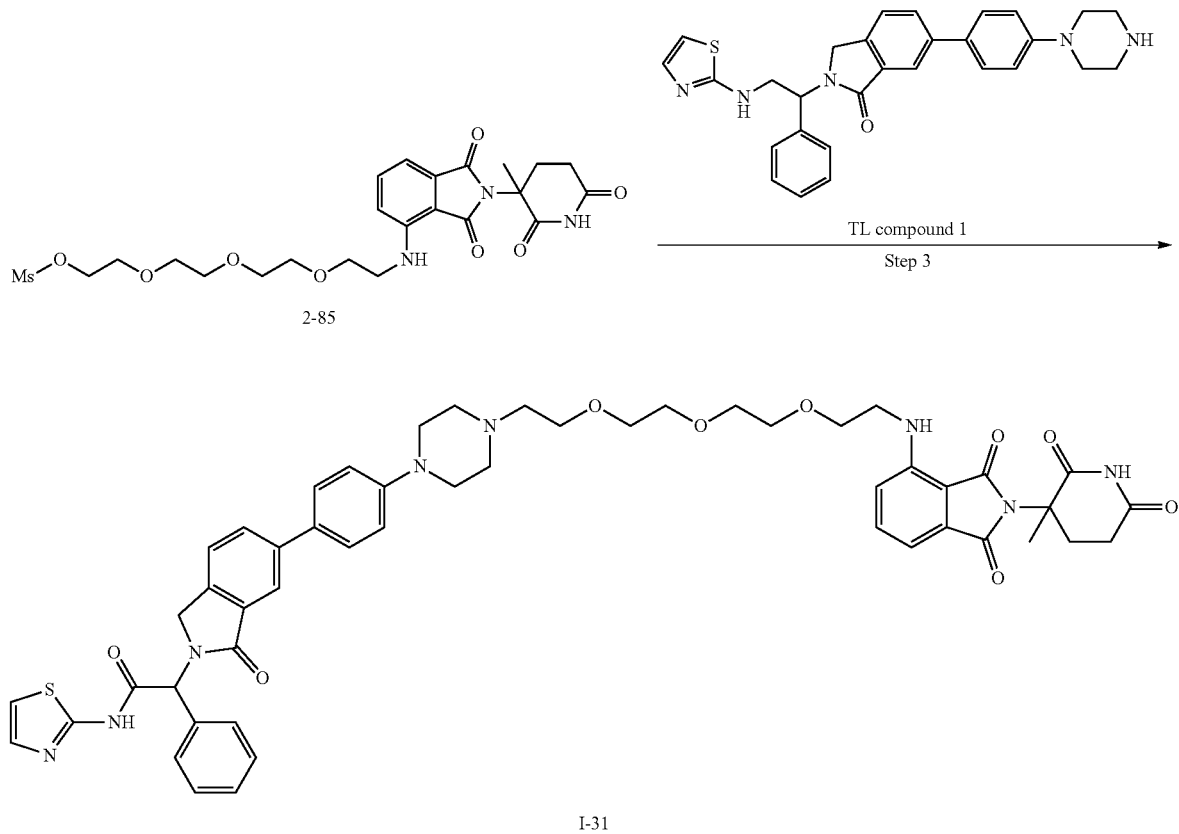

I-31

Compound I-31 was prepared according to the synthesis of Compound I-18 as shown in Example 21. Step 3 of the synthesis of Compound I-31 is shown above in Example 36. MS m/z: 955.59 [M+1]$^+$.

Example 37. Synthesis of 2-(6-(6-(4-(2-(2-(2-(2-((2-(3-methyl-2,6-dioxopiperidin-3-yl)-1,3-dioxoisoindolin-4-yl)amino)ethoxy)ethoxy)ethoxy)ethyl)piperazin-1-yl)pyridin-3-yl)-1-oxoisoindolin-2-yl)-2-phenyl-N-(thiazol-2-yl)acetamide (I-32)

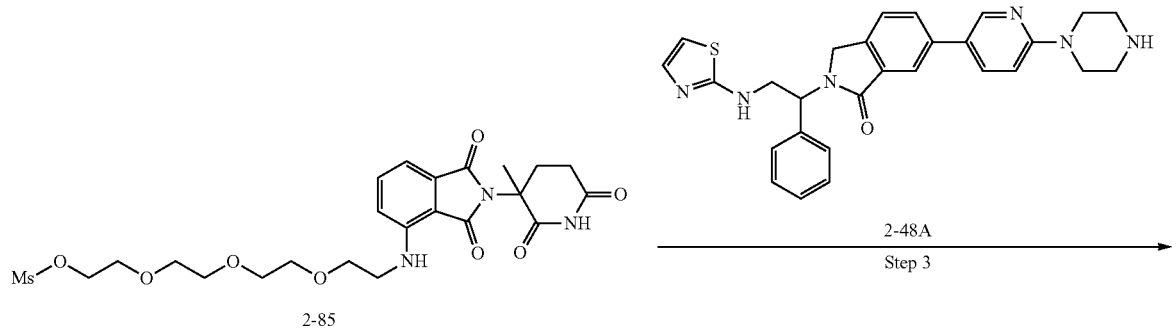

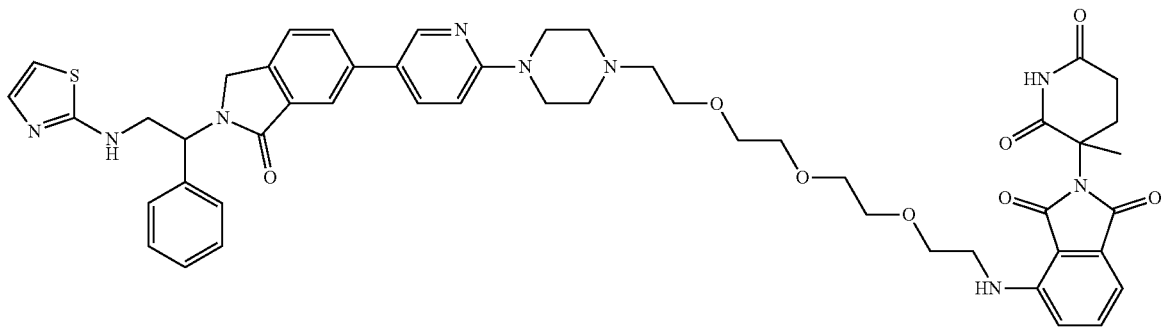

I-32

Compound I-32 was prepared according to the synthesis of Compound I-22 as shown in Example 25. Step 3 of the synthesis of Compound I-32 is shown above in Example 37. MS m/z: 956.61 [M+1]+; $^1$H NMR (500 MHz, DMSO-$d_6$) δ=12.70 (s, 1H), 10.98 (s, 1H), 8.49 (d, J=2.1 Hz, 1H), 7.97-7.88 (m, 2H), 7.86 (dd, J=7.9, 1.5 Hz, 1H), 7.61 (d, J=8.2 Hz, 1H), 7.54 (dd, J=8.4, 7.2 Hz, 1H), 7.51-7.41 (m, 4H), 7.41-7.36 (m, 2H), 7.28 (d, J=3.4 Hz, 1H), 7.10 (d, J=8.5 Hz, 1H), 6.95 (d, J=7.2 Hz, 1H), 6.93-6.88 (m, 1H), 6.62 (t, J=5.8 Hz, 1H), 6.32 (s, 1H), 4.78 (d, J=17.7 Hz, 1H), 4.00 (d, J=17.7 Hz, 1H), 3.62 (t, J=5.5 Hz, 2H), 3.60-3.47 (m, 16H), 3.47-3.40 (m, 2H), 2.75-2.43 (m, 7H), 2.04-1.96 (m, 1H), 1.87 (s, 3H).

Example 38. Synthesis of (2S,4R)-1-((2S)-2-(tert-Butyl)-4,16-dioxo-16-(4-(4-(3-oxo-2-(2-oxo-1-phenyl-2-(thiazol-2-ylamino)ethyl)isoindolin-5-yl)phenyl)piperazin-1-yl)-7,10,13-trioxa-3-azahexadecanoyl)-4-hydroxy-N-(4-(4-methylthiazol-5-yl)benzyl)pyrrolidine-2-carboxamide (I-34)

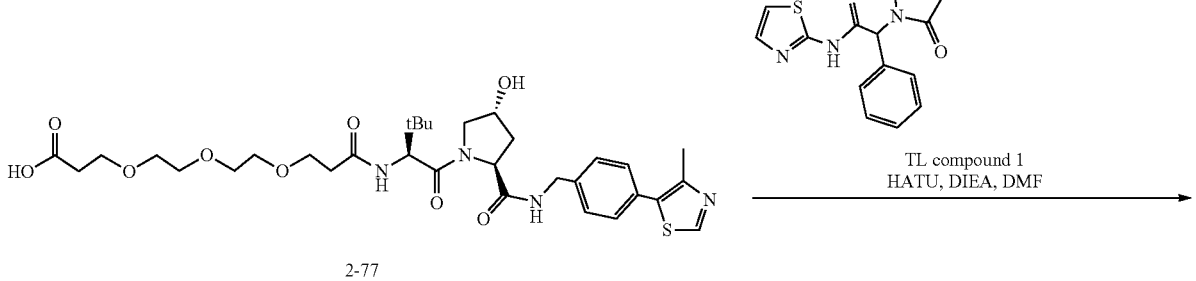

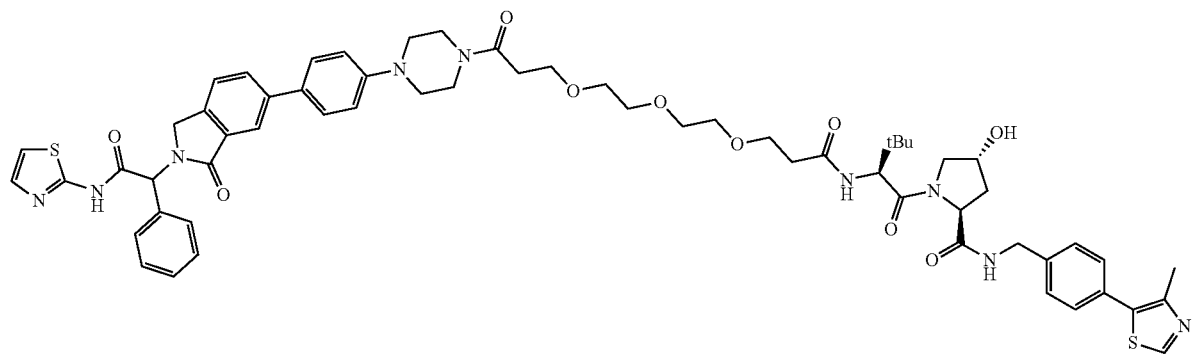

I-34

To a solution of TL compound 1 (61 mg, 0.12 mmol) and 2-77 (53 mg, 0.08 mmol) in DMF (1 mL) were added HATU (61 mg, 0.16 mmol) and DIEA (56 µL, 0.32 mmol). After stirring overnight, the reaction mixture was purified by preparative HPLC to afford 1-34 (50 mg, 52%) as a white solid. MS m/z: 1154.84 [M+1]$^+$; $^1$H NMR (500 MHz, DMSO-d$_6$) δ=12.70 (br s, 1H), 8.98 (s, 1H), 8.56 (t, J=6.3 Hz, 1H), 7.95-7.81 (m, 3H), 7.65-7.55 (m, 3H), 7.54-7.31 (m, 10H), 7.28 (d, J=3.4 Hz, 1H), 7.05 (d, J=8.5 Hz, 2H), 6.33 (s, 1H), 5.12 (d, J=3.7 Hz, 1H), 4.77 (d, J=17.7 Hz, 1H), 4.55 (d, J=9.5 Hz, 1H), 4.46-4.39 (m, 2H), 4.37-4.32 (m, 1H), 4.21 (dd, J=5.5, 15.6 Hz, 1H), 3.99 (d, J=17.7 Hz, 1H), 3.69-3.53 (m, 10H), 3.51-3.43 (m, 8H), 3.25-3.20 (m, 2H), 3.19-3.14 (m, 2H), 2.62 (t, J=6.6 Hz, 2H), 2.57-2.53 (m, 1H), 2.44 (s, 3H), 2.39-2.32 (m, 1H), 2.07-2.00 (m, 1H), 1.90 (ddd, J=4.3, 8.5, 12.9 Hz, 1H), 0.92 (s, 9H).

Example 39. EGFR Protein Expression and Purification

Constructs spanning residues 696-1022 of the human EGFR (including wild type and L858R, L858R/T790M, T790M, and T790M/V948R mutant sequences) were prepared in a GST-fusion format using the pTriEX system (Novagen) for expression in Sf9 insect cells essentially as described. (Yun, C. H. et al. The T790M mutation in EGFR kinase causes drug resistance by increasing the affinity for ATP. *Proc Natl Acad Sci USA* 105, 2070-2075 (2008); Yun, C. H. et al. Structures of lung cancer-derived EGFR mutants and inhibitor complexes: mechanism of activation and insights into differential inhibitor sensitivity. *Cancer Cell* 11, 217-227 (2007)) EGFR kinase proteins were purified by glutathione-affinity chromatography followed by size-exclusion chromatography after cleavage with TEV or thrombin to remove the GST fusion partner following established procedures. (Yun, C. H. et al. *Proc Natl Acad Sci USA* 105, 2070-2075 (2008); Yun, C. H. et al. *Cancer Cell* 11, 217-227 (2007)

Example 40. H1975, H3255 & HaCaT Target Modulation Assays

Tissue Culture

Cells were maintained in 10% FBS/RPMI supplemented with 100 µg/mL Penicillin/Streptomycin (Hyclone #SH30236.01). The cells were harvested with 0.25% Trypsin/EDTA (Hyclone #SH30042.1), re-suspended in 5% FBS/RPMI Pen/Strep and plated at 7,500 cells per well in 50 µL of media in a 384-well black plate with clear bottoms (Greiner #789068G). The cells were allowed to incubate overnight in a 37° C., 5% CO$_2$ humidified tissue culture incubator. The 12-point serial diluted test compounds were transferred to the plate containing cells by using a 50 nL Pin Head device (Perkin Elmer) and the cells were placed back in the incubator for 3 hours.

Phospho-EGFR (Y1173) Target Modulation Assay

HaCaT cells were stimulated with 10 ng/mL EGF (Peprotech # AF-100-15) for 5 minutes at room temperature. Constitutively activated EGFR mutant cell lines (H1975 and H3255) were not stimulated with EGF. The media was reduced to 20 µL using a Bio-Tek ELx 405 Select™ plate washer. Cells were lysed with 20 µL of 2× Lysis buffer containing protease and phosphatase inhibitors (2% Triton X-100, 40 mM Tris, pH 7.5, 2 mM EDTA, 2 mM EGTA, 300 mM NaCl, 2× complete cocktail inhibitor (Roche #11 697 498 001), 2× Phosphatase Inhibitor Cocktail Set II and Set III (Sigma #P5726 and #P0044)). The plates were shaken for 20 minutes. An aliquot of 25 µL from each well was transferred to prepared ELISA plates for analysis.

For the experiment studying the effect of EGF pretreatment on compound (e.g., compounds of the present application) target modulation, H1975 cells were harvested and plated in 0.5% FBS/RPMI Pen/Strep. On the following day, cells were pre-treated with 0.5% FBS/RPMI media with or without 10 ng EGF/mL for 5 minutes. Compound (i.e., compounds of the present application) was added and assay was carried out as described above.

Phospho-EGFR (Y1173) ELISA

Solid white 384-well high-binding ELISA plates (Greiner #781074) were coated with 5 µg/mL goat anti-EGFR capture antibody overnight in 50 mM carbonate/bicarbonate pH 9.5 buffer. Plates were blocked with 1% BSA (Sigma #A7030) in PBS for 1 hour at room temperature, and washes were carried out with a Bio-Tek ELx405 Select™ using 4 cycles of 100 µL TBS-T (20 mM Tris, 137 mM NaCl, 0.05% Tween-20) per well. A 25 µL aliquot of lysed cell was added to each well of the ELISA plate and incubated overnight at 4° C. with gentle shaking. A 1:1,000 anti-phospho-EGFR in 0.2% BSA/TBS-T was added and incubated for 2 hours at room temperature. After washing, 1:2,000 anti-rabbit-HRP in 0.2% BSA/TBS-T was added and incubated for 1 hour at room temperature. Chemiluminescent detection was carried out with SuperSignal ELISA Pico substrate. Signal was read on EnVision plate reader using built-in UltraLUM setting.

Example 41. Western Blotting

Cell lysates were equalized to protein content determined by Coomassie Plus™ Protein Assay Reagent (ThermoScientific #1856210) and loaded onto 4-12% NuPAGE Bis-Tris gels with MOPS running buffer with LDS Sample buffer (supplemented with DTT. Gel proteins were transferred to PVDF membranes with an iBlot® Gel Transfer Device. 1× Casein-blocked membranes were probed with primary antibodies overnight at 4° C. on an end-over-end rotisserie. Membranes were washed with TBS-T and HRP-conjugated secondary antibodies were added for 1 hour at room temperature. After washing, HRP was detected using Luminata™ Forte Western HRP Substrate reagent and recorded with a Bio-Rad VersaDoc imager.

Figure 3:
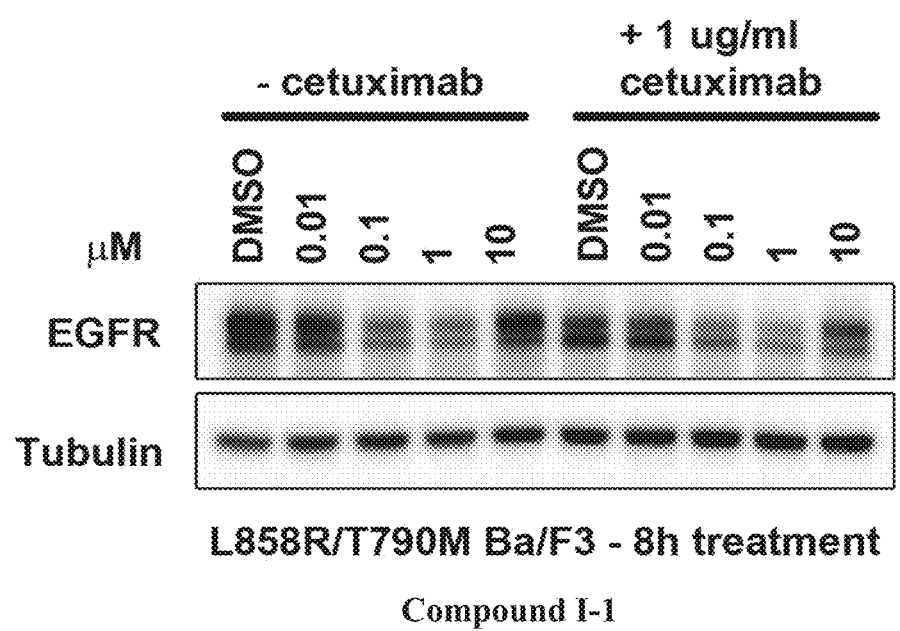
FIG. 3 is a western blot showing the levels of EGFR and tubulin in BaF3 cells expressing the EGFR L858R/T790M mutant after an 8-hour treatment with various concentrations of Compound I-1, in the absence or presence of cetuximab (1 μg/ml).
Figure 4:
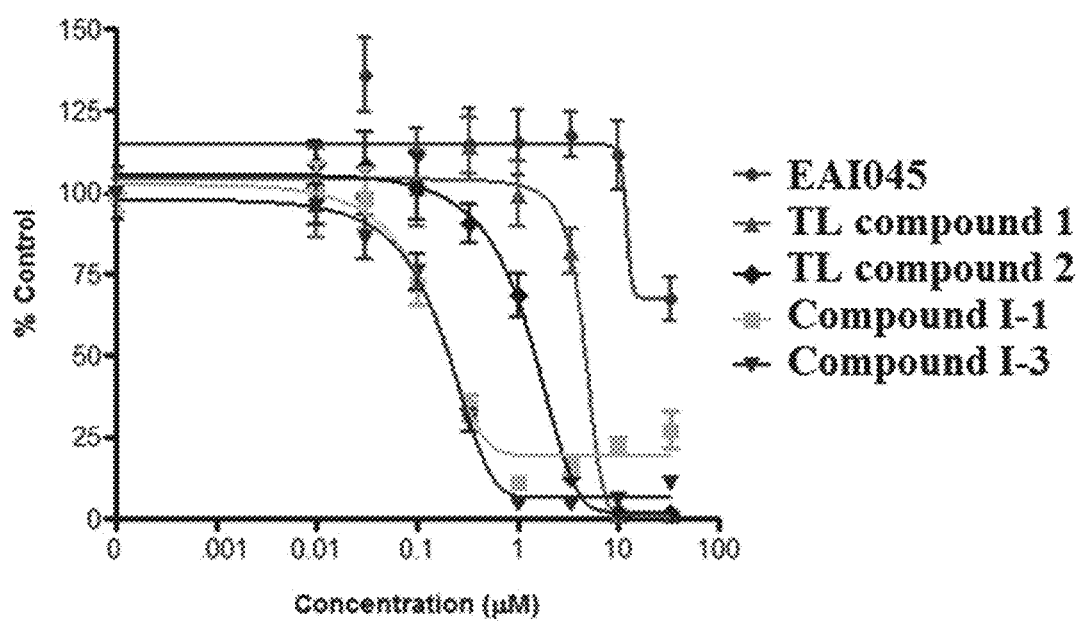
FIG. 4 is a graph showing EGFR activity in BaF3 cells expressing the EGFR L858R mutant after the cells were treated with various concentrations of EAI045 (an inhibitor of L858R/T790M EGFR mutants), TL compound 1, TL compound 2, Compound I-1, or Compound I-3. The x-axis is concentration measured in μM and the y-axis is EGFR activity measured as a percent of the control.
Figure 5A:
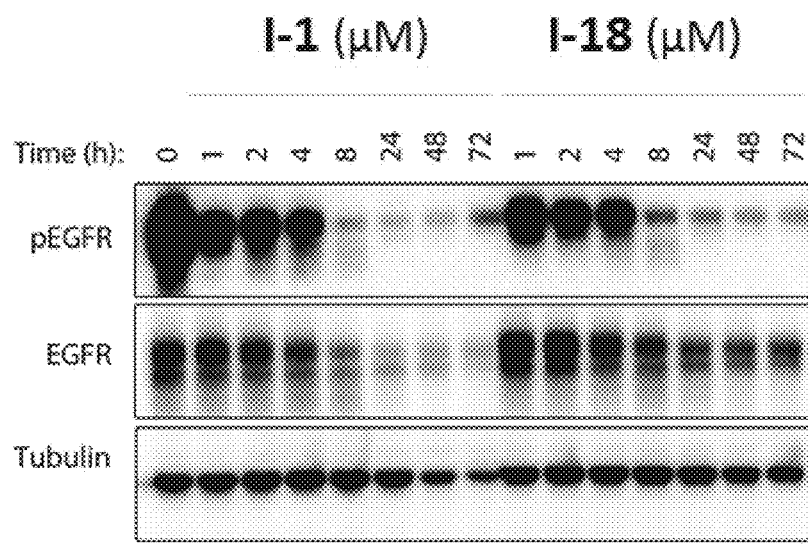
FIG. 5A is a western blot quantifying the levels of phosphorylated EGFR (pEGFR), EGFR, and tubulin in BaF3 cells expressing the EGFR L858R/T790M mutant over the course of 72 hours when exposed to Compound I-1 and Compound I-18.
Figure 5B:
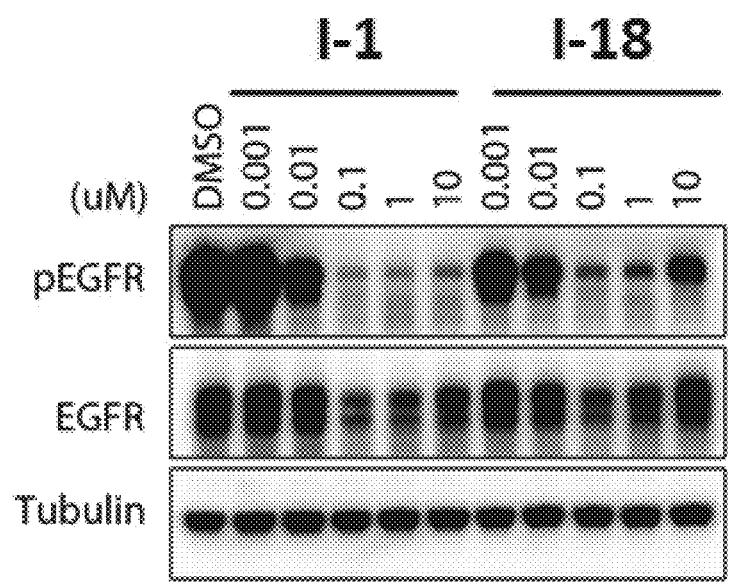
FIG. 5B is a western blot quantifying the levels of phosphorylated EGFR (pEGFR), EGFR, and tubulin in BaF3 cells expressing the EGFR L858R/T790M mutant after an 8-hour treatment of increasing concentrations of Compound I-1 and Compound I-18.
Figure 6:
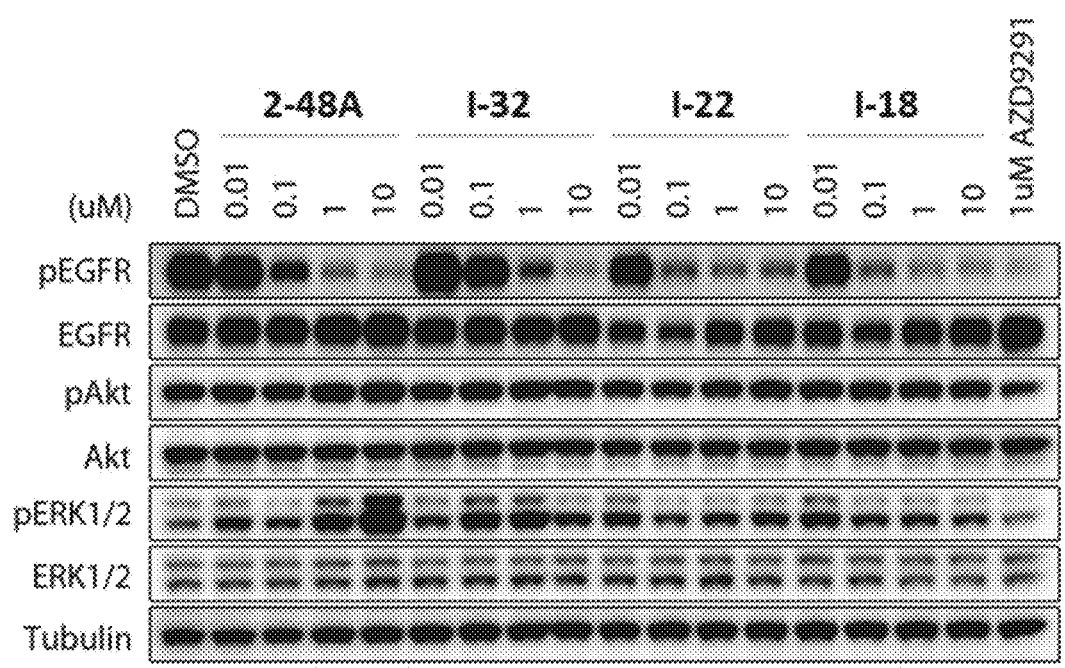
FIG. 6 is a western blot quantifying levels of phosphorylated EGFR (pEGFR), EGFR, phosphorylated AKt, Akt, phosphorylated ERK1, ERK2, phosphorylated ERK1, phosphorylated ERK2, and tubulin in a patient-derived lung cancer cell line (H1975) harboring the EGFR L858R/T790M mutant after a 24-hour treatment of increasing concentrations of intermediate 2-48A, Compound I-32, Compound I-22, and Compound I-18. The compounds were compared to known EGFR inhibitor AZD9291 tested at a concentration of 1 μM.
Figure 7:
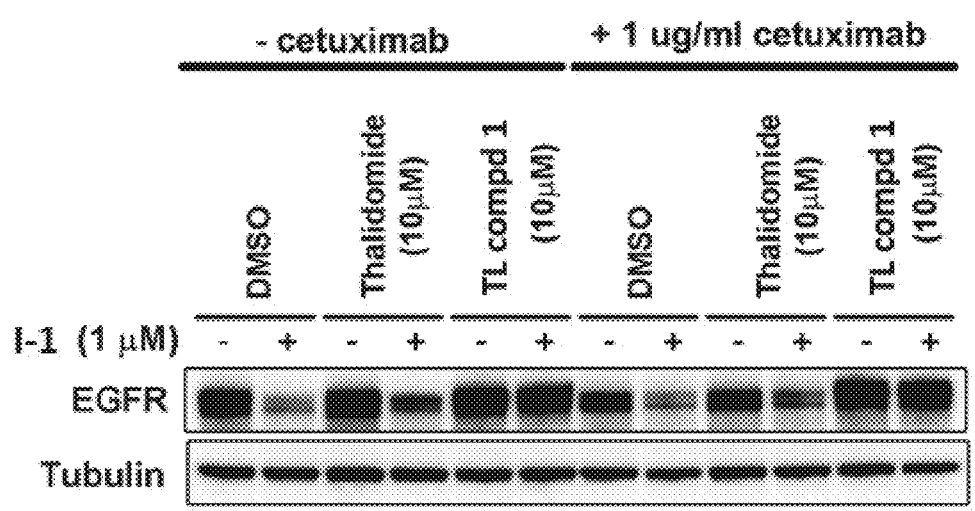
FIG. 7 is a western blot quantifying the levels of EGFR protein and tubulin after a 4 hour pretreatment of either DMSO, thalidomide (10 μM), or TL compound 1 (10 μM) followed by 24 hour Compound I-1 treatment in the presence or absence of 1 μg/mL cetuximab in BaF3 cells expressing the EGFR L858R/T790M.
Figure 8:
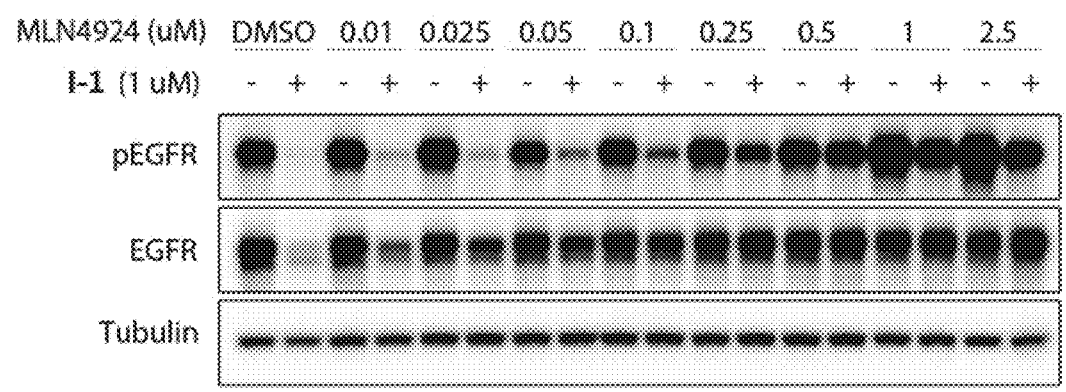
FIG. 8 is a western blot quantifying levels of phosphorylated EGFR (pEGFR), EGFR, and tubulin in BaF3 cells expressing the EGFR L858R/T790M mutant after a 4-hour pretreatment of the NEDD8-Activating Enzyme (NAE) inhibitor MLN4924 at various concentrations in the presence or absence of a 24-hour treatment of Compound I-1.

EGFR protein degradation was assessed by western blotting after treatment of T790M/L858R mutant Ba/F3 cell lines with a compound of the present application dose-dependently for 8 hour or in combination with 1 ug/mL of cetuximab. The results are shown in FIG. 3.

Example 42. Proliferation Assay

H1975, H3255 and HaCaT cell lines were plated in solid white 384-well plates (Greiner) at 500 cells per well in 10% FBS RPMI P/S media. Using a Pin Tool, 50 nL of serial diluted compounds of the present application were transferred to the cells. After 3 days, cell viability was measured by CellTiter-Glo (Promega) according to manufacturer's instructions. Luminescent readout was normalized to 0.1% DMSO-treated cells and empty wells. Data was analyzed by non-linear regression curve-fitting and EC$_{50}$ values were reported. Inhibition data of an EGFR T790M/L858R cell line for exemplary compounds of the present application combined with cetuximab (% cetuximab, 1.0 µM drug concentration with 1.0 µg/mL cetuximab) can be found in Table 2 below.

Ba/F3 Cell Proliferation Models

The EGFR mutant L858R, Del E746_A750, L858R/T790M, DelE746_A750/T790M, L858R/T790M/C797S and Del/T790M/C797S Ba/F3 cells have been previously described (Zhou, W., Ercan, D., Chen, L., Yun, C. H., Li, D., Capelletti, M., Cortot, A. B., Chirieac, L., Iacob, R. E., Padera, R., et al. "Novel mutant-selective EGFR kinase inhibitors against EGFR T790M," Nature 462, (2009), 1070-1074). All cell lines were maintained in RPMI 1640 (Cellgro; Mediatech Inc., Herndon, Calif.) supplemented with 10% FBS 100 units/mL penicillin, 100 units/mL streptomycin, and 2 mM glutamine. L858R cells were maintained in ACL-4 media (Invitrogen, Carlsbad, Calif.) supplemented with 5% FBS, 100 units/mL penicillin, 100 units/mL streptomycin, and 2 mM glutamine. The EGFR I941R mutation was introduced via site directed mutagenesis using the Quick Change Site-Directed Mutagenesis kit (Stratagene; La Jolla, Calif.) according to the manufacturer's instructions. All constructs were confirmed by DNA sequencing. The constructs were shuttled into the retroviral vector JP1540 using the BD Creator™ System (BD Biosciences). Ba/F3 cells were infected with retrovirus and according to standard protocols, as described previously (Zhou et al, Nature 2009). Stable clones were obtained by selection in puromycin (2 µg/ml).

Growth and inhibition of growth was assessed by MTS assay and was performed according to previously established methods (Zhou et al., Nature 2009). The MTS assay is a colorimetric method for determining the number of viable cells that is based on the bioreduction of MTS by cells to a formazan product that is soluble in cell culture medium and can be detected spectrophotometrically. Ba/F3 cells of different EGFR genotypes were exposed to treatment for 72 hours and the number of cells used per experiment determined empirically and has been previously established (Zhou et al., Nature 2009). All experimental points were set up in six wells and all experiments were repeated at least three times. The data was graphically displayed using GraphPad Prism version 5.0 for Windows, (GraphPad Software; www.graphpad.com). The curves were fitted using a non-linear regression model with a sigmoidal dose response.

Example 43. Mouse Efficacy Studies

EGFR-TL (T790M/L858R) and EGFR-TD (exon 19 deletion-T790M) mice were generated as previously described (Li, D., Shimamura, T., Ji, H., Chen, L., Haringsma, H. J., McNamara, K., Liang, M. C., Perera, S. A., Zaghlul, S., Borgman, C. L., et al., "Bronchial and peripheral murine lung carcinomas induced by T790M-L858R mutant EGFR respond to HKI-272 and rapamycin combination therapy," Cancer Cell 12, (2007), 81-93; Zhou et al., Nature 2009). The EGFR-L858R; T790M; C797S ("TLCS") mutant mouse cohort was established briefly as follows: The full-length HuTLCS cDNA was generated by site-directed mutagenesis using the Quickchange site directed mutagenesis kit (Agilent Technologies) and further verified by DNA sequencing. Sequence-verified targeting vectors were co-electroporated with an FLPe recombinase plasmid into v6.5 $C_{57}BL/6J$ (female)×129/sv (male) embryonic stem cells (Open Biosystems) as described elsewhere (Beard, C., Hochedlinger, K., Plath, K., Wutz, A., and Jaenisch, R., "Efficient method to generate single-copy transgenic mice by site-specific integration in embryonic stem cells," Genesis 44, (2006), 23-28). Resulting hygromycin-resistant embryonic stem clones were evaluated for transgene integration via PCR. Then, transgene-positive embryonic stem clones were injected into C57BL/6 blastocysts, and the resulting chimeras were mated with BALB/c WT mice to determine germline transmission of the TLCS transgene. Progeny of TL, TD and TLCS mice were genotyped by PCR of tail DNA.

The TL and TD mice were fed a doxycycline diet at 6 weeks of age to induce EGFR TL or TD expression, respectively. The TLCS mice were intranasally instilled with Ad-Cre (University of Iowa viral vector core) at 6 weeks of age to excise the loxP sites, activating EGFR TLCS expression.

All care of experimental animals was in accordance with Harvard Medical School/Dana-Farber Cancer Institute (DFCI) institutional animal care and use committee (IACUC) guidelines. All mice were housed in a pathogen-free environment at a DFCI animal facility and handled in strict accordance with Good Animal Practice as defined by the Office of Laboratory Animal Welfare.

Example 44. In Vivo Treatment and MRI Tumor Volume Quantification

The TL, TD and TLCS mice were monitored by MRI to quantify lung tumor burden before being assigned to various treatment study cohorts. All the treatment mice had equal amount initial tumor burden. A compound of the present application was dissolved in 10% NMP (10% 1-methyl-2-pyrrolidinone: 90% PEG-300), and was dosed at 60 mg/kg daily by oral gavage. Cetuximab was administrated at 1 mg/mouse every three days by intraperitoneal in injection. MRI evaluation was repeated every 2 weeks during the treatment. The animals were imaged with a rapid acquisition with relaxation enhancement sequence (TR=2000 ms, TE effect=25 ms) in the coronal and axial planes with a 1-mm slice thickness gating with respiratory rates. The detailed procedure for MRI scanning has been previously described (Li et al., 2007). The tumor burden volumes were quantified using 3-dimensional Slicer software.

Example 45. Bifunctional Compounds are Efficacious Against T790M/L858R Transformed Ba/F3 Cells Compounds of Table 1 were tested at a concentration of 1 µM against T790M/L858R transformed Ba/F3 cells. The assay, as described in Example 42, measured inhibition of growth as a percent of the inhibitory activity of the control. In Table 1, A is 0<% control<25, B is 25<% control<50, C is 50<% control<75, and D is 75<% control.

TABLE 1

Antiproliferative activity against T790M/L858R transformed Ba/F3 cells

| Compound | % control |
|---|---|
| I-28 | A |
| I-26 | D |
| I-10 | B |
| I-11 | B |
| I-12 | B |
| I-33 | A |
| I-29 | A |
| I-27 | D |
| I-25 | D |
| I-7 | B |
| I-17 | C |
| I-18 | A |

TABLE 1-continued

Antiproliferative activity against T790M/L858R transformed Ba/F3 cells

| Compound | % control |
|---|---|
| I-19 | D |
| I-20 | A |
| I-35 | D |
| I-8 | D |
| I-21 | C |
| I-1 | A |
| I-23 | D |
| I-22 | A |
| I-15 | C |
| I-16 | C |
| I-14 | D |
| TL Compd 1 | B |
| TL Compd 2 | D |

Example 46. Bifunctional Compounds are Potent Against T790M/L858R Transformed Ba/F3 Cells Compounds of Table 2 were tested in a T790M/L858R transformed Ba/F3 cell line as described in Example 42 and the $EC_{50}$ values were calculated. In Table 2, A is $EC_{50}<500$ nM, B is 500 nM$<EC_{50}<1000$ nM, C is 1000 nM$<EC_{50}<5000$ nM, and D is 5000 nM$<EC_{50}$.

TABLE 2

Antiproliferative activity against T790M/L858R transformed Ba/F3 cells

| Compound | T790M/L858R ($EC_{50}$) |
|---|---|
| I-29 | B |
| I-28 | B |
| I-33 | A |
| I-1 | A |
| I-10 | C |
| I-18 | A |
| I-20 | A |
| I-11 | C |
| I-12 | C |
| I-15 | C |
| I-16 | C |
| I-22 | A |
| I-14 | C |
| I-23 | D |
| I-24 | D |

Example 47. Bifunctional Compounds are Potent Against T790M/L858R/C797S Transformed Ba/F3 Cells Compounds of Table 3 were tested in a T790M/L858R transformed Ba/F3 cell line as described in Example 42 and the $EC_{50}$ values were calculated. In Table 3, A is $EC_{50}<500$ nM, B is 500 nM$<EC_{50}<1000$ nM, C is 1000 nM$<EC_{50}<5000$ nM, and D is 5000 nM$<EC_{50}$.

TABLE 3

Antiproliferative activity against T790M/L858R/C797S transformed Ba/F3 cells

| Compound | T790M/L858R/C797S ($EC_{50}$) |
|---|---|
| I-29 | D |
| I-28 | D |
| I-33 | C |
| I-1 | B |
| I-10 | D |
| I-18 | A |
| I-20 | A |
| I-11 | D |
| I-12 | D |
| I-15 | D |
| I-16 | D |
| I-22 | B |
| I-14 | D |
| I-23 | D |
| I-24 | D |

This specification has been described with reference to embodiments of the invention. However, one of ordinary skill in the art appreciates that various modifications and changes can be made without departing from the scope of the invention as set forth in the claims below. Accordingly, the specification was to be regarded in an illustrative rather than a restrictive sense, and all such modifications are intended to be included within the scope of invention.

We claim:
1. A compound of Formula:

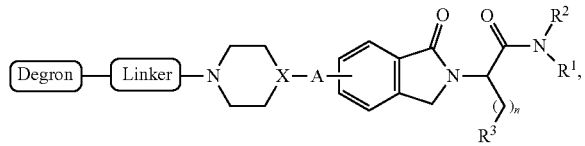

or an enantiomer, diastereomer, stereoisomer, or pharmaceutically acceptable salt thereof, wherein:
the Linker is a group that covalently binds to

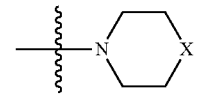

and the Degron;
the Degron is

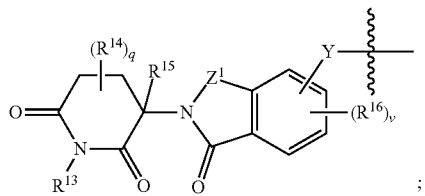

Y is a bond, $(CH_2)_{1-6}$, $(CH_2)_{0-6}$—O, $(CH_2)_{0-6}$—C(O)NR$^{11}$, $(CH_2)_{0-6}$—NR$^{11}$C(O), $(CH_2)_{0-6}$—NH, or $(CH_2)_{0-6}$—NR$^{12}$;
$Z^1$ is C(O) or C(R$^{13}$)$_2$;
$R^{11}$ is H or $C_1$-$C_6$ alkyl;
$R^{12}$ is $C_1$-$C_6$ alkyl or C(O)—$C_1$-$C_6$ alkyl;
each $R^{13}$ is independently H or $C_1$-$C_3$ alkyl;
each $R^{14}$ is independently $C_1$-$C_3$ alkyl;

$R^{15}$ is H, deuterium, $C_1$-$C_3$ alkyl, F, or Cl;
each $R^{16}$ is independently halogen, OH, $C_1$-$C_6$ alkyl, or $C_1$-$C_6$ alkoxy;
q is 0, 1, or 2; and
v is 0, 1, 2, or 3;
wherein the Degron is covalently bonded to the Linker via

A is phenyl or pyridinyl;
X is CH, C($C_1$-$C_3$) alkyl, or N;
$R^1$ is H or ($C_1$-$C_3$) alkyl;
$R^2$ is ($C_6$-$C_{10}$) aryl, or heteroaryl comprising one or two 5- to 7-membered rings and 1-4 heteroatoms selected from N, O, and S, wherein the aryl and heteroaryl are each optionally substituted with one or more $R^4$;
each $R^4$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, CN, C(O)$R^6$, C(O)O$R^6$, C(O)N$R^6R^7$, N$R^6R^7$, ($C_3$-$C_7$) cycloalkyl, heterocyclyl comprising a 5- to 7-membered ring and 1-3 heteroatoms selected from N, O, and S, ($C_6$-$C_{10}$) aryl, and heteroaryl comprising one or two 5- to 7-membered rings and 1-4 heteroatoms selected from N, O, and S, wherein the alkyl, cycloalkyl, heterocyclyl, aryl, and heteroaryl are each optionally substituted with one or more $R^5$;
each $R^5$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, and CN;
each $R^6$ is independently H or ($C_1$-$C_3$) alkyl;
each $R^7$ is independently H or ($C_1$-$C_3$) alkyl;
$R^3$ is ($C_1$-$C_3$) alkyl or

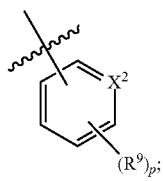

$X^2$ is N or C$R^8$;
$R^8$ is H, ($C_1$-$C_4$) alkyl, ($C_1$-$C_4$) haloalkyl, ($C_1$-$C_4$) alkoxy, ($C_1$-$C_4$) haloalkoxy, halogen, $NO_2$, $NH_2$, OH, or CN;
each $R^9$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, $NH_2$, OH, and CN;
n is 0 or 1; and
p is 0, 1, 2, or 3.

2. The compound of claim 1, wherein the Linker is

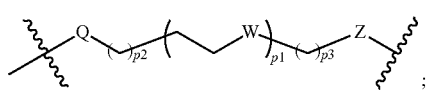

wherein
p1 is an integer selected from 0 to 12;
p2 is an integer selected from 0 to 12;
p3 is an integer selected from 0 to 6;
each W is independently absent, $CH_2$, O, S, NH, or $NR^{10}$;

Z is absent, $CH_2$, O, NH, $NR^{10}$, C(O)($CH_2$)$_{0-3}$, or NHC(O)($CH_2$)$_{0-3}$;
each $R^{10}$ is independently H or $C_1$-$C_3$ alkyl;
Q is absent or $CH_2$C(O)NH; and
wherein the Linker is covalently bonded to the Degron via the

next to Q.

3. The compound of claim 2, wherein X is N.
4. The compound of claim 2, wherein A is phenyl.
5. The compound of claim 2, wherein n is 0.
6. The compound of claim 2, wherein $R^3$ is

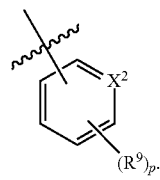

7. The compound of claim 2, wherein $R^1$ is H.
8. The compound of claim 2, wherein $R^2$ is

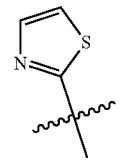

9. The compound of claim 2, wherein

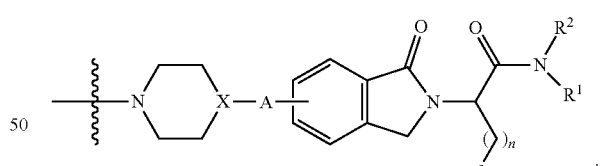

is

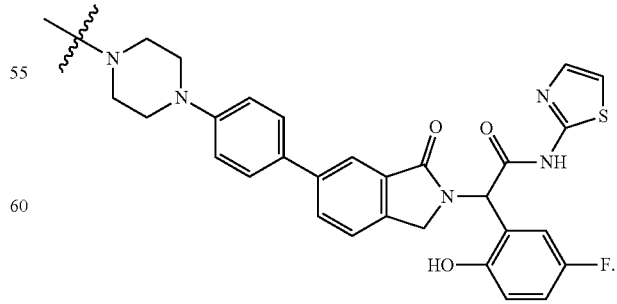

10. The compound of claim 2, wherein the Linker is selected from:

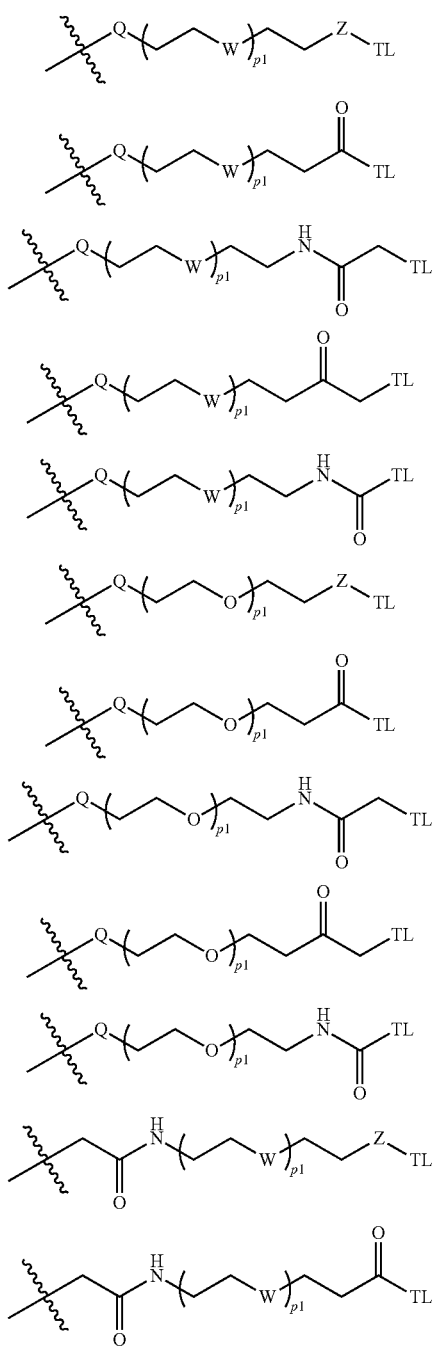
wherein TL is the connecting point to
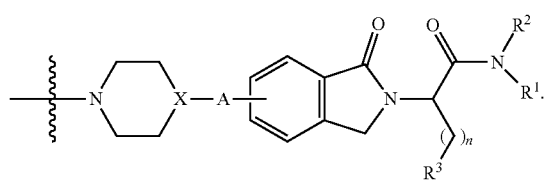
11. The compound of claim 2, wherein the Linker is selected from:
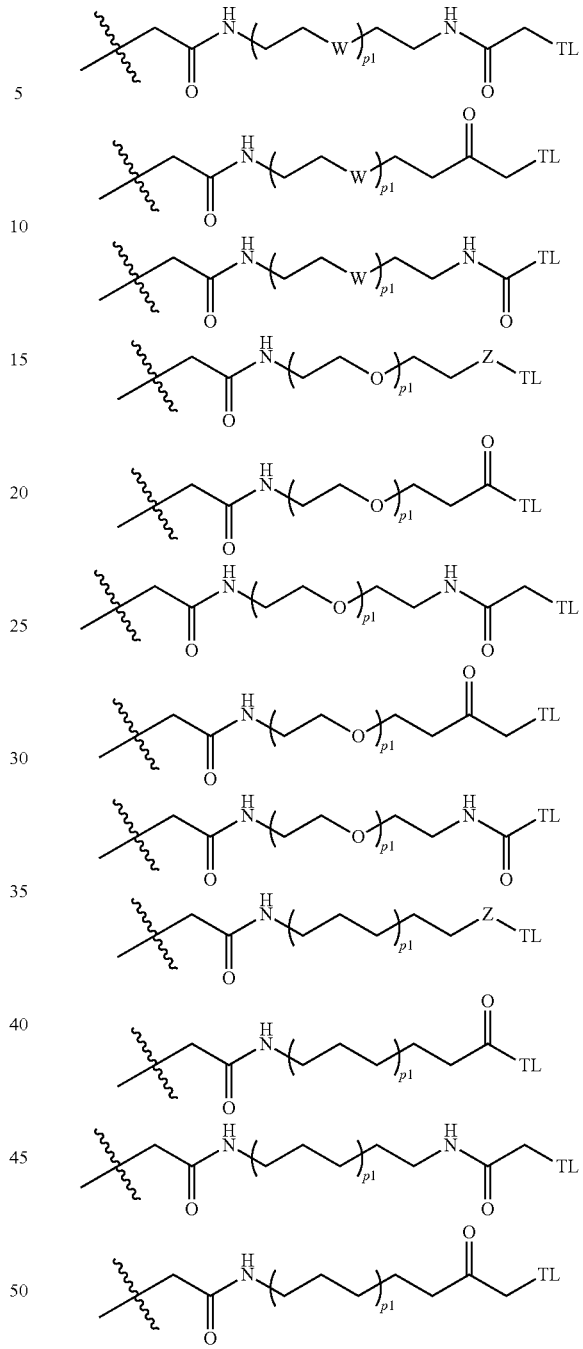
wherein TL is the connecting point to
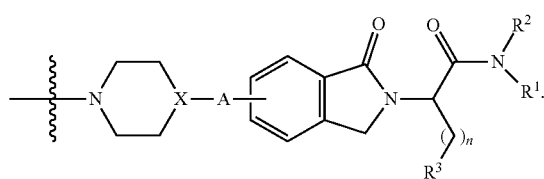
12. The compound of claim 1, wherein the compound is selected from:

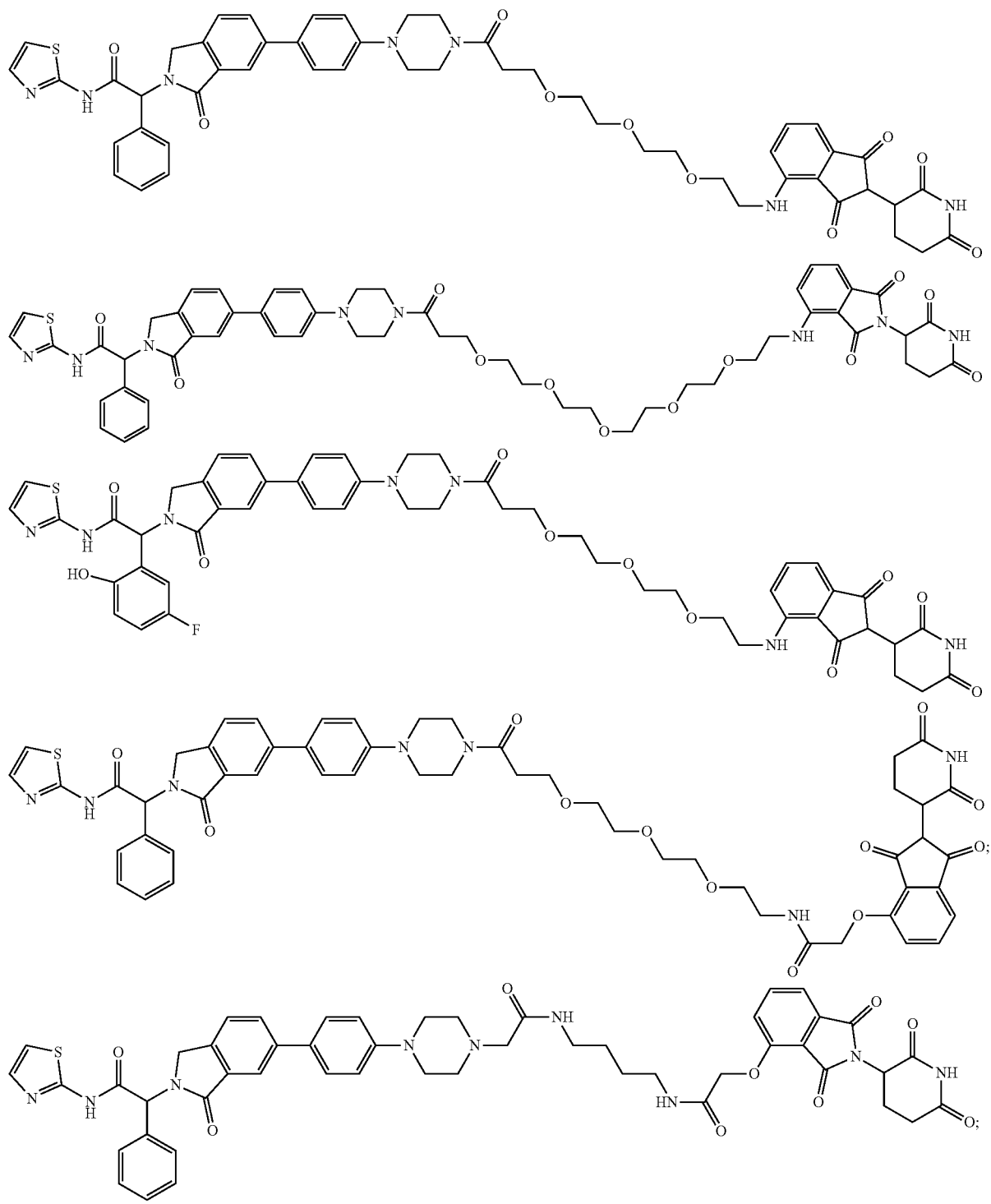

or a pharmaceutically acceptable salt thereof.

13. A pharmaceutical composition comprising a therapeutically effective amount of a compound of claim 1, or an enantiomer, diastereomer, stereoisomer, or pharmaceutically acceptable salt thereof, and a pharmaceutically acceptable carrier.

14. A method for the treatment of cancer mediated by epidermal growth factor receptor (EGFR), or a mutant thereof, comprising administering a therapeutically effective amount of a compound of claim 1 optionally in a pharmaceutically acceptable carrier to a human in need thereof.

15. The method of claim 14, wherein the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphomas, myelomas, or solid tumors.

16. The method of claim 14, wherein the disease is lung cancer.

17. The method of claim 14, wherein the disease is colon cancer.

18. The method of claim 14, wherein the disease is breast cancer.

\* \* \* \* \*